United States Patent
Verma et al.

(10) Patent No.: US 10,597,383 B2
(45) Date of Patent: Mar. 24, 2020

(54) BICYCLIC PROLINE COMPOUNDS

(71) Applicant: Genentech, Inc., South San Francisco, CA (US)

(72) Inventors: Vishal Verma, South San Francisco, CA (US); Daniel Shore, South San Francisco, CA (US); Matthew Volgraf, South San Francisco, CA (US); Anthony A. Estrada, San Mateo, CA (US); Joseph Lyssikatos, Piedmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/250,230

(22) Filed: Jan. 17, 2019

(65) Prior Publication Data

US 2019/0144428 A1    May 16, 2019

Related U.S. Application Data

(63) Continuation of application No. PCT/EP2017/068170, filed on Jul. 18, 2017.

(60) Provisional application No. 62/364,487, filed on Jul. 20, 2016.

(51) Int. Cl.
| | |
|---|---|
| *C07D 401/14* | (2006.01) |
| *C07D 401/12* | (2006.01) |
| *C07D 403/12* | (2006.01) |
| *C07D 403/14* | (2006.01) |
| *C07D 405/14* | (2006.01) |

(52) U.S. Cl.
CPC ......... *C07D 401/14* (2013.01); *C07D 401/12* (2013.01); *C07D 403/12* (2013.01); *C07D 403/14* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 3,773,919 A | | 11/1973 | Boswell et al. |
| 4,485,045 A | | 11/1984 | Regan |
| 4,544,545 A | | 1/1985 | Ryan et al. |
| 5,004,697 A | | 2/1991 | Pardridge et al. |
| 5,112,596 A | | 12/1992 | Malfroy-Camine |
| 5,268,164 A | | 7/1993 | Kozarich et al. |
| 5,506,206 A | | 9/1996 | Kozarich et al. |
| 5,686,416 A | | 11/1997 | Kozarich et al. |
| 6,645,939 B1 * | | 11/2003 | Durette ................ C07D 205/04 530/331 |
| 8,614,201 B2 * | | 12/2013 | Berthelot ............ C07D 207/48 514/117 |
| 10,179,782 B2 * | | 1/2019 | Estrada ................ C07D 403/12 |
| 2002/0025313 A1 | | 2/2002 | Micklus et al. |
| 2002/0038086 A1 | | 3/2002 | Hynynen et al. |
| 2002/0065259 A1 | | 5/2002 | Schatzberg et al. |
| 2003/0073713 A1 | | 4/2003 | Schoenhard |
| 2003/0162695 A1 | | 8/2003 | Schatzberg et al. |
| 2003/0129186 A1 | | 10/2003 | Beliveau et al. |
| 2004/0131692 A1 | | 8/2004 | Kreuter et al. |
| 2004/0204354 A1 | | 10/2004 | Nelson et al. |
| 2005/0089473 A1 | | 4/2005 | Black et al. |
| 2005/0124533 A1 | | 9/2005 | Schatzberg et al. |
| 2015/0197509 A1 * | | 7/2015 | Brotherton-Pleiss ........... C07D 231/18 514/255.05 |
| 2016/0221945 A1 * | | 8/2016 | Chen ................ C07D 403/12 |
| 2016/0264567 A1 * | | 9/2016 | Yuen ................ C07D 403/12 |
| 2016/0332999 A1 * | | 11/2016 | Kobayashi ........... C07D 453/06 |
| 2019/0023699 A1 * | | 1/2019 | Kobayashi ........... C07D 403/12 |
| 2019/0144430 A1 * | | 5/2019 | Hu ................ C07D 213/61 |

FOREIGN PATENT DOCUMENTS

| | | | | |
|---|---|---|---|---|
| CA | 2938198 A1 * | 8/2015 | ........ | C07D 453/06 |
| EP | 0133988 | 1/1984 | | |
| EP | 0102324 A2 | 7/1984 | | |
| WO | WO-2015052264 A1 * | 4/2015 | ........ | C07D 403/12 |

OTHER PUBLICATIONS

L.H. Jiang et al., 12 Current Drug Targets, 724-736 (2011) (Year: 2011).*
Z. Wang et al., 19 Drug Discovery Today, 145-150 (2014) (Year: 2014).*
S. Earley, 167 British Journal of Pharmacology, 13-22 (2012) (Year: 2012).*
L. Horvath et al., 18 Arthritis Research & Therapy (2016) (Year: 2016).*
T. Lowin et al., Arthritis Research & Therapy (2015) (Year: 2015).*
L. De Petrocellis et al., 23 Expert Opinion on Therapeutic Patents (2013) (Year: 2013).*

(Continued)

*Primary Examiner* — Alexander R Pagano
(74) *Attorney, Agent, or Firm* — Robert C. Hall

(57) ABSTRACT

The invention is concerned with the compounds of formula I:

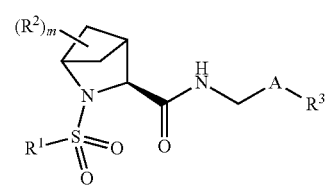

and salts thereof. In addition, the present invention relates to methods of manufacturing and methods of using the compounds of formula I as well as pharmaceutical compositions containing such compounds. The compounds may be useful in treating diseases and conditions mediated by TRPA1, such as pain.

19 Claims, No Drawings

(56) References Cited

OTHER PUBLICATIONS

D. Pretl et al., 42 Pharm. Pat. Anal. (2015) (Year: 2015).*
D.P. Corey et al., 432 Nature, 723-730 (2004) (Year: 2004).*
T. Streng et al. 53 European Urology, 391-400 (2008) (Year: 2008).*
M. Takumida et al., 129 Acta Oto-Laryngologica, 1050-1060 (2009) (Year: 2009).*
A. Elgoyhen et al., 16 Nature Reviews Neuroscience (2015) (Year: 2015).*
(International Preliminary Report on Patentability—PCT/EP2017/068170 dated Jan. 22, 2019).
(International Search Report—PCT/EP2017/068170 dated Oct. 9, 2017 Oct. 9, 2017).
Agopyan, N., et al., "TRPV1 receptors mediate particulate matter-induced apoptosis" Am J Physiol Lung Cell Mol Physiol 286:L563-L572 (Oct. 30, 2003).
Agopyan, N., et al., "Vanilloid receptor activation by 2- and 10-µm particles induces responses leading to apoptosis in human airway epithelial cells" Toxicol Appl Pharm 192:21-35 (May 28, 2003).
Ansel's Pharmaceutical Dosage Forms and Drug Delivery Systems (Table of Contents only, in 6 pages), Allen et al., 8th edition, Philadelphia, PA:Lippincott Williams & Wilkins, (2004).
Asai, Hideaki, et al., "Heat and mechanical hyperalgesia in mice model of cancer pain" Pain 117:19-29 (May 3, 2005).
Barton, N.J., et al., "Attenuation of experimental arthritis in TRPV1R knockout mice" Exp Mol Pathol 81:166-170 (Jun. 16, 2006).
Bobo et al., "Convection-enhanced delivery of macromolecules in the brain" Proc. Natl. Acad. Sci. USA 91:2076-2080 (1994).
Bolcskei, Kata, et al., "Investigation of the role of TRPV1 receptors in acute and chronic nociceptive processes using gene-deficient mice" Pain 117:368-376 (Jun. 27, 2005).
Bundgaard A Textbook of Drug Design and Development; Chapter 5 "Design and Application of Prodrugs":113-191 (1991).
Bundgaard et al., "(C) Means to Enhance Penetration (1) Prodrugs as a means to improve the delivery of peptide drugs" Advanced Drug Delivery Reviews 8:1-38 (1992).
Bundgaard, "Design of prodrugs: Bioreversible derivatives for various functional groups and chemical entities" Design of Prodrugs:1 (1985).
Chan, C.L.H., et al., "Sensory fibres expressing capsaicin receptor TRPV1 in patients with rectal hypersensitivity and faecal urgency" Lancet 361:385-391 (Feb. 1, 2003).
Coffey, S. Rodd's Chemistry of Carbon Compounds Coffey, S., Second edition, Elsevier B.V.:Elsevier B.V., vol. I-IV (2008).
de Yebenes et al., "Continuous Intracerebroventricular Infusion of Dopamine and Dopamine Agonists Through a Totally Implanted Drug Delivery System in Animal Models of Parkinson's Disease" Movement Disorders 2(3):143-158 (1987).
Dinis, Paulo, et al., "Anandamide-Evoked Activation of Vanilloid Receptor 1 Contributes to the Development of Bladder Hyper-reflexia and Nociceptive Transmission to Spinal Dorsal Horn Neurons in Cystitis" J Neurol Sci 24(50):11253-11263 (Dec. 15, 2004).
Eppstein et al., "Biological activity of liposome-encapsulated murine interferon γ is mediated by a cell membrane receptor" Proc. Natl. Acad. Sci. USA 82:3688-3692 (1985).
Fleisher et al., "Improved oral drug delivery: solubility limitations overcome by the use of prodrugs" Advanced Drug Delivery Reviews 19:115-130 (1996).
Gennaro et al. Remington: The Science and Practice of Pharmacy (Press), Philadelphia:Lippincott, Williams & Wilkins, (2000).
Geppetti, P., et al., "Activation and sensitisation of the vanilloid receptor: role in gastrointestinal inflammation and function" Brit J Pharmacol 141:1313-1320 (Mar. 29, 2004).
Ghilardi, J.R., et al., "Selective Blockade of the Capsaicin Receptor TRPV1 Attenuates Bone Cancer Pain" J Neurol Sci 25(12):3126-3131 (Mar. 23, 2005).
Gill et al., "Direct Brain Infusion of Glial Cell Line-Derived Neurotrophic Factor in Parkinson Disease" Nature Med. 9:589-595 (2003).
Goadsby, P. J., "Post-triptan Era for the Treatment of Acute Migraine" Curr Pain Head Reports 8:393-398 (Jan. 1, 2004).

Harbaugh, "Intracerebroventricular cholinergic drug administration in Alzheimer's disease: preliminary results of a double-blind study" J. Neural. Transm. 24 Suppl.:271-277 (1987).
HO Fiesers' Reagents for Organic Synthesis (Table of Contents, in 5 pages), Hoboken, New Jersey:John Wiley & Sons, Inc., vol. 23 (2007).
Honore, P., et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats" J Pharmacol Exp Ther 314(1):410-421 (Apr. 14, 2005).
Hwang et al., "Hepatic uptake and degradation of unilamellar sphingomyelin/cholesterol liposomes: A kinetic study" Proc. Natl. Acad. Sci. USA 77(7):4030-4034 (1980).
Kakeya et al., "Studies on Prodrugs of Cephalosporins.I. $^{1)}$ Synthesis and Biological Properties of Glycyloxybenzoyloxymethyl and Glycylaminobenzoyloxymethyl Esters of 7β-[2-(2-Aminothiazol-4yl)-(Z)-2-methoxyiminoacetamido]-3-3-methyl-3-cephem-4-carboxylic Acid" Chem. Pharm. Bull. 32(2):692-698 (1984).
Kimbal, E.S., et al., "Vanilloid receptor 1 antagonists attenuate disease severity in dextran sulphate sodium-induced colitis in mice" Neurogastroent Motil 16:811-818 (Jan. 5, 2004).
Kosugi, Masafumi, et al., "Activation of TRPA1 Channel Facilitates Excitatory Synaptic Transmission in Substantia Gelatinosa Neurons of the Adult Rat Spinal Cord" J Neurol Sci 27(16):4443-4451 (Apr. 18, 2007).
Kremeyer, Barbara, et al., "A Gain-of-Function Mutation in TRPA1 Causes Familial Episodic Pain Syndrome" Neuro 66:671-680 (Jun. 10, 2010).
Lalloo, Umesh G., et al., "Capsazepine inhibits cough induced by capsaicin and citric acid but not by hypertonic saline in guinea pigs" J Appl Physiol:1082-1087 (May 23, 1995).
Langer et al., "Biocompatibility of polymeric delivery systems for macromolecules" Journal of Biomedical Materials Research 15:267-277 (1981).
Menendez, L., et al., "Analgesic effects of capsazepine and resiniferatoxin on bone cancer pain in mice" Neurosci Lett 393:70-73 (Sep. 19, 2005).
Neuwelt, E. A. Implications of the Blood-Brain Barrier and Its Manipulation Neuwelt, E.A., ed.,Plenum Publishing Corporation-Springer, vol. vols. 1-2:1-434, (Jan. 1, 1989).
Notari, Robert, et al. Methods of Enzymology: Drug and Enzyme Targeting "Theory and Practice of Prodrug Kinetics" Widder, Kenneth J., eds, First edition, Waltham, MA:Academic Press, vol. 112:309-396 (Jun. 11, 1985).
Papanastassiou et al., "The potential for efficacy of the modified (ICP 34.5$^{-}$) herpes simplex virus HSV1716 following intratumoural injection into human malignant glioma: a proof of principle study" Gene Therapy 9:398-406 (2002).
Paquette, Leo. A. Organic Reactions New York, NY:Wiley and Sons, vol. 1-40:1-528 (Jul. 1, 1991).
Pomonis, J.D., et al., "N-(4-Tertiarybutylphenyl)-4-(3-cholorphyridin-2-yl) tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain" J Pharmacol Exp Ther 306(1):387-393 (Apr. 31, 2003).
Remington's Pharmaceutical Sciences (Table of Contents, total in 4 pages), Osol et al., 16th edition, Easton, Pennsylvania:Mack Publishing Company, (1980).
Robinson et al., "Discovery of the Hemifumarate and (α-L-Alanyloxy)methyl Ether as Prodrugs of an Antirheumatic Oxindole: Prodrugs for the Enolic OH Group" J. Med. Chem. 39:10-18 (1996).
Rowe, R. Handbook of Pharmaceutical Excipients Chicago:Pharmaceutical Press, (2005).
Sanchez, Maria, et al., "Expression of the transient receptor potential vanilloid 1 (TRPV1) in LNCaP and PC-3 prostate cancer cells and in human prostate tissue" Eur J Pharmacol 515:20-27 (Apr. 8, 2005).
Sculptoreanu, A., et al., "Protein kinase C contributes to abnormal capsaicin responses in DRG neurons from cats with feline interstitial cystitis" Neurosci Lett 381:42-46 (Jan. 28, 2005).

(56) References Cited

OTHER PUBLICATIONS

Sidman et al., "Controlled Release of Macromolecules and Pharmaceuticals from Synthetic Polypeptides Based on Glutamic Acid" Biopolymers 22:547-556 (1983).

Szabo, A., et al., "Role of Transient Receptor Potential Vanilloid 1 Receptors in Adjuvant-Induced Chronic Arthritis: In Vivo Study Using Gene-Deficient Mice" J Pharmacol Exp Ther 314(1):111-119 (Apr. 5, 2005).

Walker, Katherine, et al., "The VR1 Antagonist Capsazepine Reverses Mechanical Hyperalgesia in Models of Inflammatory and Neuropathic Pain" J Pharmacol Exp Ther 304(1):56-62 (Sep. 9, 2002).

Wei, Hong, et al., "Spinal transient receptor potential ankyrin 1 channel contributes to central pain hypersensitivity in various pathophysiological conditions in the rat" Pain 152:582-591 (Nov. 29, 2010).

Wei, Hong, et al., "Spinal TRPA1 ion channels contribute to cutaneous neurogenic inflammation in the rat" Neurosci Lett 479:253-256 (May 23, 2010).

Yiangou, Y., et al., "Vanilloid receptor 1 immunoreaetivity in inflamed human bowel" Lancet 357:1338-1339 (Apr. 28, 2001).

\* cited by examiner

BICYCLIC PROLINE COMPOUNDS

CROSS-REFERENCE TO RELATED APPLICATION

This application is a Continuation of PCT/EP2017/068170 filed on Jul. 18, 2017, which claims priority benefit of U.S. Provisional Application Ser. No. 62/364,487 filed on Jul. 20, 2016, the disclosures of which are incorporated herein in their entirety.

FIELD OF THE INVENTION

The invention relates to 2.1.1 bicyclic proline compounds, their manufacture, pharmaceutical compositions containing them and their use as Transient Receptor Potential (TRP) channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor.'

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., *J. Neurosci* 27, (2007) 4443-4451; Kremayer et al., *Neuron* 66 (2010) 671-680; Wei et al., *Pain* 152 (2011) 582-591); Wei et al., *Neurosci Lett* 479 (2010) 253-256)) providing additional rationale for the utility of small molecule TRPA1 inhibitors in the treatment of pain disorders.

SUMMARY OF THE INVENTION

In some embodiments, a compound or a pharmaceutically acceptable salt thereof of the following formula (I) is provided:

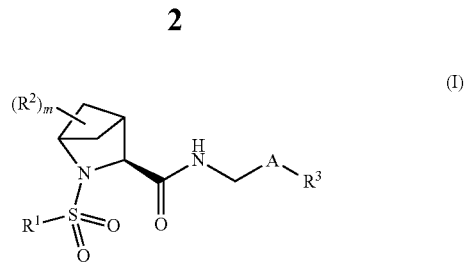

$R^1$ is selected from aryl or heteroaryl, each optionally substituted with one or more groups independently selected from halogen, —$C_{1-6}$ alkyl and —$C_{1-6}$ haloalkyl. Each $R^2$ is independently selected from —$C_{1-6}$ alkyl and m is 0, 1 or 2. $R^3$ is a 4-, 5-, 6- or 7-membered heterocycle, aryl or heteroaryl optionally substituted with one or more groups independently selected from halogen, —$C_{1-6}$ alkyl, —$C_{1-6}$ haloalkyl, —O—$C_{1-6}$ alkyl, and —CN. A is selected from $A^1$, $A^2$ and $A^3$ wherein: $A^1$ unsubstituted or substituted 5-membered heteroaryl comprising one or two nitrogen hetero atoms; $A^2$ is unsubstituted or substituted aryl; and $A^3$ is unsubstituted or substituted 6-membered heteroaryl comprising one or two nitrogen hetero atoms.

In some embodiments, a pharmaceutical composition comprising a compound of formula (I) or a pharmaceutically acceptable salt thereof, and a pharmaceutically acceptable carrier, diluent or excipient is provided.

In some embodiments, a compound of formula (I) or a pharmaceutically acceptable salt thereof is provided for use in medical therapy.

In some embodiments, a compound of formula (I) or a pharmaceutically acceptable salt thereof is provided for the treatment or prophylaxis of a respiratory disorder.

In some embodiments, a compound of formula (I) or a pharmaceutically acceptable salt thereof is provided for the preparation of a medicament for the treatment or prophylaxis of a respiratory disorder.

In some embodiments, a method for treating a respiratory disorder in a mammal is provided, the method comprising, administering a compound of formula (I) or a pharmaceutically acceptable salt thereof to the mammal.

In some embodiments, a compound of formula (I) or a pharmaceutically acceptable salt thereof is provided for modulating TRPA1 activity.

In some embodiments, a compound of formula (I) or a pharmaceutically acceptable salt thereof is provided for the treatment or prophylaxis of a disease or condition mediated by TRPA1 activity.

In some embodiments, a compound of formula (I) or a pharmaceutically acceptable salt thereof is provided for use for the preparation of a medicament for the treatment or prophylaxis of a disease or condition that is mediated by TRPA1 activity.

In some embodiments, a method for modulating TRPA1 activity is provided, the method comprising contacting TRPA1 with a compound of formula (I) or a pharmaceutically acceptable salt thereof.

In some embodiments, a method for treating a disease or condition mediated by TRPA1 activity in a mammal is provided, the method comprising administering a compound of formula (I) or a pharmaceutically acceptable salt thereof to the mammal.

DETAILED DESCRIPTION OF THE INVENTION

Definitions

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ to $R^5$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring.

"Aryl" means a cyclic aromatic hydrocarbon moiety having a mono-, bi- or tricyclic aromatic ring of 6 to 16 carbon ring atoms. The aryl group can be optionally substituted as defined herein. Examples of aryl moieties include, but are not limited to, phenyl, naphthyl, phenanthryl, fluorenyl, indenyl, pentalenyl, azulenyl, and the like, The term "aryl" also includes partially hydrogenated derivatives of the cyclic aromatic hydrocarbon moiety provided that at least one ring of the cyclic aromatic hydrocarbon moiety is aromatic, each being optionally substituted. In one embodiment the aryl has 6 to 14 carbon ring atoms (i.e., ($C_6$-$C_{14}$) aryl). In another embodiment the aryl has 6 to 10 carbon ring atoms (i.e., ($C_6$-$C_{10}$)aryl).

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a saturated or partially unsaturated carbocyclic moiety having mono- or bicyclic (including bridged bicyclic) rings and 3 to 10 carbon atoms in the ring. The cycloalkyl moiety can optionally be substituted with one or more substituents. In particular embodiments cycloalkyl contains from 3 to 8 carbon atoms (i.e., ($C_3$-$C_8$) cycloalkyl). In other particular embodiments cycloalkyl contains from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a "spirocycloalkyl" fashion such as "spirocyclopropyl":

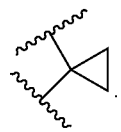

"Heterocycle" or "heterocyclyl" refers to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4 heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo [2.2.1]heptanyl, octahydroindolyl, or tetrahydroquinolinyl.

Unless otherwise indicated, the term "hydrogen" or "hydro" refers to the moiety of a hydrogen atom (—H) and not $H_2$.

The term "respiratory disorder" includes chronic obstructive pulmonary disorder (COPD), asthma, allergic rhinitis, bronchospasm, and cystic fibrosis.

Unless otherwise indicated, the term "a compound of the formula" or "a compound of formula" or "compounds of the formula" or "compounds of formula" refers to any compound selected from the genus of compounds as defined by the formula (including, if not otherwise noted, any embodiment thereof such as a pharmaceutically acceptable salt or ester of any such compound, a stereoisomer, a geometric isomer, a tautomer, a solvate, a metabolite, an isotope, a pharmaceutically acceptable salt, or a prodrug).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I, which can be useful as an intermediate for isolating or purifying a compound of formula I. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered, including but not limited to, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

In the various embodiments of the present disclosure, the 2.1.1 bicyclic proline compounds or a pharmaceutically acceptable salt thereof are of the following formula (I):

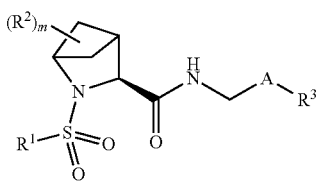

$R^1$ is selected from aryl or heteroaryl, each optionally substituted with one or more groups independently selected from halogen, —CN, —$C_{1-6}$ alkyl and —$C_{1-6}$ haloalkyl. In some embodiments, $R^1$ is selected from: (1) aryl substituted with a substituent selected from Br, Cl, F, —$CHF_2$, —$CF_3$, —$CHCl_2$ and —$CCl_3$ at any ring position; and (2) benzofuran substituted with a substituent selected from Cl, F, —$CHF_2$, —$CF_3$, —$CHCl_2$ and —$CCl_3$ at any ring position. In some embodiments, $R^1$ is selected from:

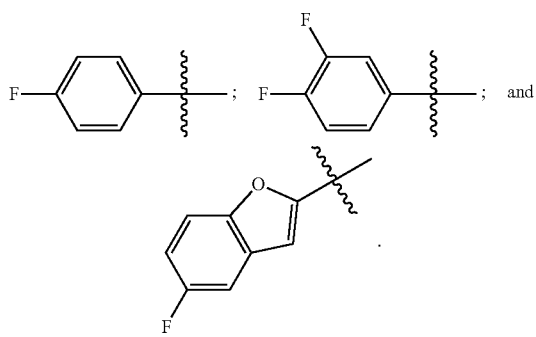

In some alternative embodiments, each F may be at a ring position other than the indicated position, and F may be replaced with —$CHF_2$ or —$CF_3$.

Each $R^2$ is independently selected from —$C_{1-6}$ alkyl and m is 0, 1 or 2. In some embodiments, $R^2$ is selected from —$CH_3$, —$CH_2CH_3$, —$CH_2CH_2CH_3$, —$CH(CH_3)_2$. In some embodiments, $R^2$ is —$CH_3$. In some embodiments, m is 0. In some embodiments, m is 1. In some embodiments, m is 2.

$R^3$ is a 4-, 5-, 6- or 7-membered heterocycle, carbocycle, aryl or heteroaryl optionally substituted with one or more groups independently selected from halogen, —$C_{1-6}$ alkyl, —$C_{1-6}$ haloalkyl, —O—$C_{1-6}$ alkyl, and —CN. In some embodiments, $R^3$ is a 5- or 6-membered optionally substituted heteroaryl comprising one or two nitrogen hetero atoms. In some embodiments, $R^3$ is selected from:

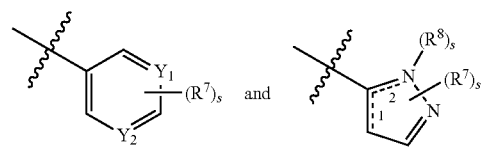

wherein: at least one of $Y_1$ and $Y_2$ is N; each s is independently 0 or 1; $R^7$ is selected from halogen, —O—$C_{1-6}$ alkyl, and —$C_{1-6}$ haloalkyl; $R^8$ is selected from H, —$C_{1-6}$ alkyl, and —$C_{1-6}$ haloalkyl; and the dashed bonds indicated at position 1 and position 2 are optional double bonds, wherein a double bond may be located only at one of position 1 and position 2, and wherein $R^8$ is absent when a double bond is present at position 2. In some embodiments, $R^7$ is selected from —$CF_3$, —$CF_2H$, —$OCF_3$ and —$OCF_2H$. In some embodiments, $R^3$ is selected from:

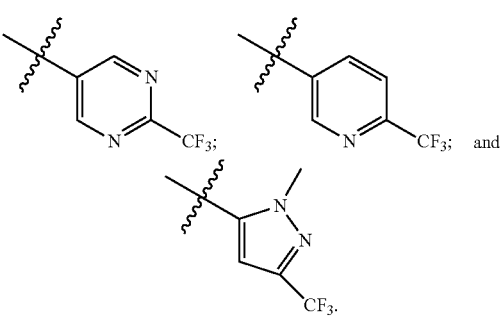

In some alternative embodiments, —$CF_3$ may be at a ring position other than the indicated position, and —$CF_3$ may be replaced with F or —$CHF_2$.

A is selected from $A^1$, $A^2$ and $A^3$.

In some embodiments A is $A^1$ wherein $A^1$ is selected from unsubstituted or substituted 5-membered heteroaryl comprising one or two nitrogen hetero atoms. In some embodiments, $A^1$ is selected from:

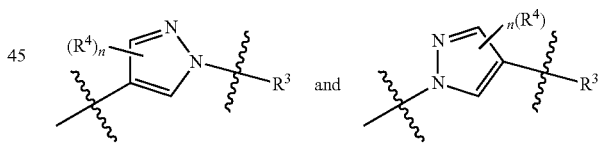

wherein n is 0 or 1 and wherein $R^4$ is selected from halogen, —O—$C_{1-6}$ alkyl and —$C_{1-6}$ haloalkyl. In some embodiments, $A^1$ is selected from:

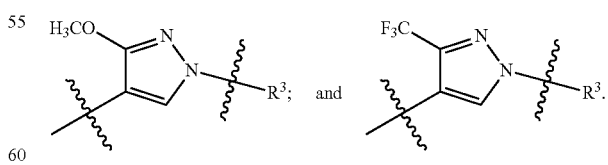

In some alternative embodiments, —$CH_3$ and —$CF_3$ may be at a ring position other than the indicated position, and may be replaced with F or —$CHF_2$.

In some embodiments A is $A^2$ wherein $A^2$ is selected from unsubstituted and substituted aryl. In some embodiments, $A^2$ is of the formula:

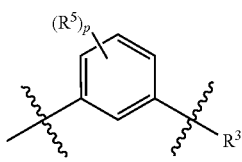

wherein p is 0 or 1 and wherein $R^5$ is selected from halogen, CN, —O—$C_{1-6}$ alkyl, —O—$C_{1-6}$ haloalkyl, —$C_{1-6}$ haloalkyl and —$C_{3-7}$ cycloalkyl. In some embodiments, $R^5$ is selected from F, Cl, —CN, —$CH_2CN$, —$CF_2H$, and —$CF_3$. In some embodiments, $A^2$ is selected from:

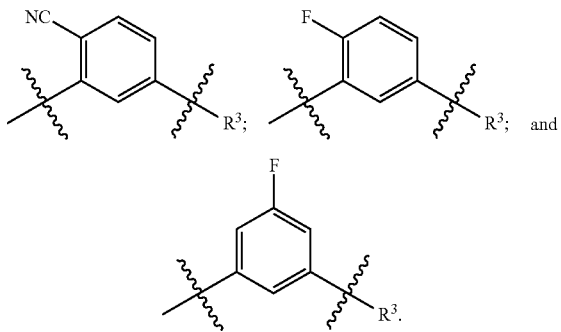

In some alternative embodiments, —CN and F may be at a ring position other than the indicated position, and may be replaced with —$CHF_2$ or —$CF_3$.

In some embodiments A is $A^3$ wherein $A^3$ is selected from unsubstituted and substituted 6-membered heteroaryl comprising one or two nitrogen hetero atoms. In some embodiments, A3 is of the formula:

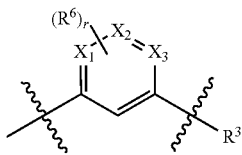

wherein: (1) $X_1$, $X_2$ and $X_3$ are independently selected from C and N wherein (i) one of $X_1$, $X_2$ and $X_3$ is N and r is 0, 1 or 2, or (ii) $X_1$ and $X_3$ are each N and r is 0 or 1; and (2) each $R^6$ is independently selected from halogen, —CN, —$C_{3-7}$ cycloalkyl, —O—$C_{1-6}$ haloalkyl, —O—$C_{1-6}$ alkyl, and —$C_{1-6}$ haloalkyl. In some embodiments, $R^6$ is selected from F, Cl, —CN, -cyclopropyl, Br, —$OCF_3$, —$CF_3$, —CFH, and —O—$CH_2$—$CF_3$. In some embodiments, $A^3$ is selected from:

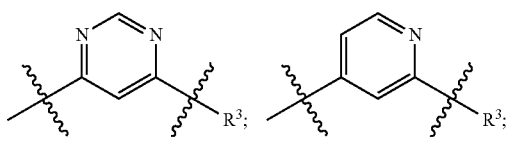

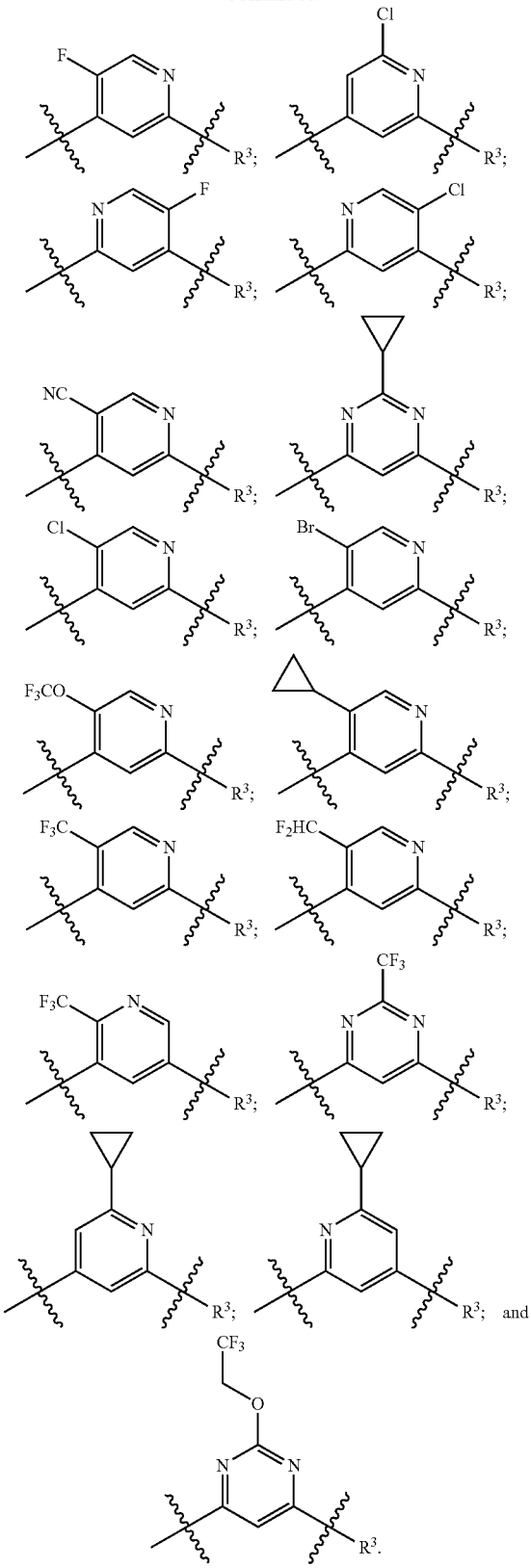

In some alternative embodiments, F, Cl, Br, -cyclopropyl, —$CHF_2$, $CF_3$, —$OCF_3$ and —O—$CH_2$—$CF_3$ may be at a ring position other than the indicated position.

In some embodiments, the 2.1.1 bicyclic proline compounds are selected from the following listing of compounds, wherein the ring substitutions may be at a ring position other than the indicated ring position and the indicated substituent may alternatively be replaced by a substituent as described elsewhere herein:
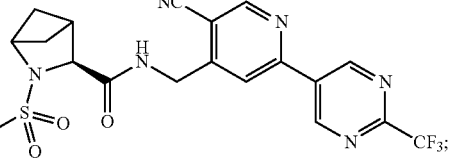
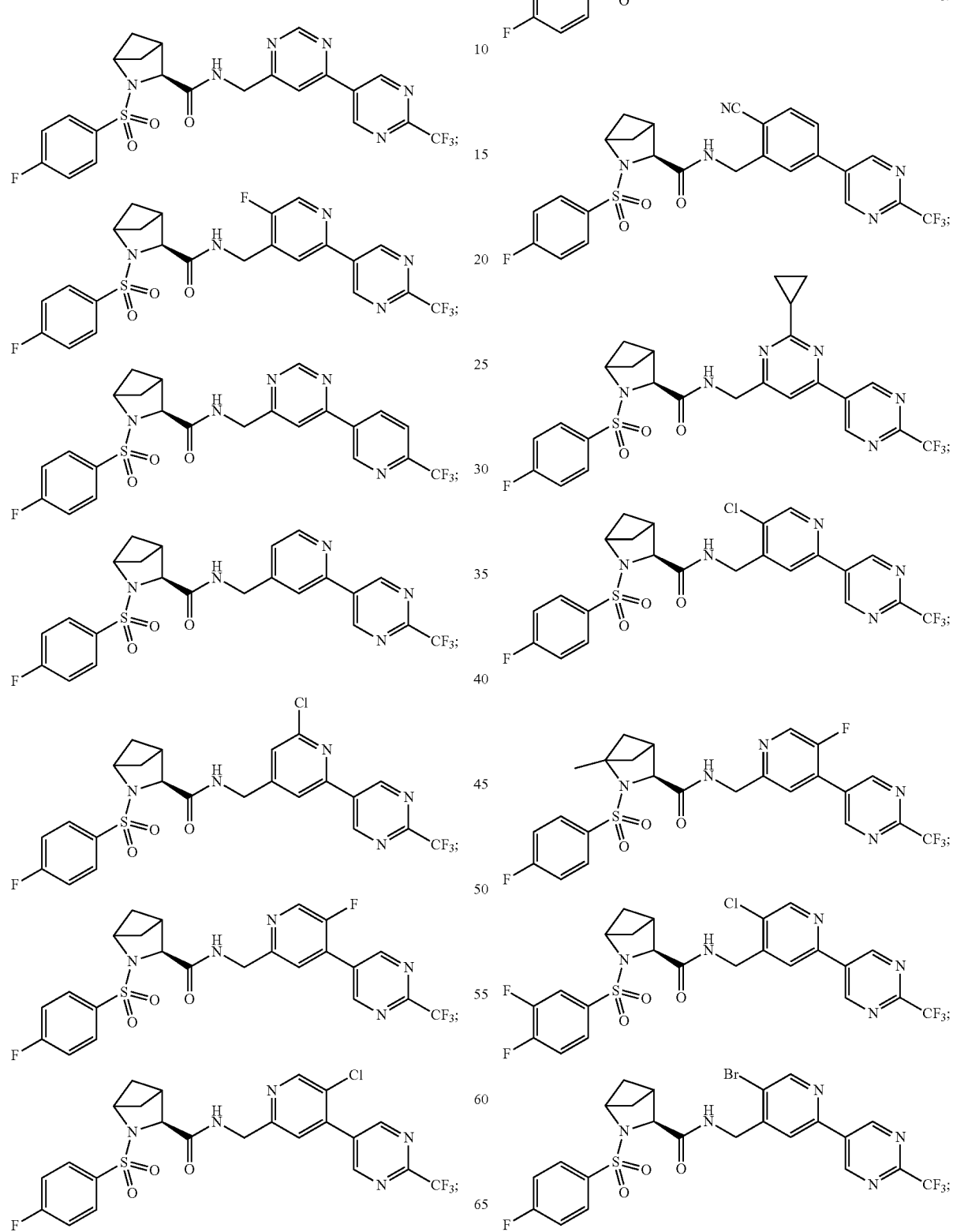

-continued
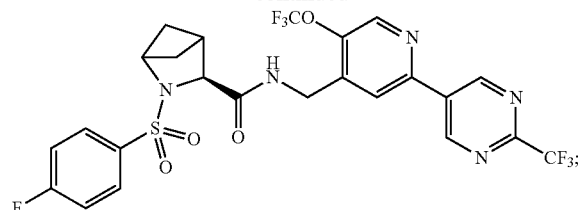
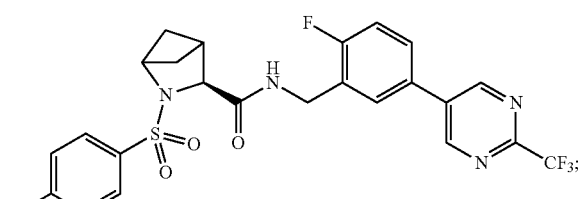
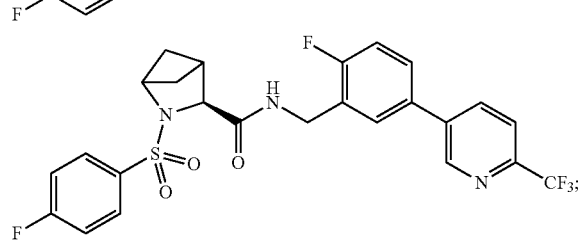
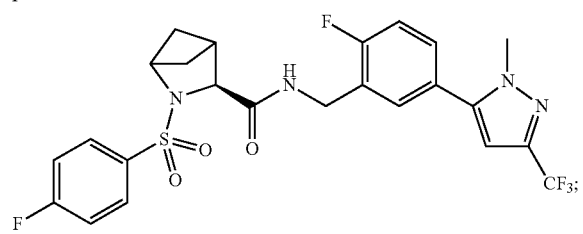
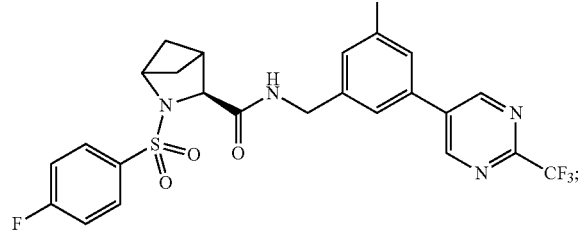
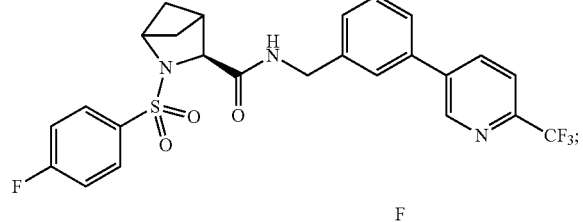
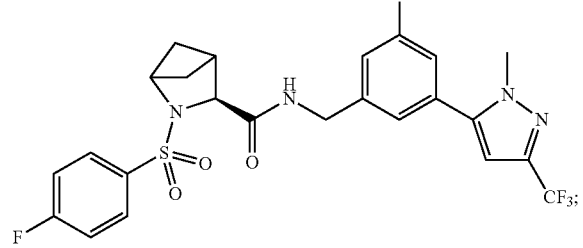
-continued
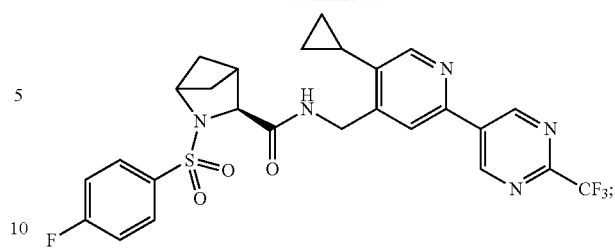
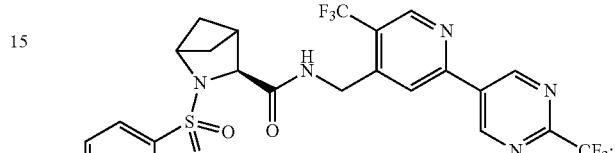
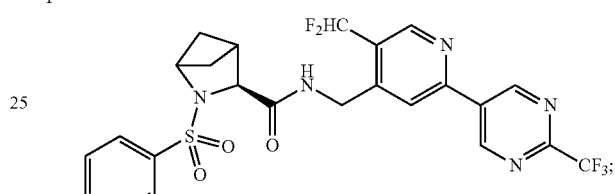
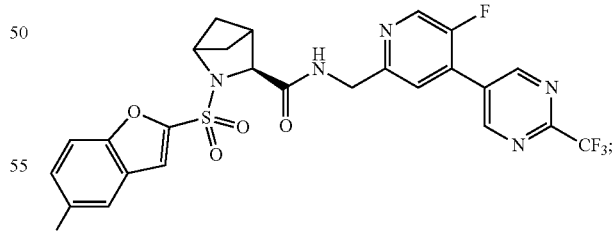
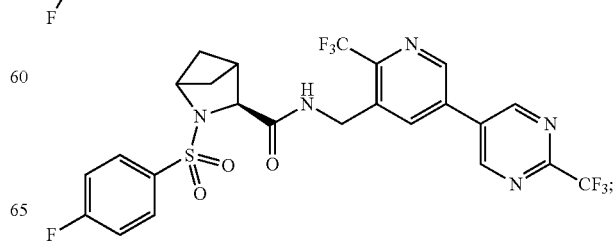

-continued

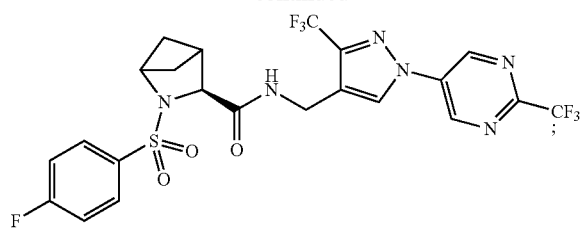

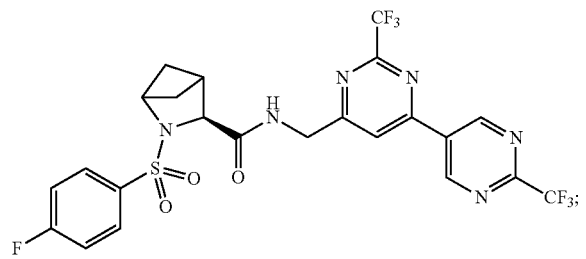

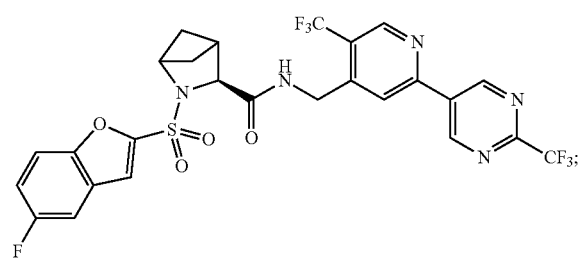

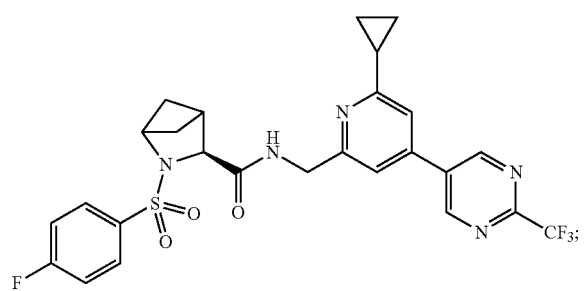

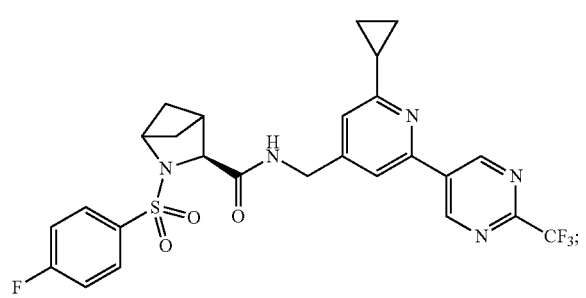

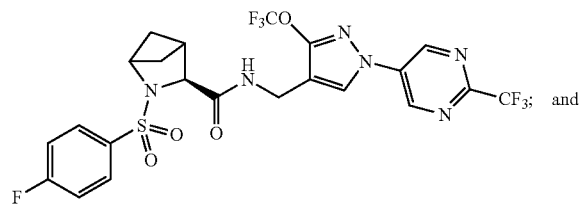

-continued

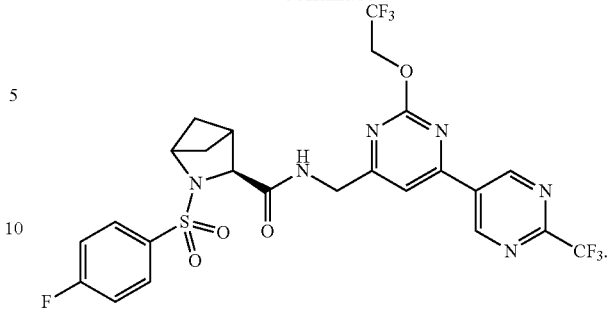

In another embodiment of the invention, the compounds of formula I are isotopically-labeled by having one or more atoms therein replaced by an atom having a different atomic mass or mass number. Such isotopically-labeled (i.e., radiolabeled) compounds of formula I are considered to be within the scope of this invention. Examples of isotopes that can be incorporated into the compounds of formula I include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula I, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula I can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula I can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula I or a pharmaceutically acceptable salt thereof and a pharmaceutically acceptable carrier.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier. The compositions of the invention can be used to selectively inhibit TRPA1 in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions or medicaments comprising a compound of formula I (or embodiments thereof including stereoisomers, geometric isomers, tautomers, solvates, metabolites, isotopes, pharmaceutically acceptable salts, and prodrugs) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, for instance oral (e.g, buccal), topical, sublingual, rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I (or embodiments thereof including stereoisomers, geometric isomers, tautomers, solvates, metabolites, isotopes, pharmaceutically acceptable salts, and prodrugs thereof) are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 0.1 mg, about 1 mg, about 5 mg, about 10 mg, about 25 mg, about 30 mg, about 50 mg, about 80 mg, about 100 mg, about 150 mg, about 250 mg, about 300 mg and about 500 mg of the compounds (or an embodiment thereof) of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention (or an embodiment thereof) per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™ Guildford Pharmaceutical).

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1 activity. Accordingly, the compounds of the invention (or an embodiment thereof) are useful as a medical therapy for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; respiratory disorders such as chronic obstructive pulmonary disease; incontinence; and disorders associated with reduced blood flow to the CNS or CNS hypoxia.

In a specific embodiment, compounds of the invention (or an embodiment thereof) can be administered as a medical therapy to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bolcskei et al., *Pain* 2005, 117(3), 368-376), sunburn, dermatitis, psoriasis, eczema, insect sting or bite, musculoskeletal disorders, bony fractures, ligamentous sprains, plantar fascitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., *Lancet,* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacal Exp Ther.,* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. *J. Pharmacal. Exp. Ther.* 2003, 306, 387; Walker, K. M. et al., *J. Pharmacal. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention (or an embodiment thereof) can be administered as a medical therapy to treat itch, which may arise from various sources, such as dermatological or inflammatory disorders.

In another specific embodiment, compounds of the invention (or an embodiment thereof) can be administered as a medical therapy to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., *Br. J. Pharmacal.* 2004, 141, 1313-20; Yiangou, Y. et al., *Lancet* 2001, 357, 1338-39; Kimball, E. S. et al., *Neurogastroenterol. Motif,* 2004, 16, 811), osteoarthritis (Szabo, A. et al., *J. Pharmacal. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention (or an embodiment thereof) can be administered as a medical therapy to treat inner ear disorders. Such disorders include, for example, hyperacusis, tinnitus, vestibular hypersensitivity, and episodic vertigo.

For example, compounds of the invention (or an embodiment thereof) can be administered as a medical therapy to treat tracheobronchial and diaphragmatic dysfunctions including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacal.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In another specific embodiment, compounds of the invention (or an embodiment thereof) can be administered as a medical therapy to treat gastrointestinal and urinary tract disorders such as, bladder overactivity, inflammatory hyperalgesia, visceral hyperreflexia of the urinary bladder, hemorrhagic cystitis (Dinis, P. et al., *J Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J Pharmacal.,* 2005, 515, 20-27), nausea, vomiting, intestinal cramping, intestinal bloating, bladder spasms, urinary urgency, defecation urgency and urge incontinence.

In another specific embodiment, compounds of the invention (or an embodiment thereof) can be administered as a medical therapy to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention (or an embodiment thereof) can be administered as a medical therapy to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention (or an embodiment thereof) are administered as a medical therapy to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound according to formula I (or an embodiment thereof) as described elsewhere herein to a subject in need thereof.

In another embodiment, the invention provides for a compound of formula I as described elsewhere herein or (or an embodiment thereof) for modulating TRPA1 activity. In some embodiments, the invention provides for a pharmaceutically acceptable salt of compound of formula I for modulating TRPA1 activity.

In another embodiment, the invention provides for a compound of formula I as described elsewhere herein, or an embodiment thereof such as a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula I (or an embodiment thereof) as described elsewhere herein to a subject in need thereof.

In another embodiment, the invention provides for a compound of formula I as described elsewhere herein or an embodiment thereof such as a pharmaceutically acceptable salt thereof for the treatment or prophylaxis of a respiratory disorder.

In another embodiment, the invention provides for the use of a compound of formula I as described elsewhere herein or an embodiment thereof such as a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound of formula I as described elsewhere herein or an embodiment thereof such as a pharmaceutically acceptable salt thereof to the mammal.

In another embodiment, the invention provides for a method for modulating TRPA1 activity, comprising contacting TRPA1 with a compound of formula I as described elsewhere herein or an embodiment thereof such as a pharmaceutically acceptable salt thereof.

In another embodiment, the invention provides for a compound of formula I as described elsewhere herein or an embodiment thereof such as a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound of formula I as described elsewhere herein or an embodiment thereof such as a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound of formula I as described elsewhere herein or an embodiment thereof such as a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder.

In one aspect, compounds of the invention demonstrate higher potency as compared to other analogues. Such representative compounds, commensurate in scope of the present invention, are shown below in Table 1 wherein "$IC_{50}$" denotes hTRPA1 CHO Ca2+ AUC EVO ($IC_{50}$) in micromolar units:

TABLE 1

| Formula | Name | $IC_{50}$ |
|---|---|---|
|  | (2S)-3-(5-fluorobenzofuran-2-yl)sulfonyl-N-[[5-fluoro-4-[2-(trifluoromethyl)pyrimidin-5-yl]-2-pyridyl[methyl]-3-azabicyclo[2.1.1]hexane-2-carboxamide | 0.00108 |
|  | (2S)-3-(4-fluorophenyl)sulfonyl-N-[[2-(trifluoromethyl)-6-[2-(trifluoromethyl)pyrimidin-5-yl]pyrimidin-4-yl]methyl]-3-azabicyclo[2.1.1]hexane-2-carboxamide | 0.00118 |

TABLE 1-continued

| Formula | Name | IC$_{50}$ |
|---|---|---|
| | (2S)-N-[[5-chloro-2-[2-(trifluoromethyl)pyrimidin-5-yl]-4-pyridyl]methyl]-3-(3,4-difluorophenyl)sulfonyl-3-azabicyclo[2.1.1]hexane-2-carboxamide | 0.00155 |
| | (2S)-3-(5-fluorobenzofuran-2-yl)sulfonyl-N-[[5-(trifluoromethyl)-2-[2-(trifluoromethyl)pyrimidin-5-yl]-4-pyridyl]methyl]-3-azabicyclo[2.1.1]hexane-2-carboxamide | 0.00185 |
| | (2S)-N-[[2-cyclopropyl-6-[2-(trifluoromethyl)pyrimidin-5-yl]pyrimidin-4-yl]methyl]-3-(4-fluorophenyl)sulfonyl-3-azabicyclo[2.1.1]hexane-2-carboxamide | 0.00215 |
| | (2S)-3-(4-fluorophenyl)sulfonyl-N-[[5-(trifluoromethyl)-2-[2-(trifluoromethyl)pyrimidin-5-yl]-4-pyridyl]methyl]-3-azabicyclo[2.1.1]hexane-2-carboxamide | 0.00261 |
| | (2S)-3-(4-fluorophenyl)sulfonyl-N-[[5-(trifluoromethoxy)-2-[2-(trifluoromethyl)pyrimidin-5-yl]-4-pyridyl]methyl]-3-azabicyclo[2.1.1]hexane-2-carboxamide | 0.00277 |

TABLE 1-continued

| Formula | Name | IC$_{50}$ |
|---|---|---|
| 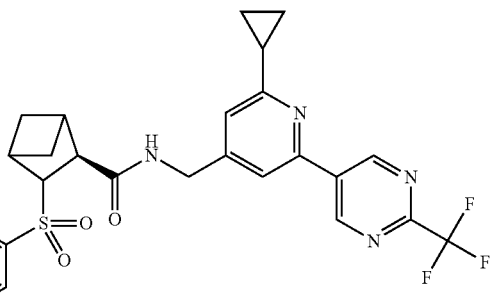 | (2S)-N-[[2-cyclopropyl-6-[2-(trifluoromethyl)pyrimidin-5-yl]-4-pyridyl]methyl]-3-(4-fluorophenyl)sulfonyl-3-azabicyclo[2.1.1]hexane-2-carboxamide | 0.00355 |
| 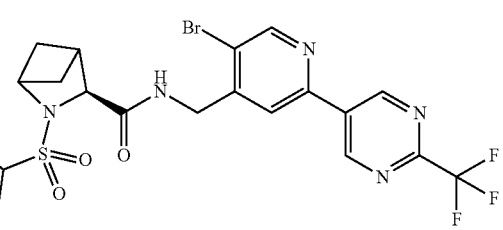 | (2S)-N-[[5-bromo-2-[2-(trifluoromethyl)pyrimidin-5-yl]-4-pyridyl]methyl]-3-(4-fluorophenyl)sulfonyl-3-azabicyclo[2.1.1]hexane-2-carboxamide | 0.00382 |
| 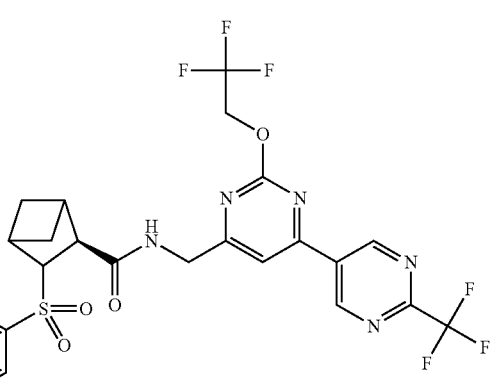 | (2S)-3-(4-fluorophenyl)sulfonyl-N-[[2-(2,2,2-trifluoroethoxy)-6-[2-(trifluoromethyl)pyrimidin-5-yl]pyrimidin-4-yl]methyl]-3-azabicyclo[2.1.1]hexane-2-carboxamide | 0.00424 |
| 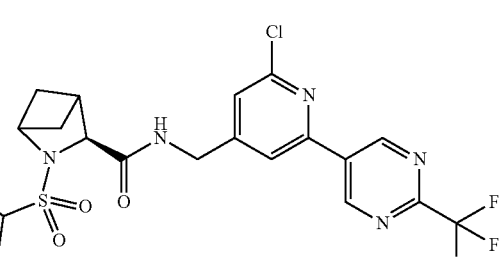 | (2S)-N-[[2-chloro-6-[2-(trifluoromethyl)pyrimidin-5-yl]-4-pyridyl]methyl]-3-(4-fluorophenyl)sulfonyl-3-azabicyclo[2.1.1]hexane-2-carboxamide | 0.00464 |
| 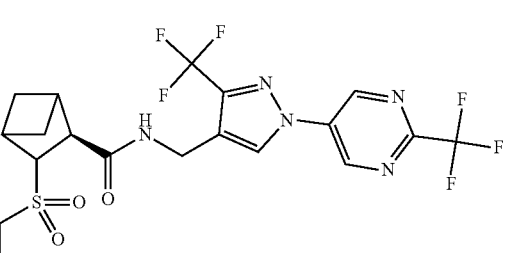 | (2S)-3-(4-fluorophenyl)sulfonyl-N-[[3-(trifluoromethyl)-1-[2-(trifluoromethyl)pyrimidin-5-yl]pyrazol-4-yl]methyl]-3-azabicyclo[2.1.1]hexane-2-carboxamide | 0.00484 |

TABLE 1-continued

| Formula | Name | IC$_{50}$ |
|---|---|---|
| 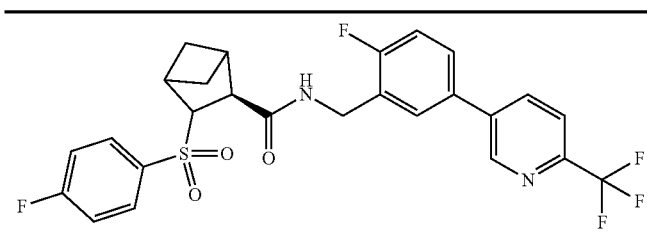 | (2S)-3-(4-fluorophenyl)sulfonyl-N-[[2-fluoro-5-[6-(trifluoromethyl)-3-pyridyl]phenyl]methyl]-3-azabicyclo[2.1.1]hexane-2-carboxamide | 0.00606 |
| 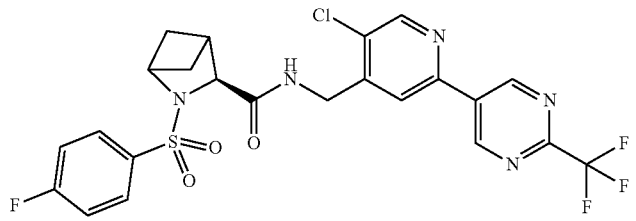 [SMILES: O=C(NCc1cc(-c2cnc(C(F)(F)F)nc2)ncc1Cl)[C@@H]1C2CC(C2)N1S(=O)(=O)c1ccc(F)cc1] | (2S)-N-[[5-chloro-4-[2-(trifluoromethyl)pyrimidin-5-yl]-2-pyridyl]methyl]-3-(4-fluorophenyl)sulfonyl-3-azabicyclo[2.1.1]hexane-2-carboxamide | 0.00608 |
| 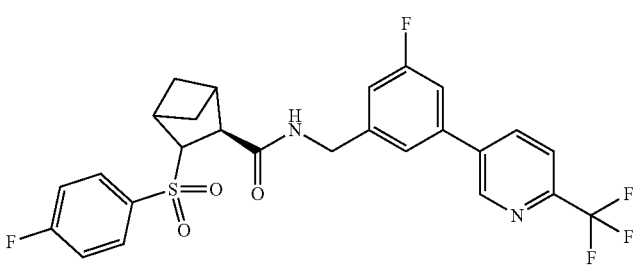 [SMILES: O=C(NCc1cc(F)cc(-c2ccc(C(F)(F)F)nc2)c1)[C@@H]1C2CC(C2)C1S(=O)(=O)c1ccc(F)cc1] | (2S)-3-(4-fluorophenyl)sulfonyl-N-[[3-fluoro-5-[6-(trifluoromethyl)-3-pyridyl]phenyl]methyl]-3-azabicyclo[2.1.1]hexane-2-carboxamide | 0.00611 |
| 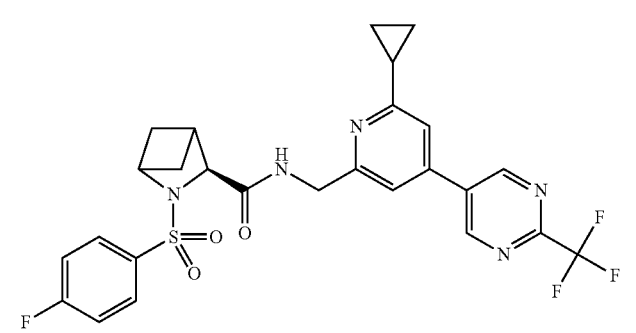 [SMILES: O=C(NCc1cc(-c2cnc(C(F)(F)F)nc2)cc(C2CC2)n1)[C@@H]1C2CC(C2)N1S(=O)(=O)c1ccc(F)cc1] | (2S)-N-[[6-cyclopropyl-4-[2-(trifluoromethyl)pyrimidin-5-yl]-2-pyridyl]methyl]-3-(4-fluorophenyl)sulfonyl-3-azabicyclo[2.1.1]hexane-2-carboxamide | 0.00724 |
| 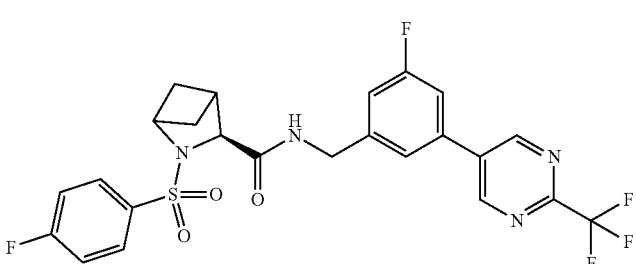 | (2S)-3-(4-fluorophenyl)sulfonyl-N-[[3-fluoro-5-[2-(trifluoromethyl)pyrimidin-5-yl]phenyl]methyl]-3-azabicyclo[2.1.1]hexane-2-carboxamide | 0.00897 |
| 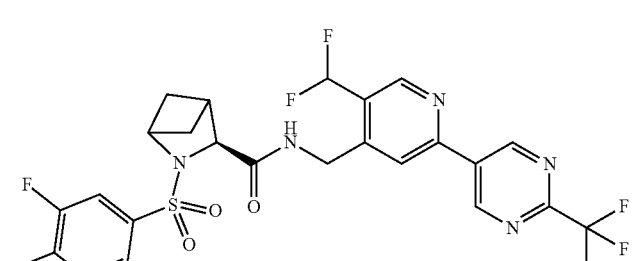 | (2S)-N-[[5-(difluoromethyl)-2-[2-(trifluoromethyl)pyrimidin-5-yl]-4-pyridyl]methyl]-3-(3,4-difluorophenyl)sulfonyl-3-azabicyclo[2.1.1]hexane-2-carboxamide | 0.00901 |

TABLE 1-continued

| Formula | Name | IC$_{50}$ |
|---|---|---|
|  | (2S)-3-(4-fluorophenyl)sulfonyl-N-[[2-fluoro-5-[2-(trifluoromethyl)pyrimidin-5-yl]phenyl]methyl]-3-azabicyclo[2.1.1]hexane-2-carboxamide | 0.00989 |
|  | (2S)-N-[[5-(difluoromethyl)-2-[2-(trifluoromethyl)pyrimidin-5-yl]-4-pyridyl]methyl]-3-(4-fluorophenyl)sulfonyl-3-azabicyclo[2.1.1]hexane-2-carboxamide | 0.00992 |

Combination Therapy

The compounds of the invention (or an embodiment thereof) may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with one or more co-therapeutic agents.

In some embodiments, the co-therapeutic agent is an opiate analgesic. Examples of opiate analgesics include morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine, pentazocine, and combinations thereof.

In some embodiments, the co-therapeutic agent is a non-opiate analgesic such as acetaminophen and/or salicylate (e.g., aspirin).

In some embodiments, the co-therapeutic agent is a non-steroidal antiinflammatory drug (NSAIDs). Examples of NSAIDs include ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, zomepirac, and combinations thereof.

In some embodiments, the co-therapeutic agent is an anticonvulsant. Examples of anticonvulsants include carbamazepine, oxcarbazepine, lamotrigine, valproate, topiramate, gabapentin, pregabalin, and combinations thereof.

In some embodiments, the co-therapeutic agent is an antidepressant. Examples of antidepressants include amitriptyline, clomipramine, desipramine, imipramine, nortriptyline, and combinations thereof.

In some embodiments, the co-therapeutic agent is a COX-2 selective inhibitor. Examples of COX-2 inhibitors include celecoxib, rofecoxib, parecoxib, valdecoxib, deracoxib, etoricoxib, lumiracoxib, and combinations thereof.

In some embodiments, the co-therapeutic agent is an alpha-adrenergic. Examples of alpha-adrenergics include doxazosin, tamsulosin, clonidine, guanfacine, dexmetatomidine, modafinil, 4-amino-6,7-dimethoxy-2-(5-methane sulfonamido-1,2,3,4-tetrahydroisoquinol-2-yl)-5-(2-pyridyl) quinazoline, and combinations thereof.

In some embodiments, the co-therapeutic agent is a barbiturate sedative. Examples of barbiturate sedatives include amobarbital, aprobarbital, butabarbital, butabital, mephobarbital, metharbital, methohexital, pentobarbital, phenobarbital, secobarbital, talbutal, theamylal, thiopental, and combinations thereof.

In some embodiments, the co-therapeutic agent is a tachykinin (NK) antagonist. Examples of tachykinin antagonists include NK-3, NK-2 or NK-1 antagonist such as (7R,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2, 4-triazol-3-one (MK-869), aprepitant, lanepitant, dapitant, 3-[[2-methoxy5-(trifluoromethoxy)phenyl]-methylamino]-2-phenylpiperidine (2S,3S), and combinations thereof.

In some embodiments, the co-therapeutic agent is a coaltar analgesic such as paracetamol.

In some embodiments, the co-therapeutic agent is a serotonin reuptake inhibitor (SRI). Examples of SRIs include paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone, fluoxetine, and combinations thereof.

In some embodiments, the co-therapeutic agent is a noradrenaline (norepinephrine) reuptake inhibitors. Examples of noradrenaline reuptake inhibitors include maprotiline, lofepramine, mirtazepine, oxaprotiline, fezolamine, tomoxetine, mianserin, buprorion, buprorion metabolite hydroxybuprorion, nomifensine and viloxazine (Vivalan®)), especially a selective noradrenaline reuptake inhibitor such as reboxetine, in particular (S,S)-reboxetine, venlafaxine duloxetine neuroleptics sedative/anxiolytics, and combinations thereof.

In some embodiments, the co-therapeutic agent is a dual serotonin-noradrenaline reuptake inhibitors. Examples of such dual inhibitors include venlafaxine metabolite O-desmethylvenlafaxine, clomipramine, clomipramine metabolite desmethylclomipramine, duloxetine, milnacipran, imipramine, and combinations thereof.

In some embodiments, the co-therapeutic agent is an acetylcholinesterase inhibitor such as donepezil.

In some embodiments, the co-therapeutic agent is an 5-HT3 antagonist such as ondansetron.

In some embodiments, the co-therapeutic agent is a metabotropic glutamate receptor (mGluR) antagonist.

In some embodiments, the co-therapeutic agent is a local anaesthetic. Examples of local anesthetics include mexiletine and lidocaine.

In some embodiments, the co-therapeutic agent is a corticosteroid such as dexamethasone.

In some embodiments, the co-therapeutic agent is an antiarrhythimic. Examples of antiarrhythmics include mexiletine and phenytoin.

In some embodiments, the co-therapeutic agent is a muscarinic antagonist. Examples of muscarinic antagonists include tolterodine, propiverine, tropsium t chloride, darifenacin, solifenacin, temiverine, ipratropium, and combinations thereof.

In some embodiments, the co-therapeutic agent is a cannabinoid.

In some embodiments, the co-therapeutic agent is a vanilloid receptor agonist such as resinferatoxin or an antagonist such as capsazepine.

In some embodiments, the co-therapeutic agent is a sedative. Examples of sedatives include glutethimide, meprobamate, methaqualone, dichloralphenazone, and combinations thereof.

In some embodiments, the co-therapeutic agent is an anxiolytic such as benzodiazepine.

In some embodiments, the co-therapeutic agent is an antidepressant such as mirtazapine.

In some embodiments, the co-therapeutic agent is a topical agent. Examples of topical agents include lidocaine, capsacin, resiniferotoxin, and combinations thereof.

In some embodiments, the co-therapeutic agent is a muscle relaxant. Examples of muscle relaxants include benzodiazepines, baclofen, carisoprodol, chlorzoxazone, cyclobenzaprine, methocarbamol, orphrenadine, and combinations thereof.

In some embodiments, the co-therapeutic agent is an anti-histamine or an H1 antagonist.

In some embodiments, the co-therapeutic agent is a NMDA receptor antagonist.

In some embodiments, the co-therapeutic agent is a 5-HT receptor agonist/antagonist.

In some embodiments, the co-therapeutic agent is a PDEV inhibitor.

In some embodiments, the co-therapeutic agent is Tramadol®.

In some embodiments, the co-therapeutic agent is a cholinergic (nicotinic) analgesic.

In some embodiments, the co-therapeutic agent is an alpha-2-delta ligand.

In some embodiments, the co-therapeutic agent is a prostaglandin E2 subtype antagonist.

In some embodiments, the co-therapeutic agent is a leukotriene B4 antagonist.

In some embodiments, the co-therapeutic agent is a 5-lipoxygenase inhibitor.

In some embodiments, the co-therapeutic agent is a 5-HT3 antagonist.

As used herein "combination" refers to any mixture or permutation of one or more compounds of the invention (or an embodiment thereof) and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In another embodiment, provided is an invention as hereinbefore described.

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention (or an embodiment thereof) can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

EXAMPLES

Although certain exemplary embodiments are depicted and described herein, the compounds of the present invention (or an embodiment thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography. Unless otherwise noted, flash chromatography was carried out using pre-packed silica gel cartridges from either ISCO or SiliCycle on an ISCO CombiFlash® chromatography instrument (from Teledyne Isco, Inc.). Reverse-phase preparative HPLC was performed using a (1) Polaris C-18 5 µM column (50×21 mm), or (2) XBridge Prep C-18 OBD 5 µM column (19×150 mm). Supercritical fluid chromatography was carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 µM, (2) 4.6 cm×5 cm, 5 µM, or (3) 15 cm×21.2 mm, 5 µM.

Mass spectrometry (MS) was performed using a (1) Sciex 15 mass spectrometer in ES+ mode, or (2) Shimadzu liquid chromatography-mass spectrometry (LCMS) 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

Example 1: Preparation 1: 2-(tert-butoxycarbonyl)-2-azabicyclo[2.1.1]hexane-3-carboxylic acid The overall reaction scheme for Example 1 was as follows:

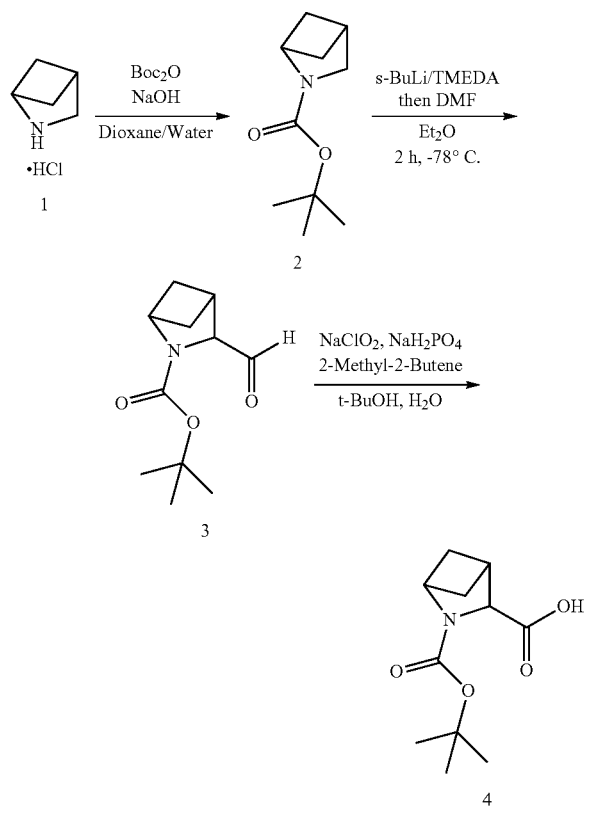

Example 1, Step 1: Preparation of tert-butyl 2-azabicyclo[2.1.1]hexane-2-carboxylate Step 1 proceeded according to the following scheme:

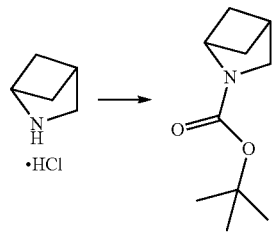

To a solution of 2-azabicyclo[2.1.1]hexane hydrochloride (20.0 g, 159 mmol) in 1,4-dioxane (300 mL) and water (300 mL) cooled to 0° C. was added sodium hydroxide (1 mol/L) in water (318 mL, 318 mmol). Di-tert-butyl dicarbonate (75 mL, 318 mmol) was then added by addition funnel over 30 min. The reaction was stirred at 0° C. for 30 min then warmed to room temperature and stirred for 18 h. The reaction mixture was concentrated in vacuo to remove dioxane and the aqueous residue was extracted with petroleum ether (3×). The combined organic layers were dried over sodium sulfate, filtered and concentrated in vacuo. The residue was adsorbed onto silica and purified by flash column chromatography with 0-50% EtOAc in heptane to yield the title compound as a pale yellow solid (25.7 g, 88%). $^1$H NMR (400 MHz, CDCl$_3$) δ 4.34 (s, 1H), 3.29 (s, 2H), 2.86-2.77 (m, 1H), 1.92-1.83 (m, 2H), 1.47 (s, 9H), 1.42-1.31 (m, 2H).

Example 1, Step 2: Preparation of tert-butyl 3-formyl-2-azabicyclo[2.1.1]hexane-2-carboxylate Step 2 proceeded according to the following scheme:

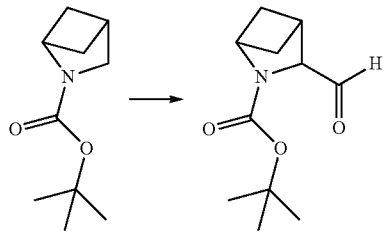

To a solution of tert-butyl 2-azabicyclo[2.1.1]hexane-2-carboxylate (9.67 g, 50.7 mmol) and N,N,N',N'-tetramethylethylenediamine (9.93 mL, 65.9 mmol) in diethyl ether (200 mL) cooled to −78° C. was added sec-butyllithium (1.4 mol/L) in cyclohexane (47 mL, 65.9 mmol) dropwise. The reaction mixture was stirred for 2 h at −78° C. then a solution of N,N-dimethylformamide (29.4 mL, 380 mmol) in diethyl ether (70 mL) was added slowly via addition funnel over 30 min. The reaction mixture was stirred for 30 min and warmed to room temperature. The reaction mixture was quenched by the addition of 60 mL of sat. aq. ammonium chloride and the layers were separated. The organic layer was washed with water (2×), dried over sodium sulfate, filtered and concentrated in vacuo. The residue was adsorbed onto silica and purified by flash column chromatography with 0-100% iPrOAc in heptane to afford the title compound as a white solid (2.97 g, 28%).

Example 1, Step 3: Preparation of 2-(tert-butoxycarbonyl)-2-azabicyclo[2.1.1]hexane-3-carboxylic acid Step 3 proceeded according to the following scheme:

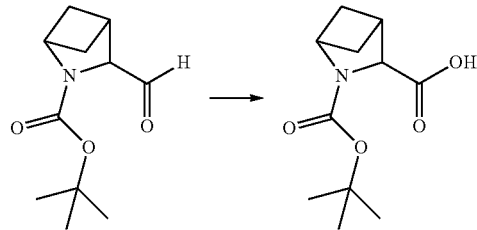 [SMILES: CC(C)(C)OC(=O)N1C2CC(C2)C1C=O ; CC(C)(C)OC(=O)N1C2CC(C2)C1C(=O)O]

To a solution of tert-butyl 2-formyl-3-azabicyclo[2.1.1]hexane-3-carboxylate (2.97 g, 14.1 mmol) in tert-butyl alcohol (120 mL) and water (28 mL) was added 2-methyl-2-butene (15 mL, 140.8 mmol), sodium dihydrogen phosphate (8.45 g, 70.4 mmol) and sodium chlorite (6.37 g, 70.4 mmol). The reaction mixture was stirred at room temperature for 1 h. The reaction mixture was then diluted with 200 mL ethyl acetate and 200 mL sat. aq. ammonium chloride. The layers were separated and the aqueous layer was extracted with EtOAc (200 mL). The organic layer was dried over sodium sulfate, filtered and concentrated in vacuo. The residue was adsorbed onto silica and purified by flash column chromatography with 10-80% 3:1 iPrOAc: MeOH in heptane to afford the desired compound as a colourless oil that solidified over time to a white solid (3.07 g, 96%). $^1$H NMR (400 MHz, CDCl$_3$-d) δ 4.36-4.29 (m, 1H), 4.24 (s, 1H), 3.19-3.10 (m, 1H), 2.08-2.03 (m, 1H), 2.03-1.97 (m, 1H), 1.65-1.55 (m, 1H), 1.51 (s, 9H), 1.49-1.39 (m, 1H).

Example 2: Preparation of 2-(tert-butoxycarbonyl)-1-methyl-2-azabicyclo[2.1.1]hexane-3-carboxylic acid The overall reaction scheme for Example 2 was as follows:

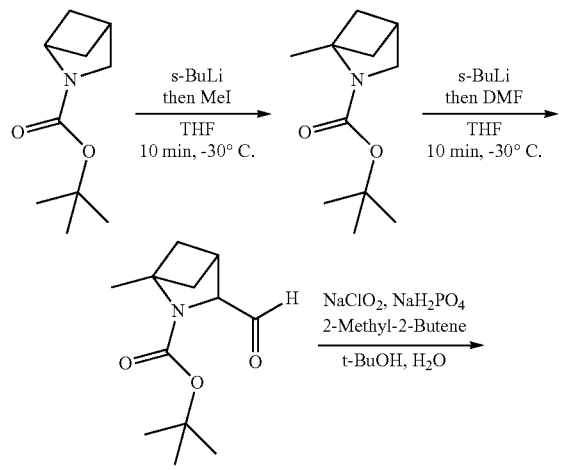

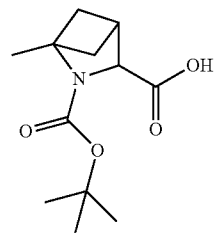

Example 2, Step 1: Preparation of tert-butyl 1-methyl-2-azabicyclo[2.1.1]hexane-2-carboxylate Step 1 proceeded according to the following scheme:

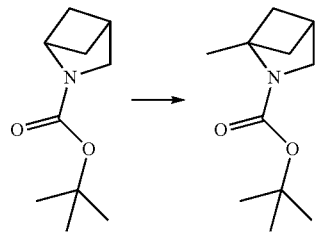

To a solution of tert-butyl 2-azabicyclo[2.1.1]hexane-2-carboxylate (1.00 g, 5.24 mmol) in tetrahydrofuran (37 mL) cooled to −30° C. was added sec-butyllithium (1.4 mol/L) in cyclohexane (7.5 mL, 6.81 mmol) and the reaction mixture was stirred at −30° C. for 10 min. Iodomethane (0.65 mL, 10.5 mmol) was then added and the reaction was stirred at −30° C. for 10 min, followed by warming to room temperature over 15 min. The reaction was quenched by the addition of aq. sat. ammonium chloride, the layers were separated, and the aqueous layer was extracted with diethyl ether (3×). The combined organic layers were dried over sodium sulfate and the crude product was concentrated in vacuo. The residue was adsorbed onto silica and purified by flash column chromatography with 0-50% EtOAc in heptane to yield the title compound as a white solid (775 mg, 75%).

Example 2, Step 2: Preparation of tert-butyl 3-formyl-1-methyl-2-azabicyclo[2.1.1]hexane-2-carboxylate Step 2 proceeded according to the following scheme:

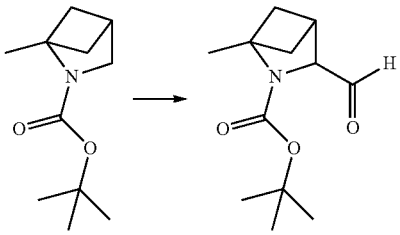 [SMILES: CC(C)(C)OC(=O)N1CC2CC1(C)C2 ; CC(C)(C)OC(=O)N1C(C=O)C2CC1(C)C2]

A solution of tert-butyl 4-methyl-3-azabicyclo[2.1.1]hexane-3-carboxylate (670 mg, 3.4 mmol) and N,N,N',N'-tetramethylethylenediamine (0.67 mL, 4.4 mmol) in diethyl ether (25 mL, 239 mmol) was cooled to −78° C. followed by dropwise addition of sec-butyllithium (1.4 mol/L) in cyclohexane (3.2 mL, 4.4 mmol). The reaction mixture was stirred for 2 h at −78° C. The reaction mixture was cannulated into a −78° C. solution of N,N-dimethylformamide (2.0 mL, 25 mmol) in diethyl ether (15 mL), stirred for 30 min, and warmed to room temperature. The reaction mixture was quenched by the addition of sat. aq. ammonium chloride and the layers were then separated. The organic layer was washed with water (2×), dried over sodium sulfate, filtered and concentrated in vacuo. The residue was adsorbed onto silica and purified by flash column chromatography with 0-100% iPrOAc in heptane to afford the title compound as a white solid (324 mg, 42%).

Example 2, Step 3: Preparation of 2-(tert-butoxycarbonyl)-1-methyl-2-azabicyclo[2.1.1]hexane-3-carboxylic acid Step 3 proceeded according to the following scheme:

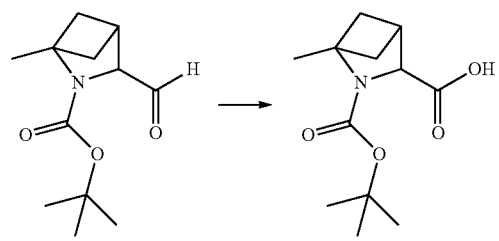 [SMILES: CC(C)(C)OC(=O)N1C(C=O)C2CC1(C)C2 ; CC(C)(C)OC(=O)N1C(C(=O)O)C2CC1(C)C2]

To a solution of tert-butyl 2-formyl-4-methyl-3-azabicyclo[2.1.1]hexane-3-carboxylate (324 mg, 1.44 mmol) in tert-butyl alcohol (12.0 mL) and water (2.9 mL) was added 2-methyl-2-butene (1.5 mL, 14.4 mmol), sodium dihydrogen phosphate (864 mg, 7.2 mmol) and sodium chlorite (651 mg, 7.2 mmol). The reaction mixture was stirred at room temperature for 1 h and then the reaction mixture was diluted with ethyl acetate and sat. aq. ammonium chloride. The layers were separated and the organic layer was washed with sat. aq. ammonium chloride. The organic layer was dried over sodium sulfate, filtered and concentrated in vacuo. The residue was adsorbed onto silica and purified by flash column chromatography with 0-80% (90:10) DCM: MeOH in DCM to afford the desired compound as a clear oil that solidified over time to a white solid (242 mg, 70%).

Example 3: Preparation of (5-fluoro-2-(2-(trifluoromethyl)pyrimidin-5-yl)pyridin-4-yl)methanamine The overall reaction scheme for Example 3 was as follows:

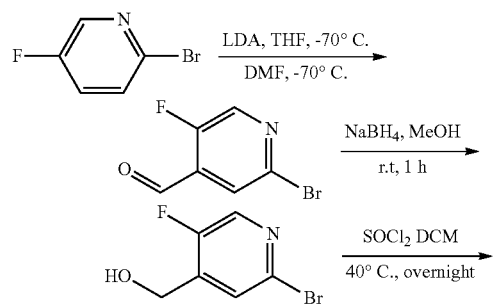

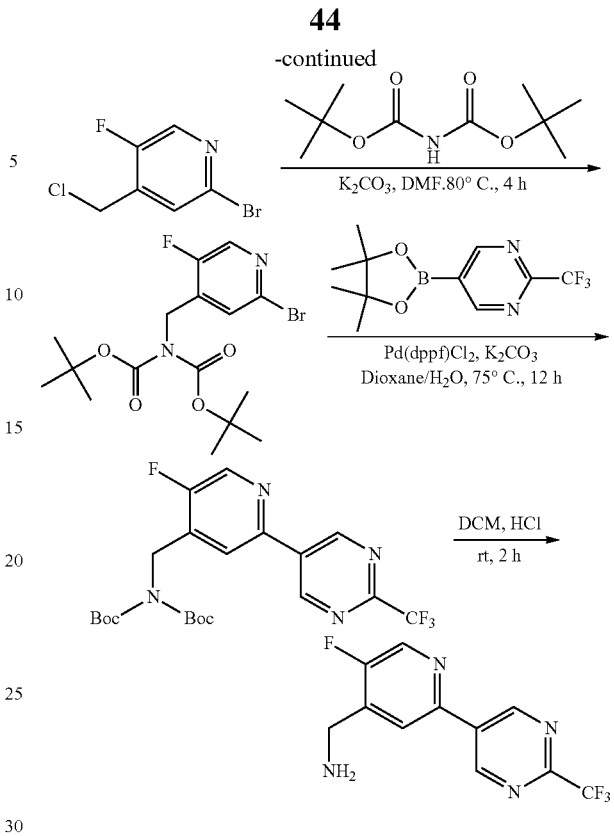

Example 3, Step 1: Preparation of 2-bromo-5-fluoroisonicotinaldehyde

Step 1 proceeded according to the following scheme:

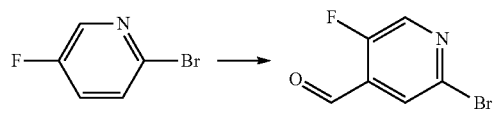 [SMILES: Fc1ccc(Br)nc1 ; O=Cc1cc(Br)ncc1F]

To a 3000-mL 4-necked round-bottom flask, that was purged and maintained with an inert nitrogen atmosphere, was added a solution of diisopropylamine (86.57 g, 1.50 equiv) in tetrahydrofuran (1500 mL) followed by the addition of n-BuLi (2.4 mol/L) (310 mL, 1.30 equiv) dropwise with stirring at −35° C. The resulting solution was stirred at −30° C. for 30 min. To this mixture was added a solution of 2-bromo-5-fluoropyridine (100 g, 568.23 mmol, 1.00 equiv) in tetrahydrofuran (200 mL) dropwise with stirring at −75° C. The resulting solution was stirred at −75° C. for an additional 2 h. To the mixture was added N,N-dimethylformamide (83.4 g, 2.00 equiv) dropwise with stirring at −70° C. The resulting solution was stirred for an additional 2 h at −70° C. and quenched by the addition of 4 N HCl. The solution pH was adjusted to 6 with 4N HCl solution. The resulting solution was extracted with 3×1000 mL of ethyl acetate. The combined organic layers were washed with 1×500 mL of brine, dried over anhydrous sodium sulfate and concentrated under vacuum to afford 125 g (crude) of 2-bromo-5-fluoropyridine-4-carbaldehyde as yellow oil.

Example 3, Step 2: Preparation of (2-bromo-5-fluoropyridin-4-yl)methanol

Step 2 proceeded according to the following scheme:

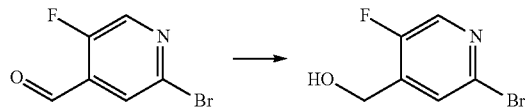 [SMILES: O=Cc1cc(Br)ncc1F ; OCc1cc(Br)ncc1F]

To a 2000-mL 4-necked round-bottom flask purged and maintained with an inert atmosphere of nitrogen was added a solution of 2-bromo-5-fluoropyridine-4-carbaldehyde (125 g, 612.75 mmol, 1.00 equiv) in methanol (1000 mL), followed by the addition of NaBH$_4$ (23.4 g, 635.44 mmol, 1.00 equiv) dropwise with stirring at 0° C. The resulting solution was stirred at room temperature for 1 h, concentrated under vacuum, diluted with 500 mL of H$_2$O, and extracted with 3×800 mL of ethyl acetate. The combined organic layers were washed with 1×500 mL of brine, dried over anhydrous sodium sulfate and concentrated under vacuum. The residue was applied onto a silica gel column eluted with ethyl acetate/petroleum ether (1:4) to afford 80 g (63%) of (2-bromo-5-fluoropyridin-4-yl)methanol as a white solid.

Example 3, Step 3: Preparation of 2-bromo-4-(chloromethyl)-5-fluoropyridine

Step 3 proceeded according to the following scheme:

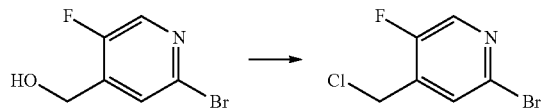 [SMILES: OCc1cc(Br)ncc1F ; Fc1cnc(Br)cc1CCl]

To a 2000-mL 4-necked round-bottom flask, purged and maintained with an inert atmosphere of nitrogen, was added a solution of (2-bromo-5-fluoropyridin-4-yl)methanol (80 g, 388.33 mmol, 1.00 equiv) in dichloromethane (800 mL), followed by the addition of thionyl chloride (240 mL) dropwise with stirring at 0° C. The resulting solution was stirred at 40° C. overnight and concentrated under vacuum to afford 90 g (crude) of 2-bromo-4-(chloromethyl)-5-fluoropyridine as yellow oil.

Example 3, Step 4: Preparation of bis-tert-butyl (2-bromo-5-fluoropyridin-4-yl)methylcarbamate Step 4 proceeded according to the following scheme:

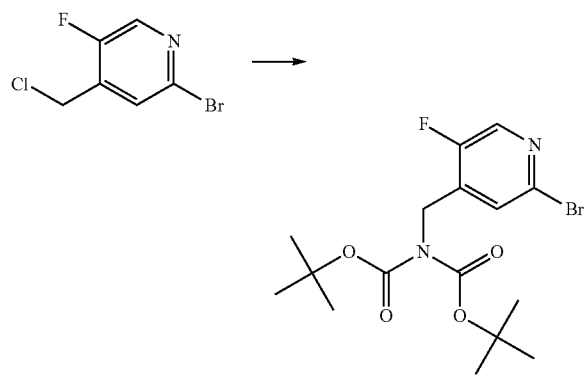

To a 2000-mL 4-necked round-bottom flask, purged and maintained with an inert atmosphere of nitrogen, was added a solution of 2-bromo-4-(chloromethyl)-5-fluoropyridine (90 g, 400.97 mmol, 1.00 equiv) in N,N-dimethylformamide (900 mL), K$_2$CO$_3$ (167 g, 1.20 mol, 2.99 equiv) and tert-butyl N-[(tert-butoxy)carbonyl]carbamate (103.7 g, 477.30 mmol, 1.19 equiv). The resulting solution was stirred at 80° C. for 4 h, quenched by the addition of 2000 mL of water/ice, and extracted with 3×800 mL of ethyl acetate. The combined organic layers were washed with 1×600 mL of brine, dried over anhydrous sodium sulfate, and concentrated under vacuum. The residue was applied onto a silica gel column eluted with ethyl acetate/petroleum ether (1:10) to afford 110 g (68%) of tert-butyl N-[(2-bromo-5-fluoropyridin-4-yl)methyl]-N-[(tert-butoxy)carbonyl]carbamate as a white solid.

Example 3, Step 5: Preparation of bis-tert-butyl (5-fluoro-2-(2-(trifluoromethyl)pyrimidin-5-yl)pyridin-4-yl)methylcarbamate Step 5 proceeded according to the following scheme:

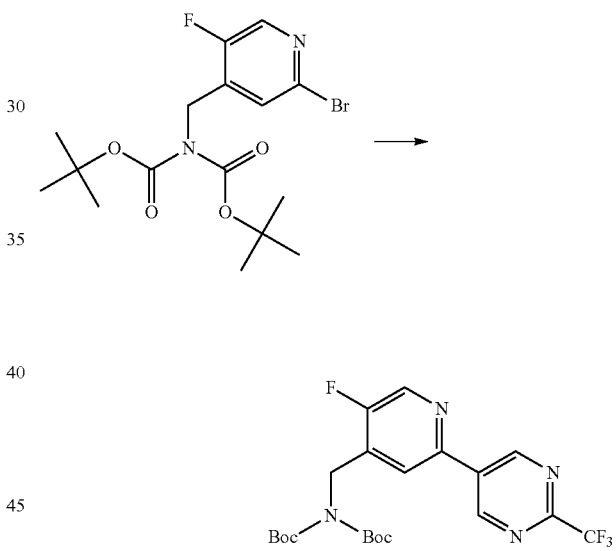

To a 2000-mL 4-necked round-bottom flask, purged and maintained with an inert atmosphere of nitrogen, was added a solution of tert-butyl N-[(2-bromo-5-fluoropyridin-4-yl)methyl]-N-[(tert-butoxy)carbonyl]carbamate (105 g, 259.09 mmol, 1.00 equiv) in dioxane (1500 mL), 5-(tetramethyl-1,3,2-dioxaborolan-2-yl)-2-(trifluoromethyl)pyrimidine (142 g, 518.16 mmol, 2.00 equiv), potassium carbonate (107.5 g, 772.20 mmol, 2.98 equiv) and water (150 mL), Pd(dppf)Cl$_2$ (20 g, 27.33 mmol, 0.11 equiv). The resulting solution was stirred at 75° C. for 12 h, cooled to room temperature, diluted with 2000 mL of ethyl acetate, and filtered. The filtrate was washed with 2×500 mL of water, dried over anhydrous sodium sulfate and concentrated under vacuum. The residue was applied onto a silica gel column eluted with ethyl acetate/petroleum ether (1:8) to afford 60 g (49%) of tert-butyl N-[(tert-butoxy)carbonyl]-N-([5-fluoro-2-[2-(trifluoromethyl)pyrimidin-5-yl]pyridin-4-yl]methyl)carbamate as a white solid.

Example 3, Step 6: Preparation of (5-fluoro-2-(2-(trifluoromethyl)pyrimidin-5-yl)pyridin-4-yl)methanamine Step 6 proceeded according to the following scheme:

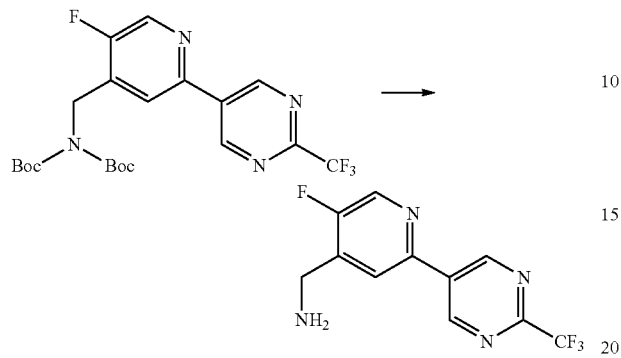

To a 1000-mL 4-necked round-bottom flask was placed a solution of tert-butyl N-[(tert-butoxy)carbonyl]-N-([5-fluoro-2-[2-(trifluoromethyl)pyrimidin-5-yl]pyridin-4-yl]methyl)carbamate (60 g, 127.00 mmol, 1.00 equiv) in dichloromethane (600 mL) followed by the introduction of hydrogen chloride (enough, gas). The resulting solution was stirred at room temperature for 2 h, concentrated under vacuum, and diluted with water. The pH value of the solution was adjusted to 9 with aqueous sodium carbonate (2 mol/L) solution. The resulting solution was extracted with 3×1000 mL of ethyl acetate. The combined organic layers were dried over anhydrous sodium sulfate and concentrated under vacuum. The residue was applied onto a silica gel column eluted with ethyl acetate/petroleum ether (9:1). The crude product was re-crystallized from EA:PE in the ratio of 1:10 to afford 20 g (58%) of [5-fluoro-2-[2-(trifluoromethyl)pyrimidin-5-yl]pyridin-4-yl]methanamine as a yellow solid. LCMS [M+H]+ 273; $^1$H-NMR (300 MHz, DMSO-d6) δ 9.65 (s, 2H), 8.67 (d, J=1.5 Hz, 1H), 8.43 (d, J=6.0 Hz, 1H), 3.88 (s, 2H), 2.17 (s, 2H).

Example 4: Preparation of [5-bromo-2-[2-(trifluoromethyl)pyrimidin-5-yl]pyridin-4-yl]methanamine hydrochloride salt The overall reaction scheme for Example 4 was as follows:

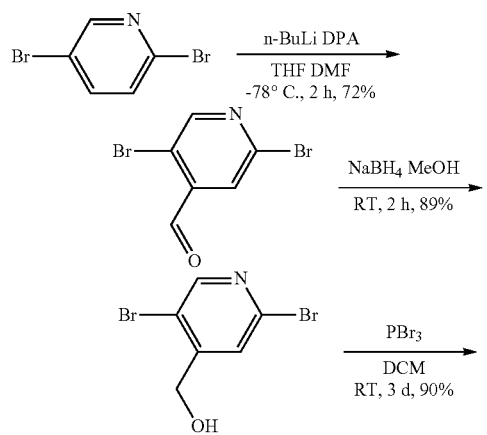

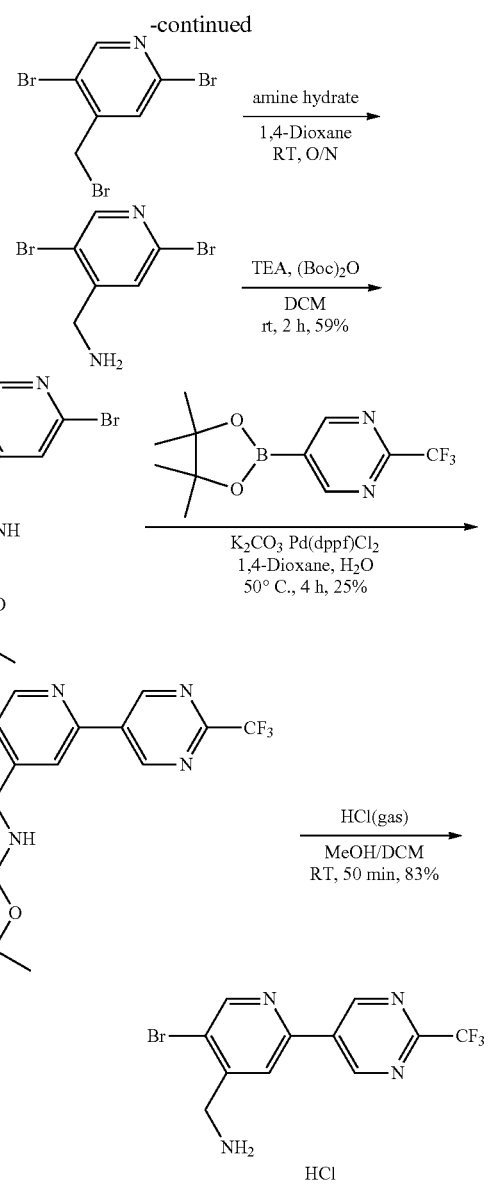

Example 4, Step 1: Preparation of 2,5-dibromoisonicotinaldehyde

Step 1 proceeded according to the following scheme:

To a 5-L 4-necked round-bottom flask, purged and maintained with an inert atmosphere of nitrogen, was placed DPA (138.5 g, 1.37 mol, 1.30 equiv) and tetrahydrofuran (1000 mL), followed by the addition of butyllithium (1265 mL, 1.20 equiv) dropwise with stirring at −30° C. The mixture was stirred at −30° C. for 30 min. To the solution was added a solution of 2,5-dibromopyridine (250 g, 1.06 mol, 1.00 equiv) in tetrahydrofuran (1000 mL) dropwise with stirring at −78° C. The mixture was stirred at −78° C. for 2 h. To this mixture was added DMF (151 g, 2.09 mol, 2.00 equiv) dropwise with stirring at −78° C. The resulting solution was stirred at −78° C. for 2 h followed by quenching with 5 L of water/ice. The pH value of the solution was adjusted to 5 with aqueous hydrogen chloride (6N), and the reaction mixture was extracted with 3×2 L of ethyl acetate. The combined organic layer was washed with 2×1.5 L of brine, dried over anhydrous sodium sulfate and concentrated under vacuum to afford 200 g (72%) of 2,5-dibromopyridine-4-carbaldehyde as a white solid.

Example 4, Step 2: Preparation of (2,5-dibromopyridin-4-yl)methanol

Step 2 proceeded according to the following scheme:

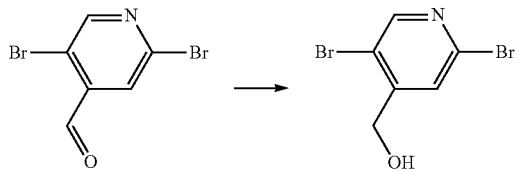 [SMILES: O=Cc1cc(Br)ncc1Br ; OCc1cc(Br)ncc1Br]

To a 3000-mL 3-necked round-bottom flask, purged and maintained with an inert atmosphere of nitrogen, was placed 2,5-dibromopyridine-4-carbaldehyde (200 g, 755.00 mmol, 1.00 equiv) and methanol (1800 mL) followed by the addition of NaBH$_4$ (30.7 g, 811.53 mmol, 1.10 equiv), in portions at 0° C. The resulting solution was stirred at room temperature for 2 h, concentrated under vacuum, and quenched by the addition of 1 L of water/ice. The resulting solution was extracted with 3×800 mL of ethyl acetate. The combined organic layer was washed with 2×500 mL of brine, dried over anhydrous sodium sulfate and concentrated under vacuum to afford 180 g (89%) of (2,5-dibromopyridin-4-yl)methanol as a white solid.

Example 4, Step 3: Preparation of 2,5-dibromo-4-(bromomethyl)pyridine

Step 3 proceeded according to the following scheme:

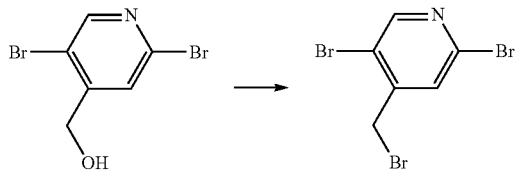 [SMILES: OCc1cc(Br)ncc1Br ; BrCc1cc(Br)ncc1Br]

To a 10-L 4-necked round-bottom flask, purged and maintained with an inert atmosphere of nitrogen, was placed (2,5-dibromopyridin-4-yl)methanol (180 g, 674.36 mmol, 1.00 equiv) and dichloromethane (6 L), followed by the addition of tribromophosphane (180 mL) dropwise with stirring. The mixture was stirred at room temperature for 24 h. To this mixture was added additional tribromophosphane (50 mL) dropwise with stirring. The resulting solution was stirred at room temperature for 3 days, quenched by the addition of 5 L of water/ice, and extracted with 2×2 L of dichloromethane. The combined organic layer was washed with 2×2 L of brine, dried over anhydrous sodium sulfate and concentrated under vacuum to afford 200 g (90%) of 2,5-dibromo-4-(bromomethyl)pyridine as a white solid.

Example 4, Step 4: Preparation of (2,5-dibromopyridin-4-yl)methanamine

Step 4 proceeded according to the following scheme:

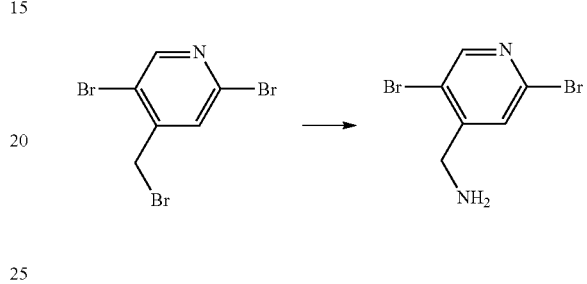

To a 10-L 4-necked round-bottom flask, purged and maintained with an inert atmosphere of nitrogen, was placed 2,5-dibromo-4-(bromomethyl)pyridine (200 g, 606.40 mmol, 1.00 equiv), 1,4-Dioxane (4 L) and amine hydrate (400 mL). The resulting solution was stirred at room temperature overnight and concentrated under vacuum to afford 220 g (crude) of (2,5-dibromopyridin-4-yl)methanamine as brown oil.

Example 4, Step 5: Preparation of tert-butyl ((2,5-dibromopyridin-4-yl)methyl)carbamate Step 5 proceeded according to the following scheme:

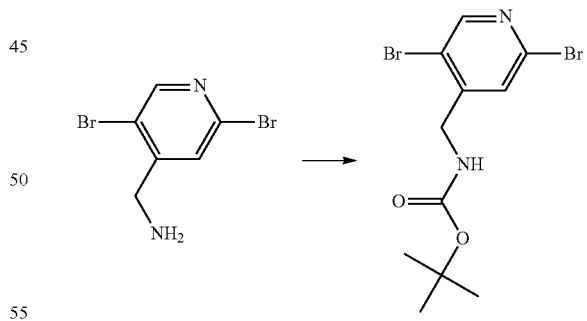

To a 5-L 3-necked round-bottom flask, purged and maintained with an inert atmosphere of nitrogen, was placed (2,5-dibromopyridin-4-yl)methanamine (220 g, 827.28 mmol, 1.00 equiv) and dichloromethane (3000 mL), followed by the addition of TEA (209 g, 2.07 mol, 2.50 equiv) and (Boc)$_2$O (271 g, 1.24 mol, 1.50 equiv), respectively in a water/ice bath. The resulting solution was stirred at room temperature for 2 h, quenched by the addition of 3 L of water, and extraction with 2×1.5 L of dichloromethane. The combined organic layer was washed with 2×1 L of brine, dried over anhydrous sodium sulfate and concentrated under vacuum. The residue was applied onto a silica gel column eluted with ethyl acetate/petroleum ether (5/95) to afford 180 g (59%) of tert-butyl N-[(2,5-dibromopyridin-4-yl)methyl]carbamate as a white solid.

Example 4, Step 6: Preparation of tert-butyl ((5-bromo-2-(2-(trifluoromethyl)pyrimidin-5-yl)pyridin-4-yl)methyl)carbamate Step 6 proceeded according to the following scheme:

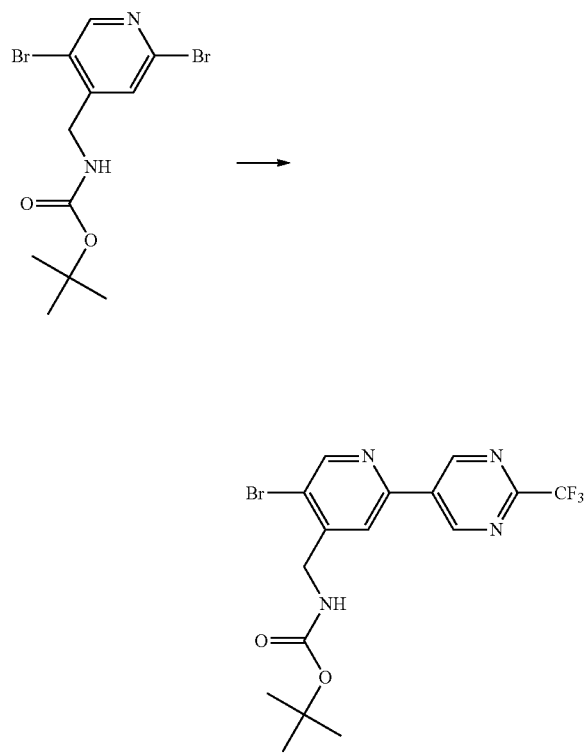

To a 1-L 3-necked round-bottom flask, purged and maintained with an inert atmosphere of nitrogen, was placed tert-butyl N-[(2,5-dibromopyridin-4-yl)methyl]carbamate (50 g, 136.59 mmol, 1.00 equiv), 5-(4,4,5,5-tetramethyl-1,3,2-dioxaborolan-2-yl)-2-(trifluoromethyl)pyrimidine (44.9 g, 1.20 equiv), 1,4-dioxane (500 mL), water (50 mL), potassium carbonate (56.6 g, 3.00 equiv) and Pd(dppf)Cl₂ (5 g, 0.05 equiv). The resulting mixture was stirred at 50° C. for 4 h and filtered. The resulting filtrate was concentrated under vacuum, diluted with 2 L of H₂O, and extracted with 3×1.5 L of ethyl acetate. The combined organic layer was washed with 2×1 L of brine and dried over anhydrous sodium sulfate and concentrated under vacuum. The residue was applied onto a silica gel column eluted with ethyl acetate/petroleum ether (10/90) to afford 45 g (25%) of tert-butyl N-([5-bromo-2-[2-(trifluoromethyl)pyrimidin-5-yl]pyridin-4-yl]methyl) carbamate as a white solid.

Example 4, Step 7: Preparation of (5-bromo-2-(2-(trifluoromethyl)pyrimidin-5-yl)pyridin-4-yl)methanamine hydrochloride Step 7 proceeded according to the following scheme:

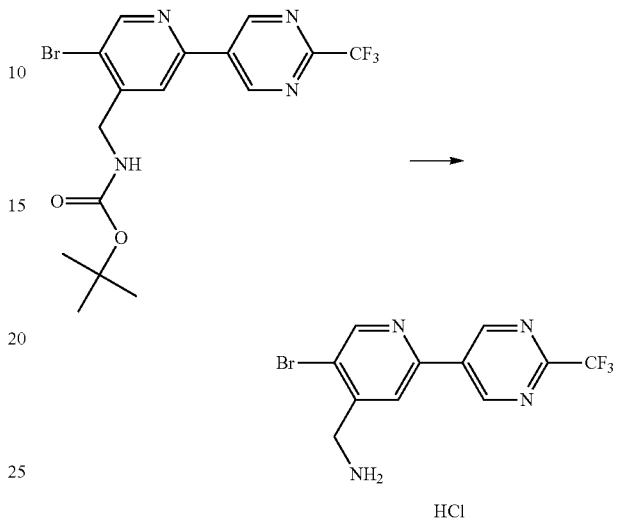

To a 1000-mL 3-necked round-bottom flask was placed tert-butyl N-([5-bromo-2-[2-(trifluoromethyl)pyrimidin-5-yl]pyridin-4-yl]methyl)carbamate (45 g, 103.87 mmol, 1.00 equiv), methanol (300 mL) and dichloromethane (300 mL). Into the above reaction system was introduced hydrogen chloride (gas). The resulting solution was stirred at room temperature for 50 min, concentrated under vacuum, diluted with 400 mL of ether, and filtered. The filter cake were dried to afford 32 g (83%) of [5-bromo-2-[2-(trifluoromethyl) pyrimidin-5-yl]pyridin-4-yl]methanamine hydrochloride salt as a white solid. LCMS [M−HCl+H]⁺ 333; ¹H NMR: (300 CDCl₃, DMSO-d₆): δ 4.26 (s, 2H), 8.74 (s, 1H), 8.95 (s, 3H), 9.00 (s, 1H), 9.74 (s, 2H).

Example 5: Preparation of (5-(trifluoromethyl)-2,4'-bipyrimidin-6'-yl)methanamine hydrochloride The overall reaction scheme for Example 5 was as follows:

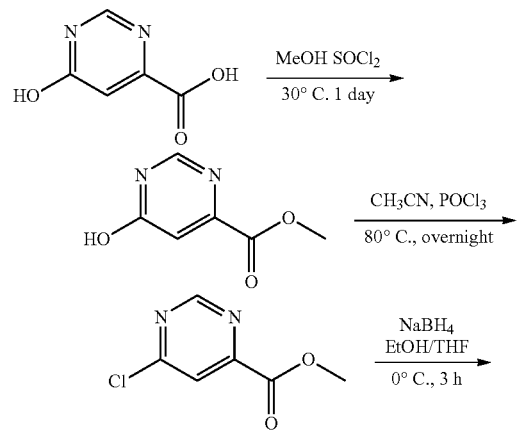

-continued

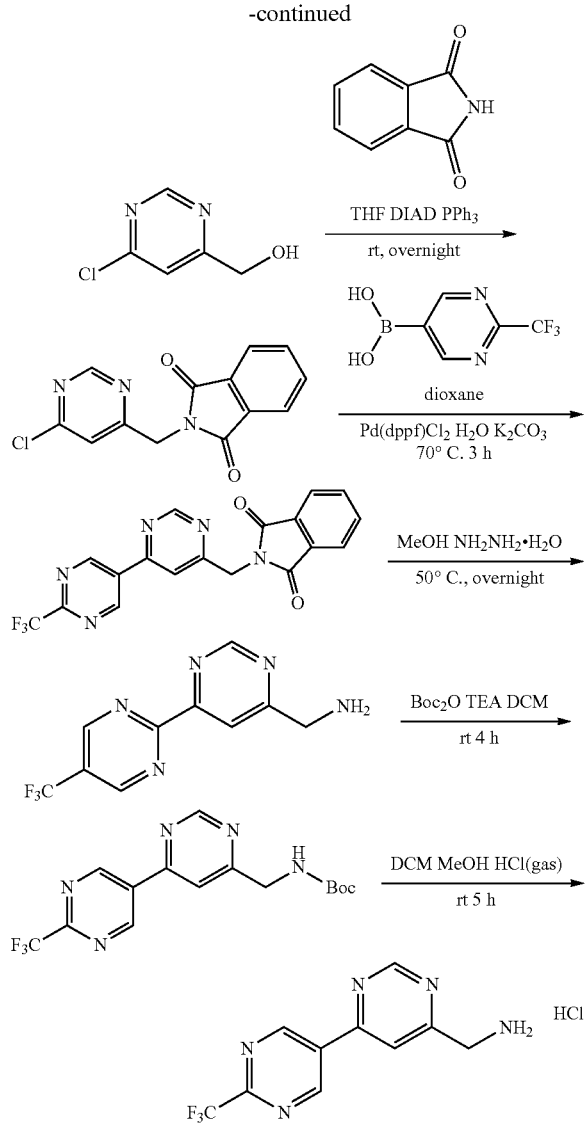

Example 5, Step 1: Preparation of methyl 6-hydroxypyrimidine-4-carboxylate

Step 1 proceeded according to the following scheme:

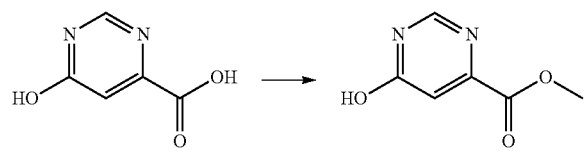

Into a 5-L 4-necked round-bottom flask, purged and maintained with an inert atmosphere of nitrogen, was placed 6-hydroxypyrimidine-4-carboxylic acid (100 g, 713.79 mmol, 1.00 equiv) and methanol (2000 mL), followed by the addition of thionyl chloride (210 g, 2.50 equiv) dropwise with stirring at 0° C. The resulting solution was stirred at 30° C. for 1 day and concentrated under vacuum to afford 115 g (crude) of methyl 6-hydroxypyrimidine-4-carboxylate as an off-white solid. LCMS [M+H]$^+$ 155.

Example 5, Step 2: Preparation of methyl 6-chloropyrimidine-4-carboxylate

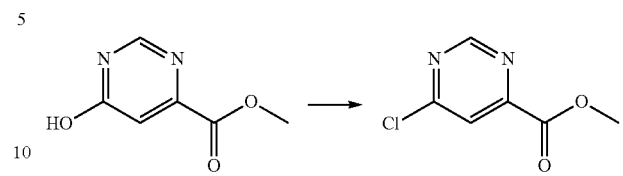

Into a 2000-mL 4-necked round-bottom flask was placed methyl 6-hydroxypyrimidine-4-carboxylate (115 g, 746.16 mmol, 1.00 equiv), CH$_3$CN (1200 mL), and POCl$_3$ (340 g, 2.22 mol, 3.00 equiv). The resulting solution was stirred at 80° C. overnight, cooled to room temperature, concentrated under vacuum, diluted with 1000 mL of EA, and quenched with 1000 mL of water/ice. The resulting solution was extracted with 3×500 mL of ethyl acetate. The combined organic layers were washed with 1×1000 mL of water and 1×1000 mL of brine, dried over anhydrous sodium sulfate, and concentrated under vacuum. The residue was applied onto a silica gel column eluted with ethyl acetate/petroleum ether (1:4) to afford 76 g (59%) of methyl 6-chloropyrimidine-4-carboxylate as a white solid. LCMS [M+H]$^+$ 173.

Example 5, Step 3: Preparation of (6-chloropyrimidin-4-yl)methanol

Step 3 proceeded according to the following scheme:

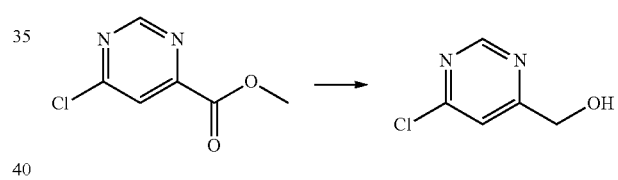

Into a 3000-mL 4-necked round-bottom flask was placed methyl 6-chloropyrimidine-4-carboxylate (80 g, 463.58 mmol, 1.00 equiv), tetrahydrofuran (1600 mL), and ethanol (160 mL), followed by the addition of NaBH$_4$ (48 g, 1.27 mol, 3.00 equiv) in several batches at 0° C. The resulting solution was stirred at 0° C. for 3 h, quenched by the addition of 1500 mL of water/ice, and extracted with 3×800 mL of ethyl acetate. The combined organic layers were washed with 1×800 mL of brine, dried over anhydrous sodium sulfate, and concentrated under vacuum. The residue was applied onto a silica gel column eluted with ethyl acetate/petroleum ether (1:2) to afford 40 g (60%) of (6-chloropyrimidin-4-yl)methanol as a yellow solid. LCMS [M+H]$^+$ 145.

Example 5, Step 4: Preparation of 2-((6-chloropyrimidin-4-yl)methyl)isoindoline-1,3-dione Step 4 proceeded according to the following scheme:

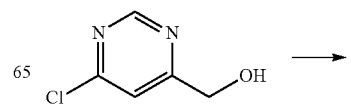

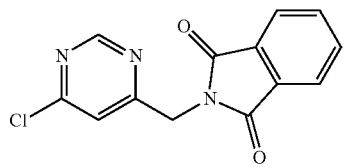

Into a 3000-mL 4-necked round-bottom flask was placed (6-chloropyrimidin-4-yl)methanol (50 g, 345.88 mmol, 1.00 equiv), tetrahydrofuran (1500 mL), 2,3-dihydro-1H-isoindole-1,3-dione (76.4 g, 519.27 mmol, 1.50 equiv), and PPh₃ (136 g, 518.51 mmol, 1.50 equiv), followed by the addition of DIAD (105 g, 519.26 mmol, 1.50 equiv) dropwise with stirring at 0° C. The resulting solution was stirred at room temperature overnight, concentrated under vacuum, diluted with 1000 mL of EA, stirred for additional 30 min, and filtered. The filter cake was washed with 1×300 mL of EA to afford 65 g (69%) of 2-[(6-chloropyrimidin-4-yl)methyl]-2,3-dihydro-1H-isoindole-1,3-dione as an off-white solid. LCMS [M+H]⁺ 274.

Example 5, Step 5: Preparation of 2-((5-(trifluoromethyl)-2,4'-bipyrimidin-6'-yl)methyl)isoindoline-1,3-dione Step 5 proceeded according to the following scheme:

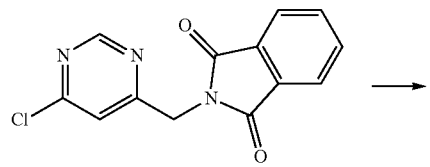

Into a 3000-mL 4-necked round-bottom flask, purged and maintained with an inert atmosphere of nitrogen, was placed 2-[(6-chloropyrimidin-4-yl)methyl]-2,3-dihydro-1H-isoindole-1,3-dione (50 g, 182.70 mmol, 1.00 equiv), 1,4-dioxane (1500 mL), water (70 mL), potassium carbonate (50 g, 361.77 mmol, 2.00 equiv), [2-(trifluoromethyl)pyrimidin-5-yl]boronic acid (91 g, 474.20 mmol, 2.50 equiv), and Pd(dppf)Cl₂ (4 g, 5.47 mmol, 0.02 equiv). The resulting solution was stirred at 70° C. for 3 h, cooled to room temperature, quenched by the addition of 3 L of water, and extracted with 3×1 L of ethyl acetate. The combined organic layers were dried over anhydrous sodium sulfate and concentrated under vacuum. The residue was applied onto a silica gel column eluted with ethyl acetate/petroleum ether (1:10) to afford 55 g (78%) of 2-([6-[2-(trifluoromethyl)pyrimidin-5-yl]pyrimidin-4-yl]methyl)-2,3-dihydro-1H-isoindole-1,3-dione as a white solid. LCMS [M+H]⁺ 386.

Example 5, Step 6: Preparation of (5-(trifluoromethyl)-2,4'-bipyrimidin-6'-yl)methanamine Step 6 proceeded according to the following scheme:

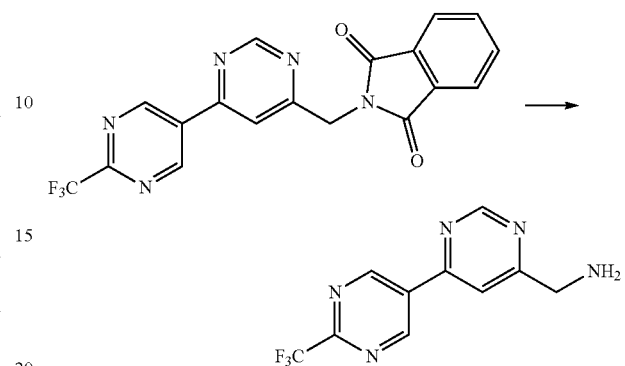

Into a 3000-mL 4-necked round-bottom flask was placed 2-([6-[2-(trifluoromethyl)pyrimidin-5-yl]pyrimidin-4-yl]methyl)-2,3-dihydro-1H-isoindole-1,3-dione (55 g, 142.75 mmol, 1.00 equiv), methanol (1500 mL), and NH₂NH₂.H₂O (110 g, 15.00 equiv). The resulting solution was at 50° C. stirred overnight, cooled to room temperature, and filtered. The filtrate diluted with 1 L of H₂O and extracted with 3×500 mL of ethyl acetate. The combined organic layers were dried over anhydrous sodium sulfate and concentrated under vacuum to afford 35 g (crude) of [6-[2-(trifluoromethyl)pyrimidin-5-yl]pyrimidin-4-yl]methanamine as a brown solid.

Example 5, Step 7: Preparation of tert-butyl (5-(trifluoromethyl)-2,4'-bipyrimidin-6'-yl)methylcarbamate Step 7 proceeded according to the following scheme:

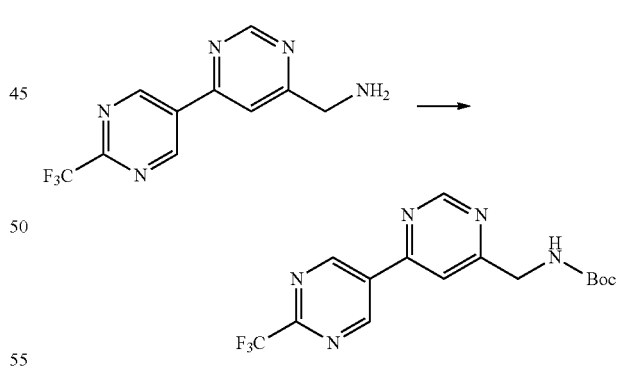

Into a 2000-mL 4-necked round-bottom flask was placed [6-[2-(trifluoromethyl)pyrimidin-5-yl]pyrimidin-4-yl]methanamine (35 g, 137.15 mmol, 1.00 equiv), dichloromethane (700 mL), TEA (20 g, 197.65 mmol, 1.50 equiv), and (Boc)₂O (44 g, 201.60 mmol, 1.50 equiv). The resulting solution was stirred at room temperature for 4 h, diluted with 2 L of H₂O, and extracted with 3×800 mL of dichloromethane. The combined organic layers were dried over anhydrous sodium sulfate and concentrated under vacuum. The residue was applied onto a silica gel column eluted with ethyl acetate/petroleum ether (1:5). This resulted in 40 g (82%) of tert-butyl N-([6-[2-(trifluoromethyl)pyrimidin-5-yl]pyrimidin-4-yl]methyl)carbamate as a yellow solid. LCMS [M+H]+ 356.

Example 5, Step 8: Preparation of (5-(trifluoromethyl)-2,4'-bipyrimidin-6'-yl)methanamine hydrochloride Step 8 proceeded according to the following scheme:

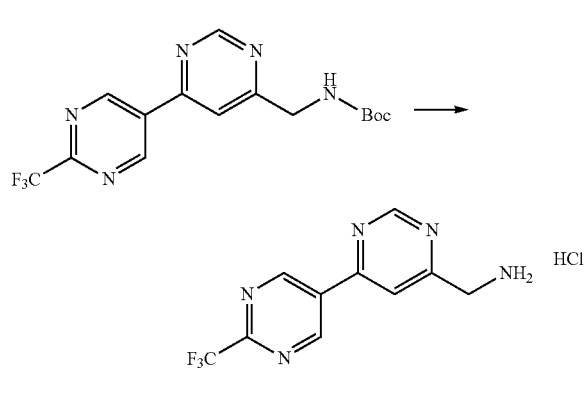

Into a 2000-mL 4-necked round-bottom flask was placed tert-butyl N-([6-[2-(trifluoromethyl)pyrimidin-5-yl]pyrimidin-4-yl]methyl)carbamate (40 g, 112.58 mmol, 1.00 equiv), dichloromethane (800 mL), and methanol (400 mL). Hydrogen chloride gas was added. The resulting solution was stirred at room temperature for 5 h, concentrated under vacuum, diluted with 200 mL of hexane, and filtered to afford 26 g (79%) of [6-[2-(trifluoromethyl)pyrimidin-5-yl]pyrimidin-4-yl]methanamine hydrochloride as a light yellow solid. LCMS [M+H]+ 256; $^{1}$H-NMR (300 MHz, DMSO) δ 9.78 (2H, s), 9.45 (1H, s), 8.67-8.76 (3H, ds), 8.62 (1H, s), 4.33-4.37 (2H, t).

Example 6: Preparation of [2-cyclopropyl-6-[2-(trifluoromethyl)pyrimidin-5-yl]pyrimidin-4-yl]methanamine The overall reaction scheme for Example 6 was as follows:

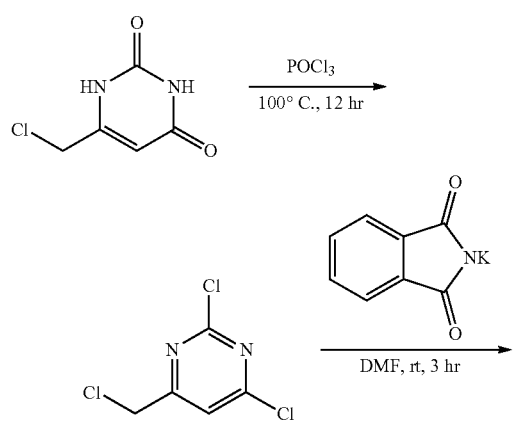

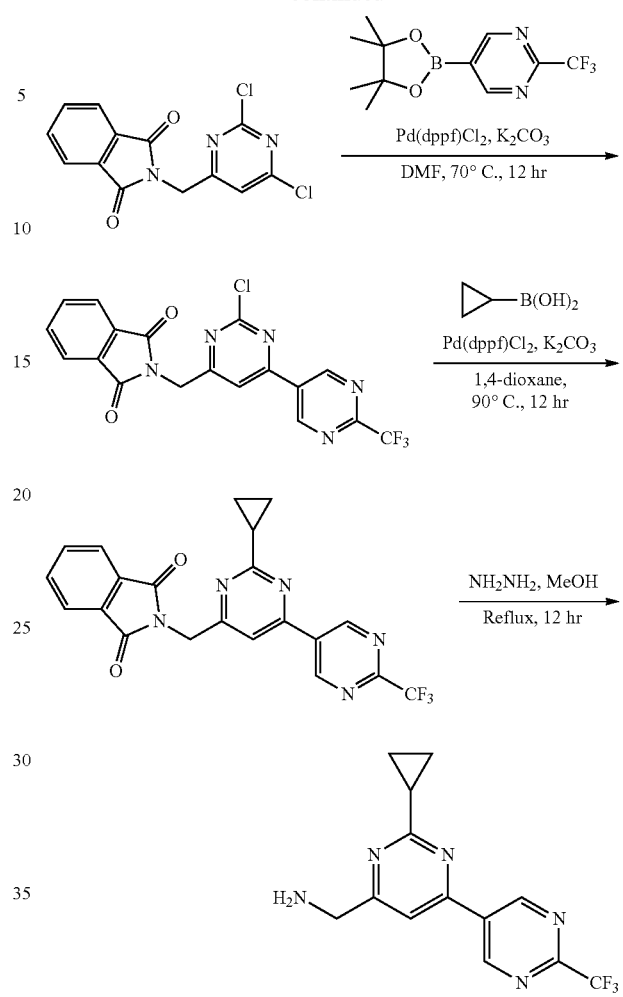

Example 6, Step 1: Preparation of 2,4-dichloro-6-(chloromethyl)pyrimidine

Step 1 proceeded according to the following scheme:

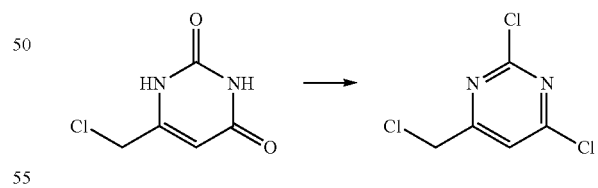

A mixture of 6-(chloromethyl)-1,2,3,4-tetrahydropyrimidine-2,4-dione (9.2 g, 57.30 mmol, 1.00 equiv) and POCl$_3$ (50 mL) was reacted by stirring for 12 hours at 100° C. in an oil bath. The reaction was then poured into water/ice, extracted with ethyl acetate, washed with brine, dried over anhydrous sodium sulfate, and concentrated under vacuum. The residue was purified by a silica gel column eluting with petroleum ether to afford the title compound (9.5 g, 84%) as a light yellow solid. LCMS [M+H+] 197.

Example 6, Step 2: Preparation of 2-[(2,6-dichloropyrimidin-4-yl)methyl]-2,3-dihydro-1H-isoindole-1,3-dione Step 2 proceeded according to the following scheme:

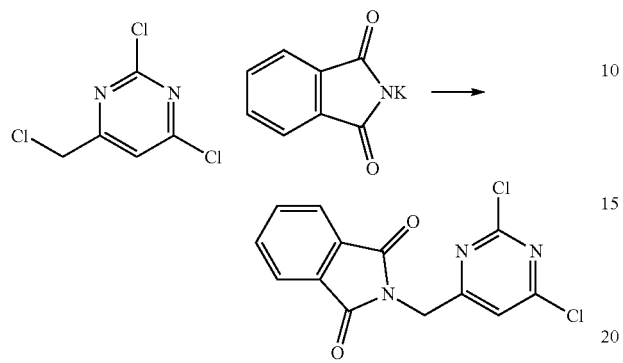

A mixture of 2-potassio-2,3-dihydro-1H-isoindole-1,3-dione (13 g, 70.19 mmol, 1.51 equiv), 2,4-dichloro-6-(chloromethyl)pyrimidine (9.2 g, 46.59 mmol, 1.00 equiv), and N,N-dimethylformamide (100 mL) was reacted by stirring for 3 hours at room temperature. The resulting solution was diluted with water. The solids were collected by filtration and dried under vacuum to afford the title compound (11.5 g, 80%) as a yellow solid. LCMS [M+H$^+$] 308.

Example 6, Step 3: Preparation of 2-([2-chloro-6-[2-(trifluoromethyl)pyrimidin-5-yl]pyrimidin-4-yl]methyl)-2,3-dihydro-1H-isoindole-1,3-dione Step 3 proceeded according to the following scheme:

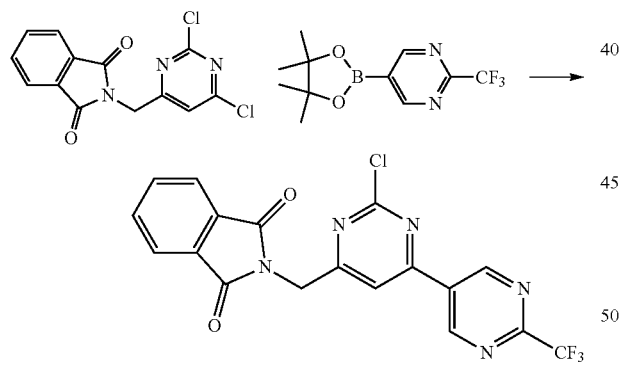

A mixture of 2-[(2,6-dichloropyrimidin-4-yl)methyl]-2,3-dihydro-1H-isoindole-1,3-dione (3.98 g, 12.91 mmol, 1.00 equiv), 5-(tetramethyl-1,3,2-dioxaborolan-2-yl)-2-(trifluoromethyl)pyrimidine (2.81 g, 10.27 mmol, 0.80 equiv), Pd(dppf)Cl$_2$ (945 mg, 1.29 mmol, 0.10 equiv), potassium carbonate (5.477 g, 39.63 mmol, 3.07 equiv), and N,N-dimethylformamide (150 mL) was stirred for 12 h at 70° C. under nitrogen. The solids were then filtered off. The resulting solution was diluted with brine, extracted with ethyl acetate, washed with brine, dried over anhydrous sodium sulfate, and concentrated under vacuum. The residue was purified by a silica gel column eluting with dichloromethane/ethyl acetate (50/1) to afford the title compound (1.75 g, 32%) as a yellow solid. LCMS [M+H$^+$] 420.

Example 6, Step 4: Preparation of 2-([2-cyclopropyl-6-[2-(trifluoromethyl)pyrimidin-5-yl]pyrimidin-4-yl]methyl)-2,3-dihydro-1H-isoindole-1,3-dione Step 4 proceeded according to the following scheme:

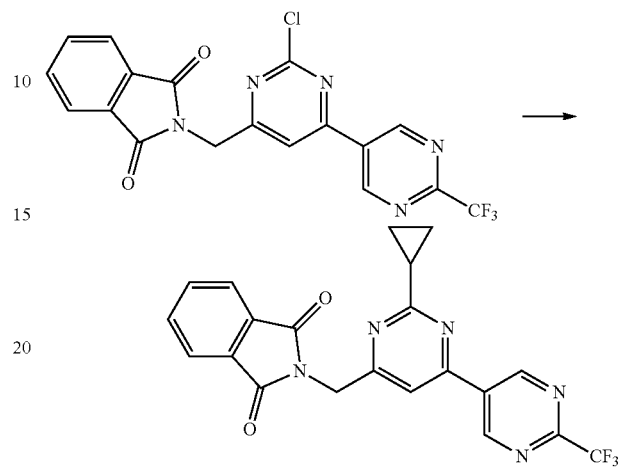

A mixture of 2-([2-chloro-6-[2-(trifluoromethyl)pyrimidin-5-yl]pyrimidin-4-yl]methyl)-2,3-dihydro-1H-isoindole-1,3-dione (190 mg, 0.45 mmol, 1.00 equiv), cyclopropylboronic acid (195 mg, 2.27 mmol, 5.02 equiv), Pd(dppf)Cl$_2$ (33 mg, 0.045 mmol, 0.10 equiv) and potassium carbonate (188 mg, 1.36 mmol, 3.01 equiv), 1,4-dioxane (10 mL) was stirred for 12 hours at 90° C. under nitrogen. The solids were filtered off. The resulting solution was diluted with brine, extracted with ethyl acetate, washed with brine, dried over anhydrous sodium sulfate, and concentrated under vacuum. The residue was purified by a silica gel column eluting with dichloromethane/ethyl acetate (50/1) to afford the title compound (175 mg, 91%) as yellow solid. LCMS [M+H$^+$] 426.

Example 6, Step 5: Preparation of [2-cyclopropyl-6-[2-(trifluoromethyl)pyrimidin-5-yl]pyrimidin-4-yl]methanamine Step 5 proceeded according to the following scheme:

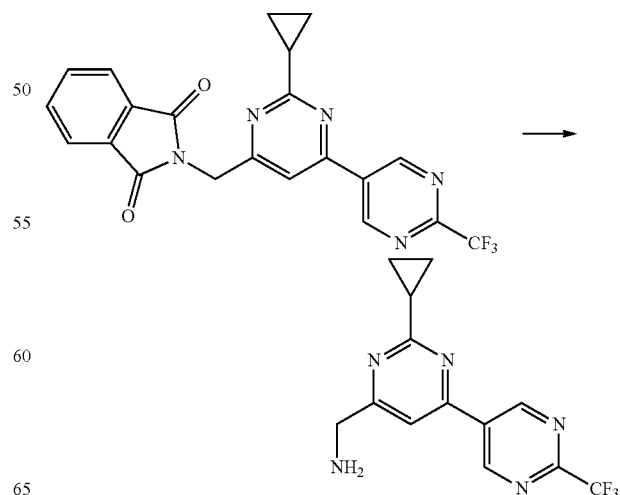

A mixture of 2-([2-cyclopropyl-6-[2-(trifluoromethyl)pyrimidin-5-yl]pyrimidin-4-yl]methyl)-2,3-dihydro-1H-isoindole-1,3-dione (175 mg, 0.41 mmol, 1.00 equiv), methanol (20 mL), NH$_2$NH$_2$.H$_2$O (206 mg, 41.1 mmol, 10.00 equiv) was heated to reflux for 12 hours in an oil bath. The resulting mixture was concentrated under vacuum and dissolved in ethyl acetate. The precipitated solids were filtered off. The resulting solution was concentrated under vacuum to afford the title compound (121 mg) as a yellow oil. LCMS [M+H$^+$] 296.

Example 7: Preparation of (2-fluoro-5-(2-(trifluoromethyl)pyrimidin-5-yl)phenyl)methanamine The overall reaction scheme for Example 7 was as follows:

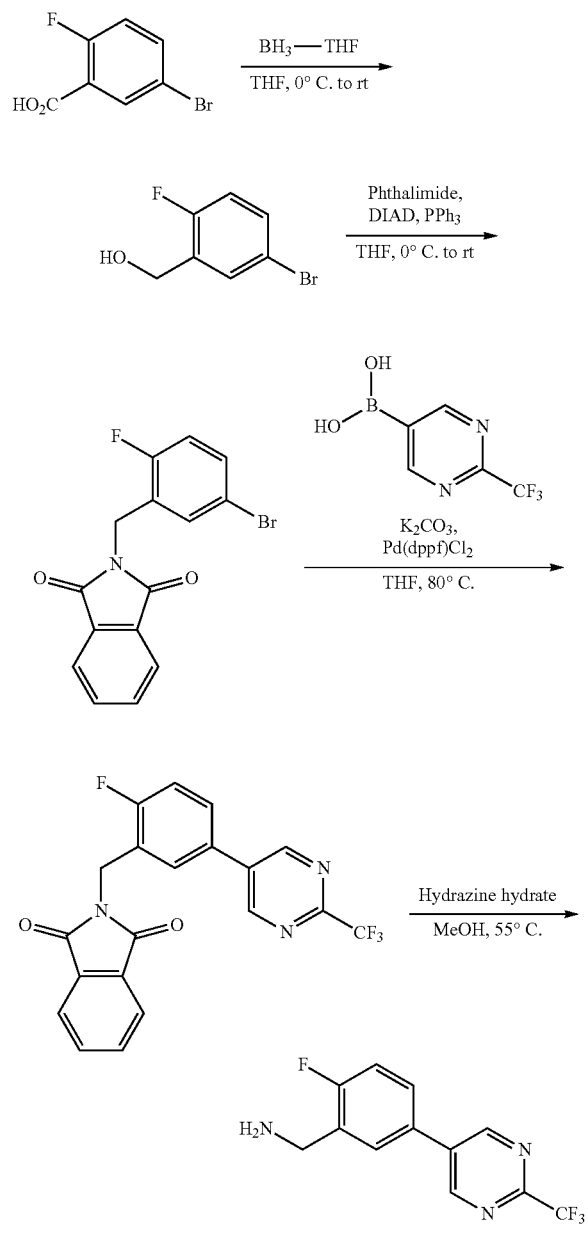

Example 7, Step 1: Preparation of (5-bromo-2-fluorophenyl)methanol

Step 1 proceeded according to the following scheme:

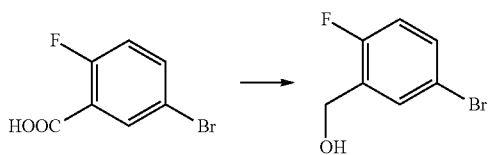 [SMILES: O=C(O)c1cc(Br)ccc1F ; OCc1cc(Br)ccc1F]

BH$_3$-THF (229 mL, 1 M in THF, 5.00 equiv) was added dropwise into a solution of 5-bromo-2-fluorobenzoic acid (10 g, 45.66 mmol, 1.00 equiv) in tetrahydrofuran (150 mL) at 0° C. under nitrogen. The resulting solution was stirred overnight at room temperature, quenched with water, extracted with ethyl acetate, washed with brine, dried over anhydrous sodium sulfate, and concentrated under vacuum. The residue was purified by a silica gel column eluting with ethyl acetate/petroleum ether (1:5) to afford the title compound (9.5 g) as light yellow oil. GCMS m/z=204, 206.

Example 7, Step 2: Preparation of 2-[(5-bromo-2-fluorophenyl)methyl]-2,3-dihydro-1H-isoindole-1,3-dione Step 2 proceeded according to the following scheme:

DIAD (18.8 g, 92.97 mmol, 2.01 equiv) was added dropwise into a stirred mixture of (5-bromo-2-fluorophenyl)methanol (9.5 g, 46.34 mmol, 1.00 equiv), 2,3-dihydro-1H-isoindole-1,3-dion (13.6 g, 92.44 mmol, 2.00 equiv), and PPh$_3$ (24.4 g, 93.03 mmol, 2.01 equiv) in tetrahydrofuran (300 mL) at 0° C. under nitrogen. The resulting solution was stirred overnight at room temperature and concentrated under vacuum. The residue was purified by a silica gel column eluting with ethyl acetate/petroleum ether (1:10) to afford the title compound (9.5 g, 61%) as a white solid. LCMS [M+H$^+$] 334; $^1$H NMR (300 MHz, CDCl$_3$) δ 7.89-7.83 (m, 2H), 7.78-7.70 (m, 2H), 7.66-7.63 (m, 1H), 7.40-7.35 (m, 1H), 7.09-7.03 (m, 1H), 4.78 (s, 2H).

Example 7, Step 3: Preparation of 2-([2-fluoro-5-[2-(trifluoromethyl)pyrimidin-5-yl]phenyl]methyl)-2,3-dihydro-1H-isoindole-1,3-dione Step 3 proceeded according to the following scheme:

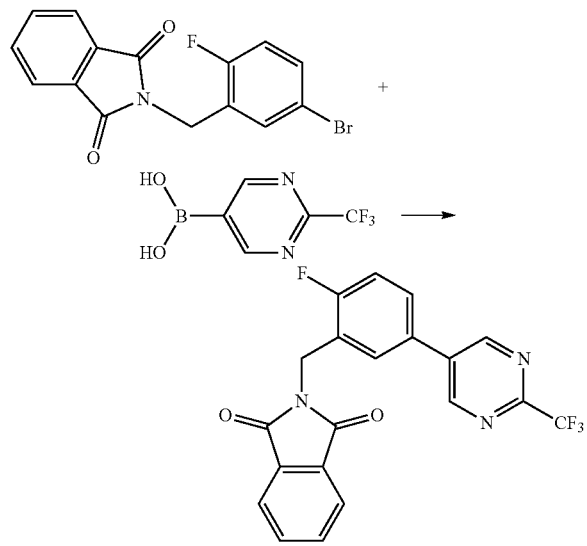

A mixture of 2-[(5-bromo-2-fluorophenyl)methyl]-2,3-dihydro-1H-isoindole-1,3-dione (2 g, 5.99 mmol, 1.00 equiv), 5-(tetramethyl-1,3,2-dioxaborolan-2-yl)-2-(trifluoromethyl)pyrimidine (2.1 g, 7.66 mmol, 1.28 equiv), Pd(dppf)Cl₂ (438 mg, 0.60 mmol, 0.10 equiv), and potassium carbonate (1.65 g, 11.94 mmol, 2.00 equiv) in tetrahydrofuran (25 mL) was stirred overnight at 80° C. The resulting mixture was concentrated under vacuum and the residue was purified by a silica gel column eluting with ethyl acetate/petroleum ether (1:100-1:10). This resulted in the title compound (1.7 g, 71%) as a light yellow solid. LCMS [M+H⁺] 402.

Example 7, Step 4: Preparation of [2-fluoro-5-[2-(trifluoromethyl)pyrimidin-5-yl]phenyl]methanamine Step 4 proceeded according to the following scheme:

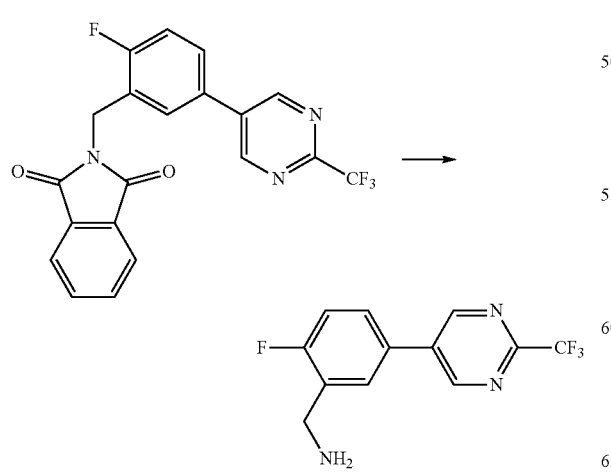

A mixture of 2-([2-fluoro-5-[2-(trifluoromethyl)pyrimidin-5-yl]phenyl]methyl)-2,3-dihydro-1H-isoindole-1,3-dione (500 mg, 1.25 mmol, 1.00 equiv) and hydrazine hydrate (623 mg, 12.45 mmol, 10.00 equiv) in methanol (10 mL) was stirred overnight at 55° C. The resulting mixture was concentrated under vacuum. The residue was dissolved in ethyl acetate. The solid was filtered out and the liquid was concentrated under vacuum. This resulted in the title compound (300 mg, crude) as light yellow oil. LCMS [M+H⁺] 272.

Example 8: Preparation of [5-(difluoromethyl)-2-[2-(trifluoromethyl)pyrimidin-5-yl]pyridin-4-yl]methanamine hydrochloride The overall reaction scheme for Example 8 was as follows:

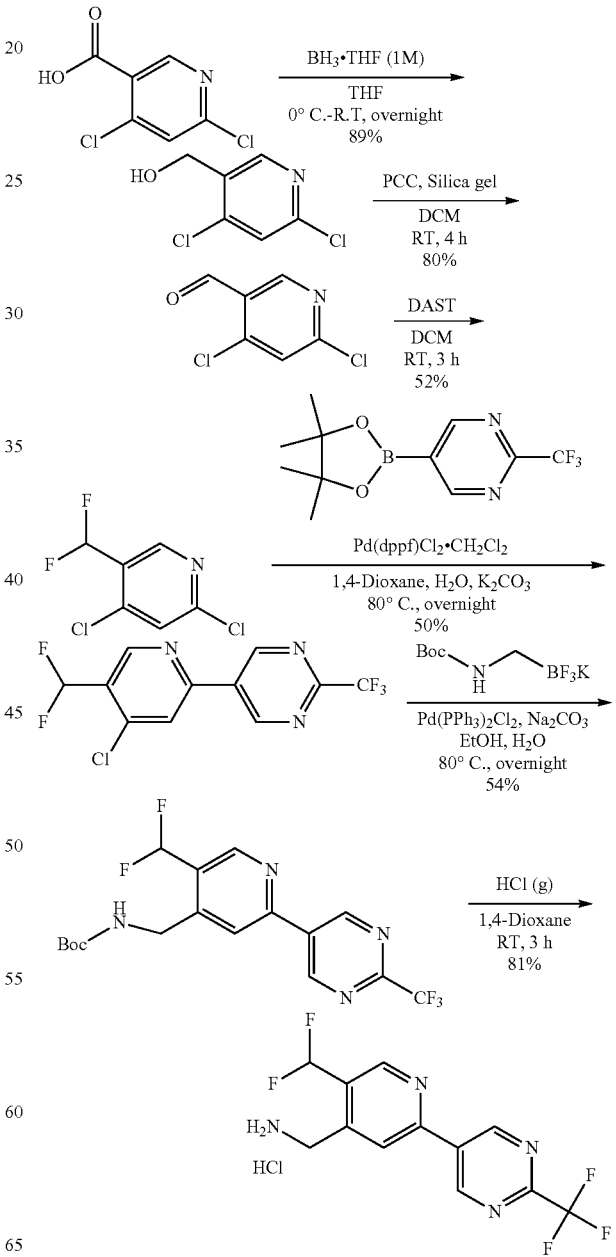

Example 8, Step 1: Preparation of (4,6-dichloropyridin-3-yl)methanol

Step 1 proceeded according to the following scheme:

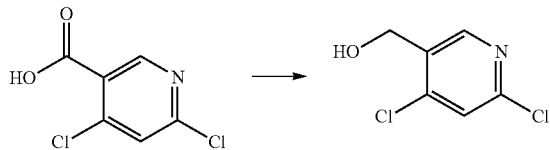 [SMILES: O=C(O)c1cnc(Cl)cc1Cl ; OCc1cnc(Cl)cc1Cl]

To a 5000-mL 4-necked round-bottom flask, purged and maintained with an inert atmosphere of nitrogen, was placed 4,6-dichloropyridine-3-carboxylic acid (95 g, 494.79 mmol, 1.00 equiv) and tetrahydrofuran (1000 mL), followed by the addition of BH$_3$.THF (1 M) (2111 mL, 4.20 equiv) dropwise with stirring at 0° C. The reaction mixture was stirred at 0° C. for 30 min and at room temperature overnight, quenched by the addition of 1000 mL of water/ice, and extracted with 3×1000 mL of ethyl acetate. The combined organic layers were dried over anhydrous sodium sulfate and concentrated under vacuum to afford 78.4 g (89%) of (4,6-dichloropyridin-3-yl)methanol as a white solid.

Example 8, Step 2: Preparation of 4,6-dichloronicotinaldehyde

Step 2 proceeded according to the following scheme:

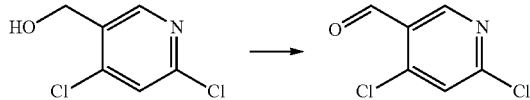

To a 2000-mL 4-necked round-bottom flask, purged and maintained with an inert atmosphere of nitrogen, was placed (4,6-dichloropyridin-3-yl)methanol (78.4 g, 440.41 mmol, 1.00 equiv), dichloromethane (1000 mL), PCC (284.83 g, 1.32 mol, 3.00 equiv) and Silica gel (235 g). The resulting mixture was stirred at room temperature for 4 h and concentrated under vacuum. The residue was applied onto a silica gel column eluted with ethyl acetate/petroleum ether (0:1-1:6) to afford 62 g (80%) of 4,6-dichloropyridine-3-carbaldehyde as a white solid.

Example 8, Step 3: Preparation of 2,4-dichloro-5-(difluoromethyl)pyridine

Step 3 proceeded according to the following scheme:

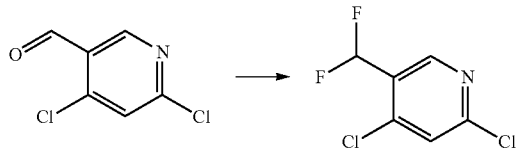 [SMILES: O=Cc1cnc(Cl)cc1Cl ; FC(F)c1cnc(Cl)cc1Cl]

To a 2000-mL 4-necked round-bottom flask, purged and maintained with an inert atmosphere of nitrogen, was placed 4,6-dichloropyridine-3-carbaldehyde (62 g, 352.27 mmol, 1.00 equiv) and dichloromethane (1000 mL), followed by the addition of DAST (113.7 g, 705.38 mmol, 2.00 equiv) dropwise with stirring at −20° C. The resulting solution was stirred at −20° C. for 30 min and at room temperature for additional 3 h, quenched by the addition of 500 mL of water dropwise with stirring, and extracted with 3×500 mL of dichloromethane. The combined organic layers were dried over anhydrous sodium sulfate and concentrated under vacuum. The residue was applied onto a silica gel column eluted with ethyl acetate/petroleum ether (0:1-1:0) to afford 36 g (52%) of 2,4-dichloro-5-(difluoromethyl)pyridine as a light yellow solid.

Example 8, Step 4: Preparation of 5-(4-chloro-5-(difluoromethyl)pyridin-2-yl)-2-(trifluoromethyl) pyrimidine Step 4 proceeded according to the following scheme:

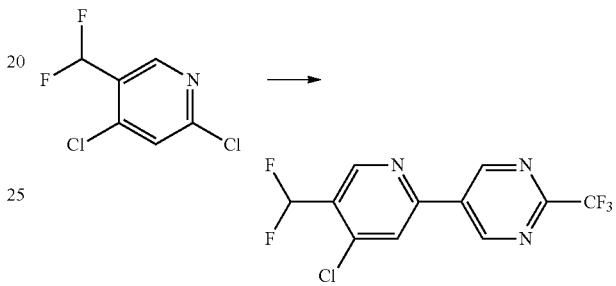

To a 3000-mL 4-necked round-bottom flask, purged and maintained with an inert atmosphere of nitrogen, was placed 2,4-dichloro-5-(difluoromethyl)pyridine (36 g, 181.82 mmol, 1.00 equiv), 1,4-dioxane (1800 mL), water (180 mL), 5-(tetramethyl-1,3,2-dioxaborolan-2-yl)-2-(trifluoromethyl) pyrimidine (60 g, 218.94 mmol, 1.20 equiv), potassium carbonate (78 g, 564.36 mmol, 3.00 equiv) and Pd(dppf) Cl$_2$.CH$_2$Cl$_2$ (15 g, 18 mmol, 0.10 equiv). The resulting solution was stirred at 80° C. overnight and filtered. The filtrate was concentrated under vacuum. The residue was applied onto a silica gel column eluted with ethyl acetate/ petroleum ether (0:1-5:95) to afford 28 g (50%) of 5-[4-chloro-5-(difluoromethyl)pyridin-2-yl]-2-(trifluoromethyl) pyrimidine as a white solid.

Example 8, Step 5: Preparation of tert-butyl ((5-(difluoromethyl)-2-(2-(trifluoromethyl)pyrimidin-5-yl)pyridin-4-yl)methyl)carbamate Step 5 proceeded according to the following scheme:

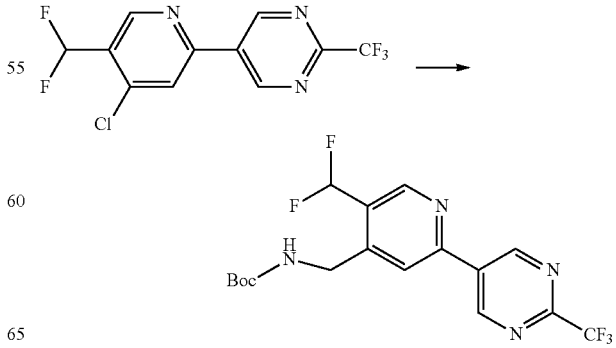

To a 3000-mL 4-necked round-bottom flask, purged and maintained with an inert atmosphere of nitrogen, was placed 5-[4-chloro-5-(difluoromethyl)pyridin-2-yl]-2-(trifluoromethyl)pyrimidine (20 g, 64.59 mmol, 1.00 equiv), ethanol (2000 mL), water (400 mL), potassium tert-butyl N-[(trifluoro-^4-boranyl)methyl]carbamate (20 g, 84.36 mmol, 1.30 equiv), sodium carbonate (22 g, 207.57 mmol, 3.20 equiv), and Pd(PPh$_3$)$_2$Cl$_2$ (5 g, 7.12 mmol, 0.11 equiv). The reaction mixture was first stirred at room temperature for 30 min and then at 80° C. overnight, followed by filtration. The filtrate was concentrated under vacuum. The residue was applied onto a silica gel column eluted with ethyl acetate/petroleum ether (0:1-1:6) to afford 14 g (54%) of tert-butyl N-[[5-(difluoromethyl)-2-[2-(trifluoromethyl)pyrimidin-5-yl]pyridin-4-yl]methyl]carbamate as a light yellow solid.

Example 8, Step 6: Preparation of (5-(difluoromethyl)-2-(2-(trifluoromethyl)pyrimidin-5-yl)pyridin-4-yl)methanamine hydrochloride Step 6 proceeded according to the following scheme:

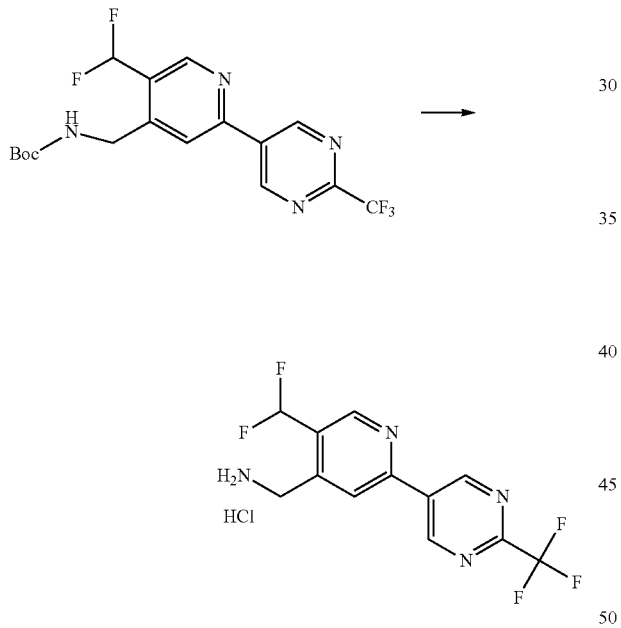

To a 1000-mL 3-necked round-bottom flask, purged and maintained with an inert atmosphere of nitrogen, was placed tert-butyl N-[[5-(difluoromethyl)-2-[2-(trifluoromethyl)pyrimidin-5-yl]pyridin-4-yl]methyl]carbamate (30 g, 74.20 mmol, 1.00 equiv) and 1,4-dioxane (500 mL). Into the above reaction mixture was introduced HCl (gas). The resulting solution was stirred at room temperature for 3 h, concentrated under vacuum, and filtered. The filter cake were washed with 1×300 mL of EA and dried to afford 20.37 g (81%) of [5-(difluoromethyl)-2-[2-(trifluoromethyl)pyrimidin-5-yl]pyridin-4-yl]methanamine hydrochloride as a yellow solid. LCMS [M−HCl+H$^+$] 305; $^1$H NMR (300 MHz, CD$_3$OD) δ 9.67 (s, 2H), 9.10 (s, 1H), 8.34 (s, 1H), 7.39-7.03 (t, 1H), 4.51 (s, 2H).

Example 9: Preparation of (2-bromo-5-(2-(trifluoromethyl)pyrimidin-5-yl)phenyl)methanamine hydrochloride The overall reaction scheme for Example 9 was as follows:

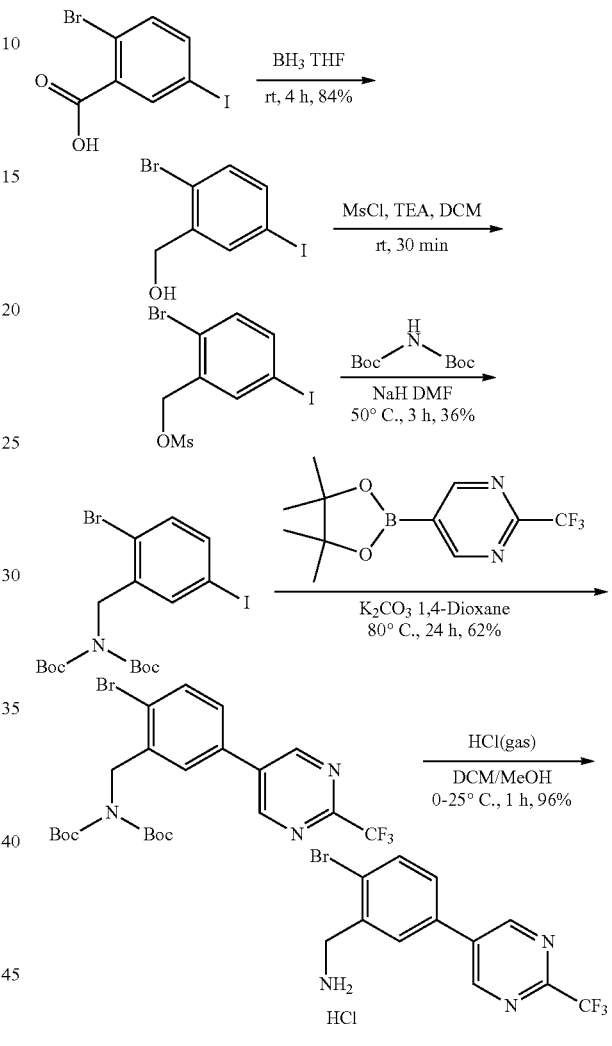

Example 9, Step 1: Preparation of (2-bromo-5-iodophenyl)methanol

Step 1 proceeded according to the following scheme:

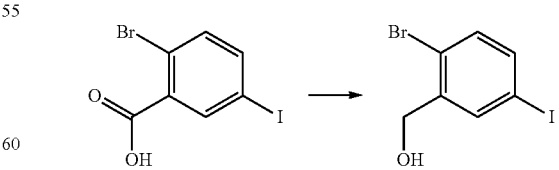

To a 5000-mL 4-necked round-bottom flask, purged and maintained with an inert atmosphere of nitrogen, was placed 2-bromo-5-iodobenzoic acid (200 g, 611.78 mmol, 1.00 equiv) and tetrahydrofuran (1500 mL), followed by the addition of borane (1834 mL, 3.00 equiv) dropwise with stirring at 0° C. The resulting solution was stirred for 4 h at room temperature, quenched by the addition of 4000 mL of water/ice, and then extracted with 2×2000 mL of ethyl acetate. The combined organic layer was washed with 2×2000 mL of brine, dried over anhydrous sodium sulfate and concentrated under vacuum. The residue was diluted with 500 mL of PE. The solids were collected by filtration to afford 160 g (84%) of (2-bromo-5-iodophenyl)methanol as a white solid.

Example 9, Step 2: Preparation of (2-bromo-5-iodophenyl)methyl methanesulfonate

Step 2 proceeded according to the following scheme:

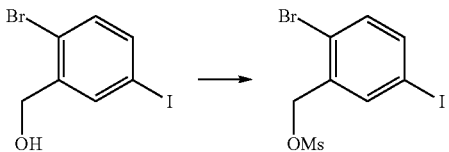 [SMILES: OCc1cc(I)ccc1Br ; CS(=O)(=O)OCc1cc(I)ccc1Br]

To a 3000-mL 4-necked round-bottom flask, purged and maintained with an inert atmosphere of nitrogen, was placed (2-bromo-5-iodophenyl)methanol (160 g, 511.30 mmol, 1.00 equiv), dichloromethane (1500 mL) and TEA (103.2 g, 1.02 mol, 2.00 equiv), followed by the addition of methanesulfonyl chloride (81.6 g, 712.35 mmol, 1.40 equiv) dropwise with stirring at 0° C. The resulting solution was stirred for 30 min at room temperature, quenched by the addition of 1000 mL of water/ice, and then extracted with 2×1500 mL of dichloromethane. The combined organic layer was washed with 1×1000 mL of brine, dried over anhydrous sodium sulfate and concentrated under vacuum to afford 200 g (crude) of (2-bromo-5-iodophenyl)methyl methanesulfonate as a light yellow solid.

Example 9, Step 3: Preparation of tert-butyl N-[(2-bromo-5-iodophenyl)methyl]-N-[(tert-butoxy)carbonyl]carbamate Step 3 proceeded according to the following scheme:

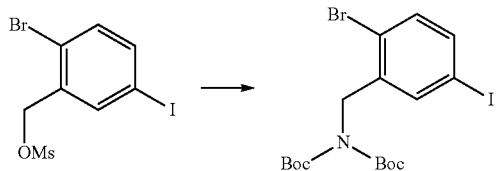 [SMILES: CS(=O)(=O)OCc1cc(I)ccc1Br ; CC(C)(C)OC(=O)N(Cc1cc(I)ccc1Br)C(=O)OC(C)(C)C]

To a 3000-mL 4-necked round-bottom flask, purged and maintained with an inert atmosphere of nitrogen, was placed tert-butyl N-[(tert-butoxy)carbonyl]carbamate (105.4 g, 485.13 mmol, 0.95 equiv) and N,N-dimethylformamide (1500 mL), followed by the addition of sodium hydride (24.5 g, 613.58 mmol, 1.20 equiv) in portions and stirring for 40 min. To this was added a solution of (2-bromo-5-iodophenyl)methyl methanesulfonate (200 g, 511.48 mmol, 1.05 equiv) in N,N-dimethylformamide (800 mL) dropwise with stirring. The resulting solution was stirred for 3 h at 50° C., quenched by the addition of 3000 mL of water/ice, and extracted with 2×1500 mL of ethyl acetate. The combined organic layer was washed with 2×1000 mL of brine, dried over anhydrous sodium sulfate, and concentrated under vacuum. The residue was applied onto a silica gel column eluted with ethyl acetate/petroleum ether (5/95) to afford 95 g (36%) of tert-butyl N-[(2-bromo-5-iodophenyl)methyl]-N-[(tert-butoxy)carbonyl]carbamate as a white solid.

Example 9, Step 4: N-([2-bromo-5-[2-(trifluoromethyl)pyrimidin-5-yl]phenyl]methyl)-N-[(tert-butoxy)carbonyl]carbamate Step 4 proceeded according to the following scheme:

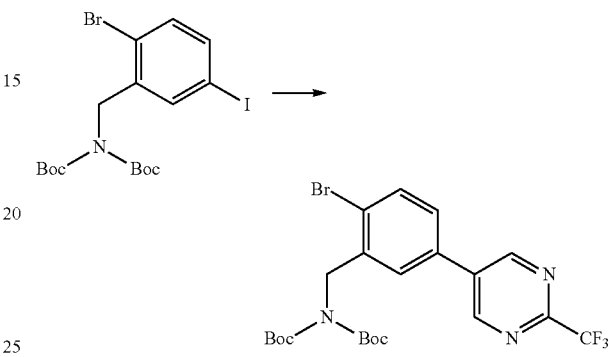

To a 1000-mL 3-necked round-bottom flask, purged and maintained with an inert atmosphere of nitrogen, was placed tert-butyl N-[(2-bromo-5-iodophenyl)methyl]-N-[(tert-butoxy)carbonyl]carbamate (70 g, 136.67 mmol, 1.00 equiv), 5-(tetramethyl-1,3,2-dioxaborolan-2-yl)-2-(trifluoromethyl)pyrimidine (52.5 g, 191.57 mmol, 1.40 equiv), 1,4-Dioxane (700 mL), K$_2$CO$_3$ (37.8 g, 2.00 equiv), and Pd(dppf)Cl$_2$ dichloromethane (10 g, 0.10 equiv). The resulting solution was stirred for 24 h at 80° C. in an oil bath, then diluted with 700 mL of EA. The solids were filtered out. The resulting mixture was concentrated under vacuum. The residue was applied onto a silica gel column eluted with ethyl acetate/petroleum ether (5/95) to afford 45 g (62%) of tert-butyl N-([2-bromo-5-[2-(trifluoromethyl)pyrimidin-5-yl]phenyl]methyl)-N-[(tert-butoxy)carbonyl]carbamate as a white solid.

Example 9, Step 5: Preparation of [2-bromo-5-[2-(trifluoromethyl)pyrimidin-5-yl]phenyl]methanamine hydrochloride Step 5 proceeded according to the following scheme:

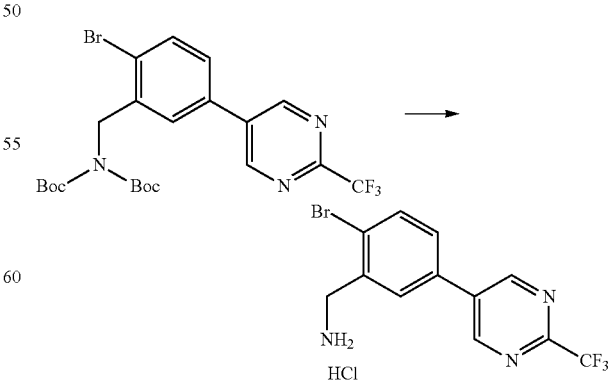

Into a 1000-mL 3-necked round-bottom flask was placed tert-butyl N-([2-bromo-5-[2-(trifluoromethyl)pyrimidin-5- yl]phenyl]methyl)-N-[(tert-butoxy)carbonyl]carbamate (45 g, 84.53 mmol, 1.00 equiv), dichloromethane (300 mL), and methanol (300 mL). Into the above hydrogen chloride (gas) was introduced. The resulting solution was stirred for 1 h at 0-25° C. in an ice/salt bath. The resulting mixture was concentrated under vacuum. The rese7due was diluted with 300 mL of ether. The solids were collected by filtration to afford 30 g (96%) of [2-bromo-5-[2-(trifluoromethyl)pyrimidin-5-yl]phenyl]methanamine hydrochloride as a white solid. LCMS [M−HCl+H+] 332; $^1$H NMR (300 MHz, DMSO-$d_6$) δ 4.23 (s, 2H), 7.88-7.94 (m, 2H), 8.26-8.28 (m, 1H), 8.64-8.76 (m, 3H), 9.49 (s, 2H).

Example 10: Preparation of (5-(trifluoromethoxy)-2-(2-(trifluoromethyl)pyrimidin-5-yl)pyridin-4-yl) methanamine

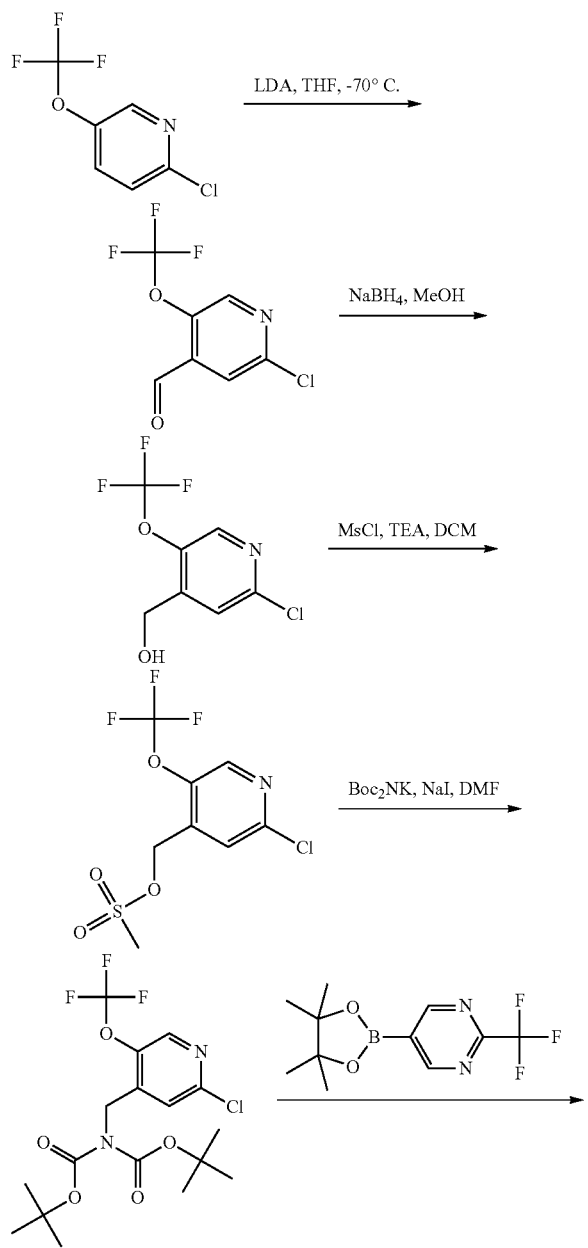

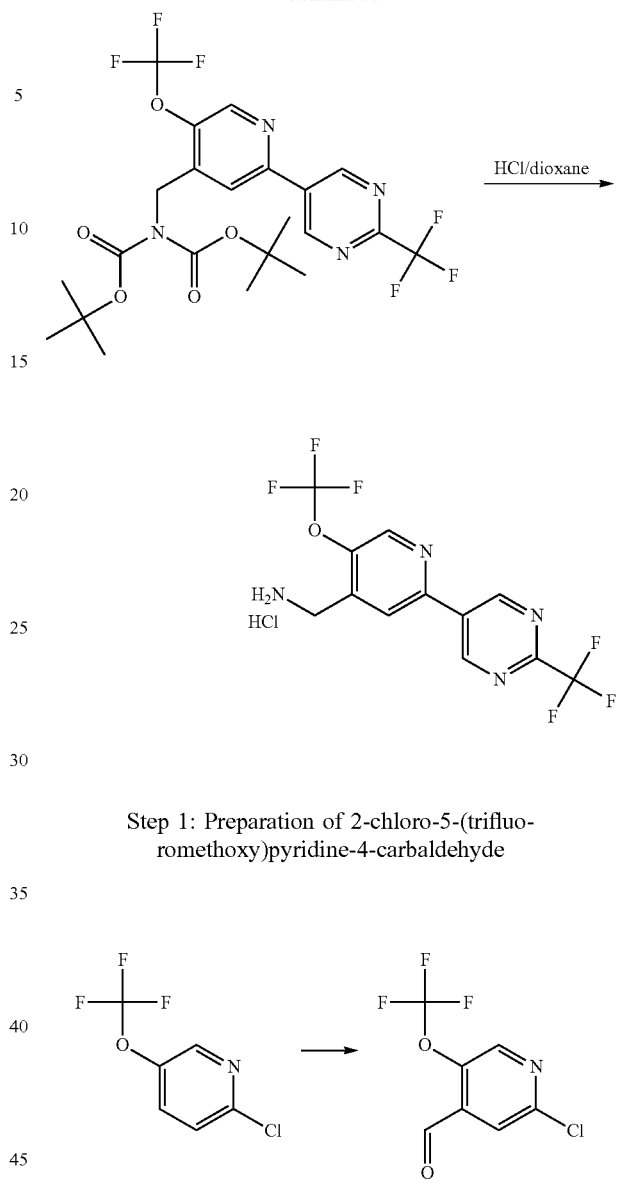

Step 1: Preparation of 2-chloro-5-(trifluoromethoxy)pyridine-4-carbaldehyde n-BuLi (20.2 mL, 2.5M in hexanes, 2.00 equiv) was added dropwise into a solution of i-Pr$_2$NH (6.38 g, 63.05 mmol, 2.49 equiv) in tetrahydrofuran (100 mL) at 0° C. under nitrogen. The resulting solution was stirred for 15 min at 0° C. To this was added 2-chloro-5-(trifluoromethoxy)pyridine (5 g, 25.311 mmol, 1.00 equiv) dropwise at −70° C. The resulting solution was allowed to react for an additional 1 h while the temperature was maintained at −70° C. To the mixture was added N,N-dimethylformamide (9.22 g, 126.14 mmol, 4.98 equiv) dropwise at −70° C. The resulting solution was allowed to react for an additional 30 min while the temperature was maintained at −70° C. The reaction was then quenched by saturated NH$_4$Cl solution, extracted with ethyl acetate, washed with hydrogen chloride (1M) and brine, dried over anhydrous sodium sulfate, and concentrated under vacuum. This resulted in the title compound (4.5 g, 79%) as light yellow oil. LCMS [M+H+] 226.

Step 2: Preparation of [2-chloro-5-(trifluoromethoxy)pyridin-4-yl]methanol

Step 4: Preparation of tert-butyl N-[(tert-butoxy)carbonyl]-N-[[2-chloro-5-(trifluoromethoxy)pyridin-4-yl]methyl]carbamate

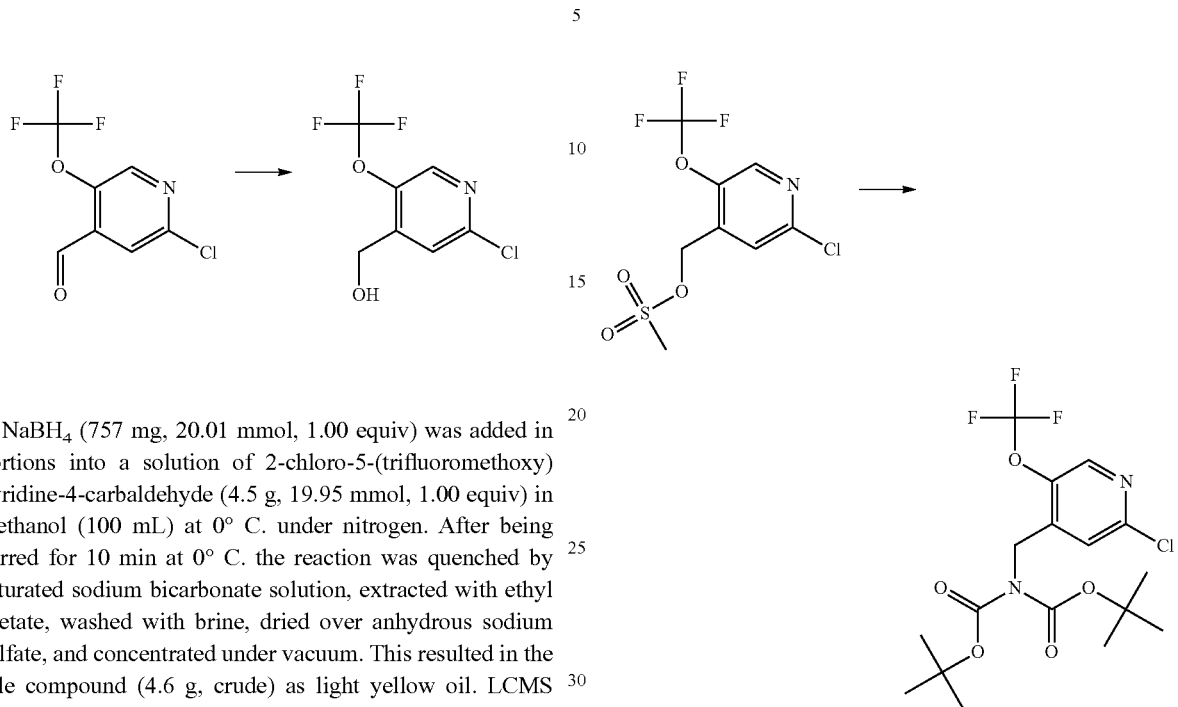

NaBH₄ (757 mg, 20.01 mmol, 1.00 equiv) was added in portions into a solution of 2-chloro-5-(trifluoromethoxy)pyridine-4-carbaldehyde (4.5 g, 19.95 mmol, 1.00 equiv) in methanol (100 mL) at 0° C. under nitrogen. After being stirred for 10 min at 0° C. the reaction was quenched by saturated sodium bicarbonate solution, extracted with ethyl acetate, washed with brine, dried over anhydrous sodium sulfate, and concentrated under vacuum. This resulted in the title compound (4.6 g, crude) as light yellow oil. LCMS [M+H⁺] 228.

Step 3: Preparation of 2-chloro-5-(trifluoromethoxy)pyridin-4-yl]methyl methanesulfonate

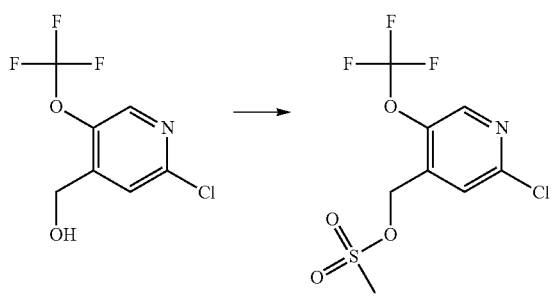 [SMILES: OCc1cc(Cl)ncc1OC(F)(F)F ; CS(=O)(=O)OCc1cc(Cl)ncc1OC(F)(F)F]

MsCl (2.8 g, 24.44 mmol, 1.21 equiv) was added dropwise into a solution of [2-chloro-5-(trifluoromethoxy)pyridin-4-yl]methanol (4.6 g, 20.21 mmol, 1.00 equiv) and TEA (6.1 g, 60.28 mmol, 2.98 equiv) in dichloromethane (100 mL). After being stirred for 15 min at 0° C. the reaction was quenched by water, extracted with ethyl acetate, washed with saturated NH₄Cl solution and brine, dried over anhydrous sodium sulfate, and concentrated under vacuum. This resulted in the title compound (7.2 g, crude) as light yellow oil. LCMS [M+H⁺] 306.

A mixture of [2-chloro-5-(trifluoromethoxy)pyridin-4-yl]methyl methanesulfonate (7.2 g, 23.56 mmol, 1.00 equiv), N,N-dimethylformamide (100 mL), NaI (3.5 g, 23.35 mmol, 0.99 equiv), and tert-butyl N-[(tert-butoxy)carbonyl]-N-potassiocarbamate (9 g, 35.25 mmol, 1.50 equiv) was stirred for 1 h at room temperature. The resulting solution was diluted with water, extracted with ethyl acetate, washed with brine, dried over anhydrous sodium sulfate, and concentrated under vacuum. The residue was purified by a silica gel column eluting with ethyl acetate/petroleum ether (1/20) to afford the title compound (7.1 g, 71%) as light yellow oil. LCMS [M+H+] 427.

Step 5: Preparation of tert-butyl N-[(tert-butoxy)carbonyl]-N-[[5-(trifluoromethoxy)-2-[2-(trifluoromethyl)pyrimidin-5-yl]pyridin-4-yl]methyl]carbamate

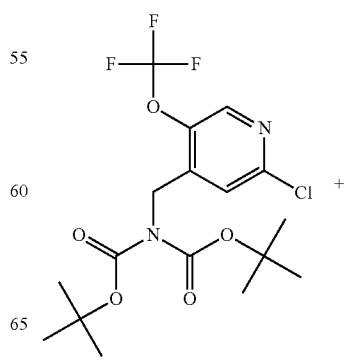

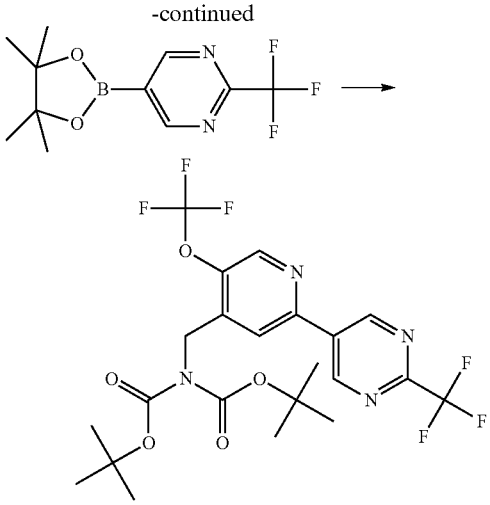

A mixture of tert-butyl N-[(tert-butoxy)carbonyl]-N-[[2-chloro-5-(trifluoromethoxy)pyridin-4-yl]methyl]carbamate (5 g, 11.72 mmol, 1.00 equiv), 5-(tetramethyl-1,3,2-dioxaborolan-2-yl)-2-(trifluoromethyl)pyrimidine (4.2 g, 15.33 mmol, 1.31 equiv), Pd(dppf)Cl$_2$ (856 mg, 1.17 mmol, 0.10 equiv), and potassium carbonate (4.8 g, 34.73 mmol, 2.96 equiv) in dioxane (100 mL) was stirred for 12 h at 85° C. under nitrogen. The resulting mixture was concentrated under vacuum. The residue was purified by a silica gel column eluting with ethyl acetate/petroleum ether (1/10) to afford the title compound (3.6 g, 57%) as a yellow solid. LCMS [M+H$^+$] 539.

Step 6: Preparation of [5-(trifluoromethoxy)-2-[2-(trifluoromethyl)pyrimidin-5-yl]pyridin-4-yl]methanamine hydrochloride

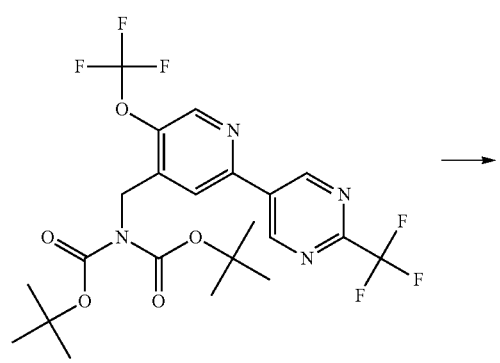

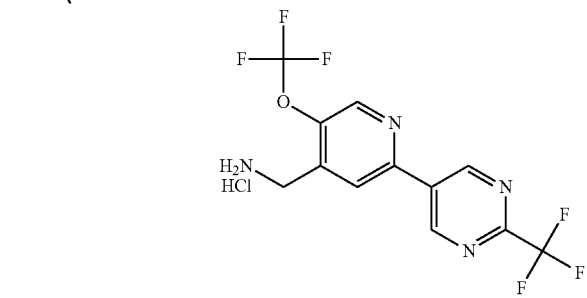

A mixture of tert-butyl N-[(tert-butoxy)carbonyl]-N-[[5-(trifluoromethoxy)-2-[2-(trifluoromethyl)pyrimidin-5-yl]pyridin-4-yl]methyl]carbamate (3.6 g, 6.69 mmol, 1.00 equiv) and 4 N of hydrogen chloride in dioxane (30 mL) was stirred for 1 h at room temperature. The solid was collected by filtration, and dried under reduced pressure. This resulted in the title compound (2.3 g, 92%) as a light yellow solid. LCMS [M+H$^+$] 339.

Example 11: Preparation of (5-(trifluoromethyl)-2-(2-(trifluoromethyl)pyrimidin-5-yl)pyridin-4-yl)methanamine The overall reaction scheme for Example 11 was as follows:

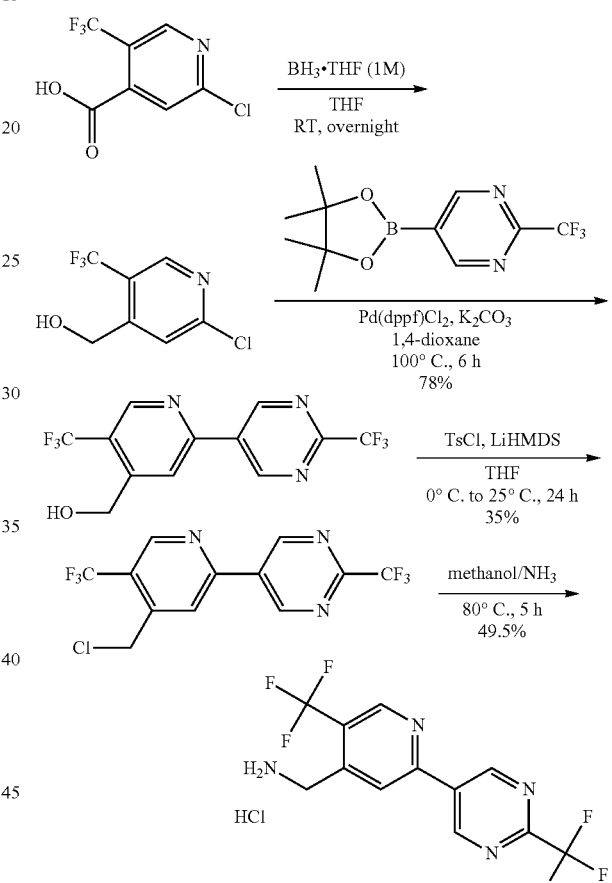

Example 11, Step 1: Preparation of [2-chloro-5-(trifluoromethyl)pyridin-4-yl]methanol Step 1 proceeded according to the following scheme:

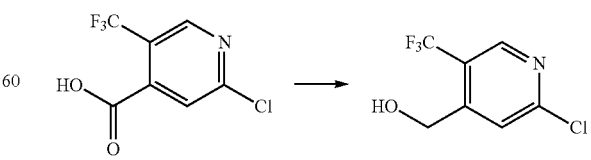

Into a 250-mL 3-necked round-bottom flask, purged and maintained with an inert atmosphere of nitrogen, was placed a solution of 2-chloro-5-(trifluoromethyl) pyridine-4-carboxylic acid (4.5 g, 19.95 mmol, 1.00 equiv) in tetrahydrofuran (40 mL) followed by the addition of BH₃.THF (1 M) (40 mL, 2.00 equiv) dropwise with stirring at 0° C. over 10 min. The resulting solution was stirred at room temperature overnight, quenched by the addition of 10 mL of methanol at 0° C., concentrated under vacuum, and extracted with ethyl acetate. The combined organic layers were washed with brine, dried over sodium sulfate, and concentrated under vacuum. The residue was purified by a silica gel column eluted with ethyl acetate/petroleum ether (1:10) to afford 3 g (crude) of [2-chloro-5-(trifluoromethyl)pyridin-4-yl]methanol as a white solid.

Example 11, Step 2: Preparation of [5-(trifluoromethyl)-2-[2-(trifluoromethyl)pyrimidin-5-yl]pyridin-4-yl]methanol Step 2 proceeded according to the following scheme:

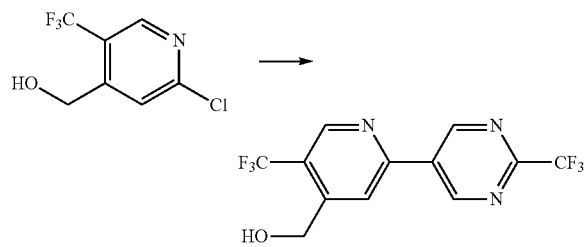

Into a 3-L 3-necked round-bottom flask, purged and maintained with an inert atmosphere of nitrogen, was placed [2-chloro-5-(trifluoromethyl)pyridin-4-yl]methanol (75.6 g, 357.33 mmol, 1.00 equiv), 1,4-dioxane (1.5 L), 5-(tetramethyl-1,3,2-dioxaborolan-2-yl)-2-(trifluoromethyl)pyrimidine (110 g, 401.39 mmol, 1.20 equiv), K₂CO₃ (148 g, 1.06 mol, 3.00 equiv), and Pd(dppf)Cl₂ (13 g, 17.77 mmol, 0.05 equiv). The resulting solution was stirred at 100° C. for 6 h under a nitrogen atmosphere, cooled to room temperature, and filtered. The filter cake was washed with 2×300 mL of EA. The filtrate was concentrated under vacuum. The residue was applied onto a silica gel column eluted with ethyl acetate/petroleum ether (1/5-1/2) to afford 90 g (78%) of [5-(trifluoromethyl)-2-[2-(trifluoromethyl)pyrimidin-5-yl]pyridin-4-yl]methanol as a white solid.

Example 11, Step 3: Preparation of 5-[4-(chloromethyl)-5-(trifluoromethyl)pyridin-2-yl]-2-(trifluoromethyl)pyrimidine Step 3 proceeded according to the following scheme:

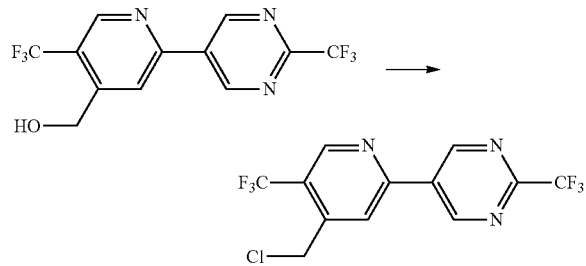

Into a 2-L 3-necked round-bottom flask, purged and maintained with an inert atmosphere of nitrogen, was placed a solution of [5-(trifluoromethyl)-2-[2-(trifluoromethyl)pyrimidin-5-yl]pyridin-4-yl]methanol (80 g, 247.53 mmol, 1.00 equiv) in tetrahydrofuran (800 mL) followed by the addition of LiHMDS (1 mol/L) (322 mL, 1.30 equiv) dropwise with stirring at 0° C. The mixture was stirred at 0° C. for 1 h. To this mixture was added 4-methylbenzene-1-sulfonyl chloride (61.2 g, 321.01 mmol, 1.30 equiv) in portions at 0° C. under a nitrogen atmosphere. The resulting solution was stirred from 0° C. to 25° C. for 24 h, cooled to 0° C., quenched by the addition of 100 mL of water, and extracted with 3×500 mL of ethyl acetate. The combined organic layers were dried over anhydrous sodium sulfate and concentrated under reduced pressure. The residue was purified by silica gel column chromatography eluted with ethyl acetate/petroleum ether (1/10) to afford 30 g (35%) of 5-[4-(chloromethyl)-5-(trifluoromethyl)pyridin-2-yl]-2-(trifluoromethyl)pyrimidine as a light yellow solid.

Example 11, Step 4: Preparation of [5-(trifluoromethyl)-2-[2-(trifluoromethyl)pyrimidin-5-yl]pyridin-4-yl]methanamine hydrochloride Step 4 proceeded according to the following scheme:

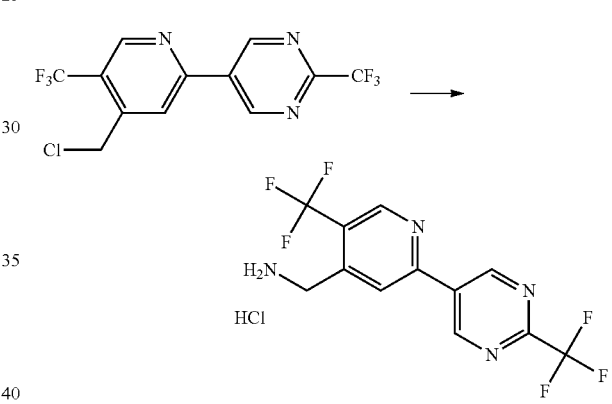

Into a 200-mL sealed tube was placed a solution of 5-[4-(chloromethyl)-5-(trifluoromethyl)pyridin-2-yl]-2-(trifluoromethyl)pyrimidine (20 g, 58.54 mmol, 1.00 equiv) in methanol/NH₃ (140 mL). The resulting solution was stirred at 80° C. in an oil bath for 5 h. This reaction was repeated twice. The reaction mixture was cooled to room temperature and concentrated under vacuum. The pH value of the aqueous solution was adjusted to 8 with saturated aqueous sodium bicarbonate. The resulting solution was extracted with 3×300 mL of dichloromethane. The combined organic layers were dried over anhydrous sodium sulfate and concentrated under vacuum. The residue was applied onto a silica gel column eluted with 10% to 30% ethyl acetate in petroleum ether to afford [5-(trifluoromethyl)-2-[2-(trifluoromethyl)pyrimidin-5-yl]pyridin-4-yl]methanamine 33 g as a light yellow solid. The residue was dissolved in 800 mL of ethyl acetate. The product was precipitated by the addition of ethyl acetate/HCl (g). The resulting mixture was concentrated under vacuum. The solids were collected by filtration. The filter cake was washed with 3×2500 mL of ether and dried to afford 31 g (49.5%) of [5-(trifluoromethyl)-2-[2-(trifluoromethyl)pyrimidin-5-yl]pyridin-4-yl]methanamine hydrochloride as a white solid. LCMS [M−HCl+H⁺] 323; ¹H NMR (300 MHz, D₂O) δ 9.48 (s, 2H), 9.06 (s, 1H), 8.21 (s, 1H), 4.49 (s, 2H).

Example 12: Preparation of [5-chloro-2-[2-(trifluoromethyl)pyrimidin-5-yl]pyridin-4-yl]methanamine hydrochloride The overall reaction scheme for Example 12 was as follows:

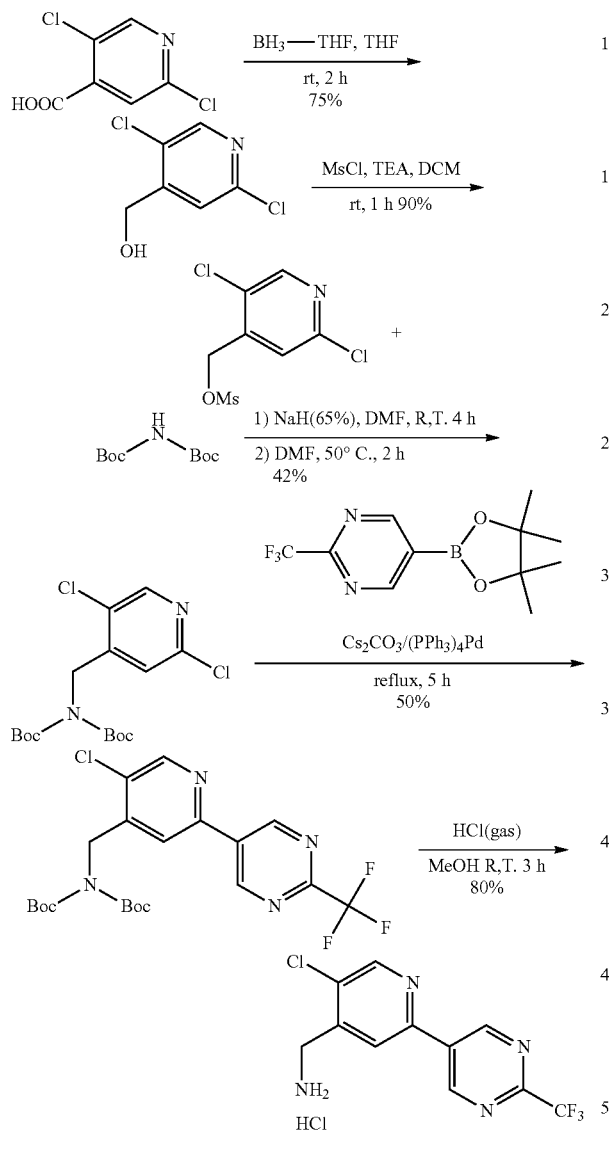

Example 12, Step 1: Preparation of (2,5-dichloropyridin-4-yl)methanol

Step 1 proceeded according to the following scheme:

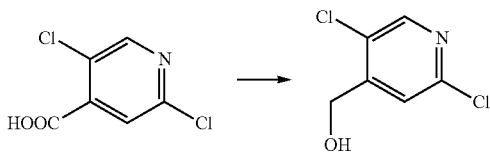 [SMILES: O=C(O)c1cc(Cl)ncc1Cl ; OCc1cc(Cl)ncc1Cl]

To a 10000-mL 4-necked round-bottom flask, purged and maintained with an inert atmosphere of nitrogen, was placed 2,5-dichloropyridine-4-carboxylic acid (200 g, 1.04 mol, 1.00 equiv) and tetrahydrofuran (2000 mL), followed by the addition of $BH_3$-THF (3140 mL, 3.00 equiv, 1M) dropwise with stirring at 0° C. The resulting solution was stirred at room temperature for 2 h, quenched by the addition of 2000 mL of water, and extracted with 3×1500 mL of ethyl acetate. The combined organic layers were washed with 2×1500 mL of water, 3×1500 mL of brine, dried over anhydrous sodium sulfate and concentrated under vacuum to afford 140 g (75%) of (2,5-dichloropyridin-4-yl)methanol as a white solid.

Example 12, Step 2: Preparation of (2,5-dichloropyridin-4-yl)methyl methanesulfonate Step 2 proceeded according to the following scheme:

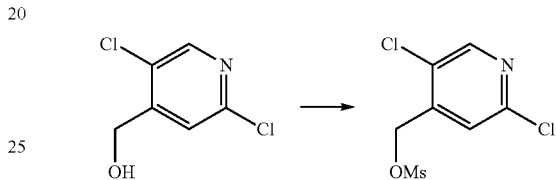

To a 3000-mL 4-necked round-bottom flask, purged and maintained with an inert atmosphere of nitrogen, was placed (2,5-dichloropyridin-4-yl)methanol (100 g, 561.75 mmol, 1.00 equiv), dichloromethane (1400 mL) and TEA (172 g, 1.70 mol, 3.00 equiv), followed by the addition of MsCl (77.3 g, 678.07 mmol, 1.20 equiv) dropwise with stirring at 0° C. The resulting solution was stirred at room temperature for 1 h, quenched by the addition of 500 mL of water. The organic layer was dried over anhydrous sodium sulfate and concentrated under vacuum to afford 129 g (90%) of (2,5-dichloropyridin-4-yl)methyl methanesulfonate as yellow oil.

Example 12, Step 3: Preparation of tert-butyl N-[(tert-butoxy)carbonyl]-N-[(2,5-dichloropyridin-4-yl)methyl]carbamate Step 3 proceeded according to the following scheme:

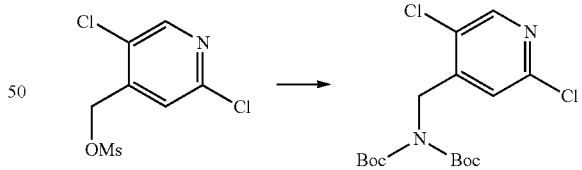

To a 5000-mL 4-necked round-bottom flask purged and, maintained with an inert atmosphere of nitrogen, was placed tert-butyl N-[(tert-butoxy)carbonyl]carbamate (104.3 g, 480.07 mmol, 0.95 equiv) and N,N-dimethylformamide (1200 mL), followed by the addition of NaH (65% in mineral oil) (21.3 g, 576.87 mmol, 1.14 equiv) in several batches at room temperature. The mixture was stirred at room temperature for 4 h. To this mixture was added a solution of (2,5-dichloropyridin-4-yl)methyl methanesulfonate (129 g, 503.70 mmol, 1.00 equiv) in N,N-dimethylformamide (200 mL) dropwise with stirring. The resulting solution stirred at 50° C. for 2 h, quenched by the addition of 2 kg of ice, and extracted with 2×1500 mL of ethyl acetate. The combined organic layers were washed with 5×800 mL of brine, dried over anhydrous sodium sulfate and concentrated under vacuum. The residue was applied onto a silica gel column eluted with ethyl acetate/petroleum ether (1:20). The crude product was re-crystallized from petroleum ether to afford 80 g (42%) of tert-butyl N-[(tert-butoxy)carbonyl]-N-[(2,5-dichloropyridin-4-yl)methyl]carbamate as a white solid.

Example 12, Step 4: Preparation of tert-butyl N-[(tert-butoxy) carbonyl]-N-([5-chloro-2-[2-(trifluoromethyl)pyrimidin-5-yl]pyridin-4-yl]methyl)carbamate Step 4 proceeded according to the following scheme:

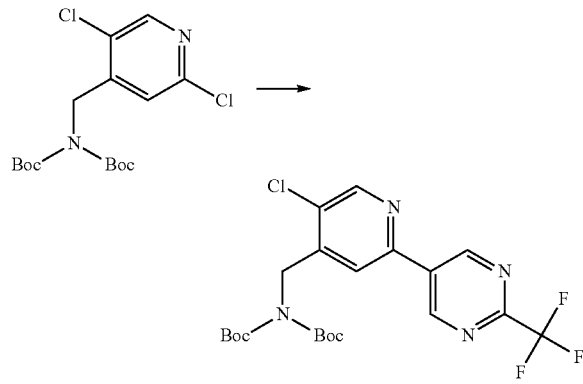

To a 2000-mL 4-necked round-bottom flask, purged and maintained with an inert atmosphere of nitrogen, was placed tert-butyl N-[(tert-butoxy)carbonyl]-N-[(2,5-dichloropyridin-4-yl)methyl]carbamate (70 g, 185.55 mmol, 1.00 equiv), 5-(tetramethyl-1,3,2-dioxaborolan-2-yl)-2-(trifluoromethyl)pyrimidine (76.5 g, 279.15 mmol, 1.50 equiv), 1,4-dioxane (700 mL), Cs$_2$CO$_3$ (0 mg, 2.00 equiv), water (200 mL) and (PPh$_3$)$_4$Pd (5.4 g). The resulting solution was refluxed for 5 h, cooled to room temperature, diluted with 500 mL of H$_2$O, and extracted with 3×500 mL of ethyl acetate. The combined organic layer was dried over anhydrous sodium sulfate and concentrated under vacuum. The residue was applied onto a silica gel column eluted with ethyl acetate/petroleum ether (1:10) to afford 45 g (50%) of tert-butyl N-[(tert-butoxy) carbonyl]-N-([5-chloro-2-[2-(trifluoromethyl)pyrimidin-5-yl]pyridin-4-yl]methyl)carbamate as a white solid.

Example 12, Step 5: Preparation of [5-chloro-2-[2-(trifluoromethyl)pyrimidin-5-yl]pyridin-4-yl]methanamine hydrochloride Step 5 proceeded according to the following scheme:

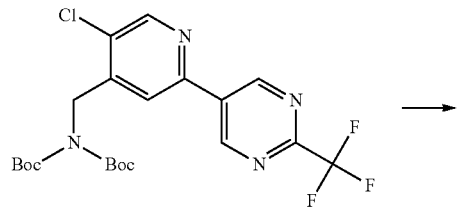

-continued

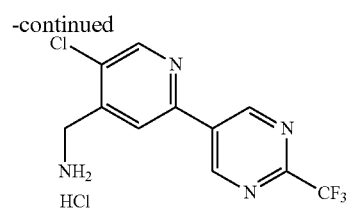

To a 2000-mL round-bottom flask was placed tert-butyl N-[(tert-butoxy)carbonyl]-N-([5-chloro-2-[2-(trifluoromethyl)pyrimidin-5-yl]pyridin-4-yl]methyl)carbamate (42 g, 85.91 mmol, 1.00 equiv) and methanol (600 mL). To the above, hydrogen chloride (gas) was bubbled through the solution. The resulting solution was stirred at room temperature for 3 h, concentrated under vacuum, and diluted with 300 mL of ether. The solids were collected by filtration and rinsed with 1×200 mL of ether to afford 22.4329 g (80%) of [5-chloro-2-[2-(trifluoromethyl)pyrimidin-5-yl]pyridin-4-yl]methanamine hydrochloride as a white solid. LCMS [M−HCl+H$^+$] 330; $^1$H NMR (300 MHz, DMSO-d6) δ 9.73 (s, 2H), 8.93 (s, 3H), 8.91 (s, 1H), 8.81-8.78 (d, J=9.0 Hz, 1H), 4.30 (s, 2H).

Example 13: Preparation of [5-fluoro-4-[2-(trifluoromethyl)pyrimidin-5-yl]pyridin-2-yl]methanamine hydrochloride The overall reaction scheme for Example 13 was as follows:

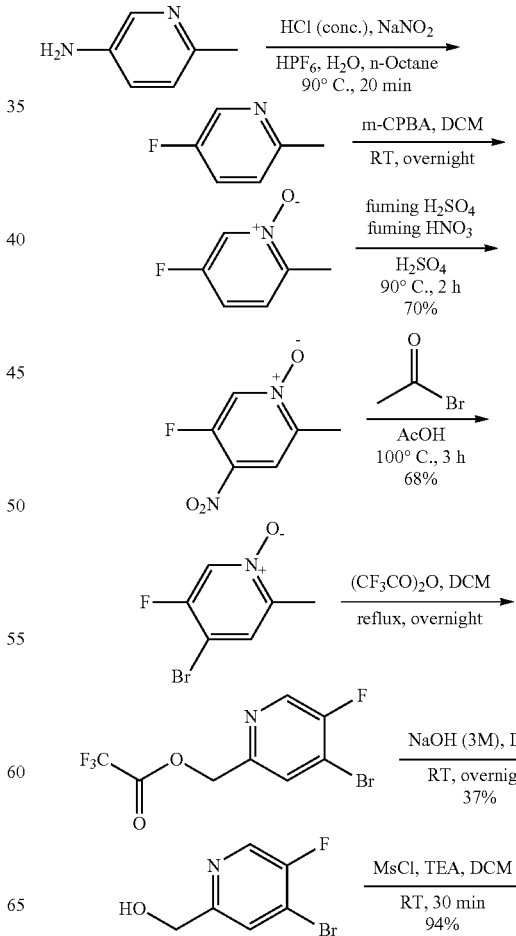

-continued

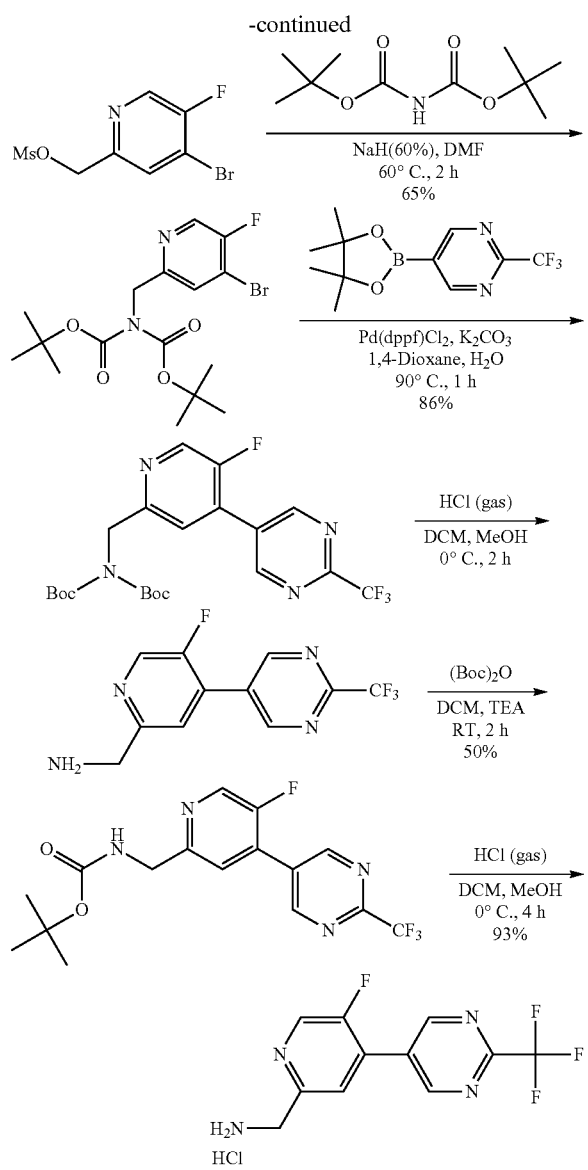

Example 13, Step 1: Preparation of
5-fluoro-2-methylpyridine

Step 1 proceeded according to the following scheme:

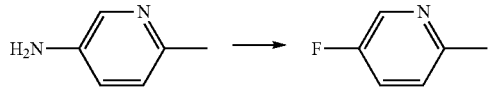

To a 10-L 4-necked round-bottom flask, purged and maintained with an inert atmosphere of nitrogen, was placed 6-methylpyridin-3-amine (350 g, 3.24 mol, 1.00 equiv) and water (400 mL), followed by the addition of aqueous hydrogen chloride (1600 mL, 12 N) dropwise with stirring at 0° C. To this was added a solution of sodium nitrite (450 g, 6.52 mol, 2.00 equiv) in water (600 mL) dropwise with stirring at 0° C. The resulting solution was stirred at 0° C. for 30 min. To the mixture was added HPF6 (60%) (1750 mL) dropwise with stirring at 0° C. The resulting solution was stirred at 0° C. for 1 h and filtered. The filter cake was washed with 2×300 mL of ice/water, 2×300 mL of EtOH, 2×300 mL of Et₂O and dried in vacuum. The residue was added to n-Octane (4 L) in several batches with stirring at 90° C. The resulting solution was stirred at 90° C. for an additional 20 min, cooled to room temperature, extracted with 3×3 L of hydrogen chloride (2 N). The aqueous layers were combined and extracted with 1×3 L of ether. The pH of the aqueous solution was adjusted to 9-10 with aqueous sodium hydroxide (40%). The resulting solution was extracted with 3×3 L of DCM. The combined organic layers were dried over anhydrous sodium sulfate. The crude solution was used directly in the next step.

Example 13, Step 2: Preparation of
5-fluoro-2-methylpyridine 1-oxide

Step 2 proceeded according to the following scheme:

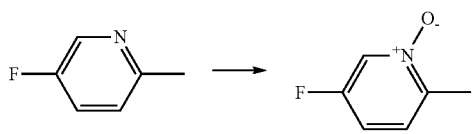

To a 10-L 4-necked round-bottom flask, purged and maintained with an inert atmosphere of nitrogen, was added the solution of 5-fluoro-2-methylpyridine from Step 1 and m-CPBA (671 g, 3.89 mol, 1.20 equiv) in portions. The resulting solution was stirred at room temperature overnight. The pH value of the solution was adjusted to 11-12 with sodium hydroxide (2 N). The resulting solution was extracted with 6×1 L of dichloromethane. The combined organic layers were washed with 1×500 mL of brine, dried over anhydrous sodium sulfate and concentrated under vacuum to afford 220 g (53% over two steps) of 5-fluoro-2-methylpyridine 1-oxide as a yellow solid.

Example 13, Step 3: Preparation of
5-fluoro-2-methyl-4-nitropyridine 1-oxide

Step 3 proceeded according to the following scheme:

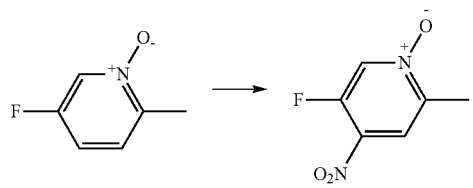

To a 5-L 4-necked round-bottom flask, purged and maintained with an inert atmosphere of nitrogen, was placed 5-fluoro-2-methylpyridin-1-ium-1-olate (220 g, 1.73 mol, 1.00 equiv) and sulfuric acid (800 mL), followed by the addition of fuming HNO₃ (1040 mL) in fuming sulfuric acid (400 mL) dropwise with stirring at 90° C. The resulting solution was stirred at 90° C. for 2 h, quenched by the addition of 10 L of ice/salt, and extracted with 3×3 L of dichloromethane. The combined organic layers were washed with 1×1.5 L of brine, dried over anhydrous sodium sulfate and concentrated under vacuum to afford 210 g (70%) of 5-fluoro-2-methyl-4-nitropyridine 1-oxide as a yellow solid.

Example 13, Step 4: Preparation of 4-bromo-5-fluoro-2-methylpyridine 1-oxide Step 4 proceeded according to the following scheme:

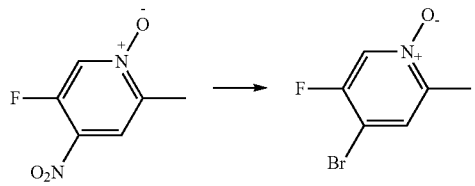

To a 5-L 4-necked round-bottom flask, purged and maintained with an inert atmosphere of nitrogen, was placed 5-fluoro-2-methyl-4-nitropyridin-1-ium-1-olate (210 g, 1.22 mol, 1.00 equiv) and AcOH (1.05 L), followed by the addition of acetyl bromide (1.58 L) dropwise with stirring at 50° C. The resulting solution was stirred at 100° C. for 3 h, cooled to room temperature and concentrated under vacuum. The residue was quenched with water/ice. The pH value of the solution was adjusted to 9-10 with aqueous sodium bicarbonate. The resulting solution was extracted with 3×1 L of dichloromethane. The organic layers were combined, dried over anhydrous sodium sulfate and concentrated under vacuum. The crude product was purified by re-crystallization from PE to afford 170 g (68%) of 4-bromo-5-fluoro-2-methylpyridine 1-oxide as a gray solid.

Example 13, Step 5: Preparation of (4-bromo-5-fluoropyridin-2-yl)methyl 2,2,2-trifluoroacetate Step 5 proceeded according to the following scheme:

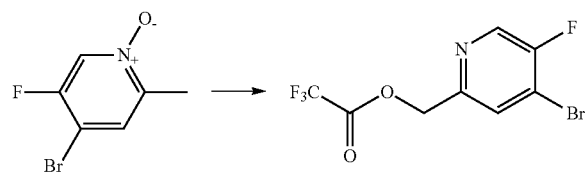

To a 2-L 4-necked round-bottom flask, purged and maintained with an inert atmosphere of nitrogen, was placed 4-bromo-5-fluoro-2-methylpyridin-1-ium-1-olate (170 g, 825.19 mmol, 1.00 equiv) and dichloromethane (800 mL), followed by the addition of trifluoroacetyl 2,2,2-trifluoroacetate (866 g, 4.12 mol, 5.00 equiv) dropwise with stirring at 0° C. The resulting solution was refluxed overnight, cooled to room temperature, and concentrated under vacuum to afford 200 g (crude) of (4-bromo-5-fluoropyridin-2-yl)methyl 2,2,2-trifluoroacetate as light yellow oil.

Example 13, Step 6: Preparation of (4-bromo-5-fluoropyridin-2-yl)methanol

Step 6 proceeded according to the following scheme:

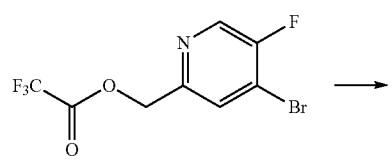

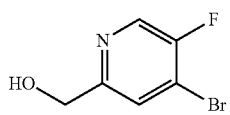

To a 2-L 4-necked round-bottom flask, purged and maintained with an inert atmosphere of nitrogen, was placed (4-bromo-5-fluoropyridin-2-yl)methyl 2,2,2-trifluoroacetate (200 g, 662.21 mmol, 1.00 equiv) and dichloromethane (400 mL), followed by the addition of sodium hydroxide (3 M) (1100 mL, 5.00 equiv) dropwise with stirring at 0° C. The resulting solution was stirred at room temperature overnight, extracted with 2×2 L of dichloromethane. The combined organic layers were washed with 1×1 L of brine, dried over anhydrous sodium sulfate and concentrated under vacuum. The residue was applied onto a silica gel column eluted with ethyl acetate/petroleum ether (3/7) to afford 50 g (37%) of (4-bromo-5-fluoropyridin-2-yl)methanol as yellow oil.

Example 13, Step 7: Preparation of (4-bromo-5-fluoropyridin-2-yl)methyl methanesulfonate Step 7 proceeded according to the following scheme:

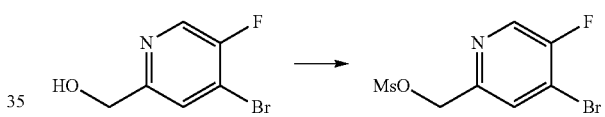

To a 1-L 4-necked round-bottom flask, purged and maintained with an inert atmosphere of nitrogen, was placed (4-bromo-5-fluoropyridin-2-yl)methanol (50 g, 242.70 mmol, 1.00 equiv), dichloromethane (500 mL) and TEA (49 g, 484.24 mmol, 2.00 equiv), followed by the addition of methanesulfonyl chloride (33.4 g, 291.57 mmol, 1.20 equiv) dropwise with stirring at 0° C. The resulting solution was stirred at room temperature for 30 min, quenched by the addition of water/ice, and extracted with 2×500 mL of dichloromethane. The combined organic layers were washed with 1×500 mL of brine, dried over anhydrous sodium sulfate and concentrated under vacuum to afford 65 g (94%) of (4-bromo-5-fluoropyridin-2-yl)methyl methanesulfonate as a yellow solid.

Example 13, Step 8: Preparation of tert-butyl N-[(4-bromo-5-fluoropyridin-2-yl)methyl]-N-[(tert-butoxy)carbonyl]carbamate Step 8 proceeded according to the following scheme:

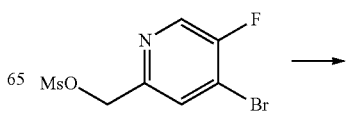

-continued

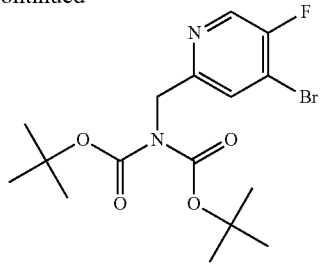

To a 3-L 4-necked round-bottom flask, purged and maintained with an inert atmosphere of nitrogen, was placed tert-butyl N-[(tert-butoxy)carbonyl]carbamate (59.7 g, 274.78 mmol, 1.20 equiv) and N,N-dimethylformamide (350 mL), followed by the addition of NaH (60%) (11 g, 1.20 equiv), in portions at 0° C. The resulting solution was stirred at 0° C. for 2 h. To this was added a solution of (4-bromo-5-fluoropyridin-2-yl)methyl methanesulfonate (65 g, 228.79 mmol, 1.00 equiv) in N,N-dimethylformamide (300 mL) dropwise with stirring at 0° C. The resulting solution was stirred at 60° C. for an additional 2 h, cooled to room temperature, quenched by the addition of 1.2 L of water/ice, and extracted with 3×500 mL of ethyl acetate. The combined organic layers were washed with 2×400 mL of water, 1×400 mL of brine, dried over anhydrous sodium sulfate and concentrated under vacuum. The residue was applied onto a silica gel column eluted with ethyl acetate/petroleum ether (1/19) to afford 60 g (65%) of tert-butyl N-[(4-bromo-5-fluoropyridin-2-yl)methyl]-N-[(tert-butoxy)carbonyl]carbamate as a yellow solid.

Example 13, Step 9: Preparation of tert-butyl N-[(tert-butoxy)carbonyl]-N-([5-fluoro-4-[2-(trifluoromethyl)pyrimidin-5-yl]pyridin-2-yl]methyl)carbamate Step 9 proceeded according to the following scheme:

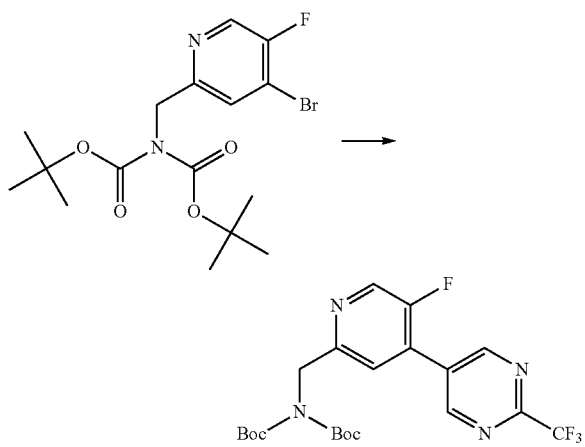

To a 2-L 4-necked round-bottom flask, purged and maintained with an inert atmosphere of nitrogen, was placed tert-butyl N-[(4-bromo-5-fluoropyridin-2-yl)methyl]-N-[(tert-butoxy)carbonyl]carbamate (60 g, 148.05 mmol, 1.00 equiv), 1,4-dioxane (900 mL), water (90 mL), potassium carbonate (61.3 g, 443.53 mmol, 3.00 equiv), 5-(4,4,5,5-tetramethyl-1,3,2-dioxaborolan-2-yl)-2-(trifluoromethyl) pyrimidine (60.8 g, 222 mmol, 1.5 equiv) and Pd(dppf)Cl$_2$ (5.4 g, 7.38 mmol, 0.05 equiv). The resulting solution was stirred at 90° C. for 1 h, cooled to room temperature, and filtered. The filtrate was extracted with 3×500 mL of ethyl acetate. The combined organic layers were washed with 1×500 mL of brine, dried over anhydrous sodium sulfate and concentrated under vacuum. The residue was applied onto a silica gel column eluted with ethyl acetate/petroleum ether (1/9) to afford 60 g (86%) of tert-butyl N-[(tert-butoxy) carbonyl]-N-([5-fluoro-4-[2-(trifluoromethyl)pyrimidin-5-yl]pyridin-2-yl]methyl)carbamate as a white solid.

Example 13, Step 10: Preparation of [5-fluoro-4-[2-(trifluoromethyl)pyrimidin-5-yl]pyridin-2-yl]methanamine Step 10 proceeded according to the following scheme:

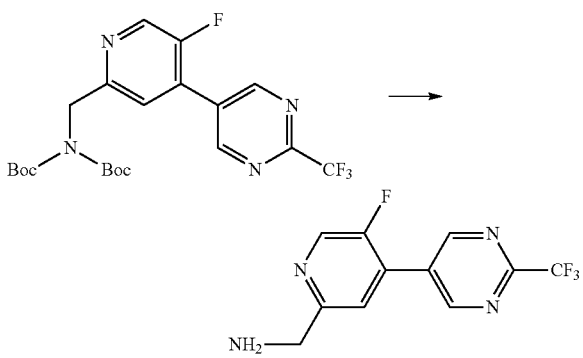

To a 2-L round-bottom flask was placed tert-butyl N-[(tert-butoxy)carbonyl]-N-([5-fluoro-4-[2-(trifluoromethyl)pyrimidin-5-yl]pyridin-2-yl]methyl)carbamate (60 g, 127.00 mmol, 1.00 equiv), methanol (600 mL), and dichloromethane (60 mL) cooled with ice/water bath. To the above, hydrogen chloride (gas) was introduced. The resulting solution was stirred at 0° C. for 2 h and concentrated under vacuum. The residue was rinsed with DCM and Et$_2$O. The solids were collected by filtration. The filter cake was washed with Et$_2$O and dried in an oven under reduced pressure to afford 45 g (crude) of [5-fluoro-4-[2-(trifluoromethyl)pyrimidin-5-yl]pyridin-2-yl]methanamine as a white solid.

Example 13, Step 11: Preparation of tert-butyl N-([5-fluoro-4-[2-(trifluoromethyl)pyrimidin-5-yl] pyridin-2-yl]methyl)carbamate Step 11 proceeded according to the following scheme:

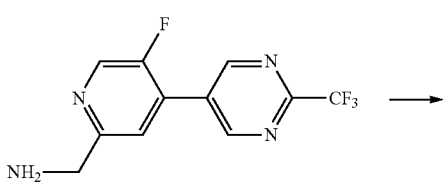

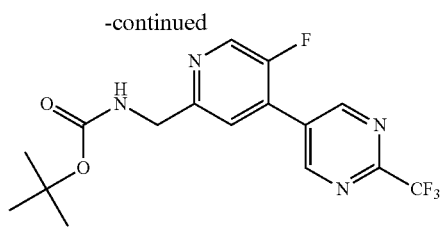

To a 1-L 4-necked round-bottom flask, purged and maintained with an inert atmosphere of nitrogen, was placed [5-fluoro-4-[2-(trifluoromethyl)pyrimidin-5-yl]pyridin-2-yl]methanamine (45 g, 165.32 mmol, 1.00 equiv) and dichloromethane (450 mL), followed by the addition of TEA (66.9 g, 661.13 mmol, 4.00 equiv) dropwise with stirring at 0° C. To this was added di-tert-butyl dicarbonate (36 g, 164.95 mmol, 1.00 equiv) dropwise with stirring at 0° C. The resulting solution was stirred at room temperature for 2 h, concentrated under vacuum, diluted with 300 mL of water, and extracted with 3×300 mL of dichloromethane. The combined organic layers were washed with 1×300 mL of brine, dried over anhydrous sodium sulfate and concentrated under vacuum. The residue was applied onto a silica gel column eluted with ethyl acetate/petroleum ether (1/3) to afford 31 g (50%) of tert-butyl N-([5-fluoro-4-[2-(trifluoromethyl)pyrimidin-5-yl]pyridin-2-yl]methyl)carbamate as a white solid.

Example 13, Step 12: Preparation of [5-fluoro-4-[2-(trifluoromethyl)pyrimidin-5-yl]pyridin-2-yl]methanamine hydrochloride Step 12 proceeded according to the following scheme:

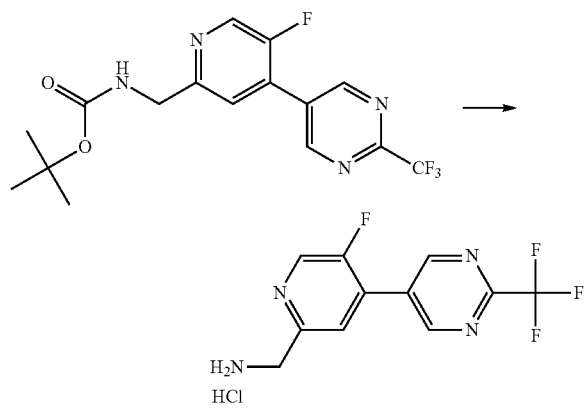

To a 1-L round-bottom flask was placed tert-butyl N-([5-fluoro-4-[2-(trifluoromethyl)pyrimidin-5-yl]pyridin-2-yl]methyl)carbamate (31 g, 83.26 mmol, 1.00 equiv), methanol (300 mL) and dichloromethane (30 mL). To the above, hydrogen chloride (g) was introduced. The resulting solution was stirred at 0° C. for 4 h. The resulting mixture was concentrated under vacuum, washed with 2×300 mL of methanol, 2×300 mL of dichloromethane and 2×300 mL of ether. The crude product was purified by re-crystallization from ether to afford 24 g (93%) of [5-fluoro-4-[2-(trifluoromethyl)pyrimidin-5-yl]pyridin-2-yl]methanamine hydrochloride as a white solid. LCMS [M−HCl+H$^+$] 273; $^1$H NMR (300 MHz, DMSO-d$_6$) δ 9.44 (2H, s), 8.89 (1H, s), 8.51-8.39 (3H, m), 8.07-8.05 (1H, m), 4.29-4.27 (2H, m).

Example 14: Preparation of (5-chloro-4-(2-(trifluoromethyl)pyrimidin-5-yl)pyridin-2-yl)methanamine hydrochloride The overall reaction scheme for Example 14 was as follows:

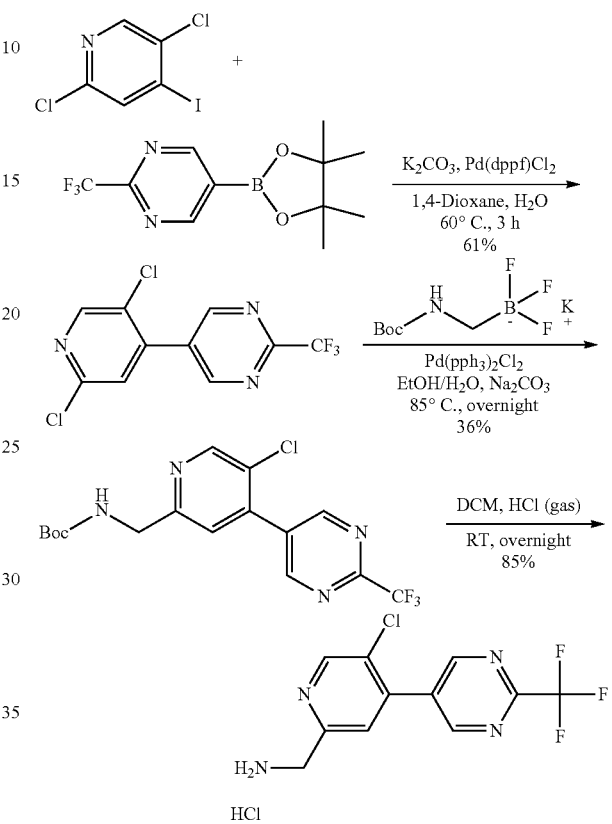

Example 14, Step 1: Preparation of 5-(2,5-dichloropyridin-4-yl)-2-(trifluoromethyl)pyrimidine Step 1 proceeded according to the following scheme:

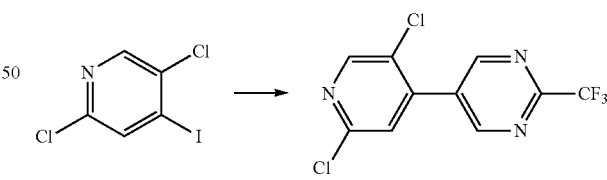

Into a 3000-mL 4-necked round-bottom flask, purged and maintained with an inert atmosphere of nitrogen, was placed 2,5-dichloro-4-iodopyridine (120 g, 438.14 mmol, 1.00 equiv), 1,4-Dioxane (1800 mL), water (180 mL), potassium carbonate (182 g, 1.32 mol, 3.00 equiv), 5-(tetramethyl-1,3,2-dioxaborolan-2-yl)-2-(trifluoromethyl)pyrimidine (132.6 g, 483.86 mmol, 1.10 equiv), and Pd(dppf)Cl$_2$ (6 g, 8.20 mmol, 0.02 equiv). The resulting solution was stirred at 60° C. for 3 h, cooled to room temperature, quenched by the addition of 4 L of water/ice, and extracted with 2×2 L of ethyl acetate. The combined organic layers were washed with 1×1 L of H$_2$O and 1×1 L of brine, dried over anhydrous sodium sulfate and concentrated under vacuum. The residue was applied onto a silica gel column with ethyl acetate/petroleum ether (1:100) to afford 78 g (61%) of 5-(2,5-dichloropyridin-4-yl)-2-(trifluoromethyl)pyrimidine as a white solid.

Example 14, Step 2: Preparation of tert-butyl N-([5-chloro-4-[2-(trifluoromethyl)pyrimidin-5-yl]pyridin-2-yl]methyl)carbamate Step 2 proceeded according to the following scheme:

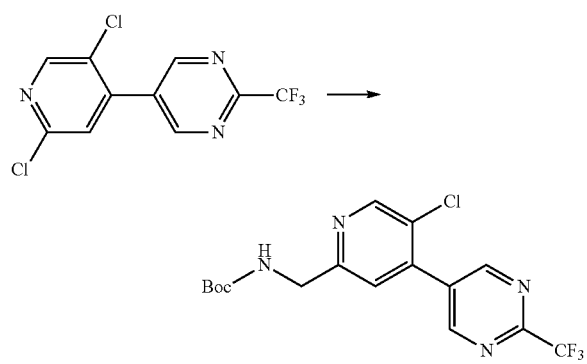

Into a 5000-mL 4-necked round-bottom flask, purged and maintained with an inert atmosphere of nitrogen, was placed 5-(2,5-dichloropyridin-4-yl)-2-(trifluoromethyl)pyrimidine (75 g, 255.05 mmol, 1.00 equiv), ethanol (2250 mL), water (450 mL), sodium carbonate (82.5 g, 778.38 mmol, 3.00 equiv), potassium (((tert-butoxycarbonyl)amino)methyl)trifluoroborate (90 g, 379.64 mmol, 1.50 equiv), and Pd(PPh$_3$)$_2$Cl$_2$ (5 g, 7.12 mmol, 0.03 equiv). The resulting solution was stirred at 85° C. overnight, cooled to room temperature, concentrated under vacuum, diluted with 2 L of EA, extracted with 2×500 mL of ethyl acetate. The combined organic layers were washed with 1×1 L of H$_2$O and 1×1 L of brine, dried over anhydrous sodium sulfate, and concentrated under vacuum. The residue was applied onto a silica gel column with ethyl acetate/petroleum ether (1:10). The crude product was re-crystallized from EA:PE in the ratio of 1:10 to afford 36 g (36%) of tert-butyl N-([5-chloro-4-[2-(trifluoromethyl)pyrimidin-5-yl]pyridin-2-yl]methyl)carbamate as a yellow solid.

Example 14, Step 3: Preparation of (5-chloro-4-(2-(trifluoromethyl)pyrimidin-5-yl)pyridin-2-yl)methanamine hydrochloride Step 3 proceeded according to the following scheme:

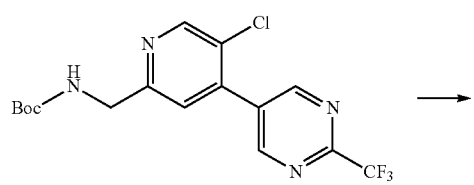

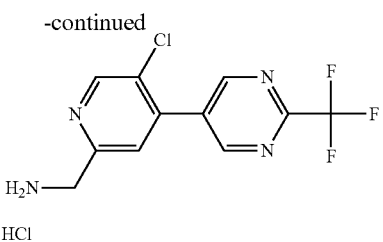

Into a 1000-mL 4-necked round-bottom flask was placed tert-butyl N-([5-chloro-4-[2-(trifluoromethyl)pyrimidin-5-yl]pyridin-2-yl]methyl)carbamate (35 g, 90.03 mmol, 1.00 equiv) and dichloromethane (600 mL). To the above, hydrogen chloride (gas) was introduced. The resulting solution was stirred at room temperature overnight. The solids were collected by filtration and washed with 1×2 L of DCM to afford 25 g (85%) of (5-chloro-4-(2-(trifluoromethyl)pyrimidin-5-yl)pyridin-2-yl)methanamine hydrochloride as an off-white solid. LCMS [M−HCl+H$^+$] 289; $^1$H NMR (300 MHz, DMSO-d$_6$) δ 9.33-9.41 (2H, s), 8.88-8.91 (1H, s), 8.79 (3H, s), 7.97-7.98 (1H, s), 4.23-4.29 (2H, m).

Example 15: Preparation of [6-[6-(trifluoromethyl)pyridin-3-yl]pyrimidin-4-yl]methanamine hydrochloride The overall reaction scheme for Example 15 was as follows:

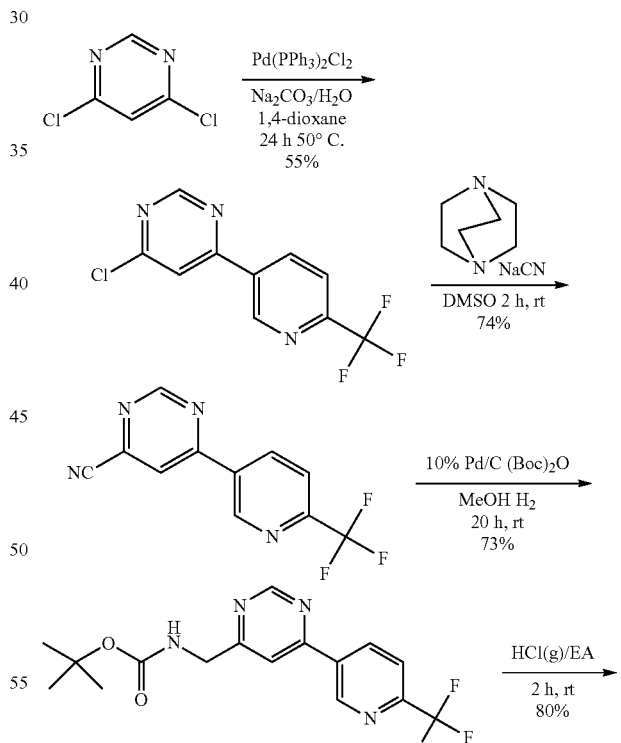

Example 15, Step 1: Preparation of 4-chloro-6-[6-(trifluoromethyl)pyridin-3-yl]pyrimidine Step 1 proceeded according to the following scheme:

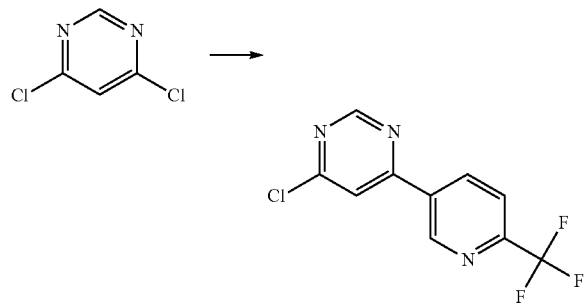

Into a 1000-mL 3-necked round-bottom flask, purged and maintained with an inert atmosphere of nitrogen, was placed a solution of [6-(trifluoromethyl)pyridin-3-yl]boronic acid (50 g, 256.66 mmol, 1.00 equiv) in 1,4-dioxane (600 mL), 4,6-dichloropyrimidine (58.51 g, 392.74 mmol, 1.50 equiv), Pd(PPh$_3$)$_2$Cl$_2$ (9.18 g, 0.05 equiv), sodium carbonate (55.5 g, 2.00 equiv), and water (120 mL). The resulting solution was stirred at 50° C. for 24 h, diluted with 1.5 L of water, and extracted with 4×200 mL of ethyl acetate. The combined organic layers were washed with 4×150 mL of brine, dried over anhydrous sodium sulfate and concentrated under vacuum. The residue was purified on a silica gel column eluted with ethyl acetate:petroleum ether (0:1-1:20) to afford 38 g (55%) of 4-chloro-6-[6-(trifluoromethyl)pyridin-3-yl]pyrimidine as an off-white solid.

Example 15, Step 2: Preparation of 6-[6-(trifluoromethyl)pyridin-3-yl]pyrimidine-4-carbonitrile Step 2 proceeded according to the following scheme:

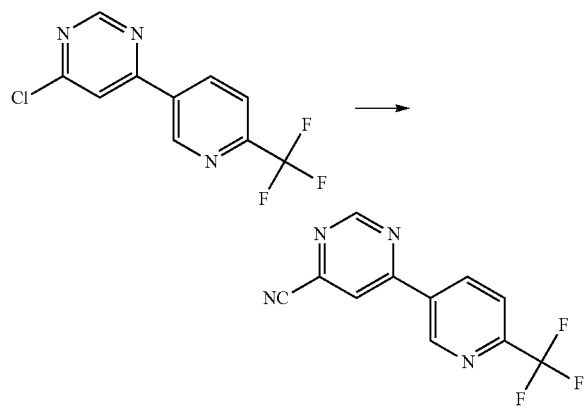

Into a 5000-mL 3-necked round-bottom flask was placed a solution of 4-chloro-6-[6-(trifluoromethyl)pyridin-3-yl]pyrimidine (230 g, 868.21 mmol, 1.00 equiv) in DMSO (2500 mL), NaCN (100 g, 2.20 equiv), 1,4-diazabicyclo[2.2.2]octane (49.69 g, 434.12 mmol, 0.50 equiv), and water (250 mL). The resulting solution was stirred at room temperature for 2 h, diluted with 2000 mL of water and extracted with 5×500 mL of ethyl acetate. The combined organic layers were washed with 4×150 mL of brine, dried over anhydrous sodium sulfate and concentrated under vacuum. The residue was purified on a silica gel column eluted with ethyl acetate:petroleum ether (1:10-1:5) to afford 165 g (74%) of 6-[6-(trifluoromethyl)pyridin-3-yl]pyrimidine-4-carbonitrile as a light yellow solid.

Example 15, Step 3: Preparation of tert-butyl N-([6-[6-(trifluoromethyl)pyridin-3-yl]pyrimidin-4-yl]methyl)carbamate Step 3 proceeded according to the following scheme:

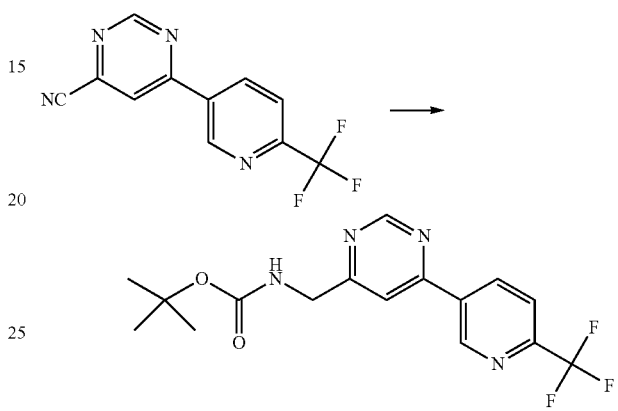

Into a 5000-mL 4-necked round-bottom flask, purged and maintained with an inert atmosphere of nitrogen, was placed a solution of 6-[6-(trifluoromethyl)pyridin-3-yl]pyrimidine-4-carbonitrile (180 g, 697.90 mmol, 1.00 equiv) in methanol (2500 mL), (Boc)$_2$O (188.22 g, 837.49 mmol, 1.20 equiv), and Pd/C (30 g, 10%). To the above H$_2$ (gas) was introduced in and the resulting solution was stirred at room temperature for 20 h. The solids were filtered out and the filtrate was concentrated under vacuum. The residue was purified on a silica gel column eluted with ethyl acetate:petroleum ether (1:10-1:3) to afford 185 g (73%) of tert-butyl N-([6-[6-(trifluoromethyl)pyridin-3-yl]pyrimidin-4-yl]methyl)carbamate as a light yellow solid.

Example 15, Step 4: Preparation of [6-[6-(trifluoromethyl)pyridin-3-yl]pyrimidin-4-yl]methanamine hydrochloride Step 4 proceeded according to the following scheme:

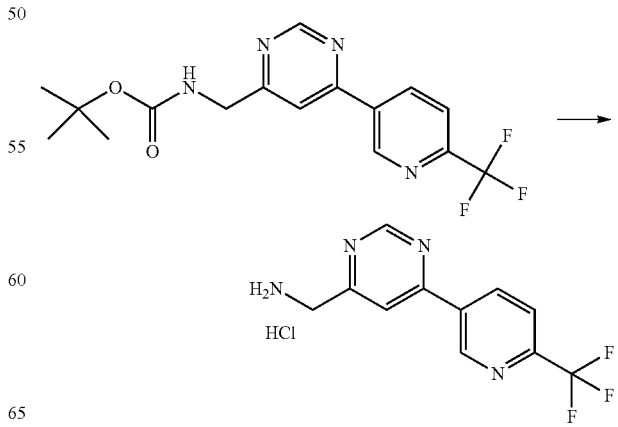

Into a 2000-mL 3-necked round-bottom flask was placed a solution of tert-butyl N-([6-[6-(trifluoromethyl)pyridin-3-yl]pyrimidin-4-yl]methyl)carbamate (185 g, 511.67 mmol, 1.00 equiv) in ethyl acetate (1500 mL). To the above hydrogen chloride (gas) was introduced and the resulting solution was stirred at room temperature for 2 h. The solids were collected by filtration and washed with 3×500 mL of EA to afford 120 g (80%) of [6-[6-(trifluoromethyl)pyridin-3-yl]pyrimidin-4-yl]methanamine hydrochloride as a light red solid. LCMS [M−HCl+H$^+$] 255; $^1$H NMR (300 MHz, D$_2$O) δ 9.17 (1H, s), 9.04 (1H, s), 8.47-8.49 (1H, d), 8.00 (1H, s), 7.86-7.89 (1H, d), 4.45 (2H, d).

Example 16: Preparation of [2-cyclopropyl-6-[2-(trifluoromethyl)pyrimidin-5-yl]pyridin-4-yl]methanamine The overall reaction scheme for Example 16 was as follows:

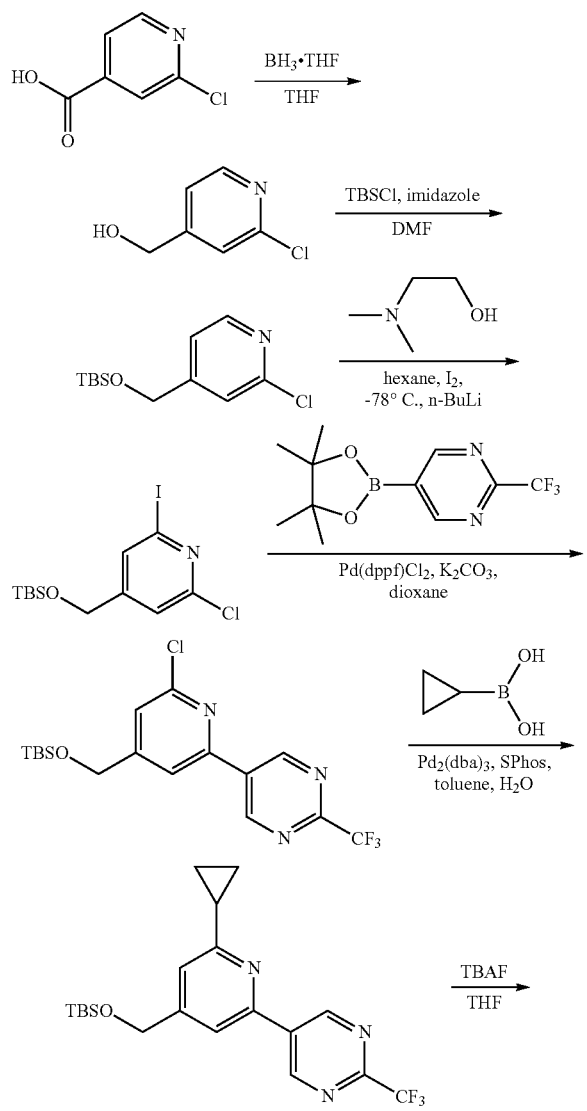

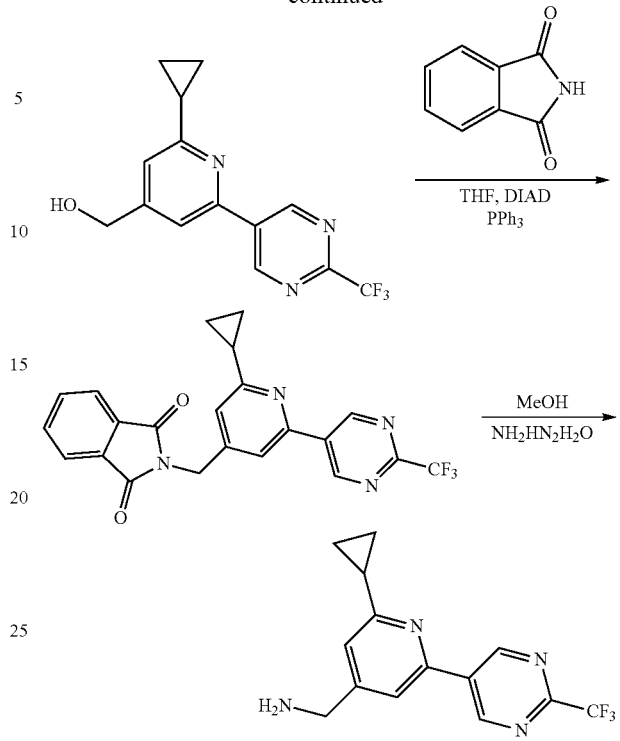

Example 16, Step 1: Preparation of (2-chloropyridin-4-yl)methanol

Step 1 proceeded according to the following scheme:

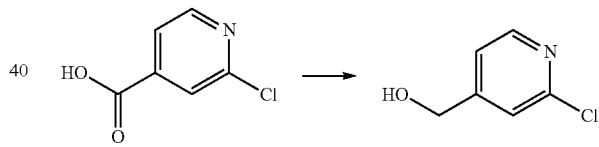

BH$_3$ THF solution (190 mL, 2.21 mol, 2.99 equiv) was added dropwise into a solution of 2-chloropyridine-4-carboxylic acid (10 g, 63.47 mmol, 1.00 equiv) in tetrahydrofuran (200 mL) at 0° C. After stirring for 12 h at room temperature, the reaction was quenched by methanol and concentrated under vacuum. The residue was purified by a silica gel column eluting with dichloromethane/ethyl acetate (50/1) to afford the title compound (11.9 g, crude) as brown oil. LCMS [M+H$^+$] 144.

Example 16, Step 2: Preparation of 4-[[(tert-butyldimethylsilyl)oxy]methyl]-2-chloropyridine Step 2 proceeded according to the following scheme:

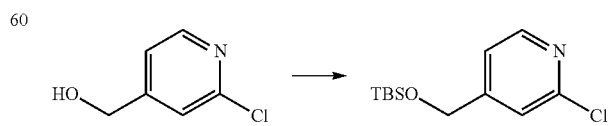

TBSCl (14.9 g, 98.85 mmol, 1.19 equiv) was added in several batches into a mixture of (2-chloropyridin-4-yl)

methanol (11.9 g, 82.89 mmol, 1.00 equiv), N,N-dimethylformamide (100 mL) and imidazole (11.2 g, 164.52 mmol, 1.99 equiv) under nitrogen. The resulting solution was stirred for 1 h at room temperature and then diluted with brine, extracted with ethyl acetate, washed with brine, and dried over anhydrous sodium sulfate. The residue was purified by a silica gel column eluting with dichloromethane/petroleum ether (2/1). This resulted in the title compound (18 g, 84%) as a light yellow solid. LCMS [M+H$^+$] 258.

Example 16, Step 3: Preparation of 4-[[(tert-butyldimethylsilyl)oxy]methyl]-2-chloro-6-iodopyridine Step 3 proceeded according to the following scheme:

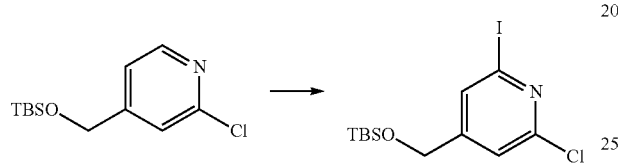

n-BuLi (46.5 mL, 2.5M in hexanes, 5.99 equiv) was added dropwise into a solution of 2-(dimethylamino)ethan-1-ol (5.1 g, 57.22 mmol, 2.95 equiv) in hexane (50 mL) at 0° C. in 1 hour under nitrogen. The resulting solution was stirred for 40 min at 0° C. To this was added a solution of 4-[[(tert-butyldimethylsilyl)oxy]methyl]-2-chloropyridine (5 g, 19.39 mmol, 1.00 equiv) in hexane (50 mL) dropwise at −70° C. in 1 hour. The resulting solution was stirred for 1.5 h while the temperature was maintained at −70° C. To the mixture was added a solution of I$_2$ (19.7 g, 77.62 mmol, 4.00 equiv) in tetrahydrofuran (200 mL) dropwise at −70° C. over 1.5 hours. After stirring for 30 min at −70° C., the reaction was quenched by 5% of Na$_2$S$_2$O$_3$, extracted with ethyl acetate, washed with brine, dried over anhydrous sodium sulfate, and concentrated under vacuum. The residue was purified by a silica gel column eluting with dichloromethane/petroleum ether (1/2) to afford the title compound (3.5 g, 47%) as yellow oil. LCMS [M+H$^+$] 384.

Example 16, Step 4: Preparation of 5-(4-[[(tert-butyldimethylsilyl)oxy]methyl]-6-chloropyridin-2-yl)-2-(trifluoromethyl)pyrimidine Step 4 proceeded according to the following scheme:

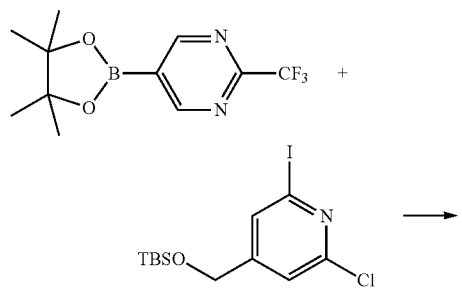

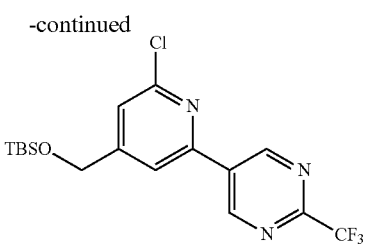

A mixture of 4-[[(tert-butyldimethylsilyl)oxy]methyl]-2-chloro-6-iodopyridine (1 g, 2.61 mmol, 1.00 equiv), 5-(tetramethyl-1,3,2-dioxaborolan-2-yl)-2-(trifluoromethyl)pyrimidine (642 mg, 2.34 mmol, 0.90 equiv), Pd(dppf)Cl$_2$ (95 mg, 0.13 mmol, 0.05 equiv), and potassium carbonate (1.08 g, 7.81 mmol, 3.00 equiv) in dioxane (10 mL)/water (1 mL) was stirred for 4 h at 60° C. under nitrogen. The solid was filtered out and the resulting solution was diluted with brine, extracted with ethyl acetate, washed with brine, dried over anhydrous sodium sulfate, and concentrated under vacuum. The residue was purified by a silica gel column eluting with ethyl acetate/petroleum ether (1/50) to afford the title compound (870 mg, 83%) as a yellow solid. LCMS [M+H$^+$] 404.

Example 16, Step 5: Preparation of 5-(4-[[(tert-butyldimethylsilyl)oxy]methyl]-6-cyclopropylpyridin-2-yl)-2-(trifluoromethyl)pyrimidine Step 5 proceeded according to the following scheme:

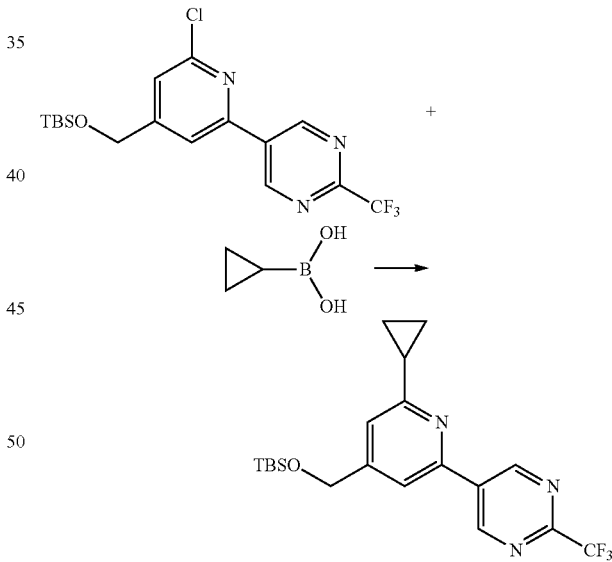

A mixture of 5-(4-[[(tert-butyldimethylsilyl)oxy]methyl]-6-chloropyridin-2-yl)-2-(trifluoromethyl)pyrimidine (870 mg, 2.15 mmol, 1.00 equiv), Pd$_2$(dba)$_3$ (111 mg, 0.12 mmol, 0.06 equiv), SPhos (88 mg, 0.21 mmol, 0.10 equiv), K$_3$PO$_4$ (1.37 g, 6.45 mmol, 3.00 equiv), and cyclopropylboronic acid (1.37 g, 15.95 mmol, 7.41 equiv) in toluene (20 mL)/water (2 mL) was stirred for 3 h at 100° C. under nitrogen. The solid was filtered out and the resulting solution was diluted with brine, extracted with ethyl acetate, dried over anhydrous sodium sulfate, and concentrated under vacuum. The residue was purified by a silica gel column eluting with ethyl acetate/petroleum ether (1/50) to afford the title compound (830 mg, 94%) as a white solid. LCMS [M+H$^+$] 410.

Example 16, Step 6: Preparation of [2-cyclopropyl-6-[2-(trifluoromethyl)pyrimidin-5-yl]pyridin-4-yl]methanol Step 6 proceeded according to the following scheme:

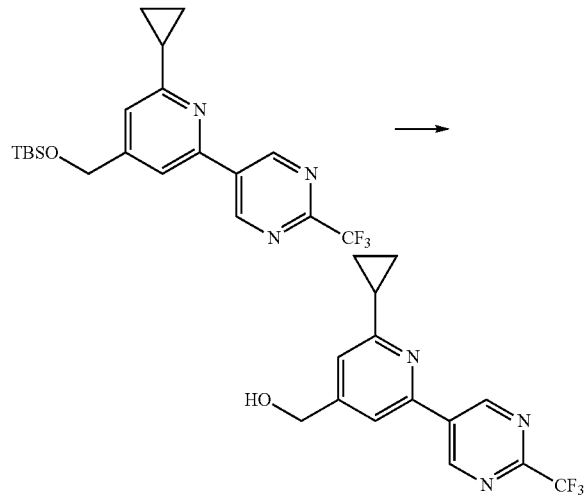

TBAF (2.43 mL, 9.29 mmol, 1.20 equiv) was added dropwise into a solution of 5-(4-[[(tert-butyldimethylsilyl)oxy]methyl]-6-cyclopropylpyridin-2-yl)-2-(trifluoromethyl)pyrimidine (830 mg, 2.03 mmol, 1.00 equiv) in tetrahydrofuran (20 mL). The resulting solution was stirred for 1 h at room temperature. The reaction solution was diluted with saturated solution of NH$_4$Cl, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (580 mg, 97%) as a yellow solid. LCMS [M+H$^+$] 296.

Example 16, Step 7: Preparation of 2-([2-cyclopropyl-6-[2-(trifluoromethyl)pyrimidin-5-yl]pyridin-4-yl]methyl)-2,3-dihydro-1H-isoindole-1,3-dione Step 7 proceeded according to the following scheme:

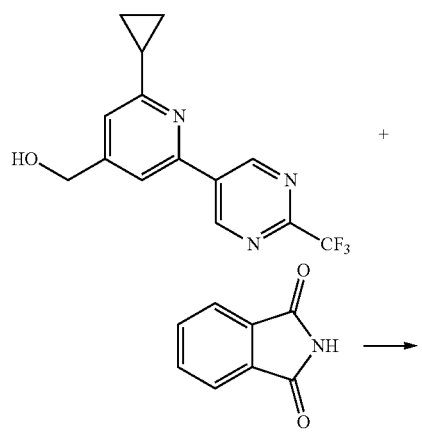

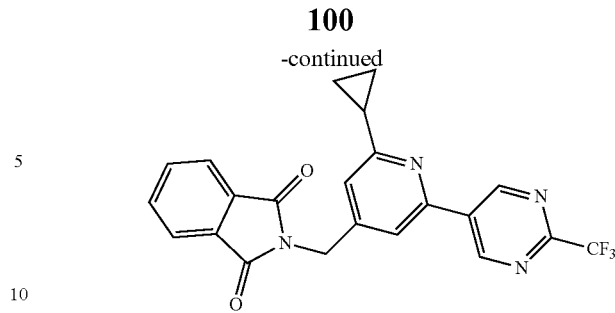

DIAD (794 mg, 3.92 mmol, 1.99 equiv) was added dropwise into a solution of [2-cyclopropyl-6-[2-(trifluoromethyl)pyrimidin-5-yl]pyridin-4-yl]methanol (580 mg, 1.96 mmol, 1.00 equiv), 2,3-dihydro-1H-isoindole-1,3-dione (578 mg, 3.93 mmol, 2.00 equiv), and PPh$_3$ (1.03 g, 3.93 mmol, 2.00 equiv) in tetrahydrofuran (50 mL) at 0° C. under nitrogen. After stirring for 12 h at room temperature the reaction was concentrated under vacuum. The residue was purified by a silica gel column eluting with dichloromethane/petroleum ether (10/1) to afford the title compound (600 mg, 72%) as a light yellow solid. LCMS [M+H$^+$] 425.

Example 16, Step 8: Preparation of [2-cyclopropyl-6-[2-(trifluoromethyl)pyrimidin-5-yl]pyridin-4-yl]methanamine Step 8 proceeded according to the following scheme:

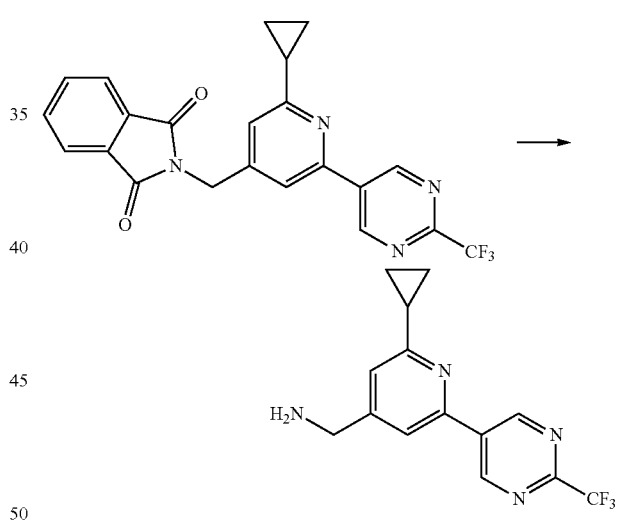

A solution of 2-([2-cyclopropyl-6-[2-(trifluoromethyl)pyrimidin-5-yl]pyridin-4-yl]methyl)-2,3-dihydro-1H-isoindole-1,3-dione (120 mg, 0.28 mmol, 1.00 equiv) and hydrazine hydrate (142 mg, 80%) in methanol (20 mL) was stirred for 3 h at 50° C. The resulting mixture was concentrated under vacuum. The residue was dissolved in ethyl acetate. The solid was filtered out and the filtrate was concentrated under vacuum. This resulted in the title compound (80 mg, 96%) as a yellow solid. LCMS [M+H$^+$] 295.

Example 17: Preparation of 2-((6-cyclopropyl-4-(2-(trifluoromethyl)pyrimidin-5-yl)pyridin-2-yl)methyl)isoindoline-1,3-dione The overall reaction scheme for Example 17 was as follows:

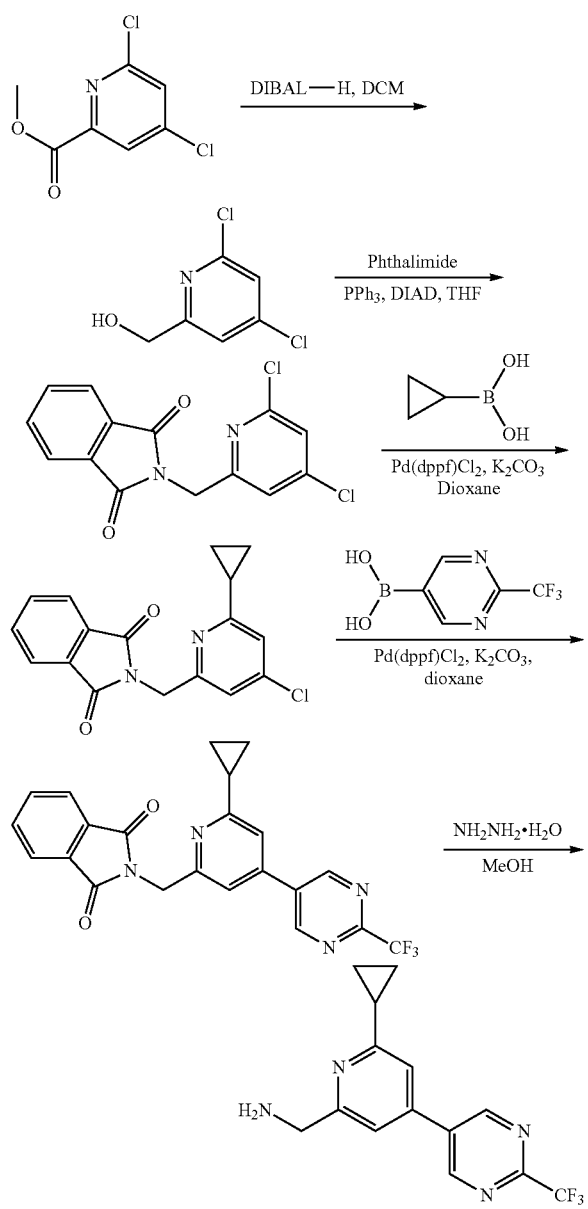

Example 17, Step 1: Preparation of 4,6-dichloropyridin-2-yl)methanol

Step 1 proceeded according to the following scheme:

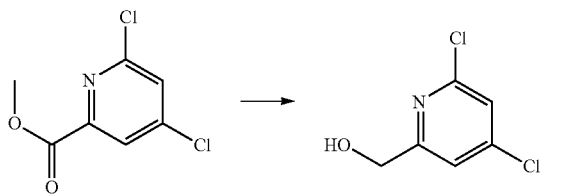

DIBAL-H (73 mL, 1 M in hexane, 3.00 equiv) was added dropwise into a solution of methyl 4,6-dichloropyridine-2-carboxylate (5 g, 24.26 mmol, 1.00 equiv) in dichloromethane (100 mL) at −78° C. under N₂. The resulting solution was stirred for overnight at room temperature. The reaction was quenched by methanol and concentrated under vacuum. The residue was purified by a silica gel column eluting with ethyl acetate/petroleum ether (1/20) to afford the title compound (9.5 g, 84%) as a light yellow solid. LCMS [M+H⁺] 178.

Example 17, Step 2: Preparation of 2-((4,6-dichloropyridin-2-yl)methyl)isoindoline-1,3-dione Step 2 proceeded according to the following scheme:

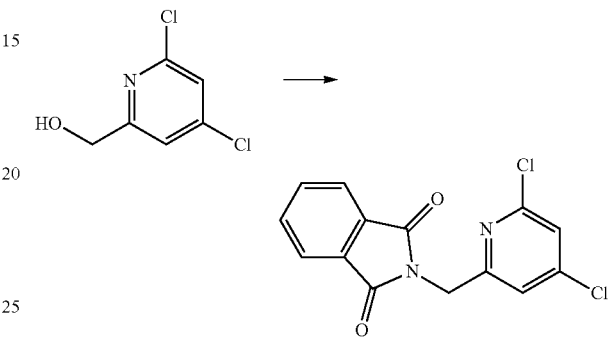

DIAD (6.87 g, 33.97 mmol, 2.00 equiv) was added dropwise into a solution of 2,3-dihydro-1H-isoindole-1,3-dione (2.50 g, 16.99 mmol, 1.00 equiv), (4,6-dichloropyridin-2-yl)methanol (4.54 g, 25.50 mmol, 1.50 equiv), and PPh₃ (8.91 g, 33.97 mmol, 2.00 equiv) in dry tetrahydrofuran (50 mL) under N₂. The resulting solution was stirred for 2 h at 0° C., concentrated under vacuum, and dissolved in ethyl acetate. The solid was collected by filtration and the filtrate was concentrated under vacuum. This resulted in the title compound (2.8 g, 54%) as a white solid. LCMS [M+H⁺] 307.

Example 17, Step 3: Preparation of 2-((4-chloro-6-cyclopropylpyridin-2-yl)methyl)isoindoline-1,3-dione Step 3 proceeded according to the following scheme:

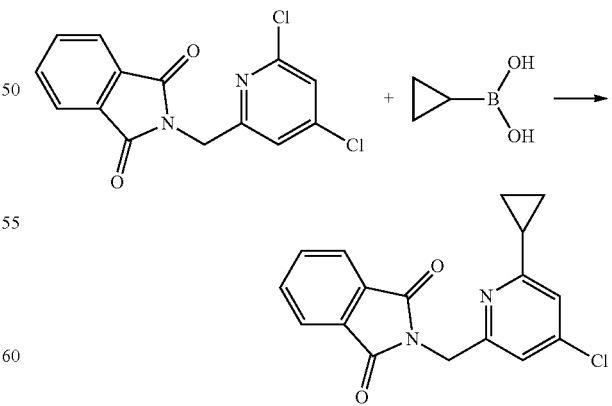

A mixture of 2-[(4,6-dichloropyridin-2-yl)methyl]-2,3-dihydro-1H-isoindole-1,3-dione (1 g, 3.25 mmol, 1.000 equiv), cyclopropylboronic acid (2.8 g, 32.59 mmol, 10.00 equiv), Pd(dppf)Cl₂·CH₂Cl₂ (270 mg, 0.33 mmol, 0.10 equiv), and potassium carbonate (1.4 g, 10.13 mmol, 3.11 equiv) in dioxane (50 mL) was stirred for 12 h at 70° C. under N₂. The solid was filtered out and the filtrate was concentrated under vacuum. The residue was purified by a silica gel column eluting with ethyl acetate/petroleum ether (1/5) to afford the title compound (700 mg, 69%) as a white solid. LCMS [M+H⁺] 313.

Example 17, Step 4: Preparation of 2-((6-cyclopropyl-4-(2-(trifluoromethyl)pyrimidin-5-yl)pyridin-2-yl)methyl)isoindoline-1,3-dione Step 4 proceeded according to the following scheme:

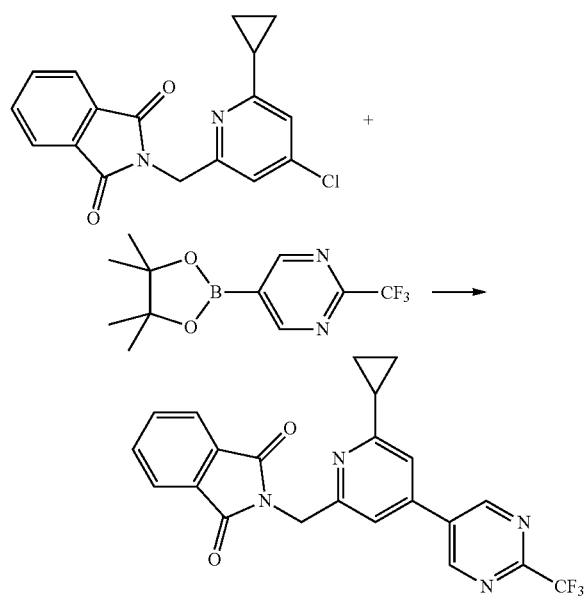

A mixture of 2-[(4-chloro-6-cyclopropylpyridin-2-yl)methyl]-2,3-dihydro-1H-isoindole-1,3-dione (700 mg, 2.23 mmol, 1.00 equiv), 5-(tetramethyl-1,3,2-dioxaborolan-2-yl)-2-(trifluoromethyl)pyrimidine (615 mg, 2.24 mmol, 1.00 equiv), Pd(dppf)Cl₂ (183 mg, 0.25 mmol, 0.11 equiv), and potassium carbonate (930 mg, 6.72 mmol, 3.00 equiv) in dioxane (30 mL) was stirred for 12 h at 100° C. under N₂. The solid was filtered out and the filtrate was concentrated under vacuum. The residue was purified by a silica gel column eluting with ethyl acetate/petroleum ether (1/4) to afford the title compound (600 mg, 63%) as a white solid. LCMS [M+H⁺] 425.

Example 17, Step 5: Preparation of 2-((6-cyclopropyl-4-(2-(trifluoromethyl)pyrimidin-5-yl)pyridin-2-yl)methyl)isoindoline-1,3-dione Step 5 proceeded according to the following scheme:

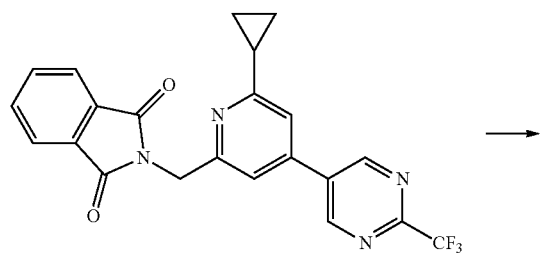

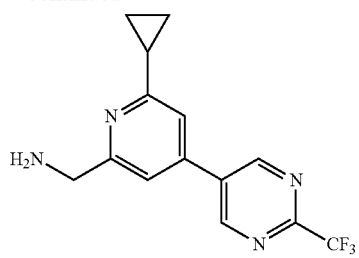

A solution of 2-([6-cyclopropyl-4-[2-(trifluoromethyl)pyrimidin-5-yl]pyridin-2-yl]methyl)-2,3-dihydro-1H-isoindole-1,3-dione (600 mg, 1.41 mmol, 1.00 equiv) and hydrazine hydrate (881 mg, 80%) in methanol (50 mL) was stirred for 2 h at 50° C. The resulting mixture was concentrated under vacuum and dissolved in ethyl acetate. The precipitated solid was filtered off. The filtrate was concentrated under vacuum to afford the title compound (400 mg, 96%) as yellow oil. [M+H⁺] 295.

Example 18: Preparation of [2-(trifluoromethyl)-6-[2-(trifluoromethyl)pyrimidin-5-yl]pyrimidin-4-yl]methanamine hydrochloride The overall reaction scheme for Example 18 was as follows:

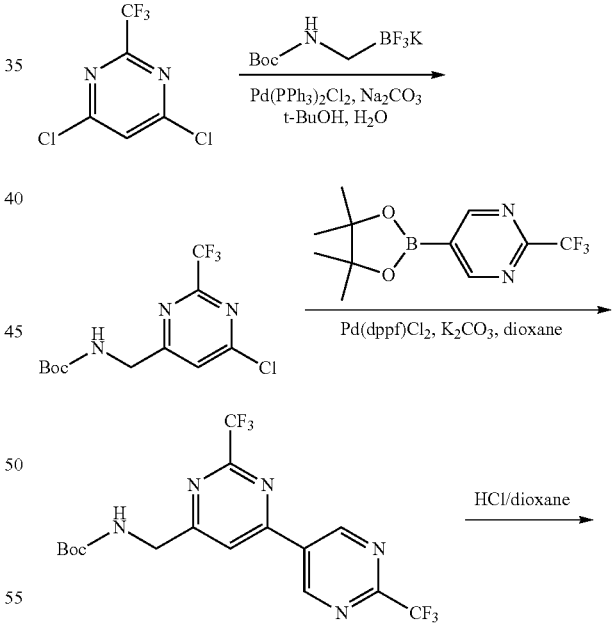

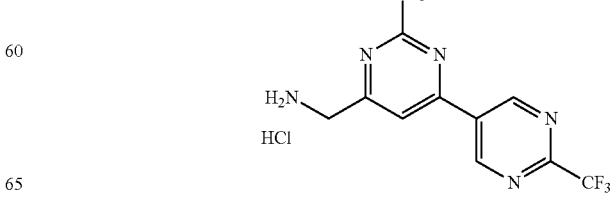

Example 18, Step 1: Preparation of tert-butyl N-[[6-chloro-2-(trifluoromethyl)pyrimidin-4-yl]methyl]carbamate Step 1 proceeded according to the following scheme:

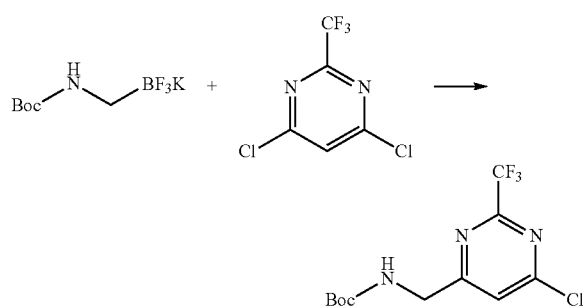

A mixture of 4,6-dichloro-2-(trifluoromethyl)pyrimidine (500 mg, 2.30 mmol, 1.00 equiv), potassium tert-butyl N-[(trifluoroboranuidyl)methyl]carbamate (546 mg, 2.30 mmol, 0.99 equiv), Pd(PPh$_3$)$_2$Cl$_2$ (162 mg, 0.23 mmol, 0.10 equiv), and sodium carbonate (488 mg, 4.60 mmol, 1.99 equiv) in t-butanol (10 mL)/water (2 mL) was stirred for 2 h at 70° C. under nitrogen. The solid was filtered off and the filtrate was diluted with water, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (450 mg, 63%) as a white solid. LCMS [M+H$^+$] 312.

Example 18, Step 2: Preparation of tert-butyl N-[[2-(trifluoromethyl)-6-[2-(trifluoromethyl)pyrimidin-5-yl]pyrimidin-4-yl]methyl]carbamate Step 2 proceeded according to the following scheme:

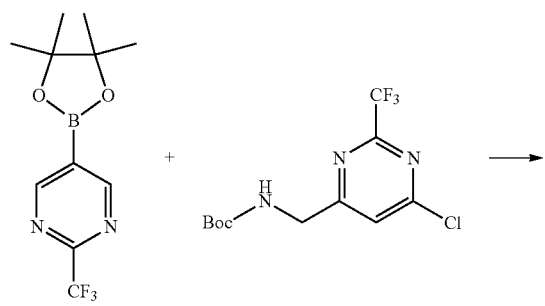

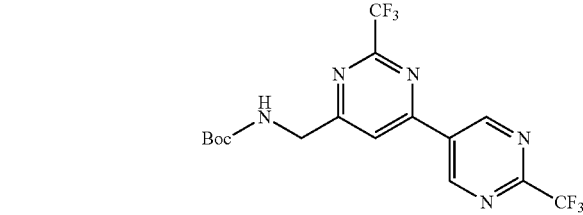

A mixture of 5-(tetramethyl-1,3,2-dioxaborolan-2-yl)-2-(trifluoromethyl)pyrimidine (450 mg, 1.64 mmol, 1.00 equiv), tert-butyl N-[[6-chloro-2-(trifluoromethyl)pyrimidin-4-yl]methyl]carbamate (396 mg, 1.27 mmol, 0.77 equiv), Pd(dppf)Cl$_2$ (106 mg, 0.14 mmol, 0.08 equiv), and potassium carbonate (400 mg, 2.89 mmol, 1.76 equiv) in dioxane (15 mL) was stirred for 3 h at 80° C. under nitrogen. The solid was filtered off. The filtrate was diluted with water, extracted with ethyl acetate, washed with brine, dried over anhydrous sodium sulfate, and concentrated under vacuum. The residue was purified by a silica gel column eluting with ethyl acetate/petroleum ether (1/5) to afford the title compound (400 mg, 58%) as a white solid. LCMS [M+H+] 424.

Example 18, Step 3: Preparation of [2-(trifluoromethyl)-6-[2-(trifluoromethyl)pyrimidin-5-yl]pyrimidin-4-yl]methanamine hydrochloride Step 3 proceeded according to the following scheme:

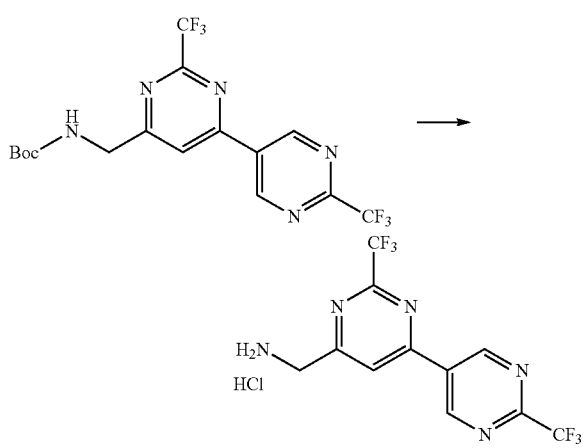

A mixture of tert-butyl N-[[2-(trifluoromethyl)-6-[2-(trifluoromethyl)pyrimidin-5-yl]pyrimidin-4-yl]methyl]carbamate (400 mg, 0.94 mmol, 1.00 equiv) and 4 N HCl in 1,4-dioxane (10 mL) was stirred for 2 h at room temperature. The resulting mixture was concentrated under vacuum to afford the title compound (220 mg) as yellow oil. LCMS [M+H$^+$] 324.

Example 19: Preparation of (2-(2,2,2-trifluoroethoxy)-2'-(trifluoromethyl)-4,5'-bipyrimidin-6-yl)methanamine hydrochloride The overall reaction scheme for Example 19 was as follows:

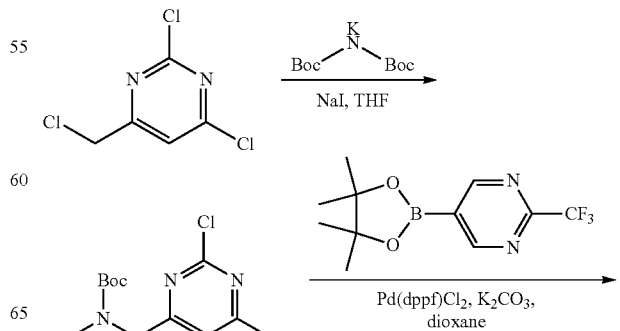

-continued

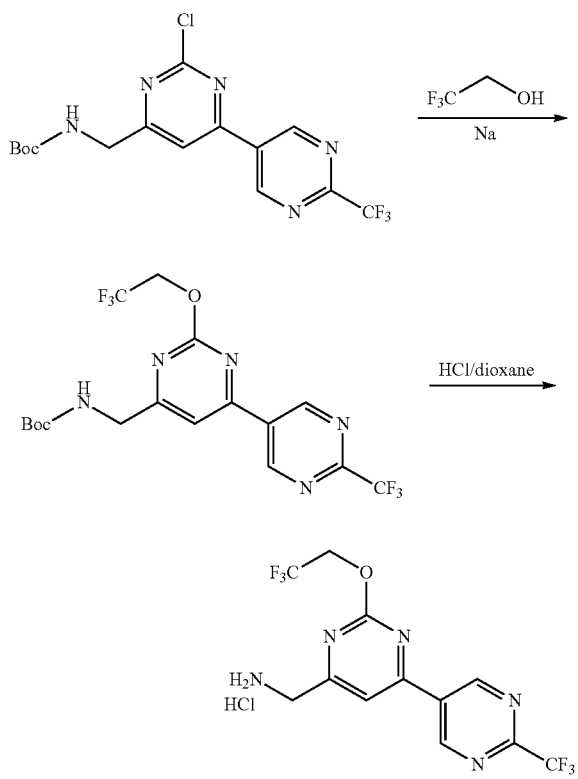

Example 19, Step 1: Preparation of tert-butyl N-[(tert-butoxy)carbonyl]-N-[(3,5-dichlorophenyl)methyl]carbamate Step 1 proceeded according to the following scheme:

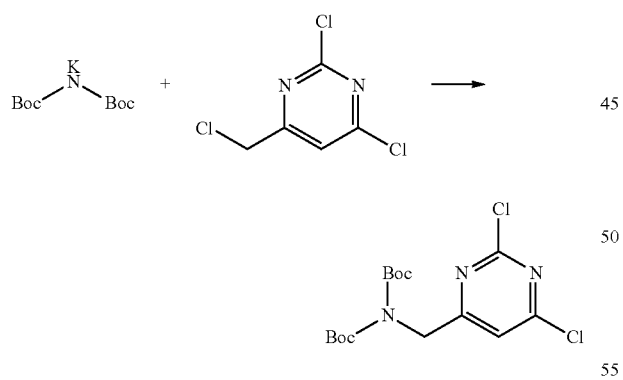

A mixture of 2,4-dichloro-6-(chloromethyl)pyrimidine (4 g, 20.25 mmol, 1.00 equiv), NaI (6.4 g, 42.69 mmol, 2.10 equiv), and potassium tert-butyl N-[(tert-butoxy)carbonyl]-N-carbamate (8.4 g, 32.89 mmol, 1.62 equiv) in tetrahydrofuran (80 mL) was stirred for 14 h at room temperature. The reaction solution was diluted with water, extracted with ethyl acetate, washed with brine, dried over anhydrous sodium sulfate, and concentrated under vacuum. The residue was purified by a silica gel column eluting with ethyl acetate/petroleum ether (1/2) to afford the title compound (3.2 g, 42%) as an off-white solid. LCMS [M+H$^+$] 378.

Example 19, Step 2: Preparation of tert-butyl (2-chloro-2'-(trifluoromethyl)-4,5'-bipyrimidin-6-yl)methylcarbamate Step 2 proceeded according to the following scheme:

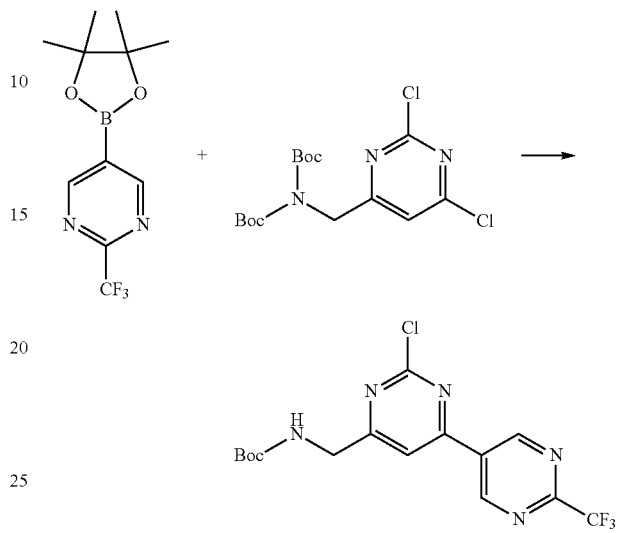

A mixture of tert-butyl N-[(tert-butoxy)carbonyl]-N-[(2,6-dichloropyrimidin-4-yl)methyl]carbamate (3.0 g, 7.93 mmol, 1.00 equiv), Pd(dppf)Cl$_2$ (562 mg, 0.76 mmol, 0.0 equiv), potassium carbonate (3.3 g, 23.96 mmol, 3.02 equiv), and 5-(tetramethyl-1,3,2-dioxaborolan-2-yl)-2-(trifluoromethyl)pyrimidine (2.19 g, 7.99 mmol, 1.00 equiv) in dioxane (100 mL)/water (10 mL) was stirred for 14 h at 80° C. under nitrogen. The resulting mixture was concentrated under vacuum. The residue was purified by a silica gel column eluting with ethyl acetate/petroleum ether (2/3) to afford the title compound (1.1 g, 36%) as a yellow solid. LCMS[M+H$^+$] 390.

Example 19, Step 3: Preparation of tert-butyl (2-(2,2,2-trifluoroethoxy)-2'-(trifluoromethyl)-4,5'-bipyrimidin-6-yl)methylcarbamate Step 3 proceeded according to the following scheme:

A mixture of 2,2,2-trifluoroethan-1-ol (8 g, 79.96 mmol, 62.33 equiv) and Na (50 mg, 2.17 mmol, 1.69 equiv) was stirred for 2 h at room temperature. To the above solution was added tert-butyl N-([2-chloro-6-[2-(trifluoromethyl)pyrimidin-5-yl]pyrimidin-4-yl]methyl)carbamate (500 mg, 1.28 mmol, 1.00 equiv), and the reaction mixture was stirred for 15 min at 0° C. The reaction was quenched by water, extracted with ethyl acetate, washed with brine, dried over anhydrous sodium sulfate, and concentrated under vacuum. The residue was purified by a silica gel column eluting with ethyl acetate/petroleum ether (1/2) to afford the title compound (420 mg, 72%) as an off-white solid. LCMS [M+H$^+$] 454.

Example 19, Step 4: Preparation of (2-(2,2,2-trifluoroethoxy)-2'-(trifluoromethyl)-4,5'-bipyrimidin-6-yl)methanamine hydrochloride Step 4 proceeded according to the following scheme:

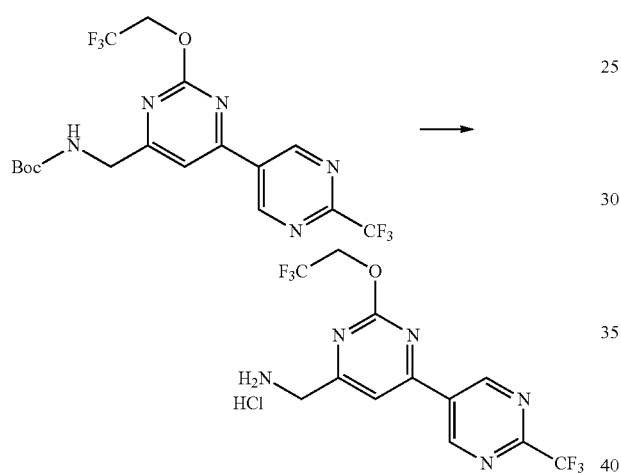

A mixture of tert-butyl N-[[2-(2,2,2-trifluoroethoxy)-6-[2-(trifluoromethyl)pyrimidin-5-yl]pyrimidin-4-yl]methyl]carbamate (400 mg, 0.88 mmol, 1.00 equiv) and saturated 4 N HCl in dioxane (15 mL) was stirred for 4 h at room temperature. The resulting mixture was concentrated under vacuum to afford the title compound (320 mg, 93%) as an off-white solid. LCMS [M+H$^+$] 354.

Example 20: Preparation of (3-methoxy-1-(2-(trifluoromethyl)pyrimidin-5-yl)-1H-pyrazol-4-yl)methanamine The overall reaction scheme for Example 20 was as follows:

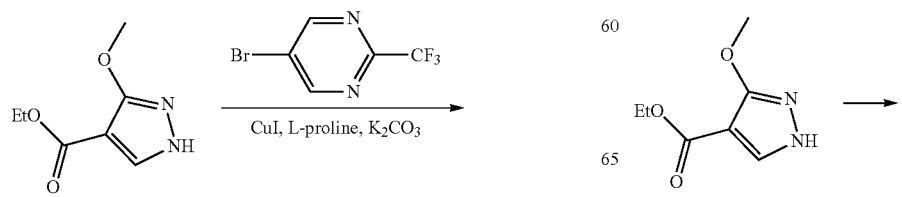

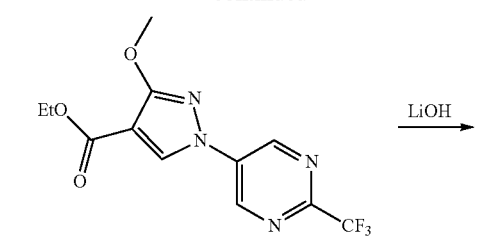

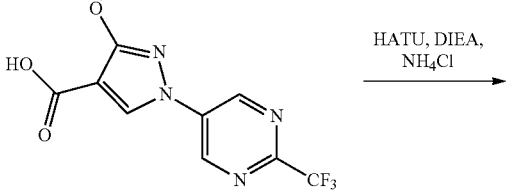

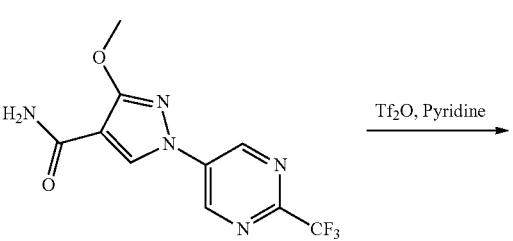

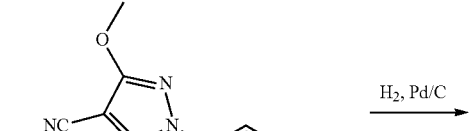

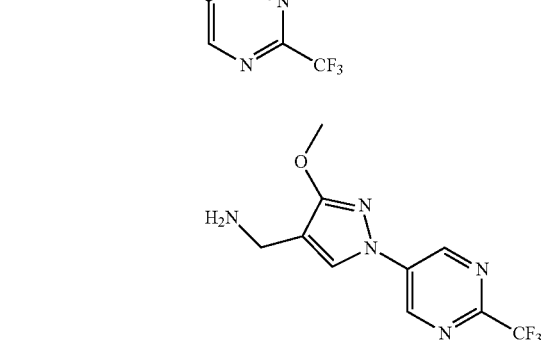

Example 20, Step 1: Preparation of ethyl 3-methoxy-1-(2-(trifluoromethyl)pyrimidin-5-yl)-1H-pyrazole-4-carboxylate Step 1 proceeded according to the following scheme:

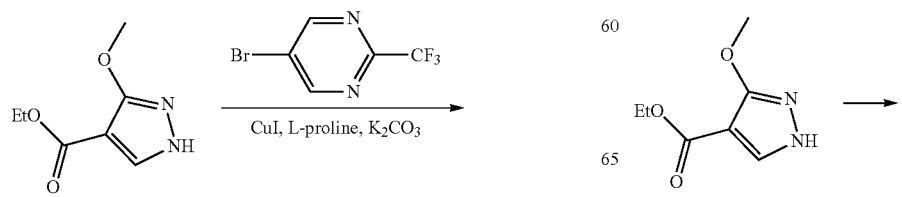

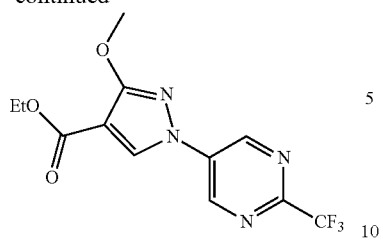

A mixture of CuI (88 mg, 0.46 mmol, 0.10 equiv), L-proline (108 mg, 0.94 mmol, 0.20 equiv), potassium carbonate (1.3 g, 9.41 mmol, 2.00 equiv), ethyl 3-methoxy-1H-pyrazole-4-carboxylate (800 mg, 4.70 mmol, 1.00 equiv), and 5-bromo-2-(trifluoromethyl)pyrimidine (1.28 g, 5.64 mmol, 1.20 equiv) in DMSO (5 mL) was stirred overnight at 100° C. under nitrogen. The reaction mixture was diluted with 40 mL of water, extracted with ethyl acetate, dried over anhydrous sodium sulfate, and concentrated under vacuum. The residue was purified by a silica gel column eluting with ethyl acetate/petroleum ether (1:5) to afford the title compound (580 mg, 39%) as a white solid.

Example 20, Step 2: Preparation of 3-methoxy-1-[2-(trifluoromethyl)pyrimidin-5-yl]-1H-pyrazole-4-carboxylic acid Step 2 proceeded according to the following scheme:

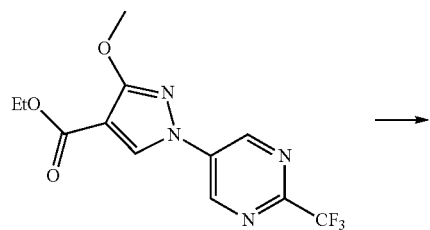

A mixture of ethyl 3-methoxy-1-[2-(trifluoromethyl)pyrimidin-5-yl]-1H-pyrazole-4-carboxylate (150 mg, 0.47 mmol, 1.0 equiv) and LiOH (22 mg, 0.92 mmol, 2.0 equiv) in THF (5 mL)/water (2 mL) was stirred for 2 h at 50° C. and diluted with 30 mL of water. The pH value of the solution was adjusted to 2 with diluted HCl. The resulting solution was extracted with ethyl acetate, dried over anhydrous sodium sulfate, and concentrated under vacuum. This resulted in the title compound (120 mg, 88%) as a white solid.

Example 20, Step 3: Preparation of 3-methoxy-1-[2-(trifluoromethyl)pyrimidin-5-yl]-1H-pyrazole-4-carboxamide Step 3 proceeded according to the following scheme:

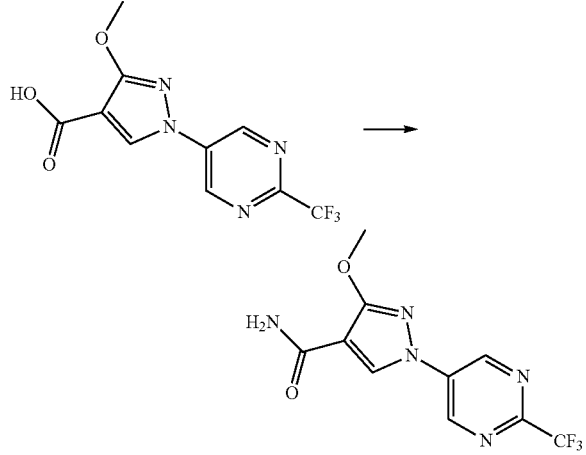

A mixture of 3-methoxy-1-[2-(trifluoromethyl)pyrimidin-5-yl]-1H-pyrazole-4-carboxylic acid (400 mg, 1.39 mmol, 1.0 equiv), HATU (792 mg, 2.08 mmol, 1.5 equiv), DIEA (540 mg, 4.18 mmol, 3.0 equiv), and NH$_4$Cl (110 mg, 2.06 mmol, 1.5 equiv) in N,N-dimethylformamide (20 ml) was stirred for 1 h at room temperature. The reaction was diluted with 30 mL of water, extracted with ethyl acetate, dried over anhydrous sodium sulfate, and concentrated under vacuum. The residue was purified by a silica gel column eluting with ethyl acetate/petroleum ether (1:3). This resulted in the title compound (300 mg, 75%) as a white solid.

Example 20, Step 4: Preparation of 3-methoxy-1-[4-(trifluoromethyl)phenyl]-1H-pyrazole-4-carbonitrile Step 4 proceeded according to the following scheme:

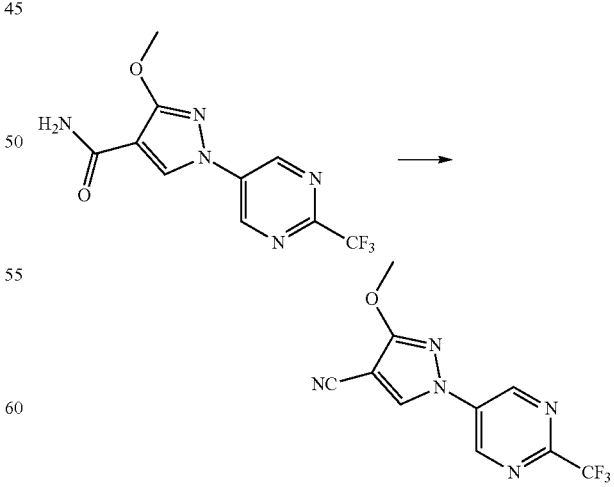

A mixture of 3-methoxy-1-[4-(trifluoromethyl)phenyl]-1H-pyrazole-4-carboxamide (300 mg, 1.05 mmol, 1.00 equiv), pyridine (347 mg, 4.39 mmol, 4.00 equiv), and Tf$_2$O (620 mg, 2.20 mmol, 2.00 equiv) in dichloromethane (30 mL) was stirred for 2 h at room temperature. The reaction was diluted with 30 mL of water, extracted with dichloromethane, dried over anhydrous sodium sulfate, and concentrated under vacuum. This resulted in the title compound 170 mg (60%) as a brown solid.

Example 20, Step 5: Preparation of (3-methoxy-1-(2-(trifluoromethyl)pyrimidin-5-yl)-1H-pyrazol-4-yl)methanamine hydrochloride Step 5 proceeded according to the following scheme:

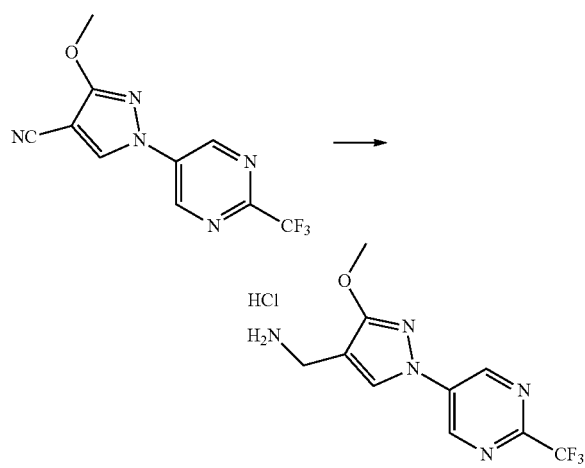

Into a 100-mL round-bottom flask purged and maintained with an atmosphere of NH₂ was placed 3-methoxy-1-[2-(trifluoromethyl)pyrimidin-5-yl]-1H-pyrazole-4-carbonitrile (170 mg, 0.63 mmol, 1.00 equiv), methanol (30 mL), hydrogen chloride (0.5 mL, 13.71 mmol, 1.00 equiv), and palladium on carbon (40 mg, 0.38 mmol, 1.00 equiv). After 30 min at room temperature the solids were filtered out. The liquid was concentrated under vacuum to afford the title compound (120 mg, 70%) of as a light yellow solid.

Example 21: Preparation of (3-methoxy-1-(2-(trifluoromethyl)pyrimidin-5-yl)-1H-pyrazol-4-yl)methanamine The overall reaction scheme for Example 21 was as follows:

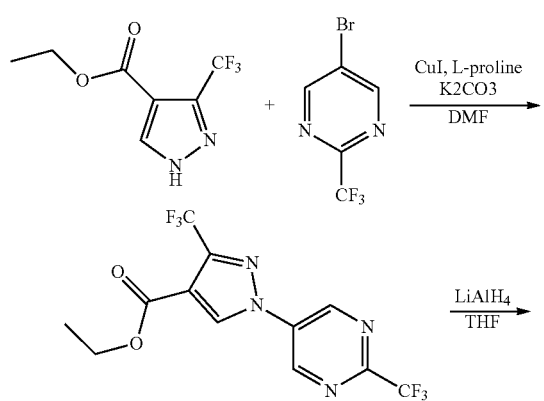

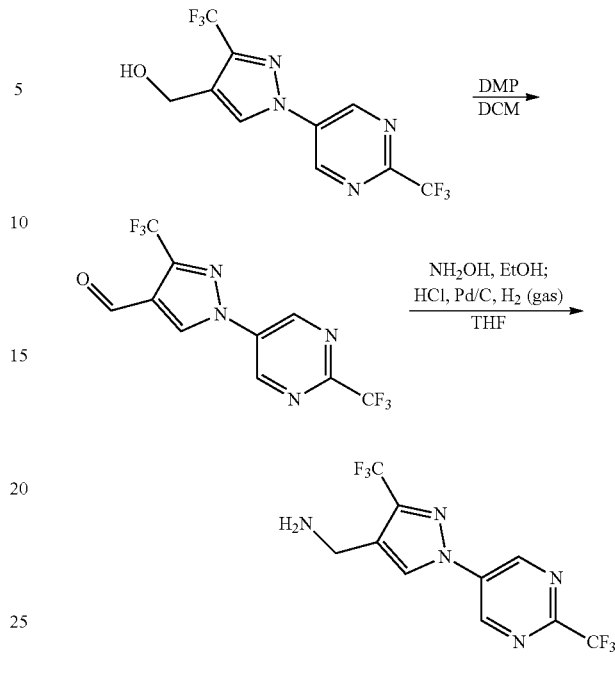

Example 21, Step 1: Preparation of ethyl 3-(trifluoromethyl)-1-(2-(trifluoromethyl)pyrimidin-5-yl)-1H-pyrazole-4-carboxylate Step 1 proceeded according to the following scheme:

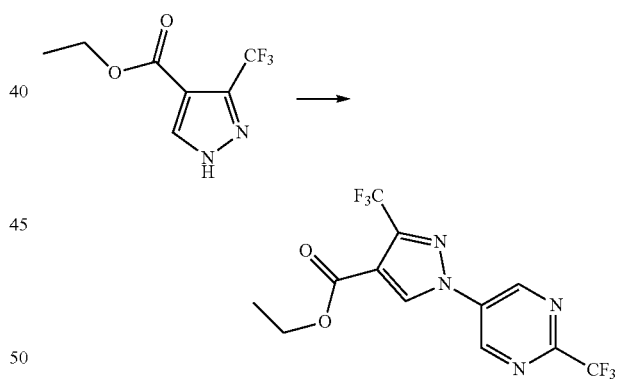

A mixture of ethyl 3-(trifluoromethyl)-1H-pyrazole-4-carboxylate (2.022 g, 9.71 mmol, 1.00 equiv) in N,N-dimethylformamide (60 mL), 5-bromo-2-(trifluoromethyl)pyridine (2.25 g, 9.96 mmol, 1.00 equiv), potassium carbonate (4.14 g, 29.96 mmol, 3.10 equiv), L-Proline (230 mg, 2.00 mmol, 0.20 equiv), and CuI (190 mg, 1.00 mmol, 0.10 equiv) was stirred overnight at 100° C. in an oil bath under nitrogen. The solid was filtered out. The resulting solution was diluted with brine, extracted with ethyl acetate, washed with brine, dried over anhydrous sodium sulfate and concentrated under vacuum. The residue was purified by a silica gel column eluting with ethyl acetate/petroleum ether (5:100) to afford the title compound (1.47 g, 43%) as a white solid. LC-MS (ESI): [M+H]⁺=354.1.

Example 21, Step 2: Preparation of [3-(trifluoromethyl)-1-[6-(trifluoromethyl)pyridin-3-yl]-1H-pyrazol-4-yl]methanol Step 2 proceeded according to the following scheme:

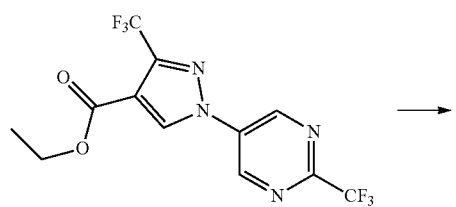

LiAlH$_4$ (190 mg, 5.01 mmol, 1.20 equiv) was added in several batches into a solution of ethyl 3-(trifluoromethyl)-1-[6-(trifluoromethyl)pyridin-3-yl]-1H-pyrazole-4-carboxylate (1.47 g, 4.16 mmol, 1.00 equiv) in tetrahydrofuran (30 mL) at 0° C. under nitrogen. The resulting solution was stirred for 30 min at 0° C. in an ice/salt bath. The reaction was then quenched by the addition of 10 mL of NaOH (1 moL/L). The resulting mixture was filtered. The solution was diluted with water, extracted with ethyl acetate, washed with brine, dried over anhydrous sodium sulfate and concentrated under vacuum. This resulted in the title compound (1.257 g, 97%) as a yellow solid. LC-MS (ESI): [M+H]$^+$=312.0.

Example 21, Step 3: Preparation of 3-(trifluoromethyl)-1-[6-(trifluoromethyl)pyridin-3-yl]-1H-pyrazole-4-carbaldehyde Step 3 proceeded according to the following scheme:

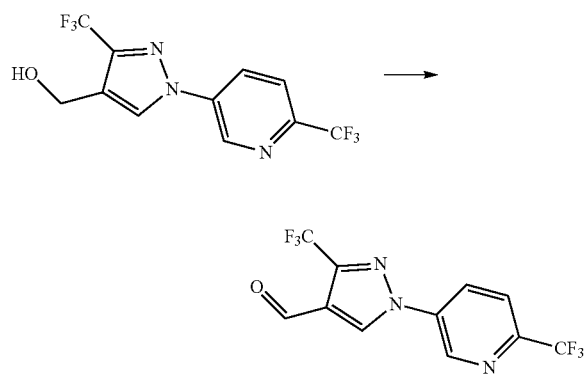 [SMILES: OCc1cn(-c2ccc(C(F)(F)F)nc2)nc1C(F)(F)F ; O=Cc1cn(-c2ccc(C(F)(F)F)nc2)nc1C(F)(F)F]

A mixture of [3-(trifluoromethyl)-1-[6-(trifluoromethyl)pyridin-3-yl]-1H-pyrazol-4-yl]methanol (1.257 g, 4.04 mmol, 1.00 equiv) in dichloromethane (40 mL), and DMP (2.06 g, 4.86 mmol, 1.20 equiv) was stirred for 3 h at room temperature. The resulting solution was diluted with ethyl acetate, washed with saturated solution of sodium bicarbonate and brine, dried over anhydrous sodium sulfate and concentrated under vacuum. The residue was purified by silica gel column eluting with ethyl acetate/petroleum ether (7:100). This resulted in the title compound (1.13 g, 90%) as a light yellow solid. LC-MS (ESI): [M+H]$^+$=310.0.

Example 21, Step 4: Preparation of [3-(trifluoromethyl)-1-[6-(trifluoromethyl)pyridin-3-yl]-1H-pyrazol-4-yl]methanamine Step 4 proceeded according to the following scheme:

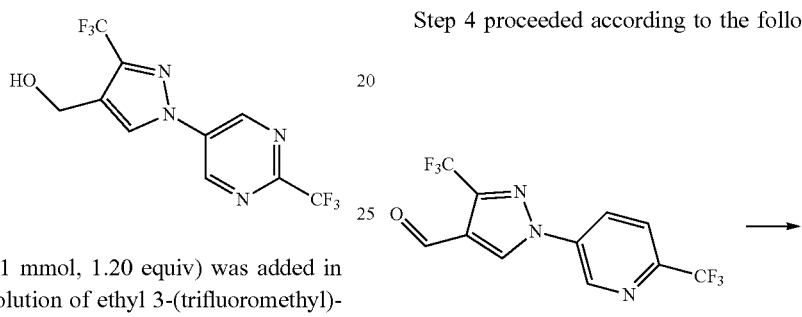

A mixture of 3-(trifluoromethyl)-1-[6-(trifluoromethyl)pyridin-3-yl]-1H-pyrazole-4-carbaldehyde (500 mg, 1.62 mmol, 1.00 equiv) in ethanol (40 mL), NH$_2$OH.HCl (230 mg, 3.31 mmol, 2.00 equiv), and water (5 mL) was stirred for 2 h at room temperature. Concentrated hydrogen chloride (2 mL), Pd/C (100 mg, 10%) was added into the mixture. The resulting mixture was stirred for 1 h at room temperature under hydrogen. The solids were filtered out. The resulting solution was diluted with water. The pH value of the solution was adjusted to 9 with sodium carbonate. The resulting solution was extracted with ethyl acetate, dried over anhydrous sodium sulfate and concentrated under vacuum. This resulted in the title compound (800 mg, crude) as a yellow solid, which was used for the next step without any further purification. LC-MS (ESI): [M+H]$^+$=311.1.

Example 22: Preparation of (S)-2-((4-fluorophenyl)sulfonyl)-N-((5-(trifluoromethyl)-2-(2-(trifluoromethyl)pyrimidin-5-yl)pyridin-4-yl)methyl)-2-azabicyclo[2.1.1]hexane-3-carboxamide The overall reaction scheme for Example 22 was as follows:

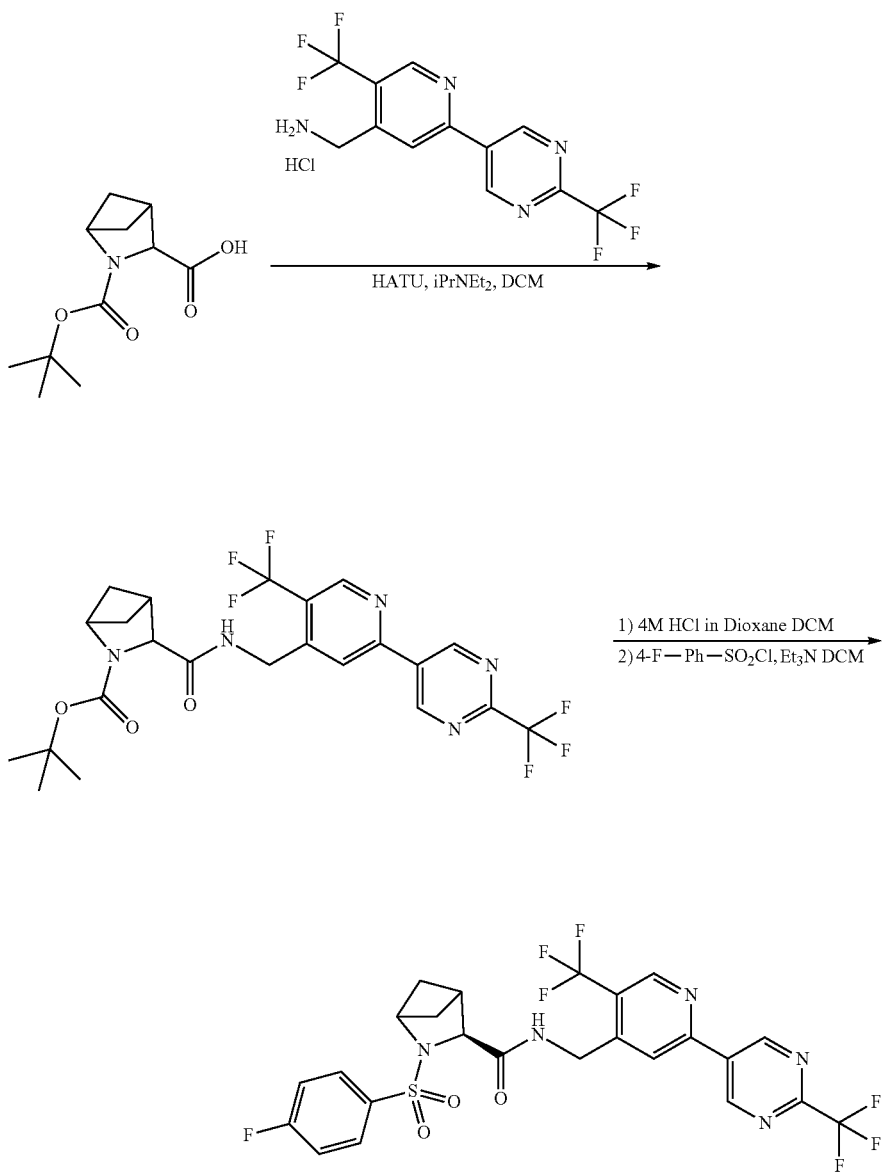

Example 22, Step 1: Preparation of tert-butyl 2-[[5-(trifluoromethyl)-2-[2-(trifluoromethyl)pyrimidin-5-yl]-4-pyridyl]methylcarbamoyl]-3-azabicyclo[2.1.1]hexane-3-carboxylate Step 1 proceeded according to the following scheme:

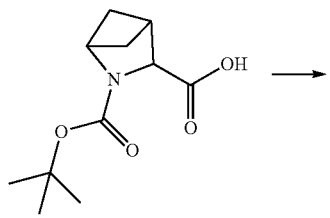

-continued

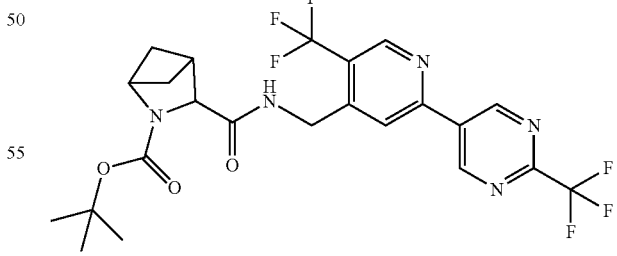

To a round bottomed flask was added 3-tert-butoxycarbonyl-3-azabicyclo[2.1.1]hexane-2-carboxylic acid (82 mg, 0.36 mmol), [5-(trifluoromethyl)-2-[2-(trifluoromethyl)pyrimidin-5-yl]-4-pyridyl]methanamine hydrochloride (136 mg, 0.38 mmol) and HATU (154 mg, 0.40 mmol). Dichloromethane (3.0 mL) was added followed by N,N-diisopropylethylamine (0.22 mL, 1.26 mmol) and the reaction mixture was stirred overnight at room temp. The reaction was quenched with sat. aq. sodium bicarbonate and extracted with DCM (3x). The combined organic extracts were washed with water (1x), brine (1x) then dried over sodium sulfated, filtered and concentrated in vacuo. The residue was adsorbed onto silica and purified by flash column chromatography with 0-100% iPrOAc in heptane to afford the title compound (155 mg, 81%).

Example 22, Step 2: Preparation of (S)-2-((4-fluorophenyl)sulfonyl)-N-((5-(trifluoromethyl)-2-(2-(trifluoromethyl)pyrimidin-5-yl)pyridin-4-yl)methyl)-2-azabicyclo[2.1.1]hexane-3-carboxamide Step 2 proceeded according to the following scheme:

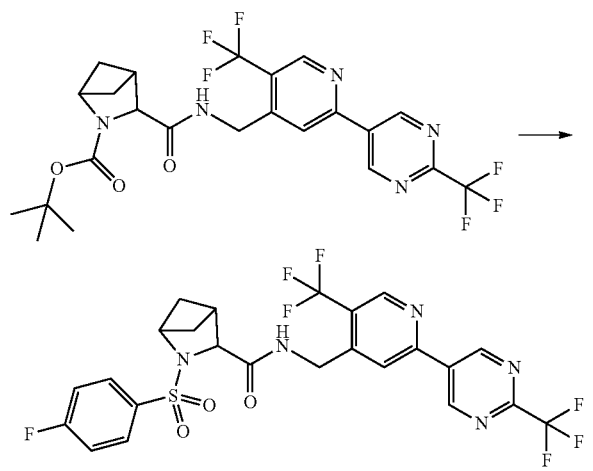

To a solution of tert-butyl 2-[[5-(trifluoromethyl)-2-[2-(trifluoromethyl)pyrimidin-5-yl]-4-pyridyl]methylcarbamoyl]-3-azabicyclo[2.1.1]hexane-3-carboxylate (155 mg, 0.29 mmol) in dichloromethane (5.0 mL) was added hydrochloric acid (4 mol/L) in 1,4-dioxane (1.2 mL, 4.8 mmol). The reaction mixture was stirred at room temp overnight. The reaction mixture was concentrated in vacuo then taken up in dichloromethane (5.0 mL). 4-Fluorobenzenesulfonyl chloride (62 mg, 0.32 mmol) and triethylamine (0.12 mL, 0.86 mmol) were added and the reaction mixture was stirred at room temperature for 2 h. The reaction mixture was diluted with DCM and water, the layers were separated and the aqueous layer was extracted with DCM (2x). The combined organic layers were dried over sodium sulfate, filtered and concentrated in vacuo. The residue was purified by chiral SFC to yield the title compound (70 mg, 41%) as a white solid. LCMS [M+H$^+$] 590.1; $^1$H NMR (400 MHz, DMSO-d$_6$) δ 9.72 (s, 2H), 9.12 (s, 1H), 9.01 (t, J=6.1 Hz, 1H), 8.37 (s, 1H), 8.09-7.99 (m, 2H), 7.57-7.48 (m, 2H), 4.83 (dd, J=17.3, 6.8 Hz, 1H), 4.50 (dd, J=17.1, 5.1 Hz, 1H), 4.31-4.23 (m, 1H), 4.03 (s, 1H), 2.87-2.80 (m, 1H), 1.97-1.90 (m, 1H), 1.82 (dd, J=10.6, 8.0 Hz, 1H), 1.77-1.69 (m, 1H), 0.41 (dd, J=10.6, 8.3 Hz, 1H).

Example 23: Preparation of (S)—N-((5-cyclopropyl-2-(2-(trifluoromethyl)pyrimidin-5-yl)pyridin-4-yl)methyl)-2-((4-fluorophenyl)sulfonyl)-2-azabicyclo[2.1.1]hexane-3-carboxamide The overall reaction scheme for Example 23 was as follows:

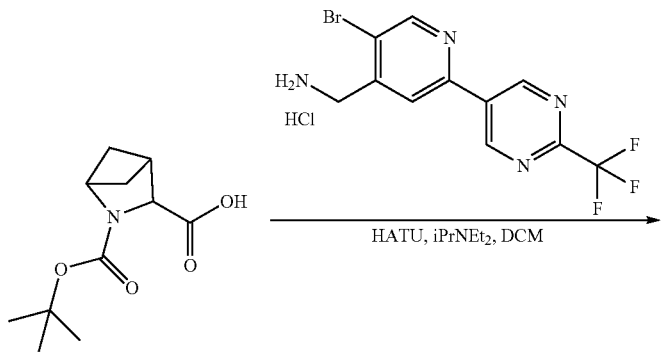

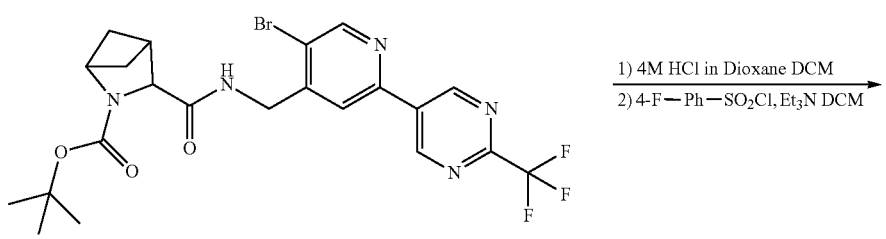

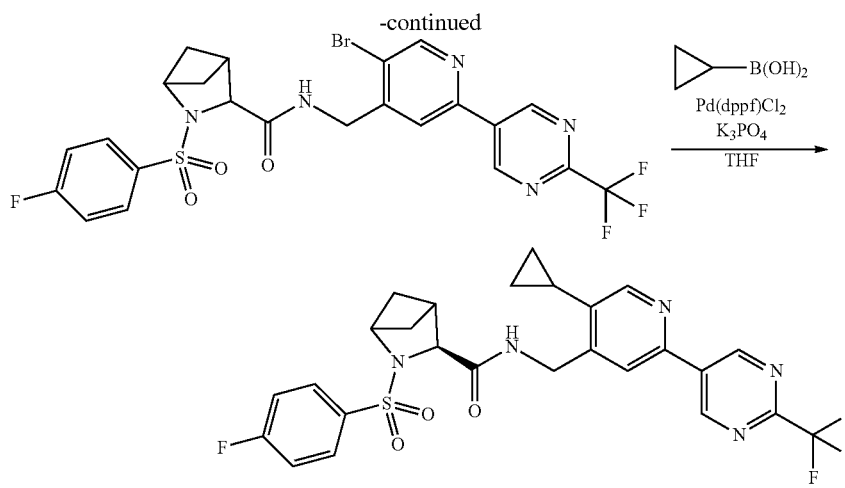

Example 23, Step 1: Preparation of tert-butyl 3-(((5-bromo-2-(2-(trifluoromethyl)pyrimidin-5-yl)pyridin-4-yl)methyl)carbamoyl)-2-azabicyclo[2.1.1]hexane-2-carboxylate Step 1 proceeded according to the following scheme:

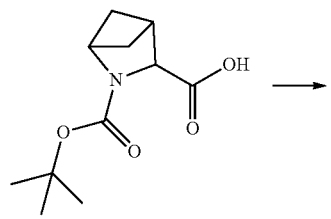

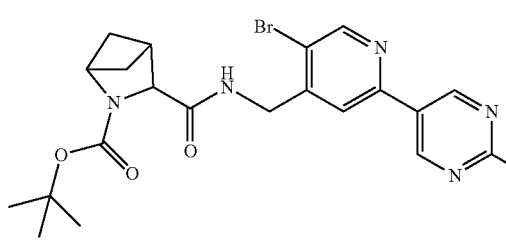

To a round bottomed flask was added 3-tert-butoxycarbonyl-3-azabicyclo[2.1.1]hexane-2-carboxylic acid (300 mg, 1.32 mmol), [5-bromo-2-[2-(trifluoromethyl)pyrimidin-5-yl]-4-pyridyl]methanamine hydrochloride (537 mg, 1.45 mmol) and HATU (563 mg, 1.45 mmol). Dichloromethane (10 mL) was added followed by N,N-diisopropylethylamine (0.81 mL, 4.62 mmol) and the reaction mixture was stirred overnight at room temp. The reaction was quenched with sat. aq. sodium bicarbonate and extracted with DCM (3×). The combined organic extracts were washed with water (1x), brine (1x) then dried over sodium sulfated, filtered and concentrated in vacuo. The residue was adsorbed onto silica and purified by flash column chromatography with 0-100% iPrOAc in heptane to afford the title compound (572 mg, 80%).

Example 23, Step 2: Preparation of N-((5-bromo-2-(2-(trifluoromethyl)pyrimidin-5-yl)pyridin-4-yl)methyl)-2-((4-fluorophenyl)sulfonyl)-2-azabicyclo[2.1.1]hexane-3-carboxamide Step 2 proceeded according to the following scheme:

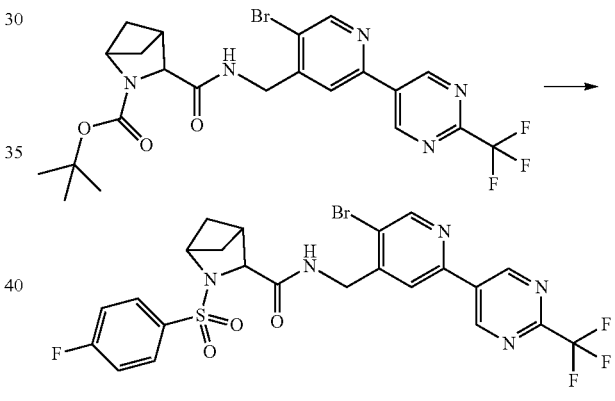

To a solution of tert-butyl 3-(((5-bromo-2-(2-(trifluoromethyl)pyrimidin-5-yl)pyridin-4-yl)methyl)carbamoyl)-2-azabicyclo[2.1.1]hexane-2-carboxylate (572 mg, 1.06 mmol) in dichloromethane (15 mL) was added hydrochloric acid (4 mol/L) in 1,4-dioxane (6.0 mL, 24 mmol). The reaction mixture was stirred at room temp for 2 h. The reaction mixture was concentrated in vacuo then taken up in dichloromethane (12 mL). 4-Fluorobenzenesulfonyl chloride (226 mg, 1.16 mmol) and triethylamine (0.44 mL, 3.16 mmol) were added and the reaction mixture was stirred at room temperature for 2 h. The reaction mixture was diluted with DCM and water, the layers were separated and the aqueous layer was extracted with DCM (2×). The combined organic layers were dried over sodium sulfate, filtered and concentrated in vacuo. The residue was adsorbed onto silica and purified by flash column chromatography with 0-100% iPrOAc in heptane to afford the desired compound as a white solid (543 mg, 86%). LCMS [M+H$^+$] 600.0; $^1$H NMR (400 MHz, DMSO-d$_6$) δ 9.65 (s, 2H), 8.97-8.91 (m, 2H), 8.18 (s, 1H), 8.08-8.00 (m, 2H), 7.56-7.47 (m, 2H), 4.63 (dd, J=17.3, 6.9 Hz, 1H), 4.33 (dd, J=17.3, 5.2 Hz, 1H), 4.28-4.23 (m, 1H), 4.03 (s, 1H), 2.88-2.80 (m, 1H), 1.97-1.90 (m, 1H), 1.89-1.79 (m, 1H), 1.76-1.70 (m, 1H), 0.47-0.37 (m, 1H).

Example 23, Step 3: Preparation of (S)—N-((5-cyclopropyl-2-(2-(trifluoromethyl)pyrimidin-5-yl)pyridin-4-yl)methyl)-2-((4-fluorophenyl)sulfonyl)-2-azabicyclo[2.1.1]hexane-3-carboxamide Step 3 proceeded according to the following scheme:

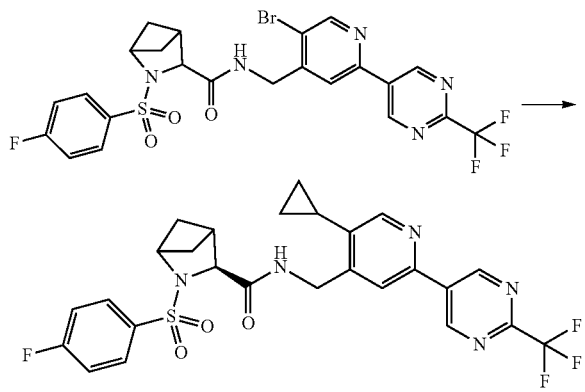

To a microwave vial was added N-[[5-bromo-2-[2-(trifluoromethyl)pyrimidin-5-yl]-4-pyridyl]methyl]-3-(4-fluorophenyl)sulfonyl-3-azabicyclo[2.1.1]hexane-2-carboxamide (100 mg, 0.17 mmol), cyclopropylboronic acid (22 mg, 0.25 mmol), [1,1'-bis(diphenylphosphino)ferrocene]palladium(II) dichloride dichloromethane adduct (14 mg, 0.017 mmol), potassium phosphate tribasic (90 mg, 0.42 mmol). Tetrahydrofuran (4.0 mL) was added, the reaction mixture was degassed with nitrogen and heated to 80° C. overnight. The reaction mixture was diluted with DCM and filtered through celite and concentrated in vacuo. The residue was adsorbed onto silica and purified by flash column chromatography with 0-100% EtOAc in Heptane to afford the desired compound as a brown foam. The residue was purified by Chiral SFC to yield the title compound (21.2 mg, 23%) as a white solid. LCMS [M+H$^+$] 562.1; $^1$H NMR (400 MHz, DMSO-d$_6$) δ 9.63 (s, 2H), 8.82 (t, J=6.0 Hz, 1H), 8.45 (s, 1H), 8.09 (s, 1H), 8.08-7.98 (m, 2H), 7.56-7.46 (m, 2H), 4.79 (dd, J=16.9, 6.8 Hz, 1H), 4.51 (dd, J=16.9, 5.3 Hz, 1H), 4.29-4.21 (m, 1H), 4.01 (s, 1H), 2.87-2.79 (m, 1H), 2.09-1.97 (m, 1H), 1.96-1.89 (m, 1H), 1.90-1.81 (m, 1H), 1.77-1.69 (m, 1H), 1.10-1.02 (m, 2H), 0.91-0.80 (m, 2H), 0.47-0.38 (m, 1H).

Example 24: Preparation of (S)—N-((5-cyano-2-(2-(trifluoromethyl)pyrimidin-5-yl)pyridin-4-yl)methyl)-2-((4-fluorophenyl)sulfonyl)-2-azabicyclo[2.1.1]hexane-3-carboxamide The overall reaction scheme for Example 24 was as follows:

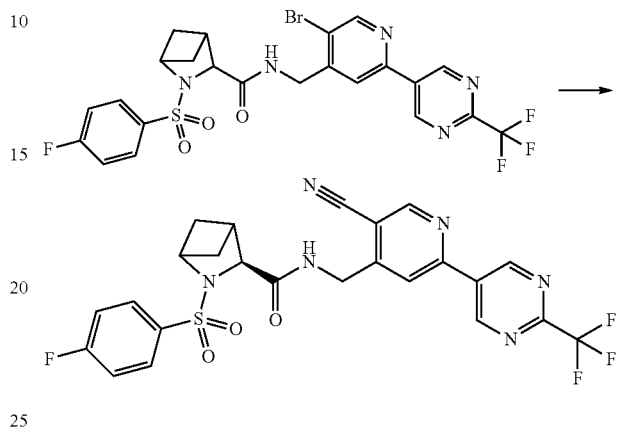

To a vial was added N-[[5-chloro-2-[2-(trifluoromethyl)pyrimidin-5-yl]-4-pyridyl]methyl]-3-(4-fluorophenyl)sulfonyl-3-azabicyclo[2.1.1]hexane-2-carboxamide (104 mg, 0.19 mmol), Zn(CN)$_2$ (44 mg, 0.37 mmol), tris(dibenzylideneacetone)dipalladium (17 mg, 0.019 mmol) and dppf (31 mg, 0.056 mmol). Degassed DMF (2.0 mL) was added and nitrogen was bubbled through the solution for 3 min. The solution was stirred for 2 h at 150° C. The resulting solution was filtered through celite and concentrated in vacuo. The residue was taken up in EtOAc and washed with water (2×) and brine (1×), dried over sodium sulfate, filtered and concentrated in vacuo. The residue was purified by Chiral SFC to yield the title compounds (28.5 mg, 28%) as a white solid. LCMS [M+H$^+$] 547.1; $^1$H NMR (400 MHz, DMSO-d$_6$) δ 9.70 (s, 2H), 9.22 (s, 1H), 9.02 (t, J=5.9 Hz, 1H), 8.32 (s, 1H), 8.07-7.97 (m, 2H), 7.57-7.46 (m, 2H), 4.78 (dd, J=17.0, 6.5 Hz, 1H), 4.54 (dd, J=17.0, 5.2 Hz, 1H), 4.29-4.21 (m, 1H), 4.00 (s, 1H), 2.88-2.80 (m, 1H), 1.96-1.88 (m, 1H), 1.88-1.78 (m, 1H), 1.76-1.68 (m, 1H), 0.46-0.36 (m, 1H).

Example 25: Preparation of (S)—N-(3-fluoro-5-(2-(trifluoromethyl)pyrimidin-5-yl)benzyl)-2-((4-fluorophenyl)sulfonyl)-2-azabicyclo[2.1.1]hexane-3-carboxamide The overall reaction scheme for Example 25 was as follows:

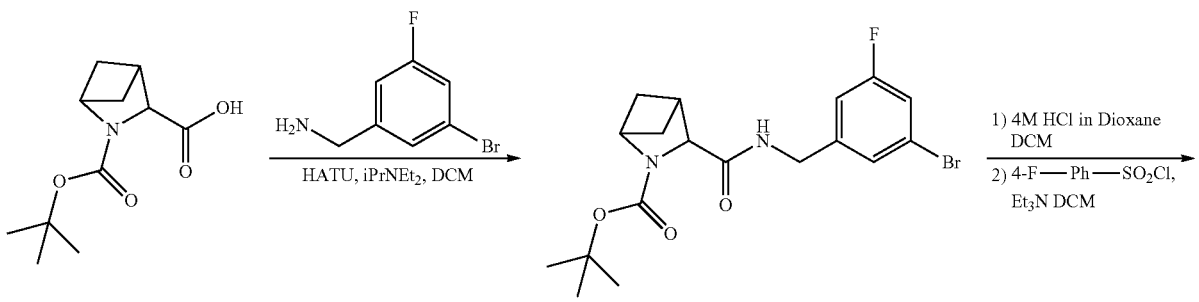

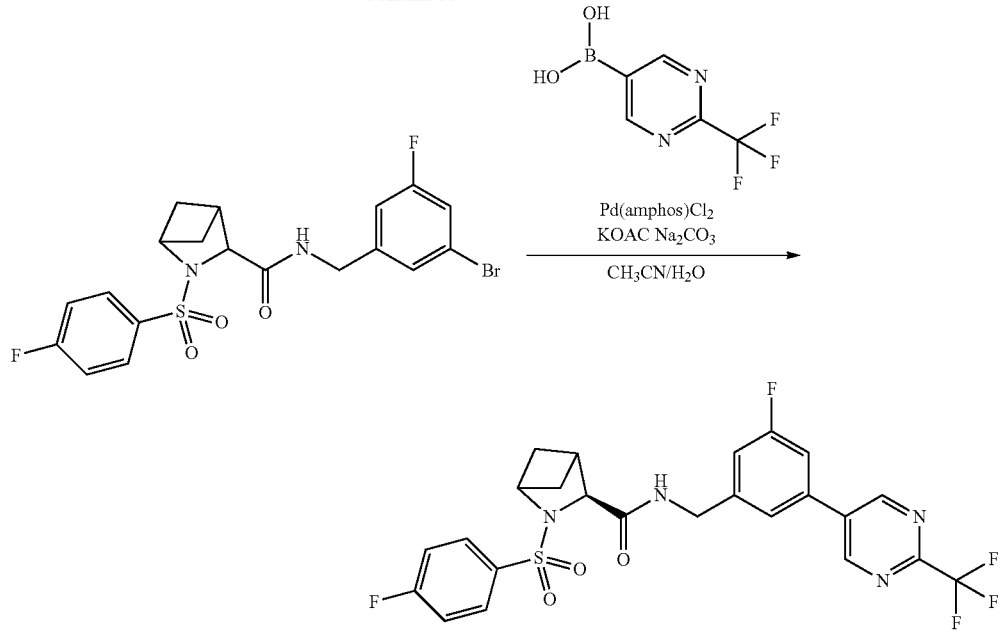

Example 25, Step 1: Preparation of tert-butyl 3-((3-bromo-5-fluorobenzyl)carbamoyl)-2-azabicyclo[2.1.1]hexane-2-carboxylate Step 1 proceeded according to the following scheme:

To a round bottomed flask was added 3-tert-butoxycarbonyl-3-azabicyclo[2.1.1]hexane-2-carboxylic acid (150 mg, 0.66 mmol), (3-bromo-5-fluorophenyl)methanamine (156 mg, 0.73 mmol) and HATU (282 mg, 0.73 mmol). Dichloromethane (5.0 mL) was added followed by N,N-diisopropylethylamine (0.29 mL, 1.65 mmol) and the reaction mixture was stirred overnight at room temp. The reaction was quenched with sat. aq. sodium bicarbonate and extracted with DCM (3×). The combined organic extracts were washed with water (1x), brine (1x) then dried over sodium sulfated, filtered and concentrated in vacuo. The residue was adsorbed onto silica and purified by flash column chromatography with 0-100% iPrOAc in heptane to afford the title compound (246 mg, 90%).

Example 25, Step 2: Preparation of N-(3-bromo-5-fluorobenzyl)-2-((4-fluorophenyl)sulfonyl)-2-azabicyclo[2.1.1]hexane-3-carboxamide Step 2 proceeded according to the following scheme:

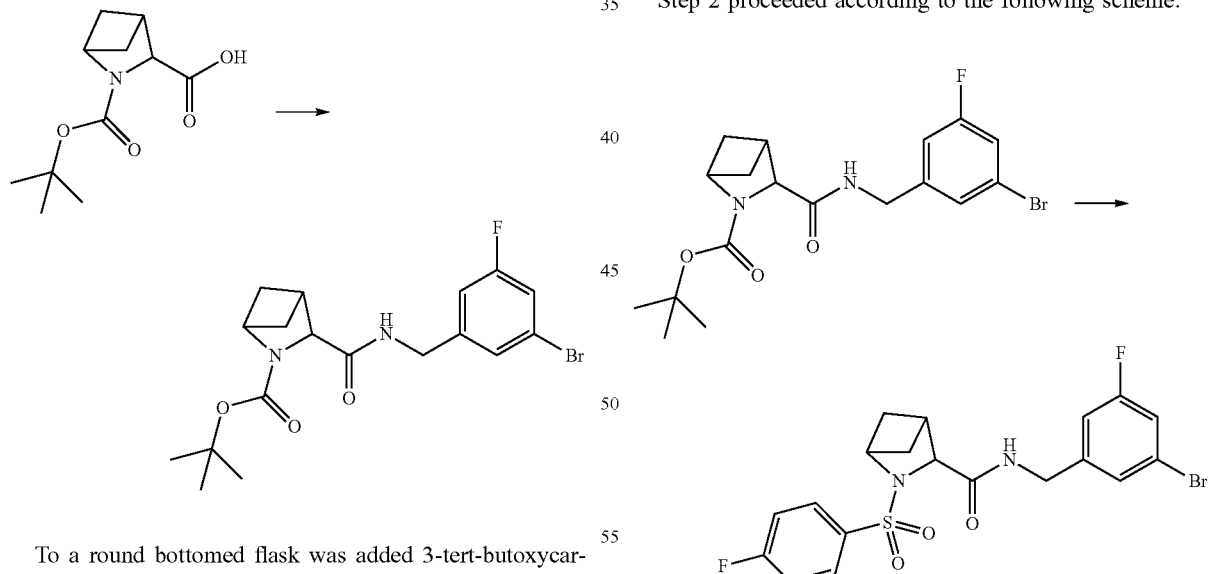

To a solution of tert-butyl 2-[(3-bromo-5-fluoro-phenyl)methylcarbamoyl]-3-azabicyclo[2.1.1]hexane-3-carboxylate (246 mg, 0.60 mmol) in dichloromethane (5.0 mL) was added hydrochloric acid (4 mol/L) in 1,4-dioxane (2.0 mL, 8.0 mmol). The reaction mixture was stirred at room temperature for 2 h. The reaction mixture was concentrated in vacuo then taken up in dichloromethane (5.0 mL). 4-Fluorobenzenesulfonyl chloride (127 mg, 0.65 mmol) and triethylamine (0.25 mL, 1.79 mmol) were added and the reaction mixture was stirred at room temperature for 2 h. The reaction mixture was diluted with DCM and water, the layers were separated and the aqueous layer was extracted with DCM (2×). The combined organic layers were dried over sodium sulfate, filtered and concentrated in vacuo to give the crude title compound (279 mg, 99%) as a brown solid which was used directly in the next step.

Example 25, Step 3: Preparation of (S)—N-(3-fluoro-5-(2-(trifluoromethyl)pyrimidin-5-yl)benzyl)-2-((4-fluorophenyl)sulfonyl)-2-azabicyclo[2.1.1]hexane-3-carboxamide Step 3 proceeded according to the following scheme:

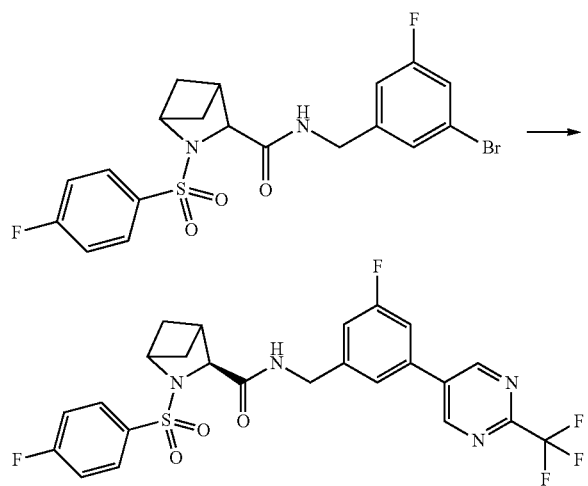

To a microwave vial was added N-[(3-bromo-5-fluorophenyl)methyl]-3-(4-fluorophenyl)sulfonyl-3-azabicyclo[2.1.1]hexane-2-carboxamide (65 mg, 0.14 mmol), 2-(trifluoromethyl)pyrimidin-5-ylboronic acid (38 mg, 0.19 mmol), bis(di-tert-butyl(4-dimethylaminophenyl)phosphine)dichloropalladium(II) (7.8 mg, 0.011 mmol), sodium carbonate (20 mg, 0.19 mmol) and potassium acetate (19 mg, 0.19 mmol). Acetonitrile (1.5 mL) and water (0.30 mL) were added and nitrogen was bubbled through the reaction mixture for 3 mins then heated to 120° C. in the microwave for 15 mins. The reaction mixture was diluted with dichloromethane, filtered through celite, eluting with dichloromethane and the filtrate was concentrated in vacuo. The residue was adsorbed onto silica and purified by flash column chromatography with 0-100% EtOAc in Heptane to afford the desired compound as a yellow foam. The residue was further purified by Chiral SFC to yield the title compound (28.4 mg, 38%) as a white solid. LCMS [M+H+] 547.1; $^1$H NMR (400 MHz, DMSO-$d_6$) δ 9.43 (s, 2H), 8.73 (t, J=6.1 Hz, 1H), 8.02-7.94 (m, 2H), 7.77-7.68 (m, 2H), 7.54-7.44 (m, 2H), 7.36-7.27 (m, 1H), 4.55 (dd, J=16.0, 6.5 Hz, 1H), 4.41 (dd, J=15.9, 5.8 Hz, 1H), 4.26-4.18 (m, 1H), 3.95 (s, 1H), 2.85-2.76 (m, 1H), 1.91-1.86 (m, 1H), 1.84-1.77 (m, 1H), 1.75-1.67 (m, 1H), 0.49-0.39 (m, 1H).

Example 26: Preparation of (S)—N-((2-chloro-6-(2-(trifluoromethyl)pyrimidin-5-yl)pyridin-4-yl)methyl)-2-((4-fluorophenyl)sulfonyl)-2-azabicyclo[2.1.1]hexane-3-carboxamide The overall reaction scheme for Example 26 was as follows:

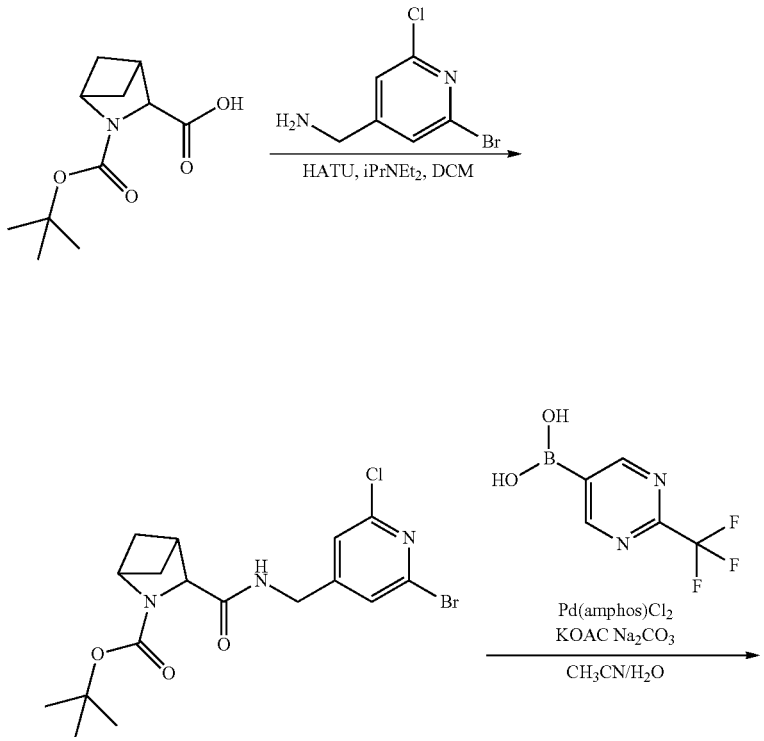

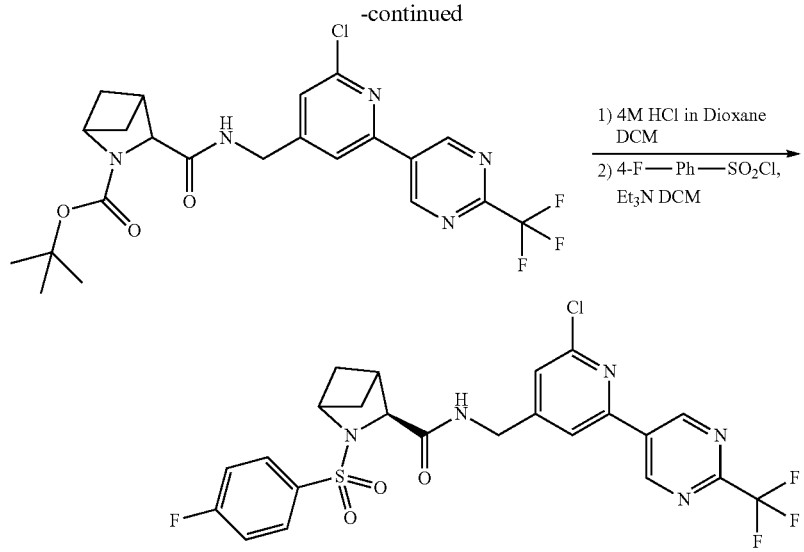

Example 26, Step 1: Preparation of tert-butyl 3-(((2-bromo-6-chloropyridin-4-yl)methyl)carbamoyl)-2-azabicyclo[2.1.1]hexane-2-carboxylate Step 1 proceeded according to the following scheme:

Example 26, Step 2: Preparation of tert-butyl 3-(((2-chloro-6-(2-(trifluoromethyl)pyrimidin-5-yl)pyridin-4-yl)methyl)carbamoyl)-2-azabicyclo[2.1.1]hexane-2-carboxylate Step 2 proceeded according to the following scheme:

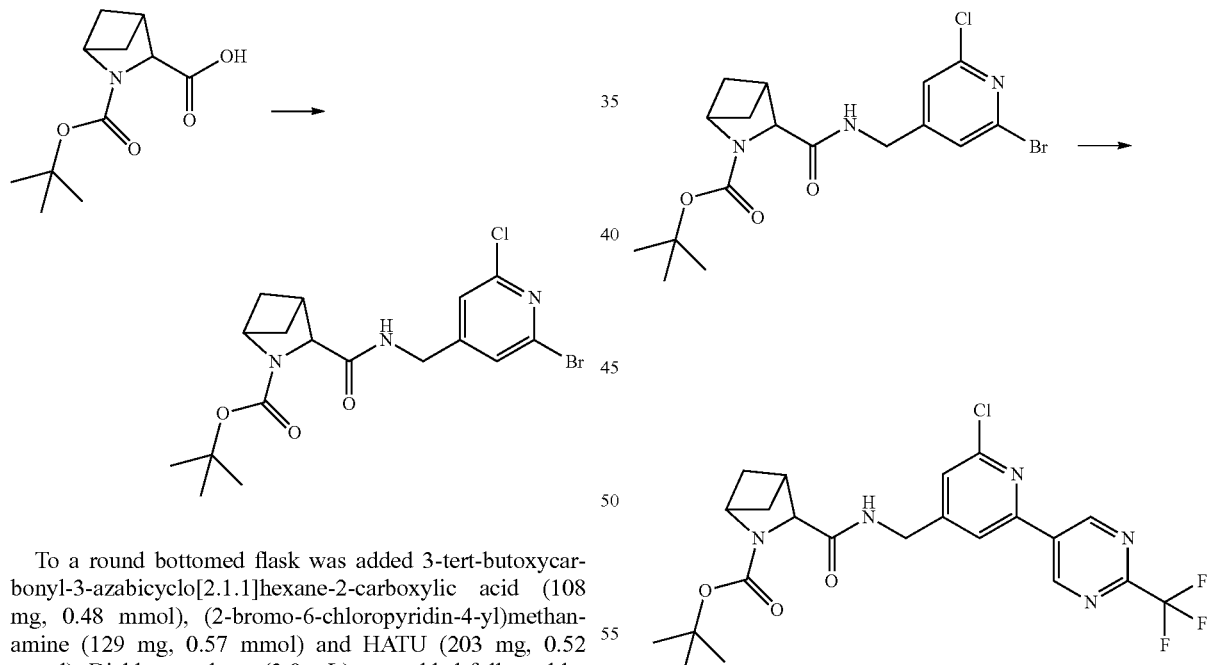

To a round bottomed flask was added 3-tert-butoxycarbonyl-3-azabicyclo[2.1.1]hexane-2-carboxylic acid (108 mg, 0.48 mmol), (2-bromo-6-chloropyridin-4-yl)methanamine (129 mg, 0.57 mmol) and HATU (203 mg, 0.52 mmol). Dichloromethane (3.0 mL) was added followed by N,N-diisopropylethylamine (0.21 mL, 1.19 mmol) and the reaction mixture was stirred overnight at room temp. The reaction was quenched with sat. aq. sodium bicarbonate and extracted with DCM (3×). The combined organic extracts were washed with water (1x), brine (1x) then dried over sodium sulfated, filtered and concentrated in vacuo. The residue was adsorbed onto silica and purified by flash column chromatography with 0-50% iPrOAc in heptane to afford the title compound (118 mg, 58%) as a pale yellow solid.

To a microwave vial was added tert-butyl 3-(((2-bromo-6-chloropyridin-4-yl)methyl)carbamoyl)-2-azabicyclo[2.1.1]hexane-2-carboxylate (118 mg, 0.27 mmol), 2-(trifluoromethyl)pyrimidin-5-ylboronic acid (52 mg, 0.27 mmol) and 1,1'-bis(diphenylphosphino)ferrocene-palladium (II)dichloride dichloromethane complex (18 mg, 0.022 mmol). Acetonitrile (3.6 mL) and 1 M potassium acetate in water (0.9 mL, 0.9 mmol) were added and nitrogen was bubbled through the reaction mixture for 3 mins then heated to 110° C. in the microwave for 30 min. The reaction mixture was diluted with dichloromethane, filtered through celite, eluting with dichloromethane and the filtrate was concentrated in vacuo. The residue was adsorbed onto silica and purified by flash column chromatography with 0-10% MeOH in DCM to afford the desired compound as a brown foam (118 mg, 87%).

Example 26, Step 3: Preparation of (S)—N-((2-chloro-6-(2-(trifluoromethyl)pyrimidin-5-yl)pyridin-4-yl)methyl)-2-((4-fluorophenyl)sulfonyl)-2-azabicyclo[2.1.1]hexane-3-carboxamide Step 3 proceeded according to the following scheme:

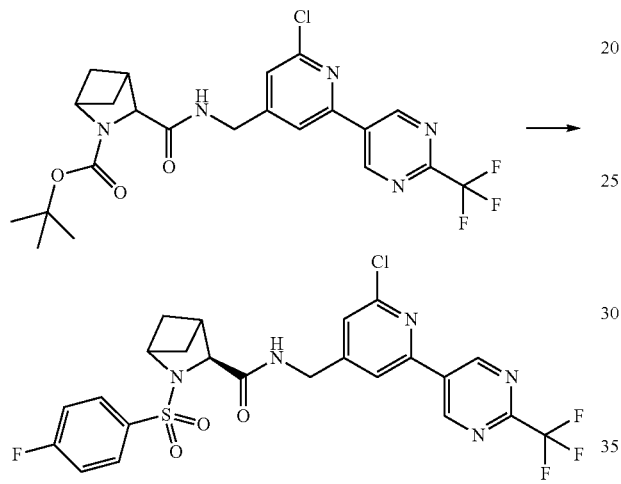

To a solution of tert-butyl 3-(((2-chloro-6-(2-(trifluoromethyl)pyrimidin-5-yl)pyridin-4-yl)methyl)carbamoyl)-2-azabicyclo[2.1.1]hexane-2-carboxylate (118 mg, 0.24 mmol) in dichloromethane (3.5 mL) was added hydrochloric acid (4 mol/L) in 1,4-dioxane (0.9 mL, 4.0 mmol). The reaction mixture was stirred at room temperature for 2 h. The reaction mixture was concentrated in vacuo then taken up in dichloromethane (5.0 mL). 4-Fluorobenzenesulfonyl chloride (51 mg, 0.26 mmol) and triethylamine (0.10 mL, 0.71 mmol) were added and the reaction mixture was stirred at room temperature for 2 h. The reaction mixture was diluted with DCM and water, the layers were separated and the aqueous layer was extracted with DCM (2×). The combined organic layers were dried over sodium sulfate, filtered and concentrated in vacuo. The residue was adsorbed onto silica and purified by flash column chromatography with 0-80% 3:1 iPrOAc:MeOH in heptane to afford the desired compound. The residue was further purified by Chiral SFC to yield the title compound (41.4 mg, 31%) as a white solid. LCMS [M+H$^+$] 556.1; $^1$H NMR (400 MHz, DMSO-d$_6$) δ 9.62 (s, 2H), 8.87 (t, J=6.1 Hz, 1H), 8.19 (d, J=1.2 Hz, 1H), 8.06-7.96 (m, 2H), 7.62 (d, J=1.2 Hz, 1H), 7.56-7.45 (m, 2H), 4.62 (dd, J=16.9, 6.6 Hz, 1H), 4.43 (dd, J=16.8, 5.5 Hz, 1H), 4.28-4.21 (m, 1H), 3.99-3.94 (m, 1H), 2.86-2.78 (m, 1H), 1.95-1.87 (m, 1H), 1.84-1.77 (m, 1H), 1.74-1.68 (m, 1H), 0.47-0.37 (m, 1H).

Example 27: Preparation of (S)—N-((5-fluoro-4-(2-(trifluoromethyl)pyrimidin-5-yl)pyridin-2-yl)methyl)-2-((4-fluorophenyl)sulfonyl)-2-azabicyclo[2.1.1]hexane-3-carboxamide The overall reaction scheme for Example 27 was as follows:

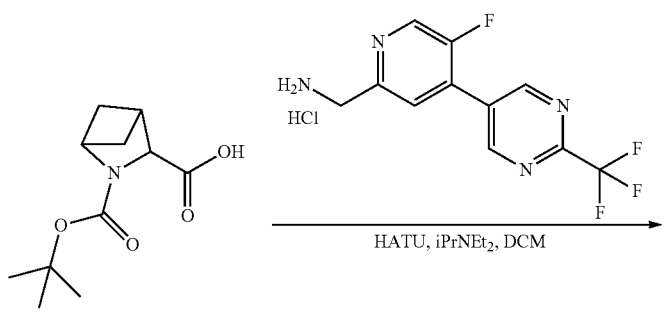

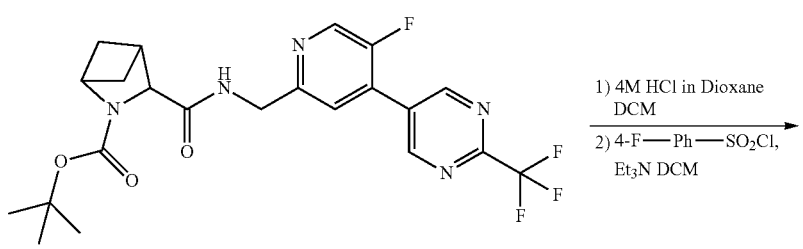

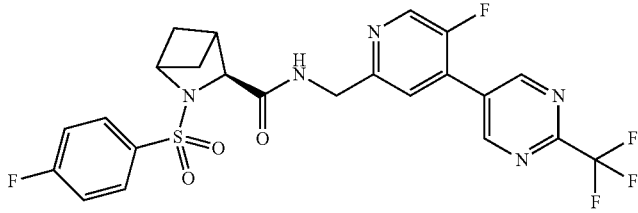

Example 27, Step 1: Preparation of tert-butyl 3-(((5-fluoro-4-(2-(trifluoromethyl)pyrimidin-5-yl)pyridin-2-yl)methyl)carbamoyl)-2-azabicyclo[2.1.1]hexane-2-carboxylate Step 1 proceeded according to the following scheme:

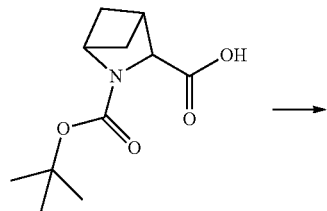

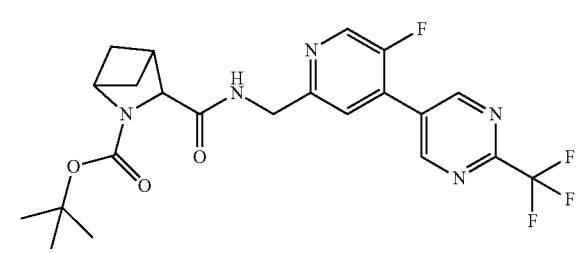

To a round bottomed flask was added 3-tert-butoxycarbonyl-3-azabicyclo[2.1.1]hexane-2-carboxylic acid (67 mg, 0.29 mmol), [5-fluoro-4-[2-(trifluoromethyl)pyrimidin-5-yl]-2-pyridyl]methanamine hydrochloride (109 mg, 0.35 mmol) and HATU (126 mg, 0.32 mmol). Dichloromethane (2.0 mL) was added followed by N,N-diisopropylethylamine (0.18 mL, 1.03 mmol) and the reaction mixture was stirred overnight at room temperature. The reaction was quenched with sat. aq. sodium bicarbonate and extracted with DCM (3×). The combined organic extracts were washed with water (1×), brine (1×) then dried over sodium sulfated, filtered and concentrated in vacuo. The residue was adsorbed onto silica and purified by flash column chromatography with 0-100% iPrOAc in heptane to afford the title compound (141 mg, 99%).

Example 27, Step 2: Preparation of (S)—N-((5-fluoro-4-(2-(trifluoromethyl)pyrimidin-5-yl)pyridin-2-yl)methyl)-2-((4-fluorophenyl)sulfonyl)-2-azabicyclo[2.1.1]hexane-3-carboxamide Step 2 proceeded according to the following scheme:

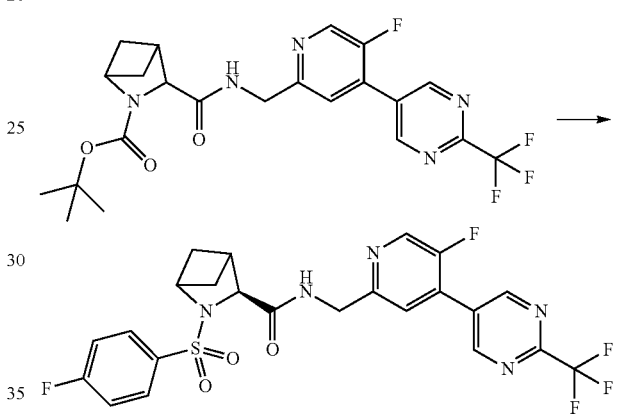

To a solution of tert-butyl 3-(((5-fluoro-4-(2-(trifluoromethyl)pyrimidin-5-yl)pyridin-2-yl)methyl)carbamoyl)-2-azabicyclo[2.1.1]hexane-2-carboxylate (142 mg, 0.30 mmol) in dichloromethane (3.0 mL) was added hydrochloric acid (4 mol/L) in 1,4-dioxane (1.0 mL, 4.0 mmol). The reaction mixture was stirred at room temperature for 2 h. The reaction mixture was concentrated in vacuo then taken up in dichloromethane (3.0 mL). 4-Fluorobenzenesulfonyl chloride (63 mg, 0.32 mmol) and triethylamine (0.12 mL, 0.88 mmol) were added and the reaction mixture was stirred at room temperature for 2 h. The reaction mixture was diluted with DCM and water, the layers were separated and the aqueous layer was extracted with DCM (2×). The combined organic layers were dried over sodium sulfate, filtered and concentrated in vacuo. The residue was purified by chiral SFC to yield the title compound (53.8 mg, 34%) as a white solid. LCMS [M+H$^+$] 540.1; $^1$H NMR (400 MHz, DMSO-d$_6$) δ 9.38 (d, J=1.2 Hz, 2H), 8.80-8.72 (m, 2H), 8.03-7.93 (m, 2H), 7.81 (d, J=6.1 Hz, 1H), 7.54-7.43 (m, 2H), 4.61 (dd, J=16.3, 6.3 Hz, 1H), 4.48 (dd, J=16.2, 5.6 Hz, 1H), 4.25-4.17 (m, 1H), 4.01-3.95 (m, 1H), 2.86-2.78 (m, 1H), 1.91-1.86 (m, 1H), 1.85-1.79 (m, 1H), 1.76-1.67 (m, 1H), 0.51-0.41 (m, 1H).

Example 28: Preparation of (S)—N-((2,2'-bis(trifluoromethyl)-[4,5'-bipyrimidin]-6-yl)methyl)-2-((4-fluorophenyl)sulfonyl)-2-azabicyclo[2.1.1]hexane-3-carboxamide The overall reaction scheme for Example 28 was as follows:

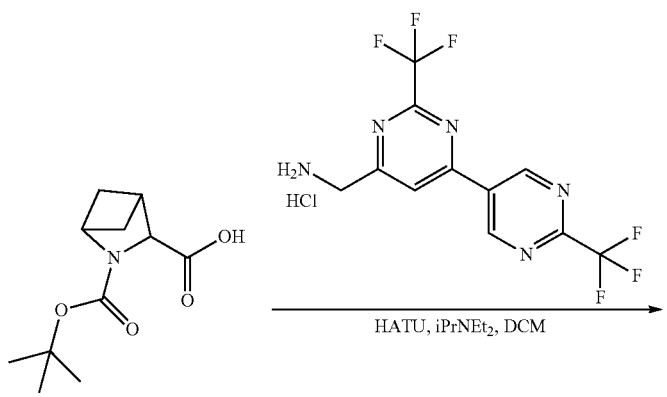

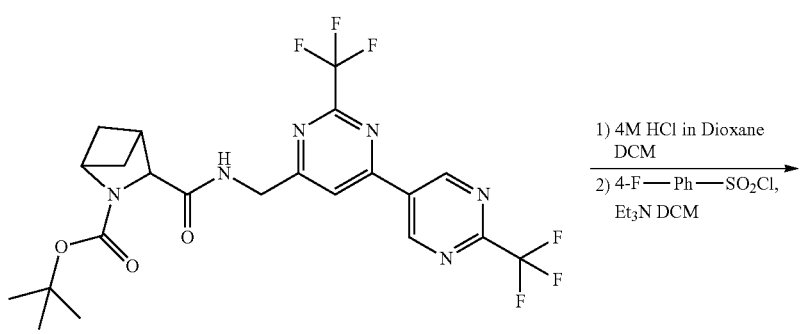

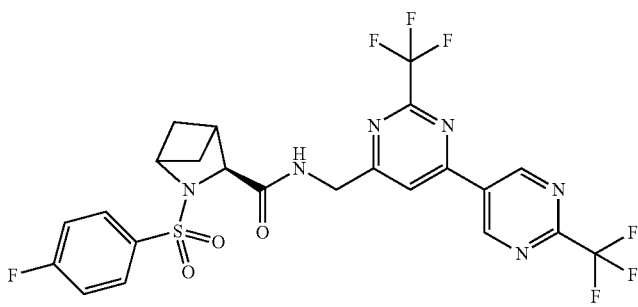

Example 28, Step 1: Preparation of tert-butyl 3-(((2,2'-bis(trifluoromethyl)-[4,5'-bipyrimidin]-6-yl)methyl)carbamoyl)-2-azabicyclo[2.1.1]hexane-2-carboxylate Step 1 proceeded according to the following scheme:

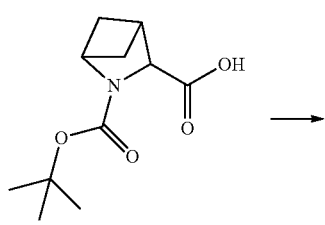

-continued

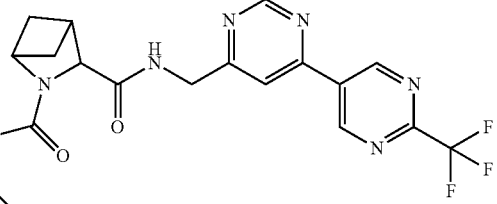

A mixture of 2-[(tert-butoxy)carbonyl]-2-azabicyclo[2.1.1]hexane-3-carboxylic acid (71 mg, 0.31 mmol, 1.00 equiv), [2-(trifluoromethyl)-6-[2-(trifluoromethyl)pyrimidin-5-yl]pyrimidin-4-yl]methanamine (50 mg, 0.15 mmol, 0.49 equiv), N,N-dimethylformamide (10 mL), DIEA (85 mg, 0.65 mmol, 2.10 equiv) and HATU (125 mg, 0.32 mmol, 1.05 equiv) was stirred for 2 h at room temperature. The reaction was poured into water, extracted with ethyl acetate, washed with brine, dried over anhydrous sodium sulfate, and concentrated under vacuum. The residue was purified by a silica gel column by elution with petroleum ether/ethyl acetate (3/1) to afford the title compound (120 mg, 72%) as a white solid. LCMS [M+H$^+$] 533.

Example 28, Step 2: Preparation of (S)—N-((2,2'-bis(trifluoromethyl)-[4,5'-bipyrimidin]-6-yl)methyl)-2-((4-fluorophenyl)sulfonyl)-2-azabicyclo[2.1.1]hexane-3-carboxamide Step 2 proceeded according to the following scheme:

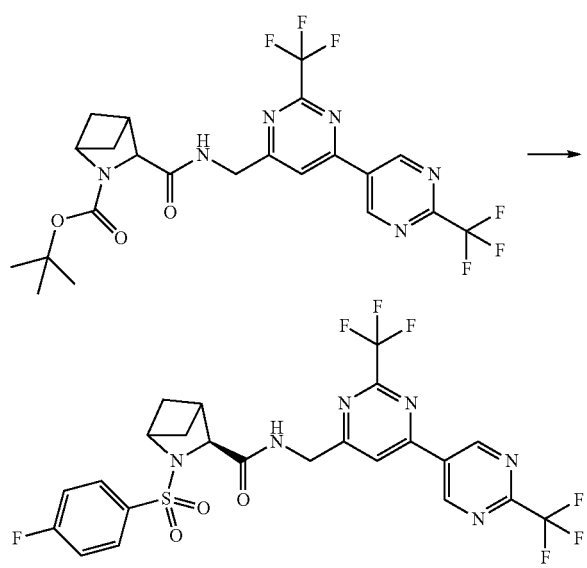

A mixture of tert-butyl 3-([[2-(trifluoromethyl)-6-[2-(trifluoromethyl)pyrimidin-5-yl]pyrimidin-4-yl]methyl]carbamoyl)-2-azabicyclo[2.1.1]hexane-2-carboxylate (110 mg, 0.21 mmol) and HCl in 1,4-dioxane (10 mL, 4 M) was stirred for 1 h at room temperature. The resulting solution was diluted with n-hexane. The solid was collected by filtration and dried under vacuum to afford a yellow solid. The solid was diluted with dichloromethane (10 mL), trimethylamine (63 mg, 0.62 mmol) and 4-fluorobenzene-1-sulfonyl chloride (60 mg, 0.31 mmol) were added and the mixture was stirred for 3 h at room temperature. The resulting mixture was concentrated under vacuum. The residue was purified by a silica gel column eluting with petroleum ether/ethyl acetate (3/1). The partially purified product was further purified by Chiral-Prep-HPLC with the following conditions: Column, Repaired IA, 21.2*150 mm, 5 um; mobile phase, Hex- and ethanol- (hold 30.0% ethanol- in 18 min); Detector, UV 254/220 nm to yield the title compound (37.0 mg 33%) as a white solid. LCMS [M+H$^+$] 591; $^1$H NMR (300 MHz, DMSO-d6) δ 9.73 (s, 2H), 9.01 (m, 1H), 8.51 (s, 1H), 8.05-8.00 (m, 2H), 7.54-7.49 (m, 2H), 4.78-4.57 (m, 2H), 4.25 (d, J=7.2, 1H), 4.01 (s, 1H), 2.83 (d, J=7.5, 1H), 1.91-1.86 (m, 2H), 1.73 (d, J=6.3, 1H), 0.46-0.39 (m, 1H).

IC$_{50}$ Determinations of Exemplified Compounds.

IC$_{50}$ (effective concentration) of compounds on the human and rat TRPA1 channels were determined using a FLIPR Tetra instrument. CHO cells expressing TRPA1 were plated into 384-well plates, incubated overnight at 37° C., and loaded with BD calcium indicator dye for 1 hr at 37° C. followed by 15 minutes. at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 20 minutes at room temperature prior to adding agonist. Following this incubation, ~EC80 concentration of cinnamaldehyde (75 uM for human TRPA1 and 45 uM for rat TRPA1) was added to active the channels and block of cinnamaldehyde induced calcium influx was measured.

IC$_{50}$ values were fit with a standard Hill function, keeping the Hill coefficient (n) fixed to 1.5. Fixing the Hill coefficient will generally reduce variability of the IC$_{50}$ determination. The IC$_{50}$ values were individually examined to make sure the MIN and MAX points were set correctly prior to validation of the results.

The above compounds of Examples 1-6, together with additional compounds made using the above procedures or purchased via commercial sources, are shown in Table 2 below where: "Ex" denotes example number and "LCMS" denotes measured molecular weight.

TABLE 2

| Ex | Structure | Name | LCMS |
| --- | --- | --- | --- |
| 1 | 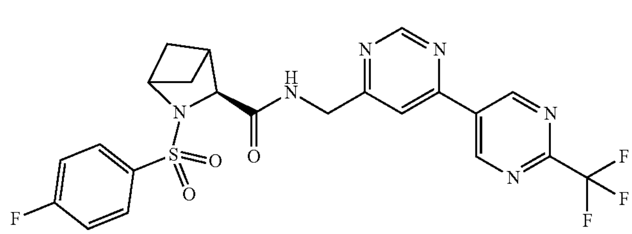 [SMILES: O=C(NCc1cc(-c2cnc(C(F)(F)F)nc2)ncn1)[C@@H]1C2CC(C2)N1S(=O)(=O)c1ccc(F)cc1] | (2S)-3-(4-fluorophenyl)sulfonyl-N-[[6-[2-(trifluoromethyl)pyrimidin-5-yl]pyrimidin-4-yl]methyl]-3-azabicyclo[2.1.1]hexane-2-carboxamide | 4.81, 523.2 |

TABLE 2-continued

| Ex | Structure | Name | LCMS |
|---|---|---|---|
| 2 | 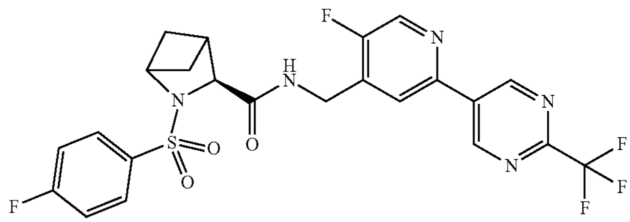 [SMILES: O=C(NCc1cc(-c2cnc(C(F)(F)F)nc2)ncc1F)[C@@H]1C2CC(C2)N1S(=O)(=O)c1ccc(F)cc1] | (2S)-3-(4-fluorophenyl)sulfonyl-N-[[5-fluoro-2-[2-(trifluoromethyl)pyrimidin-5-yl]-4-pyridyl]methyl]-3-azabicyclo[2.1.1]hexane-2-carboxamide | 5.37, 540.1 |
| 3 | 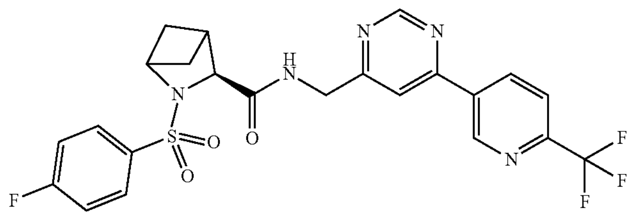 [SMILES: O=C(NCc1cc(-c2ccc(C(F)(F)F)nc2)ncn1)[C@@H]1C2CC(C2)N1S(=O)(=O)c1ccc(F)cc1] | (2S)-3-(4-fluorophenyl)sulfonyl-N-[[6-[6-(trifluoromethyl)-3-pyridyl]pyrimidin-4-yl]methyl]-3-azabicyclo[2.1.1]hexane-2-carboxamide | 5.10, 522.1 |
| 4 | 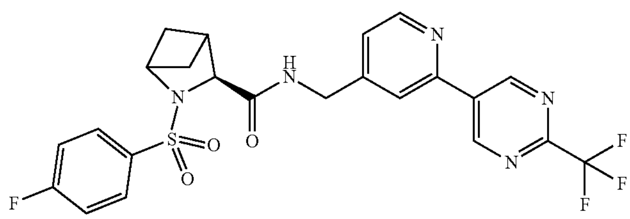 [SMILES: O=C(NCc1ccnc(-c2cnc(C(F)(F)F)nc2)c1)[C@@H]1C2CC(C2)N1S(=O)(=O)c1ccc(F)cc1] | (2S)-3-(4-fluorophenyl)sulfonyl-N-[[2-[2-(trifluoromethyl)pyrimidin-5-yl]-4-pyridyl]methyl]-3-azabicyclo[2.1.1]hexane-2-carboxamide | 5.16, 522.1 |
| 5 | 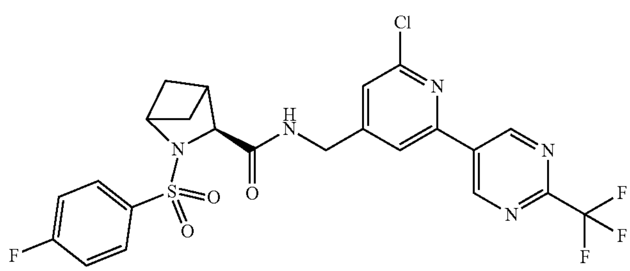 [SMILES: O=C(NCc1cc(Cl)nc(-c2cnc(C(F)(F)F)nc2)c1)[C@@H]1C2CC(C2)N1S(=O)(=O)c1ccc(F)cc1] | (2S)-N-[[2-chloro-6-[2-(trifluoromethyl)pyrimidin-5-yl]-4-pyridyl]methyl]-3-(4-fluorophenyl)sulfonyl-3-azabicyclo[2.1.1]hexane-2-carboxamide | 5.78, 556.1 |
| 6 | 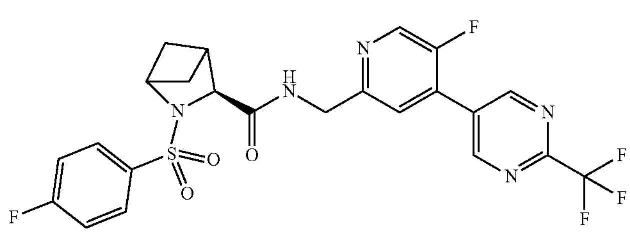 [SMILES: O=C(NCc1cc(-c2cnc(C(F)(F)F)nc2)c(F)cn1)[C@@H]1C2CC(C2)N1S(=O)(=O)c1ccc(F)cc1] | (2S)-3-(4-fluorophenyl)sulfonyl-N-[[5-fluoro-4-[2-(trifluoromethyl)pyrimidin-5-yl]-2-pyridyl]methyl]-3-azabicyclo[2.1.1]hexane-2-carboxamide | 5.23, 540.1 |
| 7 | 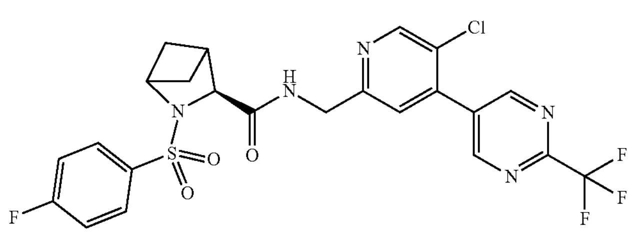 [SMILES: O=C(NCc1cc(-c2cnc(C(F)(F)F)nc2)c(Cl)cn1)[C@@H]1C2CC(C2)N1S(=O)(=O)c1ccc(F)cc1] | (2S)-N-[[5-chloro-4-[2-(trifluoromethyl)pyrimidin-5-yl]-2-pyridyl]methyl]-3-(4-fluorophenyl)sulfonyl-3-azabicyclo[2.1.1]hexane-2-carboxamide | 5.61, 556.1 |

TABLE 2-continued

| Ex | Structure | Name | LCMS |
|---|---|---|---|
| 8 | 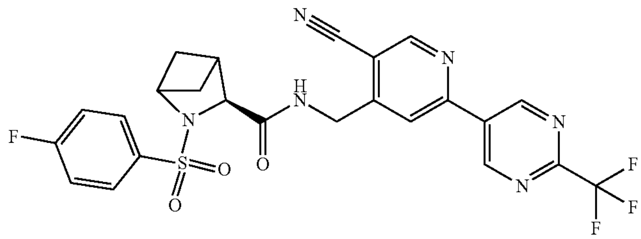 [SMILES: N#Cc1cnc(-c2cnc(C(F)(F)F)nc2)cc1CNC(=O)[C@@H]1C2CC(C2)N1S(=O)(=O)c1ccc(F)cc1] | (2S)-N-[[5-cyano-2-[2-(trifluoromethyl)pyrimidin-5-yl]-4-pyridyl]methyl]-3-(4-fluorophenyl)sulfonyl-3-azabicyclo[2.1.1]hexane-2-carboxamide | 5.62, 547.1 |
| 9 | 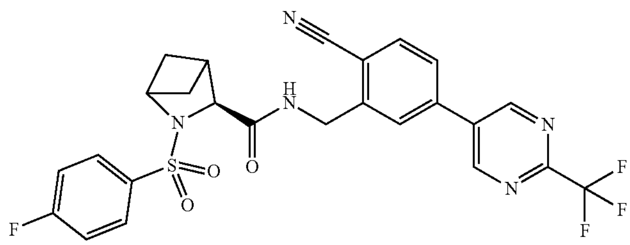 [SMILES: N#Cc1ccc(-c2cnc(C(F)(F)F)nc2)cc1CNC(=O)[C@@H]1C2CC(C2)N1S(=O)(=O)c1ccc(F)cc1] | (2S)-N-[[2-cyano-5-[2-(trifluoromethyl)pyrimidin-5-yl]phenyl]methyl]-3-(4-fluorophenyl)sulfonyl-3-azabicyclo[2.1.1]hexane-2-carboxamide | 5.62, 546.1 |
| 10 | 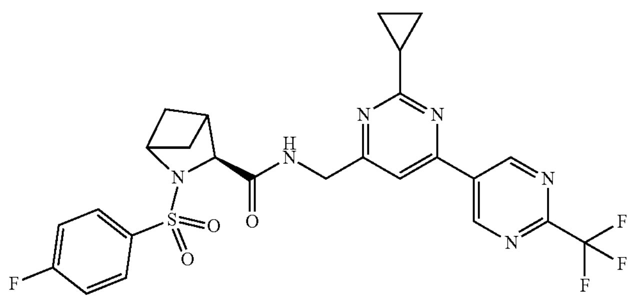 [SMILES: O=C(NCc1cc(-c2cnc(C(F)(F)F)nc2)nc(C2CC2)n1)[C@@H]1C2CC(C2)N1S(=O)(=O)c1ccc(F)cc1] | (2S)-N-[[2-cyclopropyl-6-[2-(trifluoromethyl)pyrimidin-5-yl]pyrimidin-4-yl]methyl]-3-(4-fluorophenyl)sulfonyl-3-azabicyclo[2.1.1]hexane-2-carboxamide | 6.02, 563.1 |
| 11 | 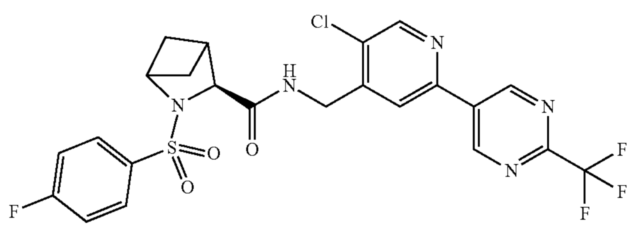 [SMILES: O=C(NCc1cc(-c2cnc(C(F)(F)F)nc2)ncc1Cl)[C@@H]1C2CC(C2)N1S(=O)(=O)c1ccc(F)cc1] | (2S)-N-[[5-chloro-4-[2-(trifluoromethyl)pyrimidin-5-yl]-2-pyridyl]methyl]-3-(4-fluorophenyl)sulfonyl-3-azabicyclo[2.1.1]hexane-2-carboxamide | 5.85, 556.1 |
| 12 | 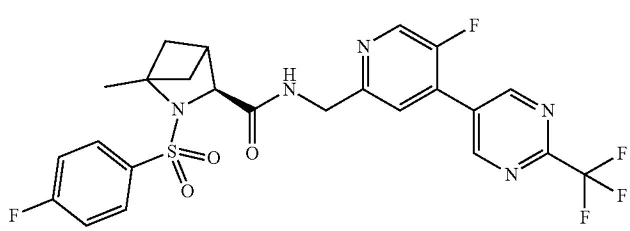 [SMILES: CC12CC(C1)[C@@H](C(=O)NCc1cc(-c3cnc(C(F)(F)F)nc3)c(F)cn1)N2S(=O)(=O)c1ccc(F)cc1] | (2S)-3-(4-fluorophenyl)sulfonyl-N-[[5-fluoro-4-[2-(trifluoromethyl)pyrimidin-5-yl]-2-pyridyl]methyl]-4-methyl-3-azabicyclo[2.1.1]hexane-2-carboxamide | 5.57, 554.1 |
| 13 | 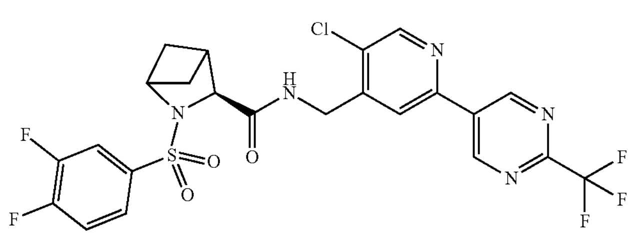 [SMILES: O=C(NCc1cc(-c2cnc(C(F)(F)F)nc2)ncc1Cl)[C@@H]1C2CC(C2)N1S(=O)(=O)c1ccc(F)c(F)c1] | (2S)-N-[[5-chloro-2-[2-(trifluoromethyl)pyrimidin-5-yl]-4-pyridyl]methyl]-3-(3,4-difluorophenyl)sulfonyl-3-azabicyclo[2.1.1]hexane-2-carboxamide | 6.02, 574.1 |

TABLE 2-continued

| Ex | Structure | Name | LCMS |
|----|-----------|------|------|
| 14 | 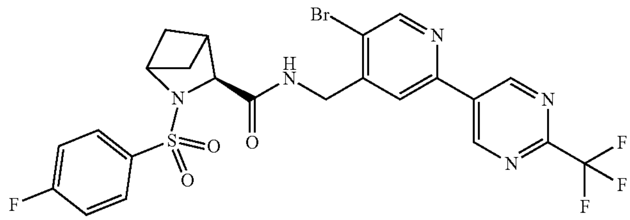 [SMILES: O=C(NCc1cc(-c2cnc(C(F)(F)F)nc2)ncc1Br)[C@@H]1C2CC(C2)N1S(=O)(=O)c1ccc(F)cc1] | (2S)-N-[[5-bromo-2-[2-(trifluoromethyl)pyrimidin-5-yl]-4-pyridyl]methyl]-3-(4-fluorophenyl)sulfonyl-3-azabicyclo[2.1.1]hexane-2-carboxamide | 5.86, 600 |
| 15 | 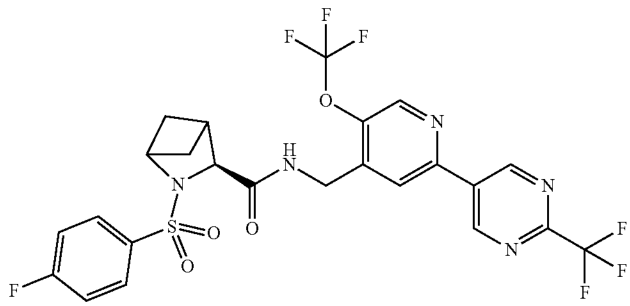 [SMILES: O=C(NCc1cc(-c2cnc(C(F)(F)F)nc2)ncc1OC(F)(F)F)[C@@H]1C2CC(C2)N1S(=O)(=O)c1ccc(F)cc1] | (2S)-3-(4-fluorophenyl)sulfonyl-N-[[5-(trifluoromethoxy)-2-[2-(trifluoromethyl)pyrimidin-5-yl]-4-pyridyl]methyl]-3-azabicyclo[2.1.1]hexane-2-carboxamide | 6.13, 606.1 |
| 16 | 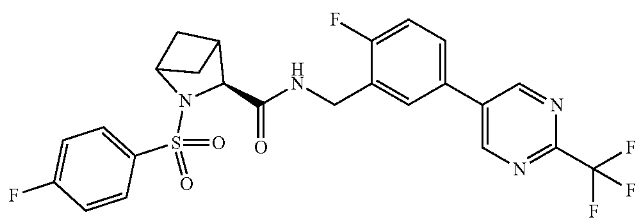 [SMILES: O=C(NCc1cc(-c2cnc(C(F)(F)F)nc2)ccc1F)[C@@H]1C2CC(C2)N1S(=O)(=O)c1ccc(F)cc1] | (2S)-3-(4-fluorophenyl)sulfonyl-N-[[2-fluoro-5-[2-(trifluoromethyl)pyrimidin-5-yl]phenyl]methyl]-3-azabicyclo[2.1.1]hexane-2-carboxamide | 5.64, 539.1 |
| 17 | 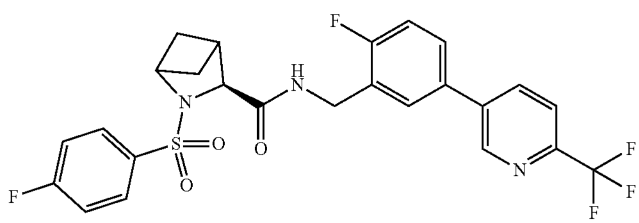 [SMILES: O=C(NCc1cc(-c2ccc(C(F)(F)F)nc2)ccc1F)[C@@H]1C2CC(C2)N1S(=O)(=O)c1ccc(F)cc1] | (2S)-3-(4-fluorophenyl)sulfonyl-N-[[2-fluoro-5-[6-(trifluoromethyl)-3-pyridyl]phenyl]methyl]-3-azabicyclo[2.1.1]hexane-2-carboxamide | 5.81, 538.1 |
| 18 | 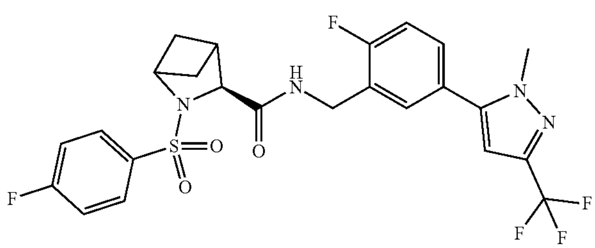 [SMILES: Cn1nc(C(F)(F)F)cc1-c1ccc(F)c(CNC(=O)[C@@H]2C3CC(C3)N2S(=O)(=O)c2ccc(F)cc2)c1] | (2S)-N-[[2-fluoro-5-[2-methyl-5-(trifluoromethyl)pyrazol-3-yl]phenyl]methyl]-3-(4-fluorophenyl)sulfonyl-3-azabicyclo[2.1.1]hexane-2-carboxamide | 5.75, 541.1 |
| 19 | 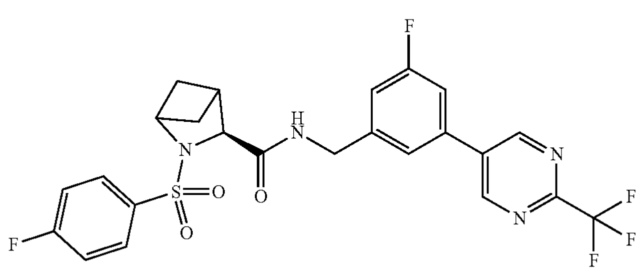 [SMILES: O=C(NCc1cc(F)cc(-c2cnc(C(F)(F)F)nc2)c1)[C@@H]1C2CC(C2)N1S(=O)(=O)c1ccc(F)cc1] | (2S)-3-(4-fluorophenyl)sulfonyl-N-[[3-fluoro-5-[2-(trifluoromethyl)pyrimidin-5-yl]phenyl]methyl]-3-azabicyclo[2.1.1]hexane-2-carboxamide | 5.69, 539.1 |

TABLE 2-continued

| Ex | Structure | Name | LCMS |
|---|---|---|---|
| 20 | 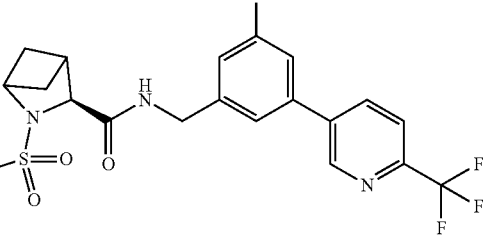 | (2S)-3-(4-fluorophenyl)sulfonyl-N-[[3-fluoro-5-[6-(trifluoromethyl)-3-pyridyl]phenyl]methyl]-3-azabicyclo[2.1.1]hexane-2-carboxamide | 5.85, 538.1 |
| 21 | 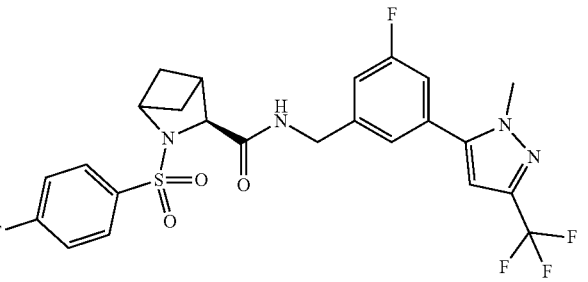 | (2S)-N-[[3-fluoro-5-[2-methyl-5-(trifluoromethyl)pyrazol-3-yl]phenyl]methyl]-3-(4-fluorophenyl)sulfonyl-3-azabicyclo[2.1.1]hexane-2-carboxamide | 5.81, 541.1 |
| 22 | 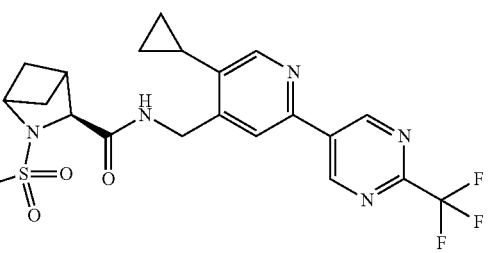 | (2S)-N-[[5-cyclopropyl-2-[2-(trifluoromethyl)pyrimidin-5-yl]-4-pyridyl]methyl]-3-(4-fluorophenyl)sulfonyl-3-azabicyclo[2.1.1]hexane-2-carboxamide | 5.77, 562.1 |
| 23 | 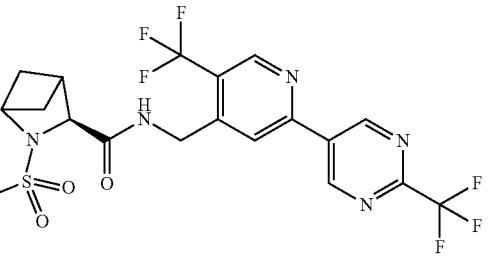 | (2S)-3-(4-fluorophenyl)sulfonyl-N-[[5-(trifluoromethyl)-2-[2-(trifluoromethyl)pyrimidin-5-yl]-4-pyridyl]methyl]-3-azabicyclo[2.1.1]hexane-2-carboxamide | 6.05, 590.1 |
| 24 | 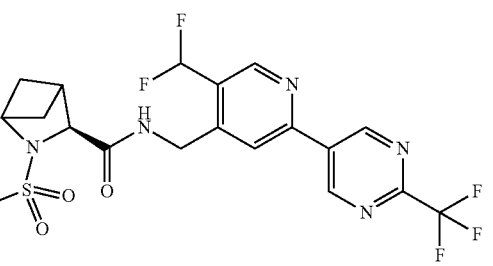 | (2S)-N-[[5-(difluoromethyl)-2-[2-(trifluoromethyl)pyrimidin-5-yl]-4-pyridyl]methyl]-3-(4-fluorophenyl)sulfonyl-3-azabicyclo[2.1.1]hexane-2-carboxamide | 5.72, 572.1 |
| 25 | 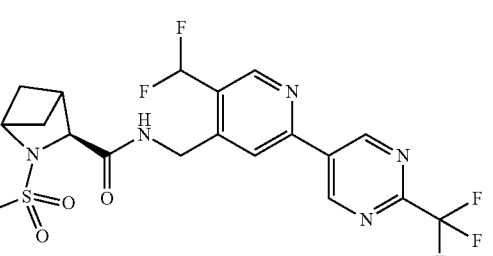 | (2S)-N-[[5-(difluoromethyl)-2-[2-(trifluoromethyl)pyrimidin-5-yl]-4-pyridyl]methyl]-3-(3,4-difluorophenyl)sulfonyl-3-azabicyclo[2.1.1]hexane-2-carboxamide | 5.85, 590.1 |

TABLE 2-continued

| Ex | Structure | Name | LCMS |
|---|---|---|---|
| 26 | 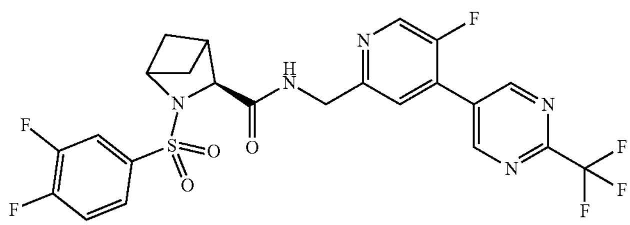 [SMILES: O=C(NCc1cc(-c2cnc(C(F)(F)F)nc2)c(F)cn1)[C@@H]1C2CC(C2)N1S(=O)(=O)c1ccc(F)c(F)c1] | (2S)-3-(3,4-difluorophenyl)sulfonyl-N-[[5-fluoro-4-[2-(trifluoromethyl)pyrimidin-5-yl]-2-pyridyl]methyl]-3-azabicyclo[2.1.1]hexane-2-carboxamide | 5.55, 558.1 |
| 27 | 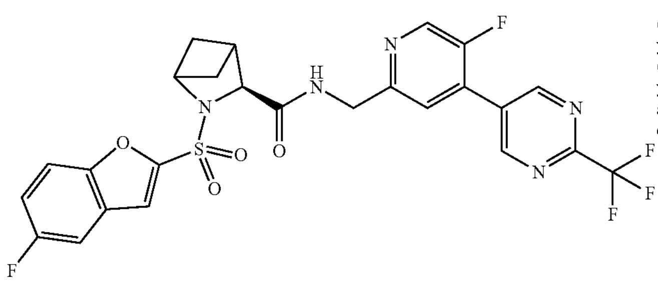 | (2S)-3-(5-fluorobenzofuran-2-yl)sulfonyl-N-[[5-fluoro-4-[2-(trifluoromethyl)pyrimidin-5-yl]-2-pyridyl]methyl]-3-azabicyclo[2.1.1]hexane-2-carboxamide | 5.82, 580.1 |
| 28 | 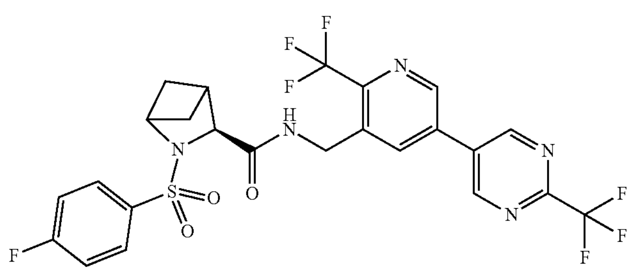 [SMILES: O=C(NCc1cc(-c2cnc(C(F)(F)F)nc2)cnc1C(F)(F)F)[C@@H]1C2CC(C2)N1S(=O)(=O)c1ccc(F)cc1] | (2S)-3-(4-fluorophenyl)sulfonyl-N-[[2-(trifluoromethyl)-5-[2-(trifluoromethyl)pyrimidin-5-yl]-3-pyridyl]methyl]-3-azabicyclo[2.1.1]hexane-2-carboxamide | 5.85, 590.1 |
| 29 | 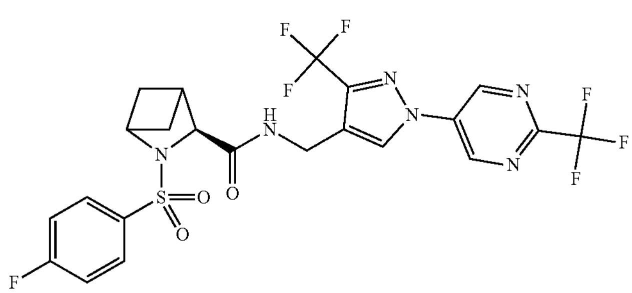 | (2S)-3-(4-fluorophenyl)sulfonyl-N-[[3-(trifluoromethyl)-1-[2-(trifluoromethyl)pyrimidin-5-yl]pyrazol-4-yl]methyl]-3-azabicyclo[2.1.1]hexane-2-carboxamide | 579 |
| 30 | 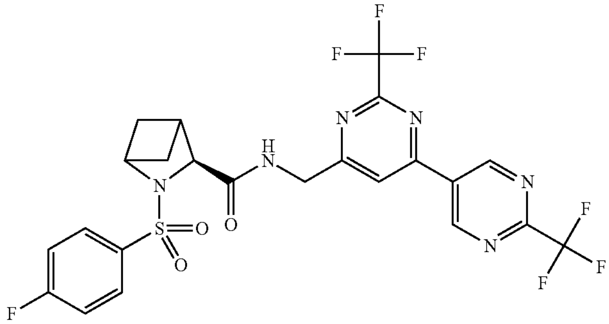 | (2S)-3-(4-fluorophenyl)sulfonyl-N-[[2-(trifluoromethyl)-6-[2-(trifluoromethyl)pyrimidin-5-yl]pyrimidin-4-yl]methyl]-3-azabicyclo[2.1.1]hexane-2-carboxamide | 591 |

TABLE 2-continued

| Ex | Structure | Name | LCMS |
|---|---|---|---|
| 31 | 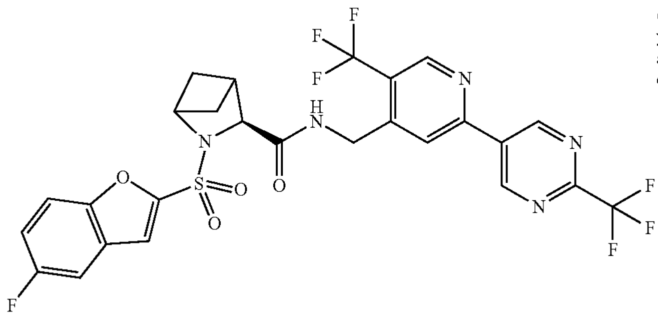 | (2S)-3-(5-fluorobenzofuran-2-yl)sulfonyl-N-[[5-(trifluoromethyl)-2-[2-(trifluoromethyl)pyrimidin-5-yl]-4-pyridyl]methyl]-3-azabicyclo[2.1.1]hexane-2-carboxamide | 6.62, 630.1 |
| 32 | 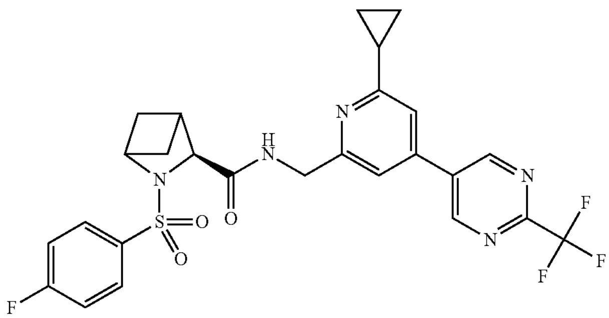 [SMILES: O=C(NCc1cc(-c2cnc(C(F)(F)F)nc2)cc(C2CC2)n1)[C@@H]1C2CC(C2)N1S(=O)(=O)c1ccc(F)cc1] | (2S)-N-[[6-cyclopropyl-4-[2-(trifluoromethyl)pyrimidin-5-yl]-2-pyridyl]methyl]-3-(4-fluorophenyl)sulfonyl-3-azabicyclo[2.1.1]hexane-2-carboxamide | 562 |
| 33 | 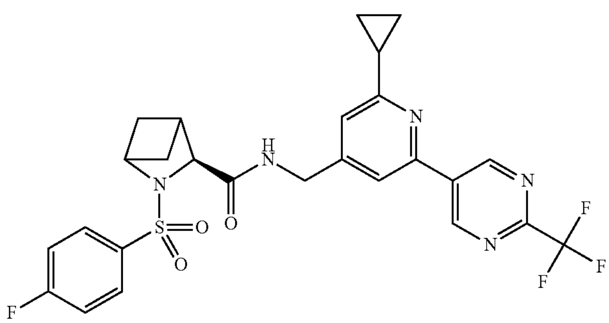 [SMILES: O=C(NCc1cc(-c2cnc(C(F)(F)F)nc2)nc(C2CC2)c1)[C@@H]1C2CC(C2)N1S(=O)(=O)c1ccc(F)cc1] | (2S)-N-[[2-cyclopropyl-6-[2-(trifluoromethyl)pyrimidin-5-yl]-4-pyridyl]methyl]-3-(4-fluorophenyl)sulfonyl-3-azabicyclo[2.1.1]hexane-2-carboxamide | 562 |
| 34 | 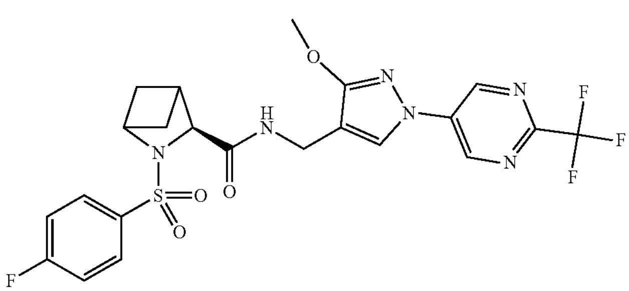 [SMILES: COc1nn(-c2cnc(C(F)(F)F)nc2)cc1CNC(=O)[C@@H]1C2CC(C2)N1S(=O)(=O)c1ccc(F)cc1] | (2S)-3-(4-fluorophenyl)sulfonyl-N-[[3-methoxy-1-[2-(trifluoromethyl)pyrimidin-5-yl]pyrazol-4-yl]methyl]-3-azabicyclo[2.1.1]hexane-2-carboxamide | 541 |

TABLE 2-continued

| Ex | Structure | Name | LCMS |
|---|---|---|---|
| 35 | 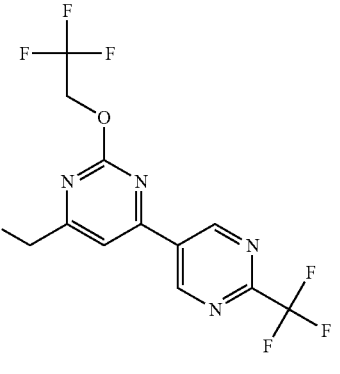 | (2S)-3-(4-fluorophenyl)sulfonyl-N-[[2-(2,2,2-trifluoroethoxy)-6-[2-(trifluoromethyl)pyrimidin-5-yl]pyrimidin-4-yl]methyl]-3-azabicyclo[2.1.1]hexane-2-carboxamide | 621 |

The IC$_{50}$ and proton $^1$H NMR results for the compounds detailed in Table 2 are reported in Table 3 below where "IC$_{50}$" denotes hTRPA1 CHO Ca2+ AUC EVO (IC$_{50}$) in micromolar units.

TABLE 3

| Ex | Structure | IC$_{50}$ | $^1$H NMR |
|---|---|---|---|
| 1 | 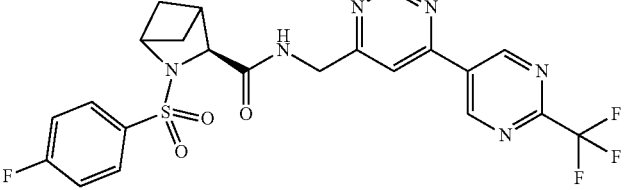 | 0.0429 | $^1$H NMR (400 MHz, DMSO) δ 9.72 (s, 2H), 9.34 (d, J = 1.3 Hz, 1H), 8.92 (t, J = 6.1 Hz, 1H), 8.26 (d, J = 1.4 Hz, 1H), 8.09-7.99 (m, 2H), 7.59-7.46 (m, 2H), 4.66 (dd, J = 17.5, 6.5 Hz, 1H), 4.48 (dd, J = 17.5, 5.5 Hz, 1H), 4.29-4.21 (m, 1H), 4.02 (d, J = 1.2 Hz, 1H), 2.89-2.80 (m, 1H), 1.96-1.82 (m, 2H), 1.77-1.69 (m, 1H), 0.49-0.39 (m, 1H). |
| 2 | 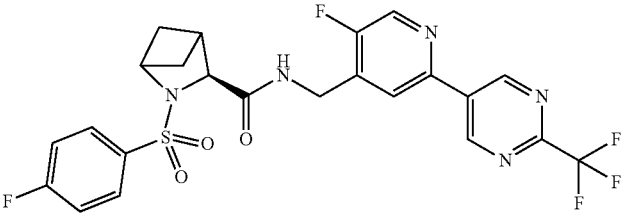 [SMILES: O=C(NCc1cc(-c2cnc(C(F)(F)F)nc2)ncc1F)[C@@H]1C2CC(C2)N1S(=O)(=O)c1ccc(F)cc1] | 0.0113 | $^1$H NMR (400 MHz, DMSO) δ 9.62 (s, 2H), 8.90 (t, J = 6.1 Hz, 1H), 8.78 (d, J = 1.2 Hz, 1H), 8.23 (d, J = 5.7 Hz, 1H), 8.07-7.97 (m, 2H), 7.57-7.46 (m, 2H), 4.68 (dd, J = 16.8, 6.6 Hz, 1H), 4.43 (dd, J = 16.8, 5.3 Hz, 1H), 4.29-4.21 (m, 1H), 4.03-3.96 (m, 1H), 2.86-2.78 (m, 1H), 1.95-1.87 (m, 1H), 1.87-1.78 (m, 1H), 1.76-1.68 (m, 1H). 0.44-0.35 (m, 1H). |
| 3 | 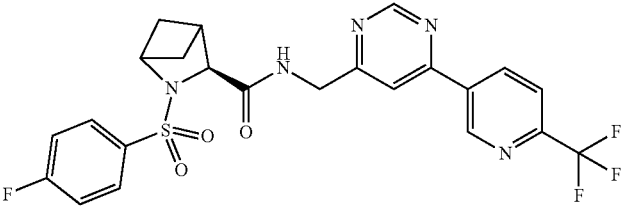 [SMILES: O=C(NCc1cc(-c2ccc(C(F)(F)F)nc2)ncn1)[C@@H]1C2CC(C2)N1S(=O)(=O)c1ccc(F)cc1] | 0.0248 | $^1$H NMR (400 MHz, DMSO) δ 9.50 (d, J = 2.1 Hz, 1H), 9.30 (d, J = 1.2 Hz, 1H), 8.89 (t, J = 6.1 Hz, 1H), 8.81 (dd, J = 8.1, 2.2 Hz, 1H), 8.21 (d, J = 1.3 Hz, 1H), 8.14-8.09 (m, 1H), 8.06-8.00 (m, 2H), 7.57-7.46 (m, 2H), 4.65 (dd, J = 17.4, 6.5 Hz, 1H), 4.47 (dd, J = 17.4, 5.5 Hz, 1H), 4.29-4.21 (m, 1H), 4.04-3.99 (m, 1H), 2.88-2.80 (m, 1H), 1.96-1.81 (m, 2H), 1.77-1.69 (m, 1H), 0.50-0.40 (m, 1H). |

TABLE 3-continued

| Ex | Structure | IC$_{50}$ | $^1$H NMR |
|---|---|---|---|
| 4 | 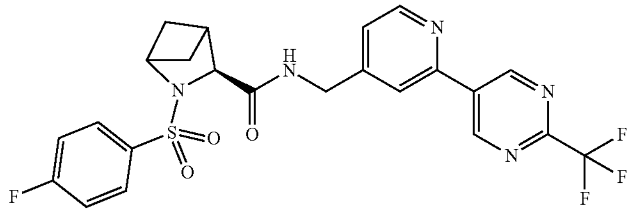 [SMILES: O=C(NCc1ccnc(-c2cnc(C(F)(F)F)nc2)c1)[C@@H]1C2CC(C2)N1S(=O)(=O)c1ccc(F)cc1] | 0.0364 | $^1$H NMR (400 MHz, DMSO) δ 9.67 (s, 2H), 8.82 (t, J = 6.1 Hz, 1H), 8.74 (d, J = 5.1 Hz, 1H), 8.17 (s, 1H), 8.06-7.96 (m, 2H), 7.56-7.44 (m, 3H), 4.60 (dd, J = 16.6, 6.6 Hz, 1H), 4.43 (dd, J = 16.6, 5.6 Hz, 1H), 4.28-4.20 (m, 1H), 4.00-3.94 (m, 1H), 2.87-2.78 (m, 1H), 1.95-1.77 (m, 2H), 1.76-1.68 (m, 1H), 0.48-0.39 (m, 1H). |
| 5 | 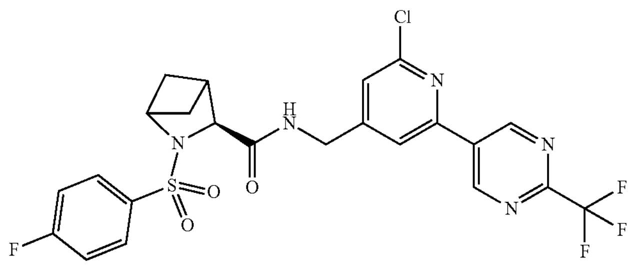 [SMILES: O=C(NCc1cc(Cl)nc(-c2cnc(C(F)(F)F)nc2)c1)[C@@H]1C2CC(C2)N1S(=O)(=O)c1ccc(F)cc1] | 0.00464 | $^1$H NMR (400 MHz, DMSO) δ 9.62 (s, 2H), 8.87 (t, J = 6.1 Hz, 1H), 8.19 (d, J = 1.2 Hz, 1H), 8.06-7.96 (m, 2H), 7.62 (d, J = 1.2 Hz, 1H), 7.56-7.45 (m, 2H), 4.62 (dd, J = 16.9, 6.6 Hz, 1H), 4.43 (dd, J = 16.9, 5.5 Hz, 1H), 4.28-4.21 (m, 1H), 3.99-3.94 (m, 1H), 2.86-2.78 (m, 1H), 1.95-1.87 (m, 1H), 1.84-1.77 (m, 1H), 1.75-1.69 (m, 1H), 0.47-0.37 (m, 1H). |
| 6 | 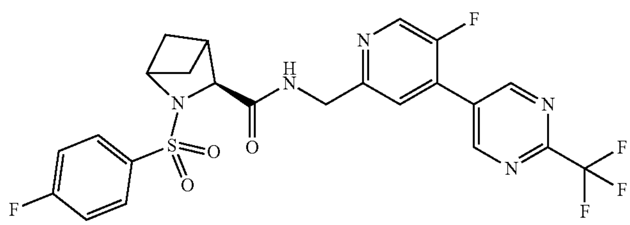 [SMILES: O=C(NCc1cc(-c2cnc(C(F)(F)F)nc2)c(F)cn1)[C@@H]1C2CC(C2)N1S(=O)(=O)c1ccc(F)cc1] | 0.0168 | $^1$H NMR (400 MHz, DMSO) δ 9.38 (d, J = 1.2 Hz, 2H), 8.80-8.72 (m, 2H), 8.03-7.93 (m, 2H), 7.81 (d, J = 6.1 Hz, 1H), 7.54-7.43 (m, 2H), 4.61 (dd, J = 16.3, 6.3 Hz, 1H), 4.48 (dd, J = 16.2, 5.6 Hz, 1H), 4.25-4.17 (m, 1H), 4.01-3.95 (m, 1H), 2.86-2.78 (m, 1H), 1.91-1.86 (m, 1H), 1.85-1.79 (m, 1H), 1.76-1.67 (m, 1H), 0.51-0.41 (m, 1H). |
| 7 | 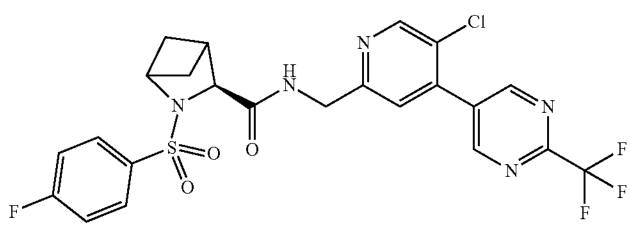 [SMILES: O=C(NCc1cc(-c2cnc(C(F)(F)F)nc2)c(Cl)cn1)[C@@H]1C2CC(C2)N1S(=O)(=O)c1ccc(F)cc1] | 0.0208 | $^1$H NMR (400 MHz, DMSO-d6) δ 9.30 (s, 2H), 8.81 (s, 1H), 8.74 (t, J = 6.0 Hz, 1H), 8.00-7.90 (m, 2H), 7.68 (s, 1H), 7.53-7.41 (m, 2H), 4.59 (dd, J = 16.5, 6.3 Hz, 1H), 4.48 (dd, J = 16.5, 5.7 Hz, 1H), 4.23-4.15 (m, 1H), 3.96 (s, 1H), 2.85-2.77 (m, 1H), 1.90-1.84 (m, 1H), 1.84-1.77 (m, 1H), 1.75-1.67 (m, 1H), 0.51-0.41 (m, 1H). |
| 8 | 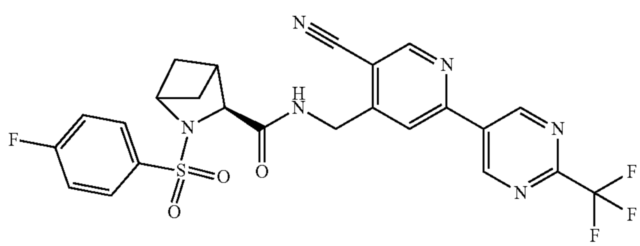 [SMILES: N#Cc1cnc(-c2cnc(C(F)(F)F)nc2)cc1CNC(=O)[C@@H]1C2CC(C2)N1S(=O)(=O)c1ccc(F)cc1] | 0.016 | $^1$H NMR (400 MHz, DMSO-d6) δ 9.70 (s, 2H), 9.22 (s, 1H), 9.02 (t, J = 5.9 Hz, 1H), 8.32 (s, 1H), 8.07-7.97 (m, 2H), 7.57-7.46 (m, 2H), 4.78 (dd, J = 17.0, 6.5 Hz, 1H), 4.54 (dd, J = 17.0, 5.2 Hz, 1H), 4.29-4.21 (m, 1H), 4.00 (s, 1H), 2.88-2.80 (m, 1H), 1.96-1.88 (m, 1H), 1.88-1.78 (m, 1H), 1.76-1.68 (m, 1H), 0.46-0.36 (m, 1H) |
| 9 | 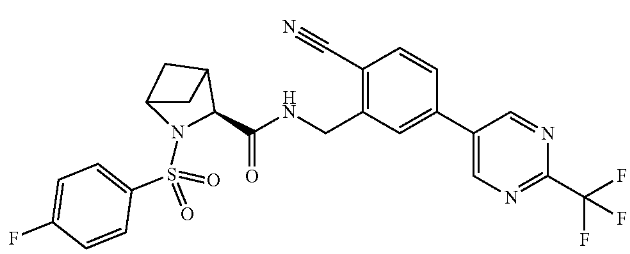 [SMILES: N#Cc1ccc(-c2cnc(C(F)(F)F)nc2)cc1CNC(=O)[C@@H]1C2CC(C2)N1S(=O)(=O)c1ccc(F)cc1] | 0.0171 | $^1$H NMR (400 MHz, DMSO-d6) δ 9.45 (s, 2H), 8.89 (t, J = 5.9 Hz, 1H), 8.12-7.93 (m, 5H), 7.54-7.43 (m, 2H), 4.74 (dd, J = 16.1, 6.5 Hz, 1H), 4.52 (dd, J = 16.0, 5.3 Hz, 1H), 4.26-4.19 (m, 1H), 3.97 (s, 1H), 2.86-2.78 (m, 1H), 1.92-1.87 (m, 1H), 1.85-1.79 (m, 1H), 1.75-1.67 (m, 1H), 0.47-0.37 (m, 1H). |

TABLE 3-continued

| Ex | Structure | IC$_{50}$ | $^1$H NMR |
|---|---|---|---|
| 10 | 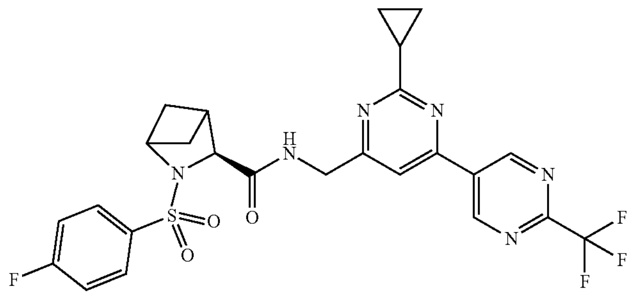 [SMILES: O=C(NCc1cc(-c2cnc(C(F)(F)F)nc2)nc(C2CC2)n1)[C@@H]1C2CC(C2)N1S(=O)(=O)c1ccc(F)cc1] | 0.00215 | $^1$H NMR (400 MHz, DMSO-d6) δ 9.68 (s, 2H), 8.84 (t, J = 6.0 Hz, 1H), 8.06-7.99 (m, 2H), 7.98 (s, 1H), 7.57-7.46 (m, 2H), 4.56 (dd, J = 17.4, 6.4 Hz, 1H), 4.41 (dd, J = 17.4, 5.5 Hz, 1H), 4.28-4.21 (m, 1H), 4.00 (s, 1H), 2.88-2.80 (m, 1H), 2.37-2.26 (m, 1H), 1.96-1.82 (m, 2H), 1.77-1.69 (m, 1H), 1.21-1.07 (m, 4H), 0.48-0.38 (m, 1H). |
| 11 | 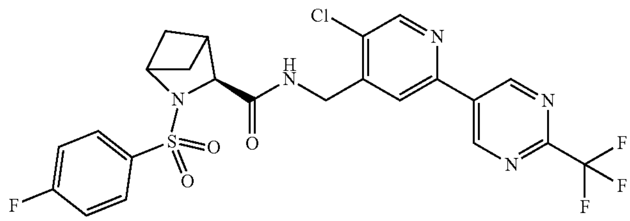 [SMILES: O=C(NCc1cc(-c2cnc(C(F)(F)F)nc2)ncc1Cl)[C@@H]1C2CC(C2)N1S(=O)(=O)c1ccc(F)cc1] | 0.00608 | $^1$H NMR (400 MHz, DMSO-d6) δ 9.65 (s, 2H), 8.92 (t, J = 6.0 Hz, 1H), 8.85 (s, 1H), 8.21 (s, 1H), 8.09-7.99 (m, 2H), 7.57-7.46 (m, 2H), 4.69 (dd, J = 17.4, 6.8 Hz, 1H), 4.39 (dd, J = 17.4, 5.2 Hz, 1H), 4.30-4.22 (m, 1H), 4.02 (s, 1H), 2.87-2.81 (m, 1H), 1.96-1.89 (m, 1H), 1.88-1.79 (m, 1H), 1.77-1.69 (m, 1H), 0.46-0.37 (m, 1H) |
| 12 | 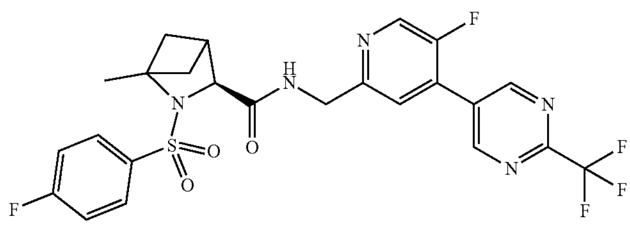 [SMILES: CC12CC(C1)[C@@H](C(=O)NCc1cc(-c3cnc(C(F)(F)F)nc3)c(F)cn1)N2S(=O)(=O)c1ccc(F)cc1] | 0.0902 | $^1$H NMR (400 MHz, DMSO-d6) δ 9.37-9.32 (m, 2H), 8.83 (t, J = 6.1 Hz, 1H), 8.76 (d, J = 2.0 Hz, 1H), 8.06-7.97 (m, 2H), 7.80 (d, J = 6.1 Hz, 1H), 7.51-7.42 (m, 2H), 4.60 (dd, J = 16.3, 6.4 Hz, 1H), 4.50 (dd, J = 16.2, 5.7 Hz, 1H), 4.24 (s, 1H), 2.78-2.71 (m, 1H), 2.00-1.91 (m, 1H), 1.70-1.62 (m, 2H), 1.47 (s, 3H), 0.87-0.77 (m, 1H) |
| 13 | 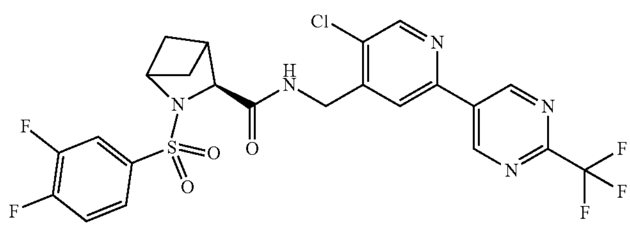 [SMILES: O=C(NCc1cc(-c2cnc(C(F)(F)F)nc2)ncc1Cl)[C@@H]1C2CC(C2)N1S(=O)(=O)c1ccc(F)c(F)c1] | 0.00155 | $^1$H NMR (400 MHz, DMSO-d6) δ 9.65 (s, 2H), 8.92 (t, J = 6.0 Hz, 1H), 8.84 (s, 1H), 8.20 (s, 1H), 8.18-8.11 (m, 1H), 7.89-7.83 (m, 1H), 7.80-7.72 (m, 1H), 4.67 (dd, J = 17.3, 6.8 Hz, 1H), 4.41 (dd, J = 17.3, 5.3 Hz, 1H), 4.34-4.27 (m, 1H), 4.11 (s, 1H), 2.90-2.82 (m, 1H), 1.97-1.91 (m, 1H), 1.88-1.82 (m, 1H), 1.79-1.74 (m, 1H), 0.54-0.44 (m, 1H). |
| 14 | 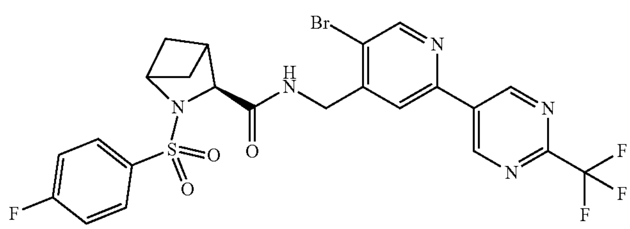 [SMILES: O=C(NCc1cc(-c2cnc(C(F)(F)F)nc2)ncc1Br)[C@@H]1C2CC(C2)N1S(=O)(=O)c1ccc(F)cc1] | 0.00382 | $^1$H NMR (400 MHz, DMSO-d6) δ 9.65 (s, 2H), 8.97-8.91 (m, 2H), 8.18 (s, 1H), 8.08-8.00 (m, 2H), 7.56-7.47 (m, 2H), 4.63 (dd, J = 17.3, 6.9 Hz, 1H), 4.33 (dd, J = 17.3, 5.2 Hz, 1H), 4.28-4.23 (m, 1H), 4.03 (s, 1H), 2.88-2.80 (m, 1H), 1.97-1.90 (m, 1H), 1.89-1.79 (m, 1H), 1.76-1.70 (m, 1H), 0.47-0.37 (m, 1H) |
| 15 | 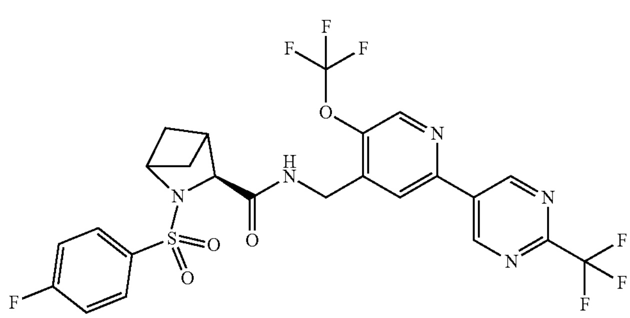 [SMILES: O=C(NCc1cc(-c2cnc(C(F)(F)F)nc2)ncc1OC(F)(F)F)[C@@H]1C2CC(C2)N1S(=O)(=O)c1ccc(F)cc1] | 0.00277 | $^1$H NMR (400 MHz, DMSO-d6) δ 9.65 (s, 2H), 8.92 (t, J = 6.1 Hz, 1H), 8.89-8.86 (m, 1H), 8.29 (s, 1H), 8.07-7.99 (m, 2H), 7.56-7.46 (m, 2H), 4.71 (dd, J = 17.2, 6.7 Hz, 1H), 4.43 (dd, J = 17.2, 5.3 Hz, 1H), 4.29-4.20 (m, 1H), 4.00 (s, 1H), 2.86-2.79 (m, 1H), 1.95-1.88 (m, 1H), 1.87-1.77 (m, 1H), 1.76-1.71 (m, 1H), 0.46-0.36 (m, 1H). |

TABLE 3-continued

| Ex | Structure | IC$_{50}$ | $^1$H NMR |
|---|---|---|---|
| 16 | 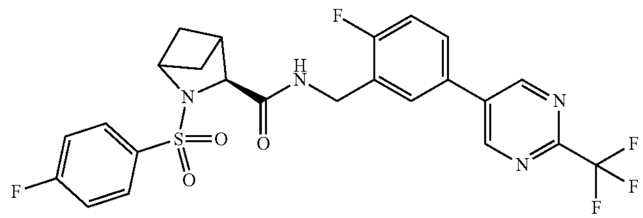 [SMILES: O=C(NCc1cc(-c2cnc(C(F)(F)F)nc2)ccc1F)[C@@H]1C2CC(C2)N1S(=O)(=O)c1ccc(F)cc1] | 0.00989 | $^1$H NMR (400 MHz, DMSO-d6) δ 9.37 (s, 2H), 8.69 (t, J = 6.0 Hz, 1H), 8.01-7.95 (m, 2H), 7.95-7.87 (m, 2H), 7.54-7.40 (m, 3H), 4.59 (dd, J = 15.9, 6.6 Hz, 1H), 4.40 (dd, J = 15.8, 5.4 Hz, 1H), 4.25-4.17 (m, 1H), 3.97 (s, 1H), 2.84-2.76 (m, 1H), 1.91-1.86 (m, 1H), 1.84-1.78 (m, 1H), 1.74-1.67 (m, 1H), 0.48-0.38 (m, 1H). |
| 17 | 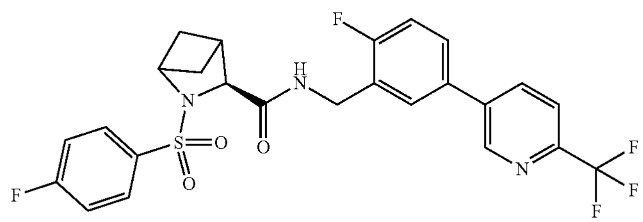 [SMILES: O=C(NCc1cc(-c2ccc(C(F)(F)F)nc2)ccc1F)[C@@H]1C2CC(C2)N1S(=O)(=O)c1ccc(F)cc1] | 0.00606 | $^1$H NMR (400 MHz, DMSO-d6) δ 9.08 (d, J = 2.3 Hz, 1H), 8.66 (t, J = 6.0 Hz, 1H), 8.34 (dd, J = 8.2, 2.3 Hz, 1H), 8.02-7.92 (m, 3H), 7.84 (dd, J = 7.2, 2.5 Hz, 1H), 7.83-7.77 (m, 1H), 7.51-7.44 (m, 2H), 7.42-7.34 (m, 1H), 4.56 (dd, J = 15.9, 6.5 Hz, 1H), 4.41 (dd, J = 15.9, 5.5 Hz, 1H), 4.25-4.17 (m, 1H), 3.96 (s, 1H), 2.84-2.75 (m, 1H), 1.91-1.86 (m, 1H), 1.83-1.77 (m, 1H), 1.75-1.67 (m, 1H), 0.50-0.40 (m, 1H). |
| 18 | 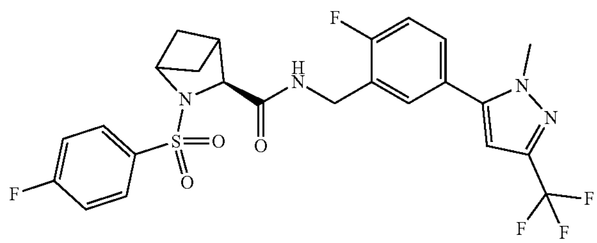 [SMILES: Cn1nc(C(F)(F)F)cc1-c1ccc(F)c(CNC(=O)[C@@H]2C3CC(C3)N2S(=O)(=O)c2ccc(F)cc2)c1] | 0.0157 | $^1$H NMR (400 MHz, DMSO-d6) δ 8.63 (t, J = 6.0 Hz, 1H), 7.99-7.89 (m, 2H), 7.61 (dd, J = 7.1, 2.3 Hz, 1H), 7.59-7.54 (m, 1H), 7.51-7.44 (m, 2H), 7.42-7.32 (m, 1H), 6.88 (s, 1H), 4.53 (dd, J = 15.8, 6.5 Hz, 1H), 4.39 (dd, J = 15.8, 5.6 Hz, 1H), 4.24-4.16 (m, 1H), 3.95 (d, J = 1.0 Hz, 1H), 3.93 (s, 3H), 2.82-2.74 (m, 1H), 1.90-1.83 (m, 1H), 1.81-1.74 (m, 1H), 1.72-1.67 (m, 1H), 0.48-0.38 (m, 1H). |
| 19 | 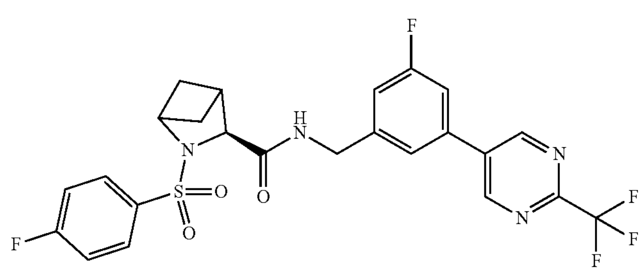 [SMILES: O=C(NCc1cc(F)cc(-c2cnc(C(F)(F)F)nc2)c1)[C@@H]1C2CC(C2)N1S(=O)(=O)c1ccc(F)cc1] | 0.00897 | $^1$H NMR (400 MHz, DMSO-d6) δ 9.43 (s, 2H), 8.73 (t, J = 6.1 Hz, 1H), 8.02-7.94 (m, 2H), 7.77-7.68 (m, 2H), 7.54-7.44 (m, 2H), 7.36-7.27 (m, 1H), 4.55 (dd, J = 16.0, 6.5 Hz, 1H), 4.41 (dd, J = 15.9, 5.8 Hz, 1H), 4.26-4.18 (m, 1H), 3.95 (s, 1H), 2.85-2.76 (m, 1H), 1.91-1.86 (m, 1H), 1.84-1.77 (m, 1H), 1.75-1.67 (m, 1H), 0.49-0.39 (m, 1H). |
| 20 | 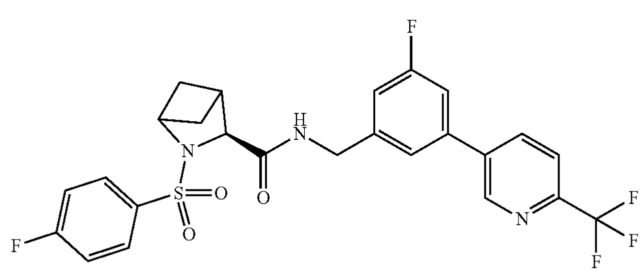 [SMILES: O=C(NCc1cc(F)cc(-c2ccc(C(F)(F)F)nc2)c1)[C@@H]1C2CC(C2)N1S(=O)(=O)c1ccc(F)cc1] | 0.00611 | $^1$H NMR (400 MHz, DMSO-d6) δ 9.13 (d, J = 2.2 Hz, 1H), 8.71 (t, J = 6.1 Hz, 1H), 8.41 (dd, J = 8.1, 2.3 Hz, 1H), 8.04-7.93 (m, 3H), 7.67-7.58 (m, 2H), 7.53-7.44 (m, 2H), 7.30-7.22 (m, 1H), 4.53 (dd, J = 15.8, 6.5 Hz, 1H), 4.41 (dd, J = 15.9, 5.7 Hz, 1H), 4.25-4.18 (m, 1H), 3.95 (s, 1H), 2.84-2.76 (m, 1H), 1.92-1.85 (m, 1H), 1.85-1.75 (m, 1H), 1.75-1.67 (m, 1H), 0.50-0.40 (m, 1H). |

TABLE 3-continued

| Ex | Structure | IC$_{50}$ | $^1$H NMR |
|---|---|---|---|
| 21 | 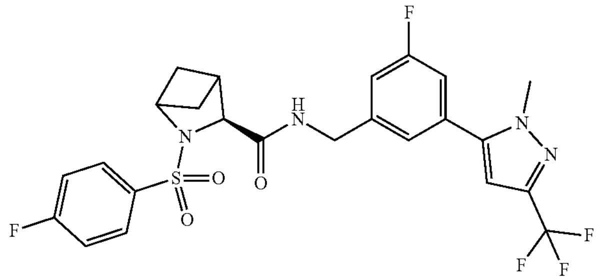 [SMILES: Cn1nc(C(F)(F)F)cc1-c1cc(F)cc(CNC(=O)[C@@H]2C3CC(C3)N2S(=O)(=O)c2ccc(F)cc2)c1] | 0.0276 | $^1$H NMR (400 MHz, DMSO-d6) δ 8.68 (t, J = 6.2 Hz, 1H), 8.00-7.92 (m, 2H), 7.54-7.44 (m, 2H), 7.44-7.36 (m, 2H), 7.31-7.22 (m, 1H), 6.96 (s, 1H), 4.50 (dd, J = 16.0, 6.4 Hz, 1H), 4.39 (dd, J = 15.9, 5.9 Hz, 1H), 4.25-4.17 (m, 1H), 3.96 (s, 3H), 3.94 (s, 1H), 2.83-2.75 (m, 1H), 1.91-1.84 (m, 1H), 1.81-1.74 (m, 1H), 1.72-1.67 (m, 1H), 0.48-0.39 (m, 1H). |
| 22 | 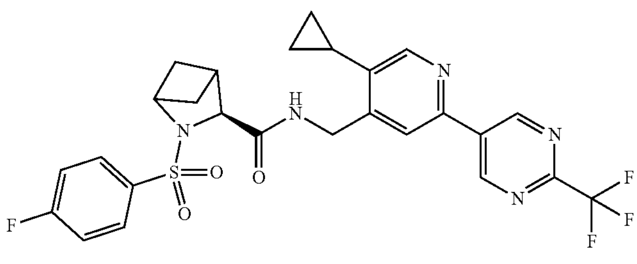 [SMILES: O=C(NCc1cc(-c2cnc(C(F)(F)F)nc2)ncc1C1CC1)[C@@H]1C2CC(C2)N1S(=O)(=O)c1ccc(F)cc1] | 0.0163 | $^1$H NMR (400 MHz, DMSO-d6) δ 9.63 (s, 2H), 8.82 (t, J = 6.0 Hz, 1H), 8.45 (s, 1H), 8.09 (s, 1H), 8.08-7.98 (m, 2H), 7.56-7.46 (m, 2H), 4.79 (dd, J = 16.9, 6.8 Hz, 1H), 4.51 (dd, J = 16.9, 5.3 Hz, 1H), 4.29-4.21 (m, 1H), 4.01 (s, 1H), 2.87-2.79 (m, 1H), 2.03 (tt, J = 8.3, 5.4 Hz, 1H), 1.96-1.89 (m, 1H), 1.90-1.81 (m, 1H), 1.77-1.69 (m, 1H), 1.10-1.02 (m, 2H), 0.91-0.80 (m, 2H), 0.47-0.38 (m, 1H). |
| 23 | 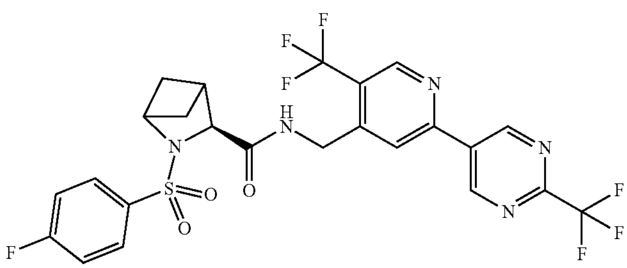 [SMILES: O=C(NCc1cc(-c2cnc(C(F)(F)F)nc2)ncc1C(F)(F)F)[C@@H]1C2CC(C2)N1S(=O)(=O)c1ccc(F)cc1] | 0.00261 | $^1$H NMR (400 MHz, DMSO-d6) δ 9.72 (s, 2H), 9.12 (s, 1H), 9.01 (t, J = 6.1 Hz, 1H), 8.37 (s, 1H), 8.09-7.99 (m, 2H), 7.57-7.48 (m, 2H), 4.83 (dd, J = 17.3, 6.8 Hz, 1H), 4.50 (dd, J = 17.1, 5.1 Hz, 1H), 4.31-4.23 (m, 1H), 4.03 (s, 1H), 2.87-2.80 (m, 1H), 1.97-1.90 (m, 1H), 1.82 (dd, J = 10.6, 8.0 Hz, 1H), 1.77-1.69 (m, 1H), 0.41 (dd, J = 10.6, 8.3 Hz, 1H). |
| 24 | 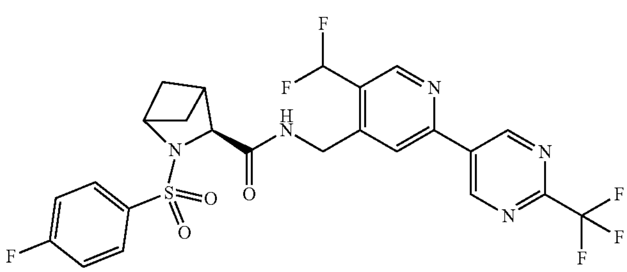 [SMILES: O=C(NCc1cc(-c2cnc(C(F)(F)F)nc2)ncc1C(F)F)[C@@H]1C2CC(C2)N1S(=O)(=O)c1ccc(F)cc1] | 0.00992 | $^1$H NMR (400 MHz, DMSO-d6) δ 9.70 (s, 2H), 8.98-8.90 (m, 2H), 8.28 (s, 1H), 8.08-7.98 (m, 2H), 7.61-7.29 (m, 3H), 4.82 (dd, J = 17.2, 6.8 Hz, 1H), 4.53 (dd, J = 17.1, 5.2 Hz, 1H), 4.29-4.22 (m, 1H), 4.01 (s, 1H), 2.87-2.79 (m, 1H), 1.96-1.88 (m, 1H), 1.82 (dd, J = 10.7, 7.9 Hz, 1H), 1.77-1.69 (m, 1H), 0.41 (dd, J = 10.7, 8.1 Hz, 1H). |
| 25 | 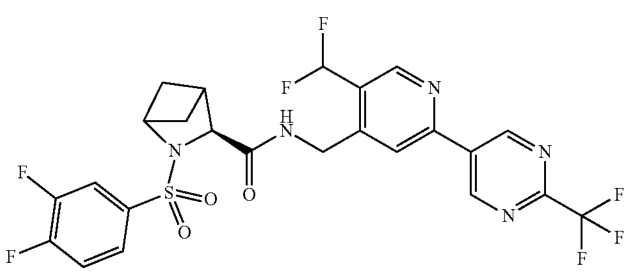 [SMILES: O=C(NCc1cc(-c2cnc(C(F)(F)F)nc2)ncc1C(F)F)[C@@H]1C2CC(C2)N1S(=O)(=O)c1ccc(F)c(F)c1] | 0.00901 | $^1$H NMR (400 MHz, DMSO-d6) δ 9.69 (s, 2H), 8.98-8.87 (m, 2H), 8.27 (s, 1H), 8.18-8.09 (m, 1H), 7.88-7.82 (m, 1H), 7.80-7.71 (m, 1H), 7.45 (t, J = 53.7 Hz, 1H), 4.81 (dd, J = 17.1, 6.7 Hz, 1H), 4.54 (dd, J = 17.2, 5.2 Hz, 1H), 4.34-4.27 (m, 1H), 4.10 (s, 1H), 2.89-2.81 (m, 1H), 1.97-1.90 (m, 1H), 1.83 (dd, J = 10.5, 7.9 Hz, 1H), 1.79-1.74 (m, 1H), 0.49 (dd, J = 10.7, 8.3 Hz, 1H). |

TABLE 3-continued

| Ex | Structure | IC$_{50}$ | $^1$H NMR |
|---|---|---|---|
| 26 | 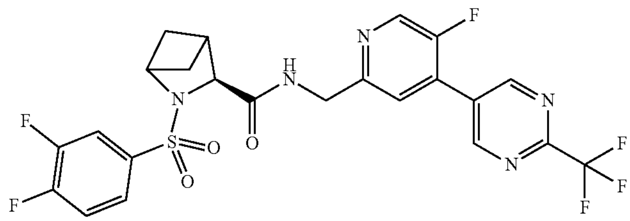 [SMILES: O=C(NCc1cc(-c2cnc(C(F)(F)F)nc2)c(F)cn1)[C@@H]1C2CC(C2)N1S(=O)(=O)c1ccc(F)c(F)c1] | 0.0106 | $^1$H NMR (400 MHz, DMSO-d6) δ 9.38 (s, 2H), 8.82-8.74 (m, 2H), 8.12-8.03 (m, 1H), 7.85-7.69 (m, 3H), 4.60 (dd, J = 16.3, 6.3 Hz, 1H), 4.48 (dd, J = 16.2, 5.7 Hz, 1H), 4.29-4.22 (m, 1H), 4.06 (s, 1H), 2.88-2.79 (m, 1H), 1.93-1.79 (m, 2H), 1.79-1.71 (m, 1H), 0.53 (dd, J = 10.3, 8.2 Hz, 1H). |
| 27 | 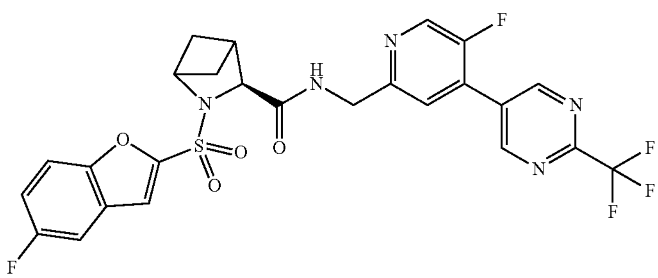 [SMILES: O=C(NCc1cc(-c2cnc(C(F)(F)F)nc2)c(F)cn1)[C@@H]1C2CC(C2)N1S(=O)(=O)c1cc2cc(F)ccc2o1] | 0.00108 | $^1$H NMR (400 MHz, DMSO-d6) δ 9.37 (s, 2H), 8.86 (t, J = 5.9 Hz, 1H), 8.76 (d, J = 2.0 Hz, 1H), 7.82 (dd, J = 9.2, 4.1 Hz, 1H), 7.80-7.75 (m, 2H), 7.65 (dd, J = 8.4, 2.7 Hz, 1H), 7.49-7.39 (m, 1H), 4.61 (dd, J = 16.2, 6.4 Hz, 1H), 4.48 (dd, J = 16.2, 5.6 Hz, 1H), 4.35-4.27 (m, 1H), 4.22 (s, 1H), 2.93-2.85 (m, 1H), 2.00-1.80 (m, 3H), 0.46 (dd, J = 10.5, 8.3 Hz, 1H). |
| 28 | 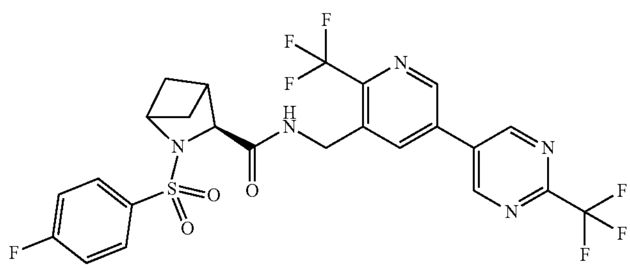 [SMILES: O=C(NCc1cc(-c2cnc(C(F)(F)F)nc2)cnc1C(F)(F)F)[C@@H]1C2CC(C2)N1S(=O)(=O)c1ccc(F)cc1] | 0.0121 | $^1$H NMR (400 MHz, DMSO-d6) δ 9.53 (s, 2H), 9.21-9.15 (m, 1H), 8.93 (t, J = 6.1 Hz, 1H), 8.55-8.49 (m, 1H), 8.05-7.95 (m, 2H), 7.55-7.45 (m, 2H), 4.81 (dd, J = 16.6, 6.6 Hz, 1H), 4.53 (dd, J = 16.4, 5.0 Hz, 1H), 4.24 (d, J = 7.2 Hz, 1H), 3.99 (s, 1H), 2.85-2.78 (m, 1H), 1.95-1.88 (m, 1H), 1.86-1.76 (m, 1H), 1.75-1.68 (m, 1H), 0.46-0.36 (m, 1H). |
| 29 | 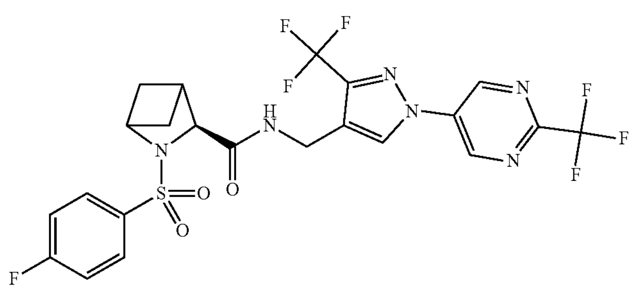 | 0.00484 | $^1$H NMR (400 MHz, CDCl3) δ 9.36 (s, 2H), 8.59 (s, 1H), 7.91-7.88 (m, 2H), 7.48-7.47 (m, 1H), 7.33-7.29 (m, 2H), 5.04-4.98 (m, 1H), 4.34-4.29 (m, 2H), 3.98 (s, 1H), 3.06-3.05 (m, 1H), 1.98 (d, J = 8 Hz, 1H), 1.74 (d, J = 7.2 Hz, 1H), 1.70-1.62 (m, 1H), 0.56 (t, J = 9.8 Hz, 1H). |
| 30 | 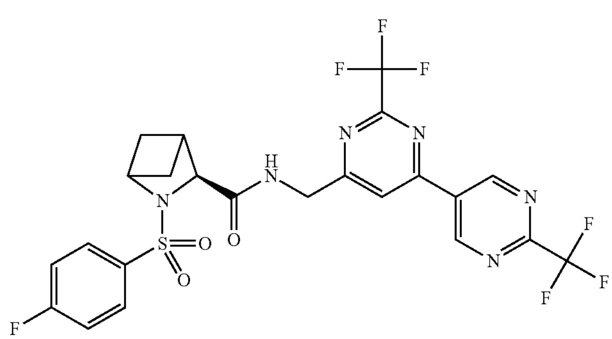 | 0.00118 | $^1$H NMR (300 MHz, DMSO-d6) δ 9.73 (s, 2H), 9.01 (m, 1H), 8.51 (s, 1H), 8.05-8.00 (m, 2H), 7.54-7.49 (m, 2H), 4.78-4.57 (m, 2H), 4.25 (d, J = 7.2, 1H), 4.01 (s, 1H), 2.83 (d, J = 7.5, 1H), 1.91-1.86 (m, 2H), 1.73 (d, J = 6.3, 1H), 0.46-0.39 (m, 1H). |

TABLE 3-continued

| Ex | Structure | IC$_{50}$ | $^1$H NMR |
|---|---|---|---|
| 31 | 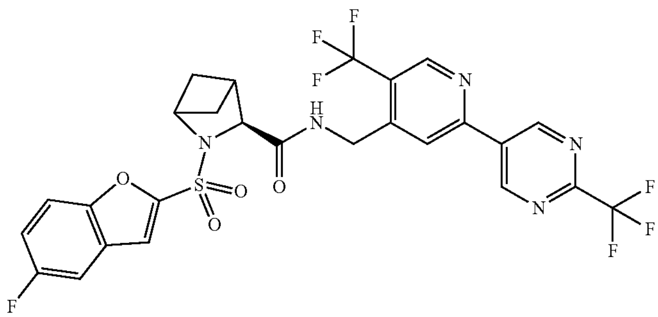 [SMILES: O=C(NCc1cc(-c2cnc(C(F)(F)F)nc2)ncc1C(F)(F)F)[C@@H]1C2CC(C2)N1S(=O)(=O)c1cc2cc(F)ccc2o1] | 0.00185 | $^1$H NMR (400 MHz, DMSO-d6) δ 9.69 (s, 2H), 9.15-9.07 (m, 2H), 8.31 (s, 1H), 7.87 (s, 1H), 7.84 (dd, J = 9.2, 4.1Hz, 1H), 7.67 (dd, J = 8.4, 2.7 Hz, 1H), 7.50-7.40 (m, 1H), 4.84 (dd, J = 17.2, 6.7 Hz, 1H), 4.49 (dd, J = 17.3, 5.0 Hz, 1H), 4.36 (d, J = 7.2 Hz, 1H), 4.28 (s, 1H), 2.96-2.88 (m, 1H), 2.05-1.98 (m, 1H), 1.93-1.84 (m, 2H), 0.52-0.43 (m, 1H). |
| 32 | 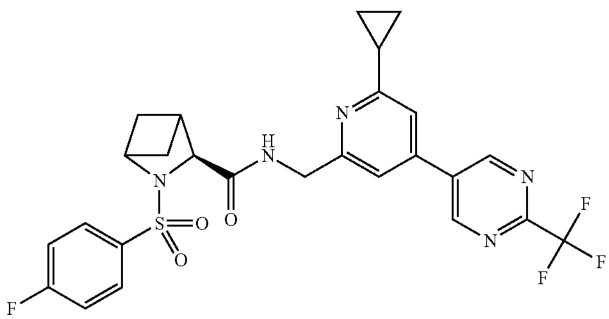 [SMILES: O=C(NCc1cc(-c2cnc(C(F)(F)F)nc2)cc(C2CC2)n1)[C@@H]1C2CC(C2)N1S(=O)(=O)c1ccc(F)cc1] | 0.00724 | $^1$H NMR (300 MHz, DMSO-d6) δ 9.48 (s, 2H), 8.70 (m, 1H), 8.02-7.97 (m, 2H), 7.74 (d, J = 1.5 Hz, 1H), 7.64 (d, J = 1.5 Hz, 1H), 7.53-7.47 (m, 2H), 4.61-4.34 (m, 2H), 4.24-4.22 (d, J = 7.1 Hz, 1H), 3.98 (d, J = 1.1 Hz, 1H), 2.83 (d, J = 7.1 Hz, 1H), 2.28-2.13 (m, 1H), 1.92-1.71 (m, 3H), 1.03-1.01 (m, 4H), 0.50-0.37 (m, 1H). |
| 33 | 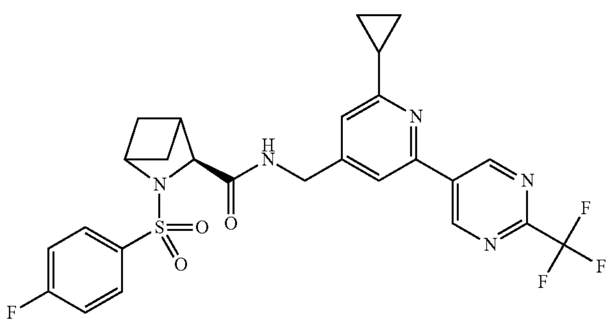 [SMILES: O=C(NCc1cc(-c2cnc(C(F)(F)F)nc2)nc(C2CC2)c1)[C@@H]1C2CC(C2)N1S(=O)(=O)c1ccc(F)cc1] | 0.00355 | $^1$H NMR (300 MHz, CDCl3) δ 9.43 (s, 2H), 7.95-7.86 (m, 2H), 7.68 (s, 1H), 7.60 (s, 1H), 7.30-7.12 (m, 3H), 4.87 (dd, J = 16.4, 7.5 Hz, 1H), 4.43-4.24 (m, 2H), 3.97 (s, 1H), 3.08-3.03 (m, 1H), 2.24-1.18 (m, 1H), 2.09-1.85 (m, 1H), 1.82-1.61 (m, 2H), 1.15-1.08 (m, 4H), 0.59-0.52 (m, 1H). |
| 34 | 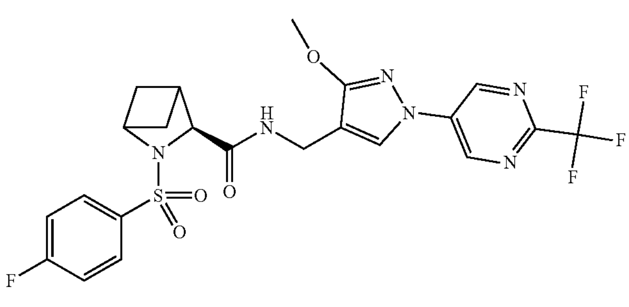 [SMILES: COc1nn(-c2cnc(C(F)(F)F)nc2)cc1CNC(=O)[C@@H]1C2CC(C2)N1S(=O)(=O)c1ccc(F)cc1] | 0.0191 | $^1$H NMR (300 MHz, DMSO-d6) δ 9.34 (s, 2H), 8.48 (s, 1H), 8.30 (t, J = 5.6 Hz, 1H), 7.99-7.94 (m, 2H), 7.51-7.45 (m, 2H), 4.28-4.05 (m, 3H), 3.99 (s, 3H), 3.93 (s, 1H), 2.79 (dd, J = 6.7, 3.3 Hz, 1H), 1.90-1.65 (m, 3H), 0.46 (t, J = 9.2 Hz, 1H). |

TABLE 3-continued

| Ex | Structure | IC$_{50}$ | $^1$H NMR |
|---|---|---|---|
| 35 | 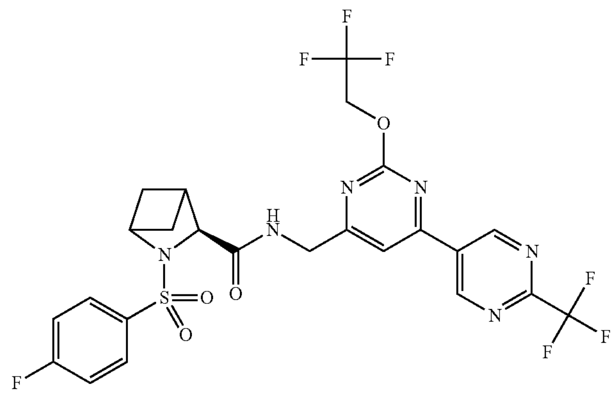 | 0.00424 | $^1$H NMR (400 MHz, CDCl3) δ 9.67 (s, 2H), 7.97-7.87 (m, 3H), 7.79 (dd, J = 8.1, 4.6 Hz, 1H), 7.37-7.27 (m, 2H), 5.14-4.88 (m, 3H), 4.45 (dd, J = 18.1, 4.3 Hz, 1H), 4.35 (dt, J = 7.6, 1.5 Hz, 1H), 4.03 (s, 1H), 3.13-3.04 (m, 1H), 2.01 (dt, J = 8.6, 2.6 Hz, 1H), 1.80-1.69 (m, 2H), 0.58 (dd, J = 10.9, 8.5 Hz, 1H). |

It is to be understood that the invention is not limited to the particular embodiments of the invention described above, as variations of the particular embodiments may be made and still fall within the scope of the appended claims. All documents cited to or relied upon herein are expressly incorporated by reference.

We claim:

1. A compound of formula (I) or a pharmaceutically acceptable salt thereof:

wherein:
  $R^1$ is selected from aryl and heteroaryl, each optionally substituted with one or more groups independently selected from halogen, —$C_{1-6}$ alkyl and —$C_{1-6}$ haloalkyl;
  m is 0, 1 or 2;
  each $R^2$ is independently selected from —$C_{1-6}$ alkyl;
  $R^3$ is a 4-, 5-, 6- or 7-membered heteraryl optionally substituted with one or more groups independently selected from halogen, —$C_{1-6}$ alkyl, —$C_{1-6}$ haloalkyl, —O—$C_{1-6}$ alkyl, and —CN; and
  A is selected from $A^1$, $A^2$ and $A^3$ wherein:
    $A^1$ unsubstituted or substituted 5-membered heteroaryl comprising one or two nitrogen hetero atoms;
    $A^2$ is unsubstituted or substituted aryl; and
    $A^3$ is unsubstituted or substituted 6-membered heteroaryl comprising one or two nitrogen hetero atoms.

2. The compound of claim 1 wherein $R^1$ is selected from:
(1) aryl substituted with a substituent selected from Cl, F, —CHF$_2$, —CF$_3$, —CHCl$_2$ and —CCl$_3$ and
(2) benzofuran substituted with a substituent selected from Cl, F, —CHF$_2$, —CF$_3$, —CHCl$_2$ and —CCl$_3$.

3. The compound of claim 2 wherein $R^1$ is selected from:

4. The compound of claim 1 wherein m is 0.

5. The compound of claim 1 wherein m is 1 or 2.

6. The compound of claim 1 wherein A is $A^1$ selected from:

wherein n is 0 or 1 and wherein $R^4$ is selected from halogen, —O—$C_{1-6}$ alkyl and —$C_{1-6}$ haloalkyl.

7. The compound of claim 6 wherein $A^1$ is selected from:

8. The compound of claim 1 wherein A is $A^2$ of the formula:

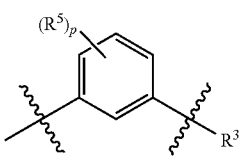

wherein p is 0 or 1 and wherein $R^5$ is selected from halogen, —CN, —O—$C_{1-6}$ alkyl, —O—$C_{1-6}$ haloalkyl, —$C_{1-6}$ haloalkyl and —$C_{3-7}$ cycloalkyl.

9. The compound of claim 8 wherein $A^2$ is selected from:

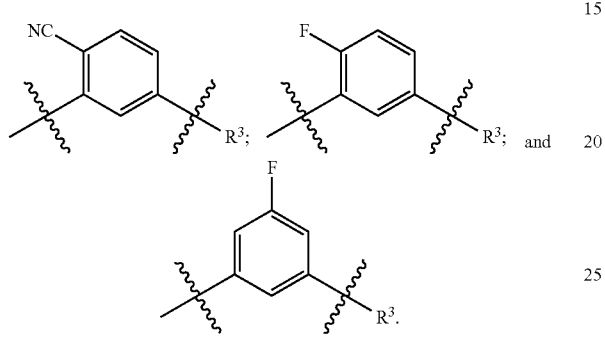

10. The compound of claim 1 wherein A is $A^3$, wherein $A^3$ is of the formula:

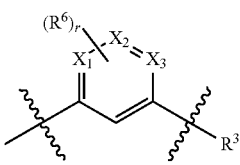

wherein:
(1) $X_1$, $X_2$ and $X_3$ are independently selected from C and N wherein
  (i) one of $X_1$, $X_2$ and $X_3$ is N and r is 0, 1 or 2, or
  (ii) $X_1$ and $X_3$ are each N and r is 0 or 1; and
(2) each $R^6$ is independently selected from halogen, —CN, —$C_{3-7}$ cycloalkyl, —O—$C_{1-6}$ haloalkyl, —O—$C_{1-6}$ alkyl, and —$C_{1-6}$ haloalkyl.

11. The compound of claim 10 wherein $A^3$ is selected from:

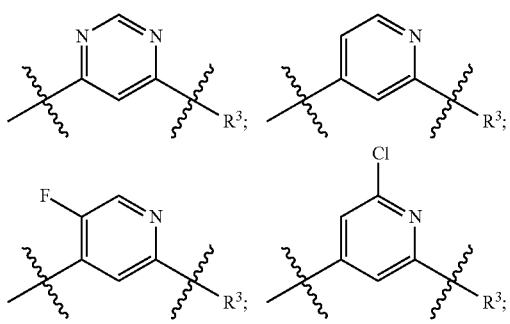

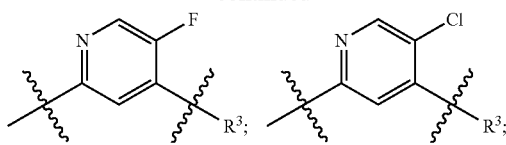

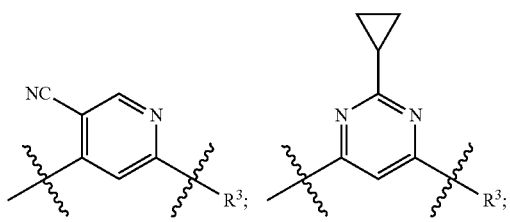

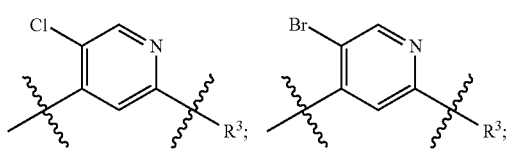

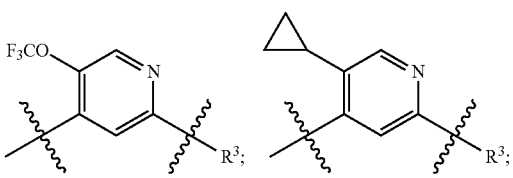

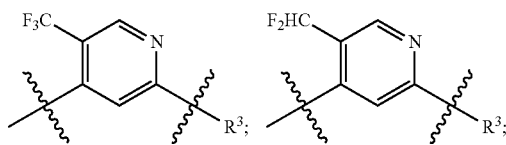

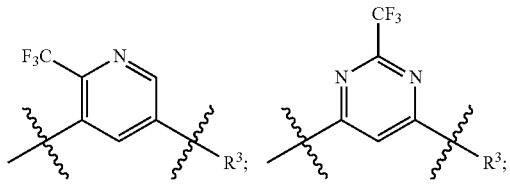

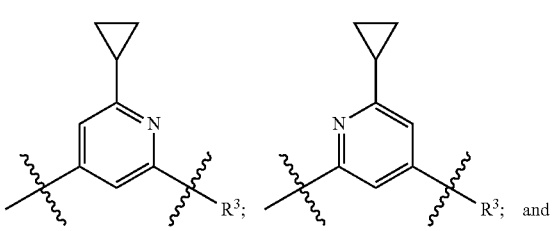

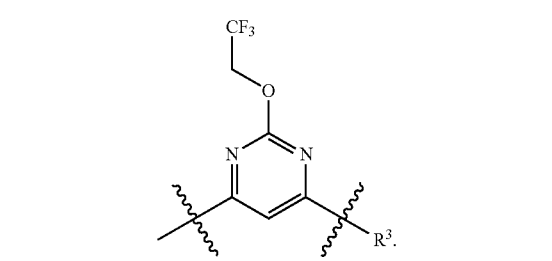

12. The compound of claim 1 wherein R³ is selected from:

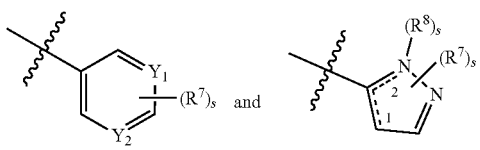

wherein:

at least one of Y₁ and Y₂ is N;

each s is independently 0 or 1;

R⁷ is selected from halogen, —O—C$_{1-6}$ alkyl, and —C$_{1-6}$ haloalkyl;

R⁸ is selected from H and —C$_{1-6}$ alkyl; and the dashed bonds indicated at position 1 and position 2 are optional double bonds, wherein a double bond may be located only at one of position 1 and position 2, and wherein R⁸ is absent when a double bond is present at position 2.

13. The compound of claim 12 wherein R³ is selected from:

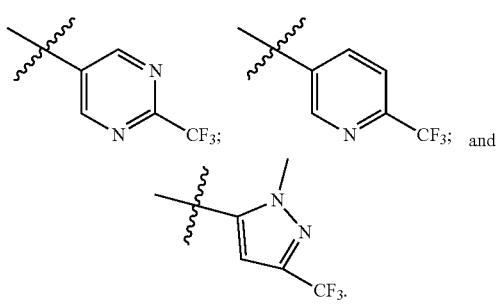

14. The compound of claim 1 selected from:

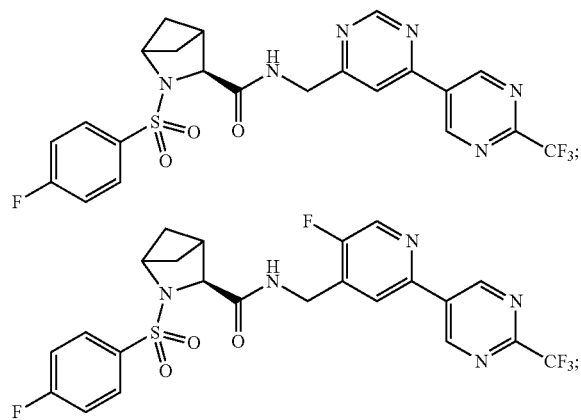

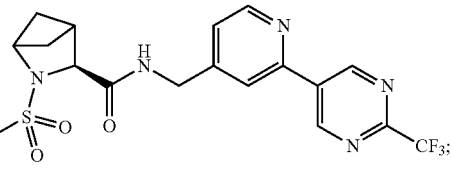

-continued

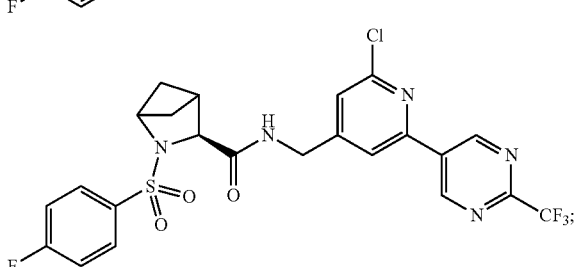

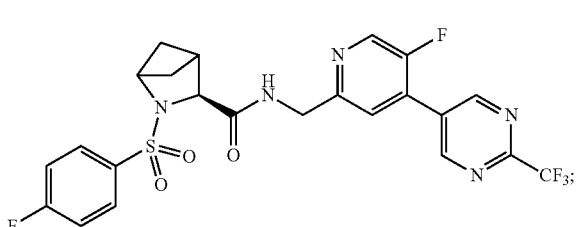

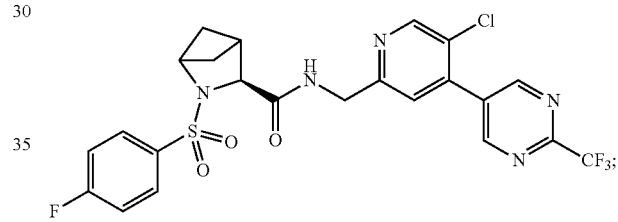

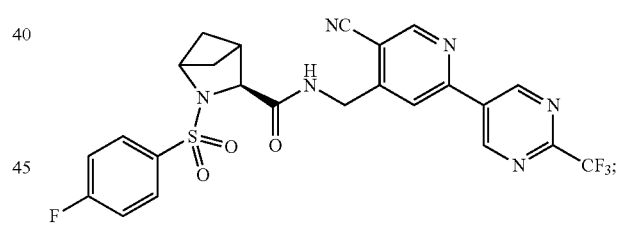

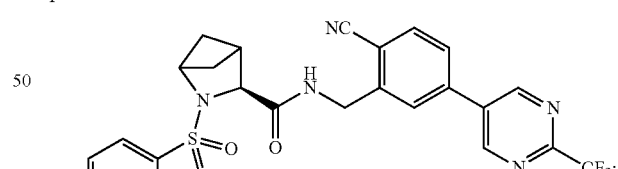

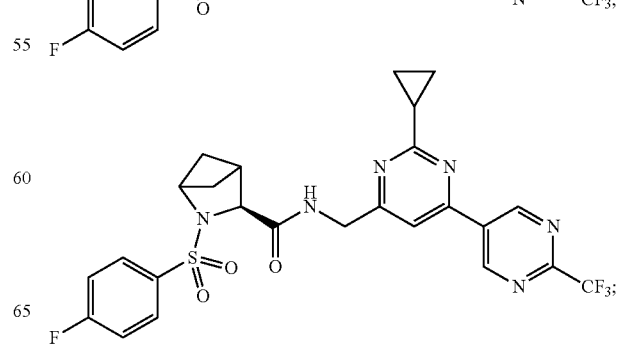

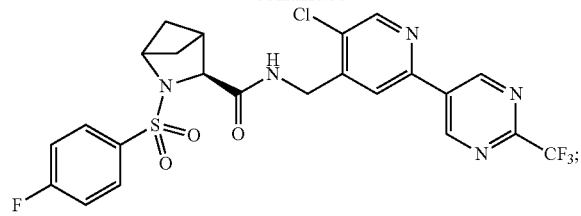
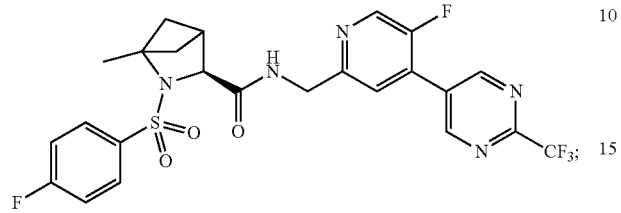
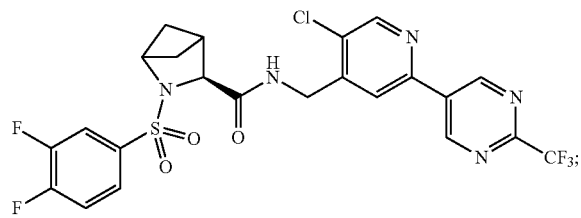
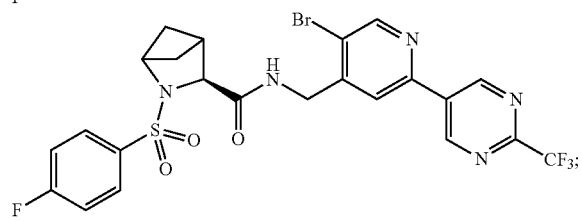
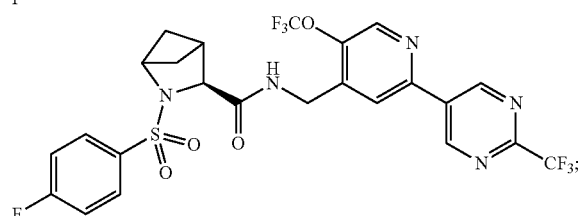
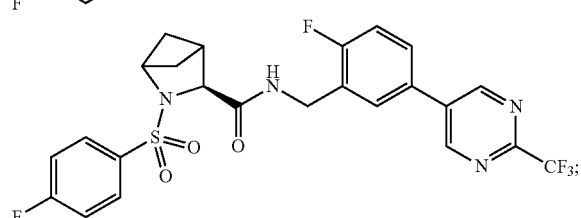
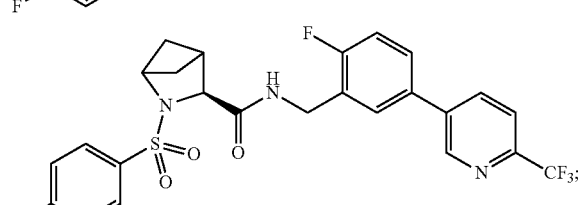
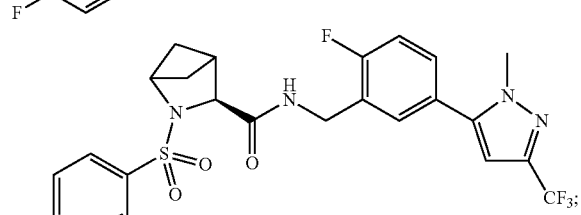
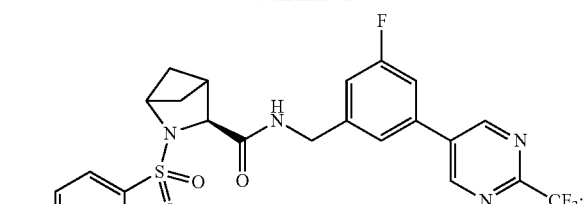
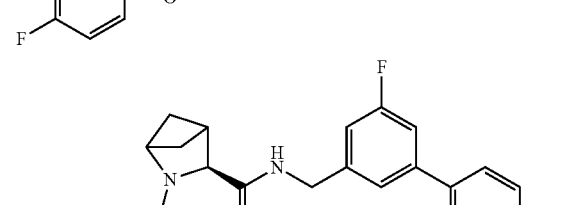
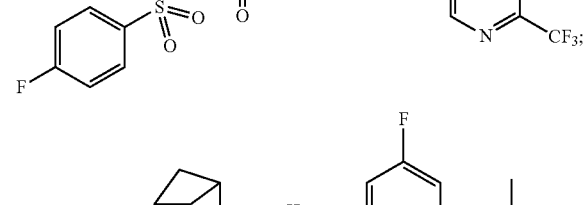
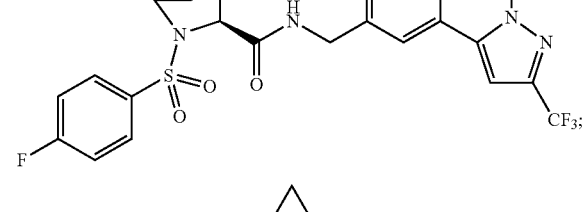
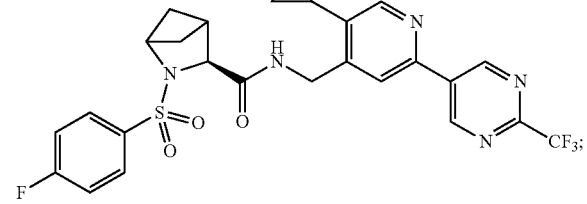
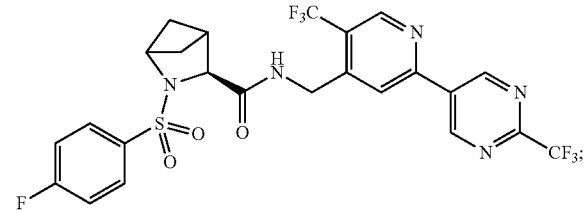
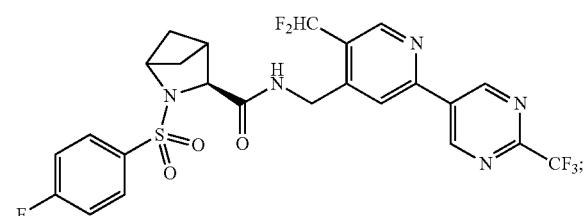
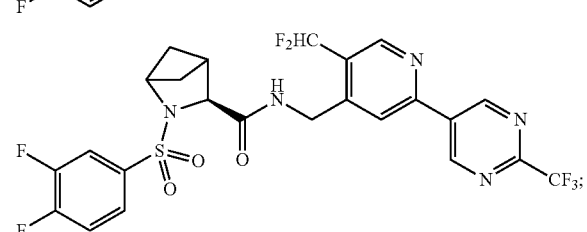

-continued
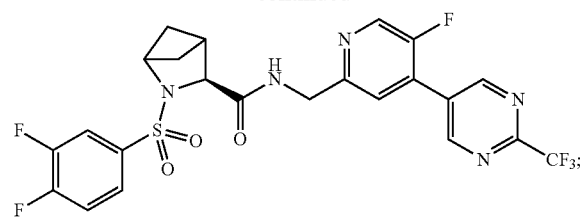
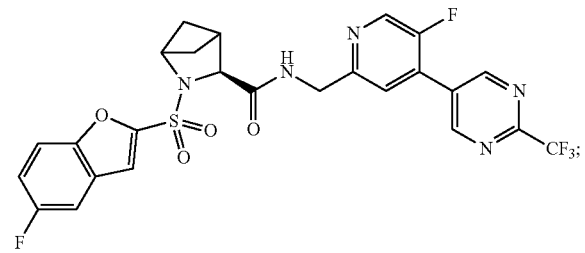
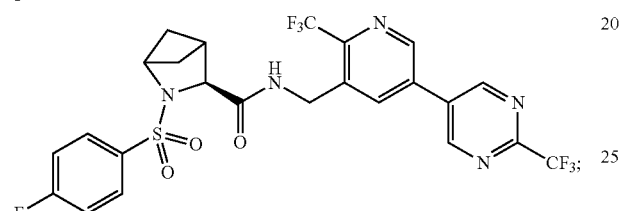
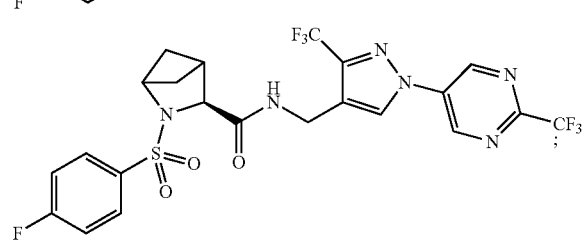
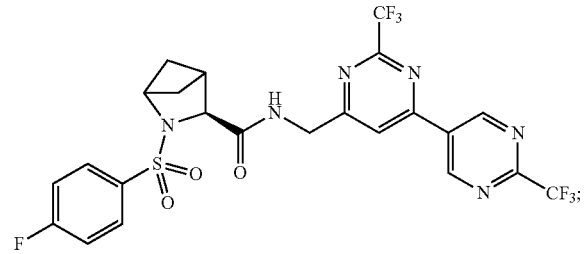
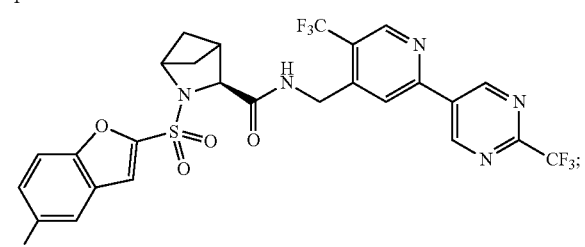
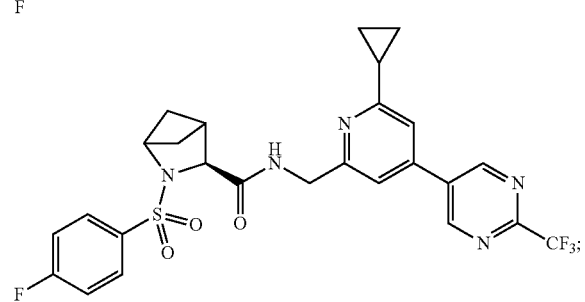
-continued
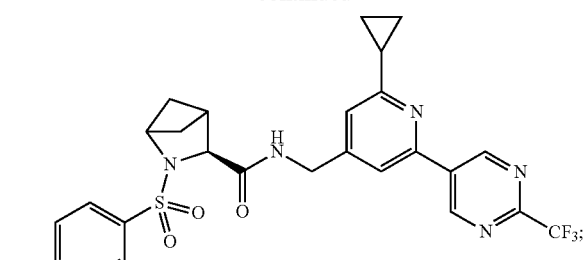
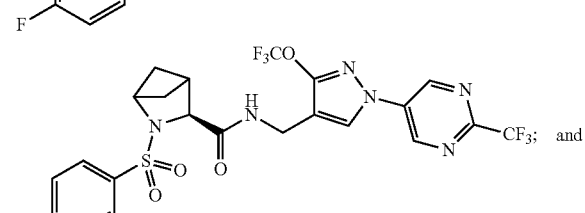
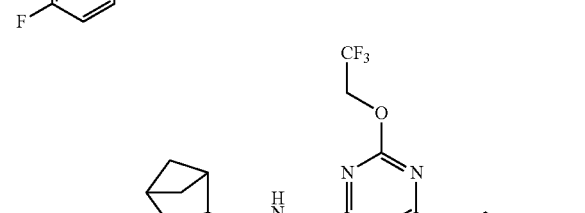
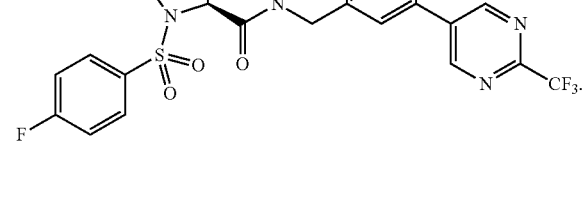
15. A compound selected from:
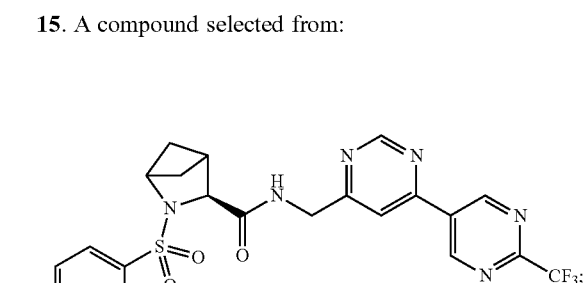
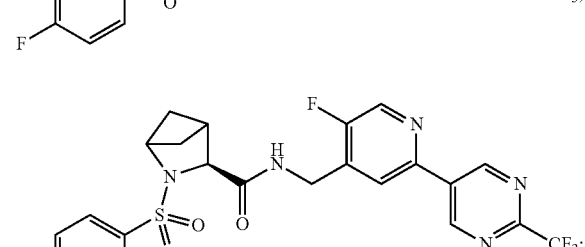
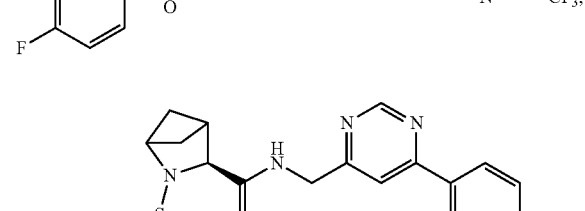

175
-continued
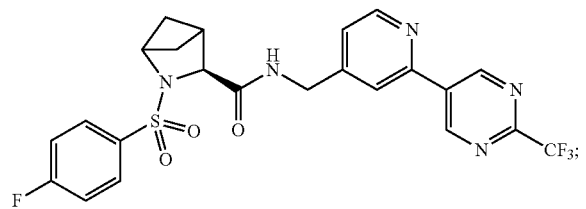
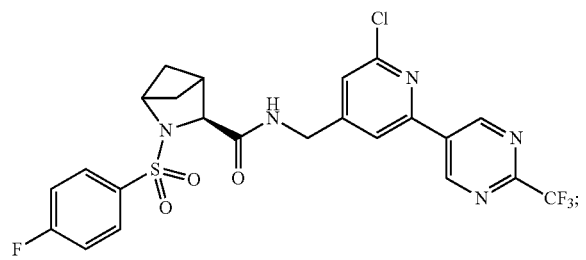
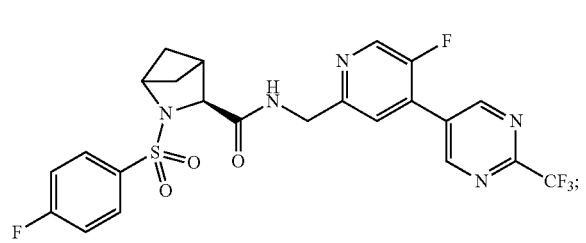
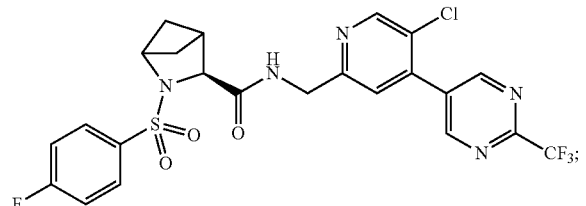
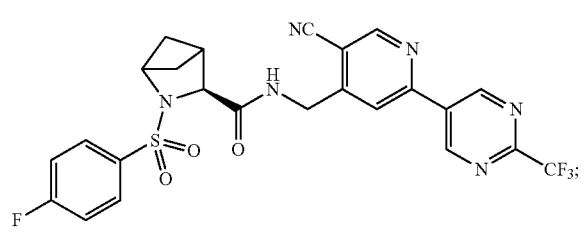
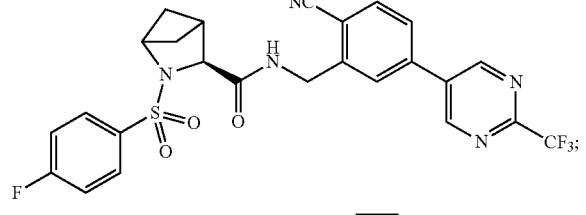
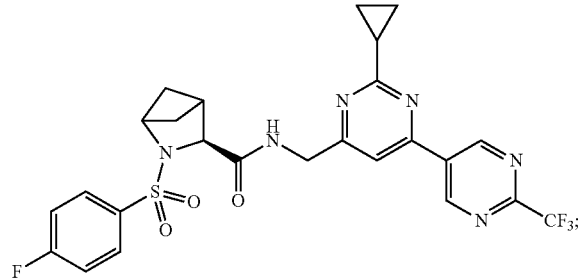
176
-continued
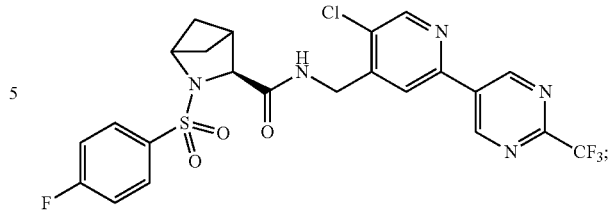
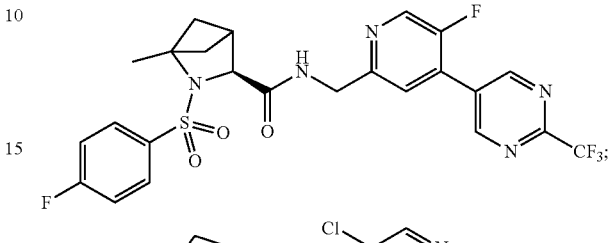
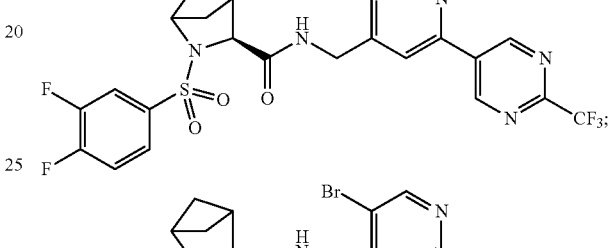
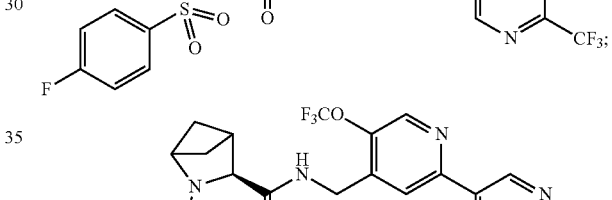
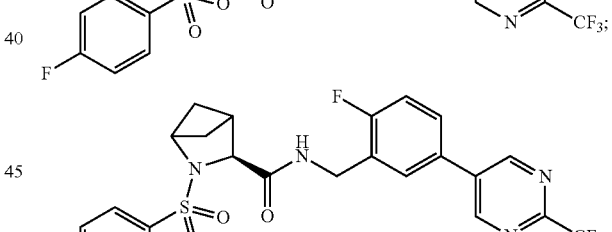
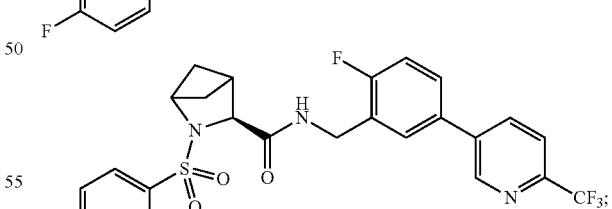
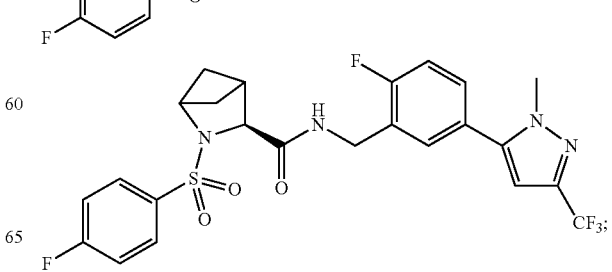

-continued
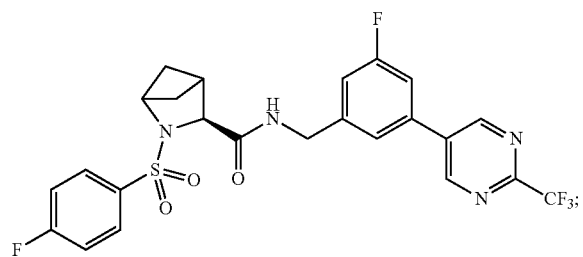
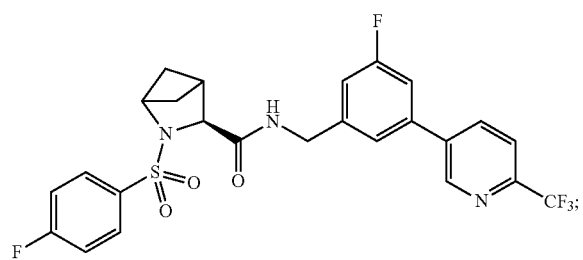
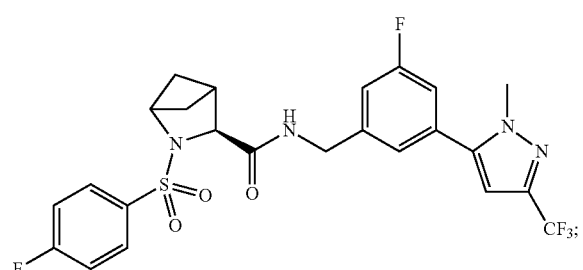
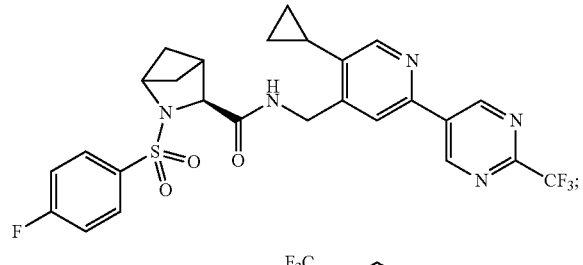
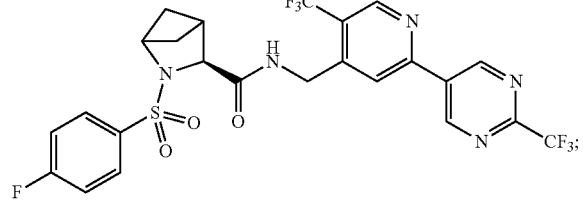
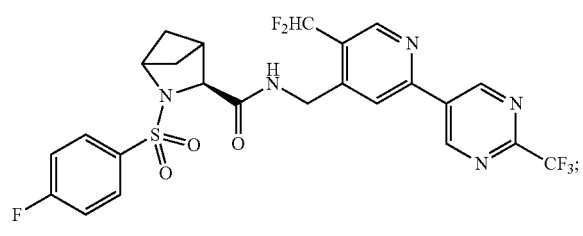
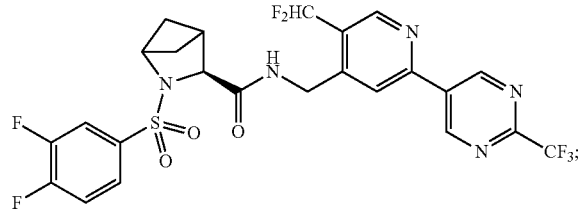
-continued
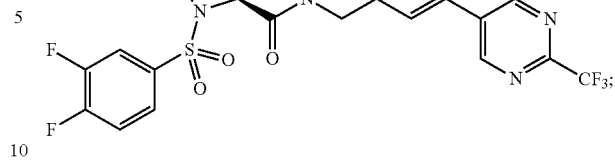
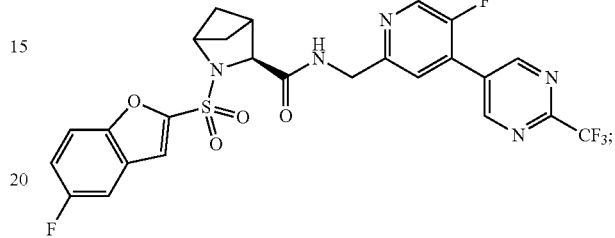
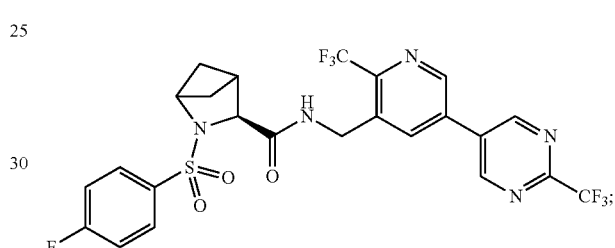
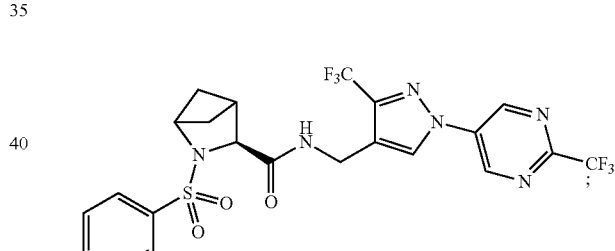
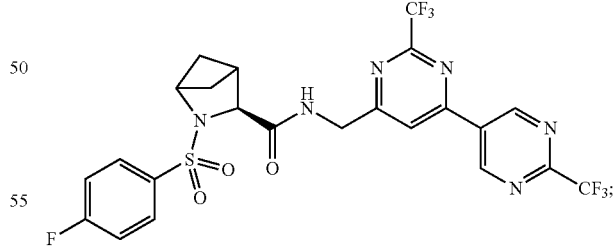
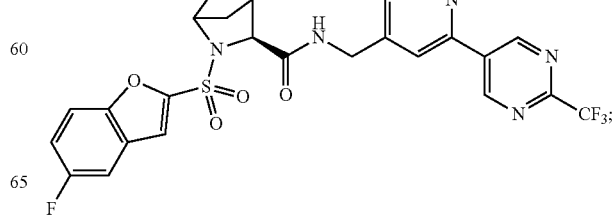

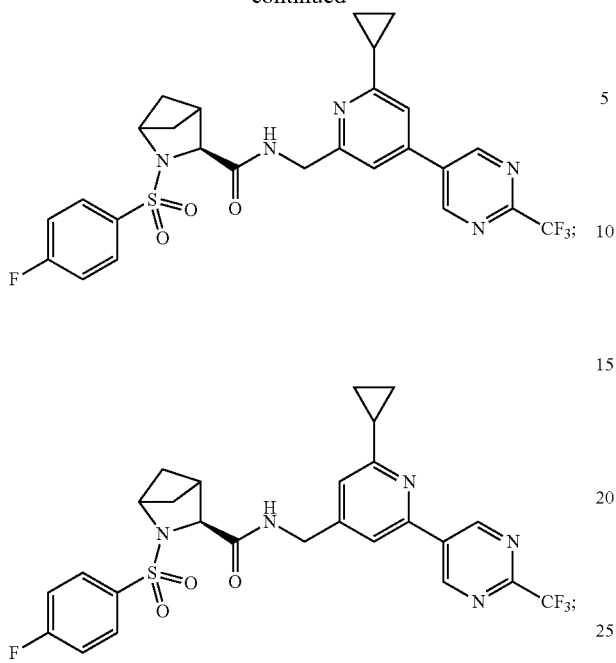

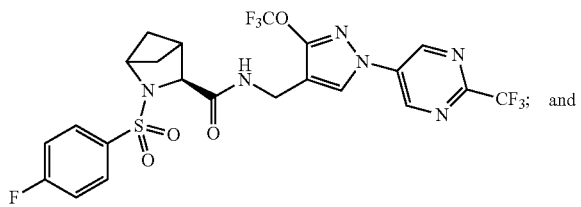

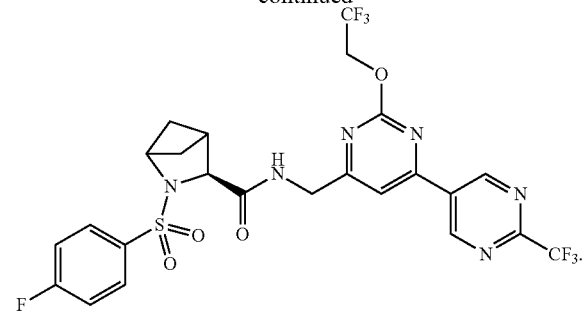

16. A pharmaceutical composition, comprising a compound as described in claim 1 or a pharmaceutically acceptable salt thereof, and a pharmaceutically acceptable carrier, diluent or excipient.

17. A method for modulating TRPA1 activity, comprising contacting TRPA1 with a compound as described in claim 1 or a salt thereof.

18. A method for treating a disease or condition mediated by TRPA1 activity in a mammal, wherein the disease or condition is pain, itch, an inflammatory disorder, chronic obstructive pulmonary disease, or incontinence, the method comprising administering a compound as described in claim 1 or a pharmaceutically acceptable salt thereof to the mammal.

19. A method for treating a disease or condition mediated by TRPA1 activity in a mammal, wherein the disease or condition is pain, arthritis, itch, cough, asthma, or inflammatory bowel disease, the method comprising administering a compound as described in claim 1 or a pharmaceutically acceptable salt thereof to the mammal.

* * * * *